(12) United States Patent
Quibell et al.

(10) Patent No.: US 7,803,803 B2
(45) Date of Patent: Sep. 28, 2010

(54) TETRAHYDROFURO[3,2-B] PYRROL-3-ONES AS CATHEPSIN K INHIBITORS

(75) Inventors: Martin Quibell, Cambridge (GB); John Paul Watts, Cambridge (GB)

(73) Assignee: Amura Therapeutics Limited, Madingley (GB)

(*) Notice: Subject to any disclaimer, the term of this patent is extended or adjusted under 35 U.S.C. 154(b) by 0 days.

(21) Appl. No.: 12/319,564

(22) Filed: Jan. 8, 2009

(65) Prior Publication Data

US 2009/0197817 A1    Aug. 6, 2009

Related U.S. Application Data

(63) Continuation of application No. PCT/GB2007/002642, filed on Jul. 13, 2007.

(51) Int. Cl.
*A61K 31/496* (2006.01)
*A61K 31/454* (2006.01)
*C07D 491/08* (2006.01)
*C12Q 1/37* (2006.01)

(52) U.S. Cl. .................. 514/254.08; 514/321; 544/373; 546/198; 435/23

(58) Field of Classification Search ........................ None
See application file for complete search history.

(56) References Cited

FOREIGN PATENT DOCUMENTS

| WO | WO-01/58886 | 8/2001 |
|---|---|---|
| WO | WO-02/057270 | 7/2002 |
| WO | WO-2005/066180 | 7/2005 |
| WO | WO-2008/007114 | 1/2008 |

OTHER PUBLICATIONS

Wolff, Manfred E. Burger's Medicinal Chemistry, 5th Ed. Part 1, pp. 975-977 (1995).*
Banker et al. "Modern Pharmaceutics", 3rd Ed. p. 596 (1996).*
Quibell, et al: "Bicyclic peptidomimetic tetrahydrofuro[3,2-b]pyrrol-3-one and hexahydrofuro[3,2-b]pyridine-3-one based scaffolds: synthesis and cysteinyl proteinase inhibition," Bioorganic & Medicinal Chemistry 12 (2004) 5689-5710.
International Search Report from Corresponding PCT Application No. PCT/GB2007/002642, (2007).
International Preliminary Report on Patentability for PCT Application No. PCT/GB2007/002642, (2008).
* cited by examiner

*Primary Examiner*—Emily Bernhardt
(74) *Attorney, Agent, or Firm*—Edwards Angell Palmer & Dodge LLP; Kathleen Williams; Weiying Yang

(57) ABSTRACT

The present invention relates to compounds of formula (I), and pharmaceutically acceptable salts thereof,

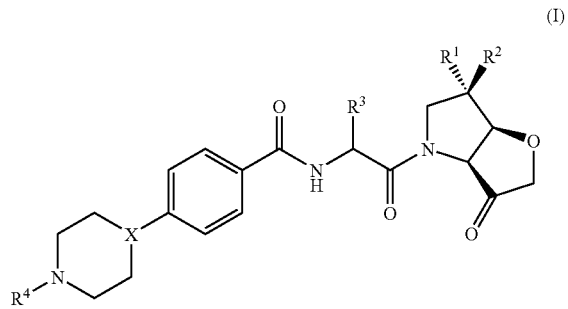

(I)

wherein:
X is CH or N;
one of $R^1$ and $R^2$ is H, and the other is selected from $OR^6$, $SR^6$, $NR^6R^7$, $N_3$, Me, Et, $CF_3$, $SOR^8$ and $SO_2R^8$;
$R^3$ is selected from tert-butylmethyl, iso-propylmethyl, sec-butyl, tert-butyl, cyclopentyl and cyclohexyl;
$R^4$ is optionally substituted $C_{1-8}$ alkyl or optionally substituted $C_{3-8}$ cycloalkyl;
$R^6$ and $R^7$ are each independently selected from H, $C_{1-8}$-alkyl and $C_{3-8}$-cycloalkyl, or $R^6$ and $R^7$ are linked to form a cyclic group together with the nitrogen to which they are attached; and
$R^8$ is $C_{1-8}$-alkyl or $C_{3-8}$-cycloalkyl.

The invention further relates to pharmaceutical compositions comprising compounds of formula (I), and the use of such compounds in the treatment of a disease selected from osteoporosis, Paget's disease, Chagas's disease, malaria, gingival diseases, hypercalaemia, metabolic bone disease, diseases involving matrix or cartilage degradation, and bone cancer disorders such as bone metastases and associated pain.

19 Claims, No Drawings

TETRAHYDROFURO[3,2-B] PYRROL-3-ONES AS CATHEPSIN K INHIBITORS

CROSS-REFERENCE TO RELATED APPLICATIONS

This application is a continuation of PCT application no. PCT/GB2007/002642, filed Jul. 13, 2007, which claims priority to GB Patent Application No. 0614044.6, filed Jul. 14, 2006. The contents of these applications are incorporated herein by reference in their entirety.

The present invention relates to compounds that are inhibitors of cysteine proteinases, pharmaceutical compositions containing said compounds, and their use in therapy. More specifically, but not exclusively, the invention relates to compounds that are inhibitors of cathepsin K and related cysteine proteinases of the CA clan. Such compounds are particularly useful for the in vivo therapeutic treatment of diseases in which participation of a cysteine proteinase is implicated.

BACKGROUND TO THE INVENTION

Proteinases form a substantial group of biological molecules which to date constitute approximately 2% of all the gene products identified following analysis of several completed genome sequencing programmes. Proteinases have evolved to participate in an enormous range of biological processes, mediating their effect by cleavage of peptide amide bonds within the myriad of proteins found in nature. This hydrolytic action is performed by initially recognising, then binding to, particular three-dimensional electronic surfaces displayed by a protein, which align the bond for cleavage precisely within the proteinase catalytic site. Catalytic hydrolysis then commences through nucleophilic attack of the amide bond to be cleaved either via an amino acid side-chain of the proteinase itself, or through the action of a water molecule that is bound to and activated by the proteinase. Proteinases in which the attacking nucleophile is the thiol side-chain of a Cys residue are known as cysteine proteinases. The general classification of 'cysteine proteinase' contains many members found in a wide range of organisms from viruses, bacteria, protozoa, plants and fungi to mammals.

Cathepsin K and indeed many other crucial proteinases belong to the papain-like CAC1 family. Cysteine proteinases are classified into 'clans' based upon a similarity in the three-dimensional structure or a conserved arrangement of catalytic residues within the proteinase primary sequence. Additionally, 'clans' may be further classified into 'families' in which each proteinase shares a statistically significant relationship with other members when comparing the portions of amino acid sequence which constitute the parts responsible for the proteinase activity (see Barrett, A. J et al, in 'Handbook of Proteolytic Enzymes', Eds. Barrett, A. J., Rawlings, N. D., and Woessner, J. F. Publ. Academic Press, 1998, for a thorough discussion).

To date, cysteine proteinases have been classified into five clans, CA, CB, CC, CD and CE (Barrett, A. J. et al, 1998). A proteinase from the tropical papaya fruit 'papain' forms the foundation of clan CA, which currently contains over 80 distinct and complete entries in various sequence databases, with many more expected from the current genome sequencing efforts. Proteinases of clan CA/family C1 have been implicated in a multitude of house-keeping roles and disease processes. e.g. human proteinases such as cathepsin K (osteoporosis, osteoarthritis), cathepsin S (multiple sclerosis, rheumatoid arthritis, autoimmune disorders), cathepsin L (metastases), cathepsin B (metastases, arthritis), cathepsin F (antigen processing), cathepsin V (T-cell selection), dipeptidyl peptidase I (granulocyte serine proteinase activation) or parasitic proteinases such as falcipain (malaria parasite *Plasmodium falciparum*) and cruzipain (*Trypanosoma cruzi* infection). Recently a bacterial proteinase, staphylopain (*S. aureus* infection) has also been tentatively assigned to clan CA.

X-ray crystallographic structures are available for a range of the above mentioned proteinases in complex with a range of inhibitors e.g. papain (PDB entries, 1pad, 1pe6, 1pip, 1pop, 4pad, 5pad, 6pad, 1ppp, 1the, 1csb, 1huc), cathepsin K (1au0, 1au2, 1au3, 1au4, 1atk, 1mem, 1bgo, 1ayw, 1ayu, 1nl6, 1nlj, 1q6k, 1snk, 1tu6), cathepsin L (1cs8, 1mhw), cathepsin S (1glo, 1ms6, 1npz), cathepsin V (1fh0), dipeptidyl peptidase I (1jqp, 1k3b), cathepsin B (1gmy, 1csb), cathepsin F (1m6d), cruzain (a recombinant form of cruzipain see Eakin, A. E. et al, 268(9), 6115-6118, 1993) (1ewp, 1aim, 2aim, 1F29, 1F2A, 1F2B, 1F2C), staphylopain (1cv8). Each of the structures displays a similar overall active-site topology, as would be expected by their 'clan' and 'family' classification and such structural similarity exemplifies one aspect of the difficulties involved in discovering a selective inhibitor of cathepsin K suitable for human use. However, subtle differences in terms of the depth and intricate shape of the active site groove of each CAC1 proteinase are evident, which may be exploited for selective inhibitor design. Additionally, many of the current substrate-based inhibitor complexes of CAC1 family proteinases show a series of conserved hydrogen bonds between the inhibitor and the proteinase backbone, which contribute significantly to inhibitor potency. Primarily a bidentate hydrogen-bond is observed between the proteinase Gly66 (C=O)/inhibitor N—H and the proteinase Gly66 (NH)/inhibitor (C=O), where the inhibitor (C=O) and (NH) are provided by an amino acid residue <u>NHCHRCO</u> that constitutes the S2 sub-site binding element within the inhibitor (see Berger, A. and Schecter, I. *Philos. Trans. R. Soc. Lond.* *[Biol.]*, 257, 249-264, 1970 for a description of proteinase binding site nomenclature). A further hydrogen-bond between the proteinase main-chain (C=O) of asparagine or aspartic acid (158 to 163, residue number varies between proteinases) and an inhibitor (N—H) is often observed, where the inhibitor (N—H) is provided by the S1 sub-site binding element within the inhibitor. Thus, the motif X—<u>NHCHR CO</u>—NH—Y is widely observed amongst the prior art substrate-based inhibitors of CAC1 proteinases.

Cathepsin K is thought to be significant in diseases involving excessive loss of bone or cartilage. Bone consists of a protein matrix incorporating hydroxyapatite crystals. About 90% of the structural protein of the matrix is type I collagen, with the remainder comprising various non-collagenous proteins such as osteocalcin, proteoglycans, osteopontin, osteonectin, thrombospondin, fibronectin and bone sialoprotein.

Skeletal bone is not a static structure but continually undergoes a cycle of bone resorption and replacement. Bone resorption is carried out by osteoclasts, which are multi-nuclear cells of haematopoietic lineage. Osteoclasts adhere to the bone surface and form a tight sealing zone. The membrane on the apical surface of the osteoclasts is folded so as to create a closed extracellular compartment between the osteoclast and the bone surface, which is acidified by proton pumps in the osteoclast membrane. Proteolytic enzymes are secreted into the compartment from the osteoclast. The high acidity in the compartment causes the hydroxyapatite at the surface of the bone to be dissolved and the proteolytic enzymes break down the protein matrix causing a resorption lacuna to be formed. Following bone resorption, osteoblasts produce a new protein matrix that is subsequently mineralised.

In disease states such as osteoporosis and Paget's disease, the bone resorption and replacement cycle is disrupted leading to a net loss of bone with each cycle. This leads to weakening of the bone and therefore to increased risk of bone fracture.

Cathepsin K is expressed at a high level in osteoclasts and is therefore thought to be essential for bone resorption. Thus, selective inhibition of cathepsin K is likely to be effective in the treatment of diseases involving excessive bone loss. These include osteoporosis, gingival diseases such as gingivitis and periodontitis, Paget's disease, hypercalaemia of malignancy and metabolic bone disease.

In addition to osteoclasts, high levels of cathepsin K are also found in chondroclasts from the synovium of osteoarthritic patients. It therefore appears that cathepsin K inhibitors will be of use in the treatment of diseases involving matrix or cartilage degradation, in particular osteoarthritis and rheumatoid arthritis.

Elevated levels of cathepsin K are also found in metastatic neoplastic cells which suggests that cathepsin K inhibitors may also be useful for treating certain neoplastic diseases.

In the prior art, the development of cysteine proteinase inhibitors for human use has recently been an area of intense activity (e.g. see Deaton, D. N. and Kumar, S., Prog. Med. Chem. 42, 245-375, 2004; Bromme, D. and Kaleta, J., Curr. Pharm. Des., 8, 1639-1658, 2002; Kim, W. and Kang, K., Expert Opin. Ther. Patents, 12(3), 419-432, 2002; Leung-Toung, R. et al. Curr. Med. Chem., 9, 979-1002, 2002; Lecaille, F. et al., Chem. Rev., 102, 4459-4488, 2002; Hernandez, A. A. and Roush, W. R., Curr. Opin. Chem. Biol., 6, 459-465, 2002). Considering the CAC1 family members, particular emphasis has been placed upon the development of inhibitors of human cathepsins, primarily cathepsin K (osteoporosis), cathepsin S (autoimmune disorders), cathepsin L (metastases), cathepsin B (metastases, arthritis), cathepsin F (antigen processing), cathepsin V (T-cell selection) and dipeptidyl peptidase I (granulocyte serine proteinase activation), through the use of peptide and peptidomimetic nitriles (e.g. see WO-A-03041649, WO-A-03037892, WO-A-03029200, WO-A-02051983, WO-A-02020485, US-A-20020086996, WO-A-01096285, WO-A-0109910, WO-A-0051998, WO-A-0119816, WO-A-9924460, WO-A-0049008, WO-A-0048992, WO-A-0049007, WO-A-0130772, WO-A-0055125, WO-A-0055126, WO-A-0119808, WO-A-0149288, WO-A-0147886), linear and cyclic peptide and peptidomimetic ketones (e.g. see Veber, D. F. and Thompson, S. K., Curr. Opin. Drug Discovery Dev., 3(4), 362-369, 2000, WO-A-02092563, WO-A-02017924, WO-A-01095911, WO-A-0170232, WO-A-0178734, WO-A-0009653, WO-A-0069855, WO-A-0029408, WO-A-0134153 to WO-A-0134160, WO-A-0029408, WO-A-9964399, WO-A-9805336, WO-A-9850533), ketoheterocycles (e.g. see WO-A-02080920, WO-A-03042197, WO-A-WO-A-03024924, WO-A-0055144, WO-A-0055124), monobactams (e.g. see WO-A-0059881, WO-A-9948911, WO-A-0109169), α-ketoamides (e.g. see WO-A-03013518), cyanoamides (WO-A-01077073, WO-A-01068645), dihydro pyrimidines (e.g. see WO-A-02032879) and cyanoaminopyrimidines (e.g. see WO-A-03020278, WO-A-03020721).

The prior art describes potent in vitro inhibitors, but also highlights the many difficulties in developing a human therapeutic. For example, WO-A-9850533 and WO-A-0029408 describe compounds that may be referred to as cyclic ketones (e.g. 1'a-f) and are inhibitors of cysteine proteinases with a particular reference towards papain family proteinases and as a most preferred embodiment, cathepsin K. WO-A-9850533 describes compounds subsequently detailed in the literature as potent inhibitors of cathepsin K with good oral bioavailability (Witherington, J., 'Tetrahydrofurans as Selective Cathepsin K Inhibitors', RSC meeting, Burlington House, London, 1999). The compounds of WO-A-9850533 were reported to bind to cathepsin K through the formation of a reversible covalent bond between the tetrahydrofuran carbonyl and the active site catalytic cysteine residue (Witherington, J., 1999). Additionally, the same cyclic ketone compounds are described in WO-A-9953039 as part of a wide-ranging description of inhibitors of cysteine proteinases associated with parasitic diseases, with particular reference to the treatment of malaria by inhibition of falcipain.

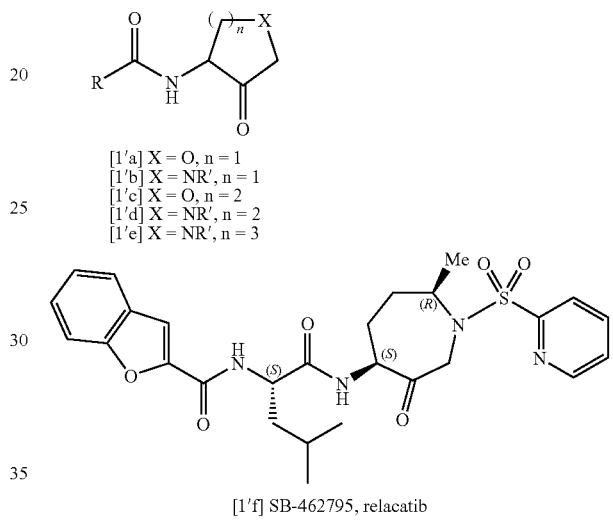

[1'a] X = O, n = 1
[1'b] X = NR', n = 1
[1'c] X = O, n = 2
[1'd] X = NR', n = 2
[1'e] X = NR', n = 3

[1'f] SB-462795, relacatib

Prior Art Cyclic Inhibitors of Cathepsin K

The initial cyclic inhibitors of GSK were based upon potent, selective and reversible 3-amido-tetrahydrofuran-4-ones [1'a], 3-amidopyrrolidin-4-ones [1'b], 4-amido-tetrahydropyran-3-ones [1'c], 4-amidopiperidin-3-ones [1'd] and 4-amidoazepan-3-ones [1'e, 1'f] (shown above) [see (a) Marquis, R. W. et al, J. Med. Chem. 2001, 44, 725, and references cited therein; (b) Marquis, R. W. et al, J. Med. Chem. 2001, 44, 1380, and references cited therein; (c) Yamashita, D. S. et al, J. Med. Chem. 2006, 49(5), 1597-1612].

Further studies revealed that cyclic ketones [1'], in particular the five-membered ring analogues [1'a] and [1'b], suffered from configurational instability due to facile epimerisation at the centre situated α to the ketone [Marquis, R. W. et al, J. Med. Chem. 2001, 44, 1380; Fenwick, A. E. et al, J. Bioorg. Med. Chem. Lett. 2001, 11, 199; WO 00/69855]. This precluded the pre-clinical optimisation of inhibitors of formulae [1'a-d] and led to the development of the configurationally more stable azepanone series [1'e], providing the cathepsin K inhibitor clinical candidate relacatib [1'f]. However, literature clearly states that azepanones are still prone to epimerisation and indeed relacatib [1'f] is reported to exist as a 9:1 thermodynamic mixture of 4-S and 4-R isomers [Yamashita, D. S. et al, J. Med. Chem., 2006, 49(5), 1597-1612]. As an alternative to the ring expansion approach, alkylation of the α-carbon removes the ability of cyclic ketones [1'] to undergo α-enolisation and hence leads to configurational stability. However, studies have shown that α-methylation in the 3-amidopyrrolidin-4-one [1'b] system results in a substantial loss in potency versus cathepsin K from $K_{i,app}$≈0.18 to 50 nM.

The cyclic ketone compounds of WO-A-0069855 are considered to be an advance on compounds of WO-A-9850533 due to the presence of the □-substituent on the cyclic ketone ring system that provides improved chiral stability to the α-carbon of the cyclic ketone ring system. However, the compounds of WO-A-0069855 and indeed those of WO-A-9850533 describe a requirement for the presence of the potential hydrogen-bonding motif X—NHCHRCO—NH—Y that is widely observed amongst the prior art substrate-based inhibitors of CAC1 proteinases.

More recent studies have investigated 5,5-bicyclic systems as inhibitors of CAC1 proteinases, for example, N-(3-oxo-hexahydrocyclopenta[b]furan-3a-yl)acylamide bicyclic ketones [2'] [(a) Quibell, M.; Ramjee, M. K., WO 02/57246; (b) Watts, J. et al, Bioorg. Med. Chem. 2004, 12, 2903-2925], tetrahydrofuro[3,2-b]pyrrol-3-one based scaffolds [3'] [(a) Quibell, M. WO02/57270; (b) Quibell, M. et al, Bioorg. Med. Chem., 2004, 12, 5689-5710], cis-6-oxohexahydro-2-oxa-1,4-diazapentalene and cis-6-oxo-hexahydropyrrolo[3,2-c]pyrazole based scaffolds [4'] [Wang, Y. et al, Bioorg. Med. Chem. Lett., 2005, 15, 1327-1331], and cis-hexahydropyrrolo[3,2-b]pyrrol-3-one based scaffolds [5'] (a) Quibell, M. WO04/07501; (b) Quibell, M. et al, Bioorg. Med. Chem., 2005, 13, 609-625].

[2']

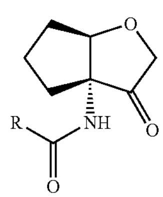

[3']

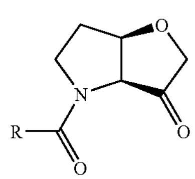

[4']

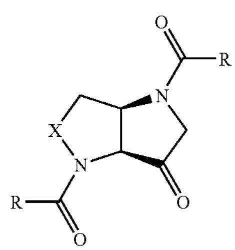

X = O
X = NH

[5']

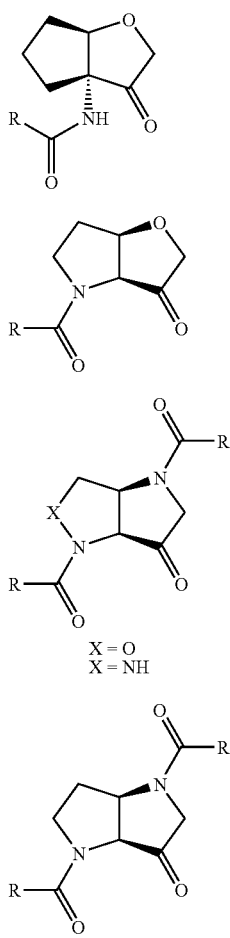

5,5-bicyclic Inhibitors of CAC1 Cysteinyl Proteinases

Studies have shown that the above-described 5,5-bicyclic systems exhibit promising potency as inhibitors of a range of therapeutically attractive mammalian and parasitic CAC1 cysteinyl proteinase targets. Moreover, the 5,5-bicyclic series are chirally stable due to a marked energetic preference for a cis-fused rather than a trans-fused geometry. This chiral stability provides a major advance when compared to monocyclic systems that often show limited potential for preclinical development due to chiral instability.

PCT applications WO-A-02057270 and WO-A-04007501 describe bicyclic compounds in which the chirality of the α-aminoketone is stabilised (for a review of energetic considerations within fused ring systems see (a) Toromanoff, E. *Tetrahedron Report No* 96, 36, 2809-2931, 1980; (b) Eliel, E. L. et. al. *Stereochemistry of Organic Compounds*, Wiley: New York, 1-1267, 1994). These compounds do not contain the X—NHCHRCO—NH—Y motif and yet the compounds are highly potent inhibitors across a broad range of CAC1 cysteine proteinases. In particular, certain of the compounds are potent and selective inhibitors of a range of mammalian and parasitic CAC1 proteinases.

More recently, Quibell, M. et al (*Bioorg. Med. Chem.* 12, 5689-5710, 2004) disclosed two potent and selective cathepsin K inhibitors having a tetrahydrofuro[3,2-b]pyrrol-3-one core, along with in vitro potency and in vitro selectivity data. Further kinetic parameters such as enzyme association (kon) and dissociation (koff) rates were disclosed, as well as basic physiochemical parameters such as plasma and microsome stability, Caco-2 permeability and LogD ($pH_{7.4}$) measurements.

The present inventors have now discovered a small genus of tetrahydrofuro[3,2-b]pyrrol-3-ones that exhibit potent in vitro inhibition versus human cathepsin K. Advantageously, the claimed compounds also display favourable pharmacokinetic properties and a highly preferred subset exhibit potent osteoclast activity versus human cells.

STATEMENT OF INVENTION

A first aspect of the invention relates to a compound of formula (I), or a pharmaceutically acceptable salt, hydrate, complex or pro-drug thereof, (I)

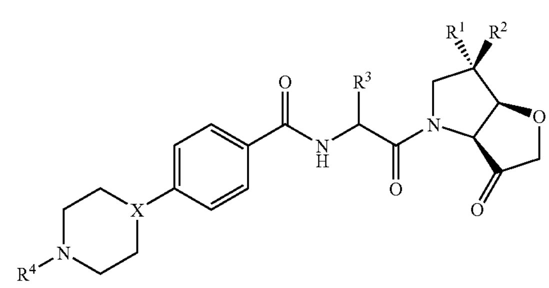

wherein:

X is CH or N;

one of $R^1$ and $R^2$ is H, and the other is selected from $OR^6$, $SR^6$, $NR^6R^7$, $N_3$, Me, Et, $CF_3$, $SOR^8$ and $SO_2R^8$;

$R^3$ is selected from tert-butylmethyl, iso-propylmethyl, sec-butyl, tert-butyl, cyclopentyl and cyclohexyl;

$R^4$ is optionally substituted $C_{1-8}$ alkyl or optionally substituted $C_{3-8}$ cycloalkyl;

$R^6$ and $R^7$ are each independently selected from H, $C_{1-8}$-alkyl and $C_{3-8}$-cycloalkyl, or $R^6$ and $R^7$ are linked to form a cyclic group together with the nitrogen to which they are attached; and $R^8$ is $C_{1-8}$-alkyl or $C_{3-8}$-cycloalkyl.

As mentioned above, compounds of formula (I) exhibit surprisingly high efficacies for human cathepsin K. Indeed, all of the compounds prepared to date exhibit potent in vitro inhibition versus human cathepsin K with Ki<50 nM. Furthermore, preferred compounds of formula (I) also exhibit desirable pharmacokinetic properties and potent cross species osteoclast activity, contrary to many cathepsin K inhibitors known in the art. In addition, preferred compounds of formula (I) also exhibit surprisingly good stability in plasma and microsome assays.

A second aspect of the invention relates to a pharmaceutical or veterinary composition comprising a compound of formula (I) and a pharmaceutically acceptable or veterinarily acceptable diluent, excipient and/or carrier.

A third aspect of the invention relates to a process for preparing a pharmaceutical or veterinary composition as defined above, said process comprising admixing a compound of the invention with a pharmaceutically acceptable or veterinarily acceptable diluent, excipient and/or carrier.

A fourth aspect of the invention relates to compounds of formula (I) for use in medicine.

A fifth aspect of the invention relates to the use of a compound of formula (I) in the preparation of a medicament for treating a disease selected from osteoporosis, Paget's disease, Chagas's disease, malaria, gingival diseases, hypercalaemia, metabolic bone disease, diseases involving matrix or cartilage degradation, and bone cancer disorders such as bone metastases and associated pain.

A sixth aspect of the invention relates to a method of inhibiting a cysteine proteinase in a cell, said method comprising contacting said cell with a compound of formula (I).

A seventh aspect of the invention relates to method of inhibiting a cysteine proteinase in a subject, said method comprising administering to the subject a pharmacologically effective amount of a compound of formula (I).

An eighth aspect of the invention relates to a method of treating a disease selected from osteoporosis, Paget's disease, Chagas's disease, malaria, gingival diseases, hypercalaemia, metabolic bone disease, diseases involving matrix or cartilage degradation, and bone cancer disorders such as bone metastases and associated pain, in a subject, said method comprising administering to the subject a pharmacologically effective amount of a compound of formula (I).

A ninth aspect of the invention relates to the use of a compound according to the invention in an assay for identifying further candidate compounds capable of inhibiting one or more cysteine proteinases.

A tenth aspect of the invention relates to the use of a compound of formula (I) in the validation of a known or putative cysteine proteinase as a therapeutic target.

An eleventh aspect of the invention relates to a process of preparing a compound of formula (I).

DETAILED DESCRIPTION

The term 'alkyl' as applied herein includes stable straight and branched chain aliphatic carbon chains which may be optionally substituted. Preferred examples include methyl, ethyl, n-propyl, isopropyl, n-butyl, isobutyl, t-butyl, pentyl, isopentyl, hexyl, heptyl and any simple isomers thereof. Suitable substituents include, for example, one or more $C_{1-6}$ alkoxy, OH, COOH, COOMe, $NH_2$, $NMe_2$, NHMe, $NO_2$, CN, $CF_3$ and/or halo groups. Additionally, where the alkyl group contains two or more contiguous carbon atoms, an alkene group (—CH=CH—) or alkyne group (—C≡C—) may be present. Furthermore, the alkyl group may optionally contain one or more heteroatoms for example, to give ethers, thioethers, sulphones, sulphonamides, substituted amines, amidines, guanidines, carboxylic acids, carboxamides. If the heteroatom is located at a chain terminus then it is appropriately substituted with one or two hydrogen atoms. For example, the group $CH_3$—$CH_2$—O—$CH_2$—$CH_2$— is defined within 'alkyl' as a $C_4$ alkyl that contains a centrally positioned heteroatom whereas the group $CH_3$—$CH_2$—$CH_2$—$CH_2$— is defined within 'alkyl' as an unsubstituted $C_4$ alkyl.

Preferably, the alkyl group is a $C_{1-8}$ alkyl group, more preferably a $C_{1-6}$ group, even more preferably a $C_{1-4}$ alkyl group.

As used herein, the term "cycloalkyl" refers to a cyclic alkyl group (i.e. a carbocyclic ring) which may be substituted (mono- or poly-) or unsubstituted. Suitable substituents include, for example, one or more $C_{1-6}$ alkyl, $C_{1-6}$ alkoxy, OH, COOH, COOMe, $NH_2$, $NMe_2$, NHMe, $NO_2$, CN, $CF_3$ and/or halo groups. Preferably, the cycloalkyl group is a $C_{3-8}$ cycloalkyl group, more preferably a $C_{3-6}$-cycloalkyl, even more preferably a $C_{3-4}$ cycloalkyl group. Examples include cyclopropyl, cyclobutyl, cyclopentyl, cyclohexyl and the like. In addition, the carbocyclic ring itself may optionally contain one or more heteroatoms, for example, to give a heterocycloalkyl group such as tetrahydrofuran, pyrrolidine, piperidine, piperazine or morpholine.

'Halogen' or 'halo' as applied herein encompasses F, Cl, Br, I.

'Heteroatom' as applied herein encompasses O, S, P and N, more preferably, O, S and N.

The present invention includes all salts, hydrates, solvates, complexes and prodrugs of the compounds of this invention. The term "compound" is intended to include all such salts, hydrates, solvates, complexes and prodrugs, unless the context requires otherwise.

In particular, the skilled person will appreciate that the ketone group of the bicycle core of compounds of formula (I) may exist in alternative forms such as the hydrate (as shown below), and the invention extends to all such alternative forms.

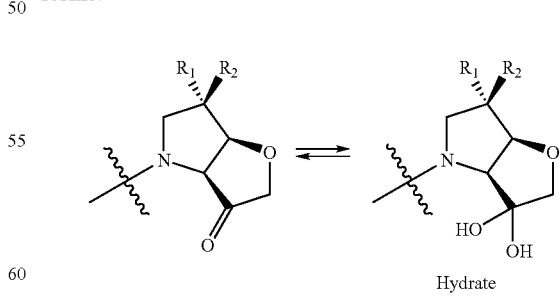

Hydrate

Abbreviations and symbols commonly used in the peptide and chemical arts are used herein to describe compounds of the present invention, following the general guidelines presented by the IUPAC-IUB Joint Commission on Biochemical Nomenclature as described in *Eur. J. Biochem.*, 158, 9-, 1984.

Compounds of formula (I) and the intermediates and starting materials used in their preparation are named in accordance with the IUPAC rules of nomenclature in which the characteristic groups have decreasing priority for citation as the principle group.

In one preferred embodiment, the compound of the invention is of formula Ia

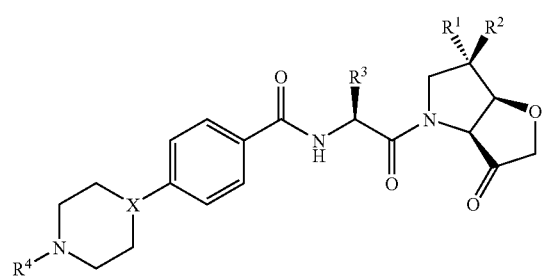

wherein X, $R^1$, $R^2$, $R^3$ and $R^4$ are as defined above.

In more preferred embodiment, $R^3$ is cyclohexyl such that the central moiety is the amino acid (S)-cyclohexylglycine.

In one highly preferred embodiment, $R^3$ is cyclopentyl such that the central moiety is the amino acid (S)-cyclopentylglycine.

In one preferred embodiment, $R^3$ is iso-propylmethyl such that the central moiety is the amino acid (S)-leucine.

In one preferred embodiment, $R^3$ is tert-butyl such that the central moiety is the amino acid (S)-tert-butylglycine.

In another preferred embodiment, $R^3$ is sec-butyl of S-configuration such that the central moiety is the amino acid (2S,3S)-isoleucine.

In another preferred embodiment, $R^3$ is tert-butylmethyl such that the central moiety is the amino acid (S)-tert-butylalanine.

In one highly preferred embodiment, $R^3$ is tert-butylmethyl such that the central moiety is the amino acid (S)-tert-butylalanine.

In one preferred embodiment, X is CH.

In another preferred embodiment, X is N.

In one preferred embodiment, $R^4$ is an unsubstituted $C_{3-6}$ cycloalkyl group.

In one preferred embodiment, $R^4$ is a $C_{1-6}$ alkyl group optionally substituted by one or more $C_{1-6}$ alkoxy groups.

Even more preferably, $R^4$ is selected from methyl, ethyl, n-propyl, isopropyl, cyclopropyl, n-butyl, s-butyl, i-butyl, tert-butyl, cyclobutyl and 2-methoxyethyl.

Yet even more preferably, $R^4$ is selected from methyl, ethyl, n-propyl, isopropyl, cyclopropyl, cyclobutyl and 2-methoxyethyl.

In one preferred embodiment, $R^3$ is selected from tert-butylmethyl, sec-butyl, tert-butyl, cyclopentyl and cyclohexyl.

In another preferred embodiment, $R^3$ is cyclopentyl or cyclohexyl.

In one preferred embodiment, $R^6$ and $R^7$ are each independently H, $C_{1-4}$-alkyl or $C_{3-6}$-cycloalkyl.

In more preferred embodiment, $R^6$ and $R^7$ are each independently selected from H, methyl, ethyl, isopropyl, n-propyl, iso-butyl, sec-butyl, tert-butyl, cyclopropyl and cyclobutyl.

In another preferred embodiment, $R^6$ and $R^7$ are linked to form an alkylene group,

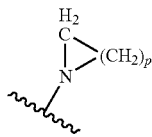

wherein p is 1, 2, 3 or 4.

In one preferred embodiment, one of $R^1$ and $R^2$ is H, and the other is selected from Me, Et, $CF_3$, OH, OMe, OEt, O"Pr, $O^iPr$, O-cyclopropyl, O-cyclobutyl, SH, SMe, SEt, S"Pr, $S^iPr$, S-cyclopropyl, S-cyclobutyl, $NH_2$, NHMe, NHEt, NH"Pr, $NH^iPr$, NH-cyclopropyl, NH-cyclobutyl, $NMe_2$, $N_3$, SOMe, SOEt, SO"Pr, $SO^iPr$, SO-cyclopropyl, SO-cyclobutyl, $SO_2Me$, $SO_2Et$, $SO_2"Pr$, $SO_2{}^iPr$, $SO_2$-cyclopropyl, $SO_2$-cyclobutyl and

More preferably, one of $R^1$ and $R^2$ is H, and the other is selected from OH, OMe, OEt, O"Pr, $O^iPr$, O-cyclopropyl, O-cyclobutyl, SH, SMe, SEt, S"Pr, S"Pr, S-cyclopropyl, S-cyclobutyl, $NH_2$, NHMe, NHEt, NH"Pr, $NH^iPr$, NH-cyclopropyl, NH-cyclobutyl, $NMe_2$, $N_3$, SOMe, SOEt, SO"Pr, $SO^iPr$, SO-cyclopropyl, SO-cyclobutyl, $SO_2Me$, $SO_2Et$, $SO_2"Pr$, $SO_2{}^iPr$, $SO_2$-cyclopropyl, $SO_2$-cyclobutyl and

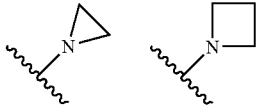

Even more preferably, one of $R^1$ and $R^2$ is H, and the other is selected from OH, OMe, OEt, O"Pr, $O^iPr$, O-cyclopropyl, O-cyclobutyl, SH, SMe, SEt, S"Pr, $S^iPr$, S-cyclopropyl, S-cyclobutyl, $NH_2$, NHMe, NHEt, NH"Pr, $NH^iPr$, $NMe_2$ and $N_3$.

In one highly preferred embodiment, $R^1$ is OH, OMe, OEt, SMe, $NH_2$, NHMe, $NMe_2$ or $N_3$ and $R^2$ is H; or $R^2$ is OH, OMe, OEt, SMe, $NH_2$, NHMe, $NMe_2$ or $N_3$ and $R^1$ is H.

In an even more preferred embodiment, $R^1$ is OH, OMe, OEt, $NH_2$, NHMe, SMe or $N_3$, and $R^2$ is H; or $R^2$ is OH, OMe, $NH_2$ or $N_3$, and $R^1$ is H.

In one highly preferred embodiment, the compound of the invention is selected from the following:

N—((S)-1-((3aS,6S,6aS)-6-hydroxy-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide N—((S)-1-((3aS,6S,6aS)-6-hydroxy-3-oxodihydro-2H-furo[3,2-b]pyrrol-4(5H,6H,6aH)-yl)-4,4-dimethyl-1-oxopentan-2-yl)-4-(4-isopropylpiperazin-1-yl)benzamide 4-(4-cyclopropylpiperazin-1-yl)-N—((S)-1-((3aS,6S,6aS)-6-hydroxy-3-oxodihydro-2H-furo[3,2-b]pyrrol-4(5H,6H,6aH)-yl)-4,4-dimethyl-1-oxopentan-2-yl)benzamide 4-(4-cyclobutylpiperazin-1-yl)-N—((S)-1-((3aS,6S,6aS)-6-hydroxy-3-oxodihydro-2H-furo[3,2-b]pyrrol-4(5H,6H,6aH)-yl)-4,4-dimethyl-1-oxopentan-2-yl)benzamide 4-(1-cyclopropylpiperidin-4-yl)-N—((S)-1-((3aS,6S,6aS)-6-hydroxy-3-oxodihydro-2H-furo[3,2-b]pyrrol-4(5H,6H,6aH)-yl)-4,4-dimethyl-1-oxopentan-2-yl)benzamide 4-(1-cyclobutylpiperidin-4-yl)-N—((S)-1-((3aS,6S,6aS)-6-hydroxy-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-hydroxy-3-oxodihydro-2H-furo[3,2-b]pyrrol-4(5H,6H,6aH)-yl)-4-methyl-1-oxopentan-2-yl)-4-(4-propylpiperazin-1-yl)benzamide N—((S)-1-((3aS,6S,6aS)-6-hydroxy-3-oxodihydro-2H-furo[3,2-b]pyrrol-4(5H,6H,6aH)-yl)-4-methyl-1-oxopentan-2-yl)-4-(4-isopropylpiperazin-1-yl)benzamide 4-(4-cyclopropylpiperazin-1-yl)-N—((S)-1-((3aS,6S,6aS)-6-hydroxy-3-oxodihydro-2H-furo[3,2-b]pyrrol-4(5H,6H,6aH)-yl)-4-methyl-1-oxopentan-2-yl)benzamide 4-(4-cyclobutylpiperazin-1-yl)-N—((S)-1-((3aS,6S,6aS)-6-hydroxy-3-oxodihydro-2H-furo[3,2-b]pyrrol-4(5H,6H,6aH)-yl)-4-methyl-1-oxopentan-2-yl)benzamide 4-(1-cyclopropylpiperidin-4-yl)-N—((S)-1-((3aS,6S,6aS)-6-hydroxy-3-oxodihydro-2H-furo[3,2-b]pyrrol-4(5H,6H,6aH)-yl)-4-methyl-1-oxopentan-2-yl)benzamide 4-(1-cyclobutylpiperidin-4-yl)-N—((S)-1-((3aS,6S,6aS)-6-hydroxy-3-oxodihydro-2H-furo[3,2-b]pyrrol-4(5H,6H,6aH)-yl)-4-methyl-1-oxopentan-2-yl)benzamide 4-(4-ethylpiperazin-1-yl)-N-((2S,3S)-1-((3aS,6S,6aS)-6-hydroxy-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aS)-6-hydroxy-3-oxodihydro-2H-furo[3,2-b]pyrrol-4(5H,6H,6aH)-yl)-3-methyl-1-oxopentan-2-yl)-4-(4-propylpiperazin-1-yl)benzamide N-((2S,3S)-1-((3aS,6S,6aS)-6-hydroxy-3-oxodihydro-2H-furo[3,2-b]pyrrol-4(5H,6H,6aH)-yl)-3-methyl-1-oxopentan-2-yl)-4-(4-isopropylpiperazin-1-yl)benzamide 4-(4-cyclopropylpiperazin-1-yl)-N-((2S,3S)-1-((3aS,6S,6aS)-6-hydroxy-3-oxodihydro-2H-furo[3,2-b]pyrrol-4(5H,6H,6aH)-yl)-3-methyl-1-oxopentan-2-yl)benzamide 4-(4-cyclobutylpiperazin-1-yl)-N-((2S,3S)-1-((3aS,6S,6aS)-6-hydroxy-3-oxodihydro-2H-furo[3,2-b]pyrrol-4(5H,6H,6aH)-yl)-3-methyl-1-oxopentan-2-yl)benzamide 4-(1-cyclopropylpiperidin-4-yl)-N-((2S,3S)-1-((3aS,6S,6aS)-6-hydroxy-3-oxodihydro-2H-furo[3,2-b]pyrrol-4(5H,6H,6aH)-yl)-3-methyl-1-oxopentan-2-yl)benzamide 4-(1-cyclobutylpiperidin-4-yl)-N-((2S,3S)-1-((3aS,6S,6aS)-6-hydroxy-3-oxodihydro-2H-furo[3,2-b]pyrrol-4(5H,6H,6aH)-yl)-3-methyl-1-oxopentan-2-yl)benzamide 4-(4-ethylpiperazin-1-yl)-N—((S)-1-((3aS,6S,6aS)-6-hydroxy-3-oxodihydro-2H-furo[3,2-b]pyrrol-4(5H,6H,6aH)-yl)-3,3-dimethyl-1-oxobutan-2-yl)benzamide N—((S)-1-((3aS,6S,6aS)-6-hydroxy-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide N—((S)-1-((3aS,6S,6aS)-6-hydroxy-3-oxodihydro-2H-furo[3,2-b]pyrrol-4(5H,6H,6aH)-yl)-3,3-dimethyl-1-oxobutan-2-yl)-4-(4-isopropylpiperazin-1-yl)benzamide 4-(4-cyclopropylpiperazin-1-yl)-N—((S)-1-((3aS,6S,6aS)-6-hydroxy-3-oxodihydro-2H-furo[3,2-b]pyrrol-4(5H,6H,6aH)-yl)-3,3-dimethyl-1-oxobutan-2-yl)benzamide 4-(4-cyclobutylpiperazin-1-yl)-N—((S)-1-((3aS,6S,6aS)-6-hydroxy-3-oxodihydro-2H-furo[3,2-b]pyrrol-4(5H,6H,6aH)-yl)-3,3-dimethyl-1-oxobutan-2-yl)benzamide 4-(1-cyclopropylpiperidin-4-yl)-N—((S)-1-((3aS,6S,6aS)-6-hydroxy-3-oxodihydro-2H-furo[3,2-b]pyrrol-4(5H,6H,6aH)-yl)-3,3-dimethyl-1-oxobutan-2-yl)benzamide 4-(1-cyclobutylpiperidin-4-yl)-N—((S)-1-((3aS,6S,6aS)-6-hydroxy-3-oxodihydro-2H-furo[3,2-b]pyrrol-4(5H,6H,6aH)-yl)-3,3-dimethyl-1-oxobutan-2-yl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)benzamide N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)-4-(4-methylpiperazin-1-yl)benzamide 4-(4-ethylpiperazin-1-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide 4-(4-isopropylpiperazin-1-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)-4-(4-(2-methoxyethyl)piperazin-1-yl)benzamide 4-(4-cyclopropylpiperazin-1-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide 4-(4-cyclobutylpiperazin-1-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)-4-(1-propylpiperidin-4-yl)benzamide 4-(1-isopropylpiperidin-4-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)-4-(1-(2-methoxyethyl)piperidin-4-yl)benzamide 4-(1-cyclopropylpiperidin-4-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide 4-(1-cyclobutylpiperidin-4-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)-4-(4-methylpiperazin-1-yl)benzamide 4-(4-ethylpiperazin-1-yl)-N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)benzamide N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)-4-(4-propylpiperazin-1-yl)benzamide 4-(4-isopropylpiperazin-1-yl)-N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)benzamide N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)-4-(4-(2-methoxyethyl)piperazin-1-yl)benzamide 4-(4-cyclopropylpiperazin-1-yl)-N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)benzamide 4-(4-cyclobutylpiperazin-1-yl)-N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)benzamide N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)-4-(1-propylpiperidin-4-yl)benzamide 4-(1-cyclopropylpiperidin-4-yl)-N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)benzamide 4-(1-cyclobutylpiperidin-4-yl)-N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)benzamide N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)-4-(4-methylpiperazin-1-yl)benzamide 4-(4-ethylpiperazin-1-yl)-N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)-4-(4-propylpiperazin-1-yl)benzamide 4-(4-isopropylpiperazin-1-yl)-N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)-4-(1-(2-methoxyethyl)piperazin-4-yl)benzamide 4-(4-cyclopropylpiperazin-1-yl)-N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)benzamide 4-(4-cyclobutylpiperazin-1-yl)-N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)-4-(1-methylpiperidin-4-yl)benzamide 4-(1-ethylpiperidin-4-yl)-N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)-4-(1-propylpiperidin-4-yl)benzamide 4-(1-isopropylpiperidin-4-yl)-N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)-4-(1-(2-methoxyethyl)piperidin-4-yl)benzamide 4-(1-cyclopropylpiperidin-4-yl)-N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)benzamide 4-(1-cyclobutylpiperidin-4-yl)-N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)benzamide N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)-4-(4-methylpiperazin-1-yl)benzamide 4-(4-ethylpiperazin-1-yl)-N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)benzamide N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide 4-(4-isopropylpiperazin-1-yl)-N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)benzamide N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)-4-(4-(2-methoxyethyl)piperazin-1-yl)benzamide 4-(4-cyclopropylpiperazin-1-yl)-N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)benzamide 4-(4-cyclobutylpiperazin-1-yl)-N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)benzamide N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)-4-(1-propylpiperidin-4-yl)benzamide 4-(1-cyclopropylpiperidin-4-yl)-N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)benzamide 4-(1-cyclobutylpiperidin-4-yl)-N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)benzamide N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)benzamide N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(1-methylpiperidin-4-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(1-ethylpiperidin-4-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(1-(2-methoxyethyl)piperidin-4-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)benzamide N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)-4-(4-methylpiperazin-1-yl)benzamide N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)-4-(4-ethylpiperazin-1-yl)benzamide N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)-4-(4-isopropylpiperazin-1-yl)benzamide N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)-4-(4-(2-methoxyethyl)piperazin-1-yl)benzamide 4-(4-cyclopropylpiperazin-1-yl)-N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)benzamide 4-(4-cyclobutylpiperazin-1-yl)-N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)-4-(1-propylpiperidin-4-yl)benzamide N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)-4-(1-isopropylpiperidin-4-yl)benzamide N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)-4-(1-(2-methoxyethyl)piperidin-4-yl)benzamide 4-(1-cyclopropylpiperidin-4-yl)-N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)benzamide 4-(1-cyclobutylpiperidin-4-yl)-N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)-4-(4-methylpiperazin-1-yl)benzamide N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)-4-(4-ethylpiperazin-1-yl)benzamide N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)-4-(4-propylpiperazin-1-yl)benzamide N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)-4-(4-isopropylpiperazin-1-yl)benzamide N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)-4-(4-(2-methoxyethyl)piperazin-1-yl)benzamide 4-(4-cyclopropylpiperazin-1-yl)-N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)benzamide 4-(4-cyclobutylpiperazin-1-yl)-N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)benzamide N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)-4-(1-propylpiperidin-4-yl)benzamide 4-(1-cyclopropylpiperidin-4-yl)-N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)benzamide 4-(1-cyclobutylpiperidin-4-yl)-N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(4-methylpiperazin-1-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(4-ethylpiperazin-1-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(4-propylpiperazin-1-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(4-isopropylpiperazin-1-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(4-(2-methoxyethyl)piperazin-1-yl)benzamide 4-(4-cyclopropylpiperazin-1-yl)-N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)benzamide 4-(4-cyclobutylpiperazin-1-yl)-N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(1-methylpiperidin-4-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(1-ethylpiperidin-4-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(1-propylpiperidin-4-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(1-isopropylpiperidin-4-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(1-(2-methoxyethyl)piperidin-4-yl)benzamide 4-(1-cyclopropylpiperidin-4-yl)-N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)benzamide 4-(1-cyclobutylpiperidin-4-yl)-N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)benzamide N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)-4-(4-methylpiperazin-1-yl)benzamide N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)-4-(4-ethylpiperazin-1-yl)benzamide N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)-4-(4-isopropylpiperazin-1-yl)benzamide N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)-4-(4-(2-methoxyethyl)piperazin-1-yl)benzamide 4-(4-cyclopropylpiperazin-1-yl)-N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)benzamide 4-(4-cyclobutylpiperazin-1-yl)-N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)benzamide N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)-4-(1-propylpiperidin-4-yl)benzamide 4-(1-cyclopropylpiperidin-4-yl)-N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)benzamide 4-(1-cyclobutylpiperidin-4-yl)-N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(1-methylpiperidin-4-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(1-ethylpiperidin-4-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(1-(2-methoxyethyl)piperidin-4-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(1-methylpiperidin-4-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(1-ethylpiperidin-4-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(1-(2-methoxyethyl)piperidin-4-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)benzamide N—((S)-1-((3aS,6S,6aR)-6-amino-3-oxodihydro-2H-furo[3,2-b]pyrrol-4(5H,6H,6aH)-yl)-4,4-dimethyl-1-oxopentan-2-yl)-4-(1-propylpiperazin-1-yl)benzamide N—((S)-1-((3aS,6S,6aR)-6-amino-3-oxodihydro-2H-furo[3,2-b]pyrrol-4(5H,6H,6aH)-yl)-4,4-dimethyl-1-oxopentan-2-yl)-4-(1-cyclopropylpiperazin-1-yl)benzamide N—((S)-1-((3aS,6S,6aR)-6-amino-3-oxodihydro-2H-furo[3,2-b]pyrrol-4(5H,6H,6aH)-yl)-4,4-dimethyl-1-oxopentan-2-yl)-4-(1-cyclobutylpiperazin-1-yl)benzamide N-((2S,3S)-1-((3aS,6S,6aR)-6-amino-3-oxodihydro-2H-furo[3,2-b]pyrrol-4(5H,6H,6aH)-yl)-3-methyl-1-oxopentan-2-yl)-4-(4-ethylpiperazin-1-yl)benzamide N-((2S,3S)-1-((3aS,6S,6aR)-6-amino-3-oxodihydro-2H-furo[3,2-b]pyrrol-4(5H,6H,6aH)-yl)-3-methyl-1-oxopentan-2-yl)-4-(4-propylpiperazin-1-yl)benzamide N-((2S,3S)-1-((3aS,6S,6aR)-6-amino-3-oxodihydro-2H-furo[3,2-b]pyrrol-4(5H,6H,6aH)-yl)-3-methyl-1-oxopentan-2-yl)-4-(4-isopropylpiperazin-1-yl)benzamide N-((2S,3S)-1-((3aS,6S,6aR)-6-amino-3-oxodihydro-2H-furo[3,2-b]pyrrol-4(5H,6H,6aH)-yl)-3-methyl-1-oxopentan-2-yl)-4-(4-cyclopropylpiperazin-1-yl)benzamide N-((2S,3S)-1-((3aS,6S,6aR)-6-amino-3-oxodihydro-2H-furo[3,2-b]pyrrol-4(5H,6H,6aH)-yl)-3-methyl-1-oxopentan-2-yl)-4-(4-cyclobutylpiperazin-1-yl)benzamide N—((S)-1-((3aS,6S,6aR)-6-amino-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide N—((S)-1-((3aS,6S,6aR)-6-amino-3-oxodihydro-2H-furo[3,2-b]pyrrol-4(5H,6H,6aH)-yl)-3,3-di-methyl-1-oxobutan-2-yl)-4-(4-cyclopropylpiperazin-1-yl)benzamide N—((S)-1-((3aS,6S,6aR)-6-amino-3-oxodihydro-2H-furo[3,2-b]pyrrol-4(5H,6H,6aH)-yl)-3,3-di-methyl-1-oxobutan-2-yl)-4-(4-cyclobutylpiperazin-1-yl)benzamide N—((S)-2-((3aS,6S,6aR)-6-amino-3-oxodihydro-2H-furo[3,2-b]pyrrol-4(5H,6H,6aH)-yl)-1-cyclopentyl-2-oxoethyl)-4-(4-propylpiperazin-1-yl)benzamide N—((S)-2-((3aS,6S,6aR)-6-amino-3-oxodihydro-2H-furo[3,2-b]pyrrol-4(5H,6H,6aH)-yl)-1-cyclopentyl-2-oxoethyl)-4-(4-cyclopropylpiperazin-1-yl)benzamide N—((S)-2-((3aS,6S,6aR)-6-amino-3-oxodihydro-2H-furo[3,2-b]pyrrol-4(5H,6H,6aH)-yl)-1-cyclopentyl-2-oxoethyl)-4-(4-cyclobutylpiperazin-1-yl)benzamide N—((S)-2-((3aS,6S,6aR)-6-amino-3-oxodihydro-2H-furo[3,2-b]pyrrol-4(5H,6H,6aH)-yl)-1-cyclohexyl-2-oxoethyl)-4-(4-ethylpiperazin-1-yl)benzamide N—((S)-2-((3aS,6S,6aR)-6-amino-3-oxodihydro-2H-furo[3,2-b]pyrrol-4(5H,6H,6aH)-yl)-1-cyclohexyl-2-oxoethyl)-4-(propylpiperazin-1-yl)benzamide N—((S)-2-((3aS,6S,6aR)-6-amino-3-oxodihydro-2H-furo[3,2-b]pyrrol-4(5H,6H,6aH)-yl)-1-cyclohexyl-2-oxoethyl)-4-(isopropylpiperazin-1-yl)benzamide N—((S)-2-((3aS,6S,6aR)-6-amino-3-oxodihydro-2H-furo[3,2-b]pyrrol-4(5H,6H,6aH)-yl)-1-cyclohexyl-2-oxoethyl)-4-(cyclopropylpiperazin-1-yl)benzamide N—((S)-2-((3aS,6S,6aR)-6-amino-3-oxodihydro-2H-furo[3,2-b]pyrrol-4(5H,6H,6aH)-yl)-1-cyclohexyl-2-oxoethyl)-4-(cyclobutylpiperazin-1-yl)benzamide N—((S)-1-((3aS,6S,6aR)-6-(methylamino)-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide 4-(4-cyclopropylpiperazin-1-yl)-N—((S)-1-((3aS,6S,6aR)-6-(methylamino)-3-oxodihydro-2H-furo[3,2-b]pyrrol-4(5H,6H,6aH)-yl)-4,4-dimethyl-1-oxopentan-2-yl)benzamide 4-(4-cyclobutylpiperazin-1-yl)-N—((S)-1-((3aS,6S,6aR)-6-(methylamino)-3-oxodihydro-2H-furo[3,2-b]pyrrol-4(5H,6H,6aH)-yl)-4,4-dimethyl-1-oxopentan-2-yl)benzamide 4-(1-cyclopropylpiperidin-4-yl)-N—((S)-1-((3aS,6S,6aR)-6-(methylamino)-3-oxodihydro-2H-furo[3,2-b]pyrrol-4(5H,6H,6aH)-yl)-4,4-dimethyl-1-oxopentan-2-yl)benzamide 4-(1-cyclobutylpiperidin-4-yl)-N—((S)-1-((3aS,6S,6aR)-6-(methylamino)-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aR)-6-(methylamino)-3-oxodihydro-2H-furo[3,2-b]pyrrol-4(5H,6H,6aH)-yl)-4-methyl-1-oxopentan-2-yl)-4-(4-propylpiperazin-1-yl)benzamide 4-(4-cyclopropylpiperazin-1-yl)-N—((S)-1-((3aS,6S,6aR)-6-(methylamino)-3-oxodihydro-2H-furo[3,2-b]pyrrol-4(5H,6H,6aH)-yl)-4-methyl-1-oxopentan-2-yl)benzamide 4-(4-cyclobutylpiperazin-1-yl)-N—((S)-1-((3aS,6S,6aR)-6-(methylamino)-3-oxodihydro-2H-furo[3,2-b]pyrrol-4(5H,6H,6aH)-yl)-4-methyl-1-oxopentan-2-yl)benzamide 4-(4-ethylpiperazin-1-yl)-N-((2S,3S)-1-((3aS,6S,6aR)-6-(methylamino)-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aR)-6-(methylamino)-3-oxodihydro-2H-furo[3,2-b]pyrrol-4(5H,6H,6aH)-yl)-3-methyl-1-oxopentan-2-yl)-4-(4-propylpiperazin-1-yl)benzamide 4-(4-isopropylpiperazin-1-yl-N-((2S,3S)-1-((3aS,6S,6aR)-6-(methylamino)-3-oxodihydro-2H-furo[3,2-b]pyrrol-4(5H,6H,6aH)-yl)-3-methyl-1-oxopentan-2-yl)-)benzamide 4-(4-(2-methoxyethyl)piperazin-1-yl)-N-((2S,3S)-1-((3aS,6S,6aR)-6-(methylamino)-3-oxodihydro-2H-furo[3,2-b]pyrrol-4(5H,6H,6aH)-yl)-3-methyl-1-oxopentan-2-yl)benzamide 4-(4-cyclopropylpiperazin-1-yl)-N-((2S,3S)-1-((3aS,6S,6aR)-6-(methylamino)-3-oxodihydro-2H-furo[3,2-b]pyrrol-4(5H,6H,6aH)-yl)-3-methyl-1-oxopentan-2-yl)benzamide 4-(4-cyclobutylpiperazin-1-yl)-N-((2S,3S)-1-((3aS,6S,6aR)-6-(methylamino)-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aR)-6-(methylamino)-3-oxodihydro-2H-furo[3,2-b]pyrrol-4(5H,6H,6aH)-yl)-3-methyl-1-oxopentan-2-yl)-4-(1-propylpiperidin-4-yl)benzamide 4-(1-isopropylpiperidin-4-yl)-N-((2S,3S)-1-((3aS,6S,6aR)-6-(methylamino)-3-oxodihydro-2H-furo[3,2-b]pyrrol-4(5H,6H,6aH)-yl)-3-methyl-1-oxopentan-2-yl)benzamide 4-(1-cyclopropylpiperidin-4-yl)-N-((2S,3S)-1-((3aS,6S,6aR)-6-(methylamino)-3-oxodihydro-2H-furo[3,2-b]pyrrol-4(5H,6H,6aH)-yl)-3-methyl-1-oxopentan-2-yl)benzamide 4-(1-cyclobutylpiperidin-4-yl)-N-((2S,3S)-1-((3aS,6S,6aR)-6-(methylamino)-3-oxodihydro-2H-furo[3,2-b]pyrrol-4(5H,6H,6aH)-yl)-3-methyl-1-oxopentan-2-yl)benzamide N—(S)-1-((3aS,6S,6aR)-6-(methylamino)-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide 4-(4-cyclopropylpiperazin-1-yl)-N—((S)-1-((3aS,6S,6aR)-6-(methylamino)-3-oxodihydro-2H-furo[3,2-b]pyrrol-4(5H,6H,6aH)-yl)-3,3-dimethyl-1-oxobutan-2-yl)benzamide 4-(4-cyclobutylpiperazin-1-yl)-N—((S)-1-((3aS,6S,6aR)-6-(methylamino)-3-oxodihydro-2H-furo[3,2-b]pyrrol-4(5H,6H,6aH)-yl)-3,3-dimethyl-1-oxobutan-2-yl)benzamide N—((S)-1-((3aS,6S,6aR)-6-(methylamino)-3-oxodihydro-2H-furo[3,2-b]pyrrol-4(5H,6H,6aH)-yl)-3,3-dimethyl-1-oxobutan-2-yl)-4-(1-propylpiperidin-4-yl)benzamide 4-(1-cyclopropylpiperidin-4-yl)-N—((S)-1-((3aS,6S,6aR)-6-(methylamino)-3-oxodihydro-2H-furo[3,2-b]pyrrol-4(5H,6H,6aH)-yl)-3'3-di-methyl-1-oxobutan-2-yl)benzamide 4-(1-cyclobutylpiperidin-4-yl)-N—((S)-1-((3aS,6S,6aR)-6-(methylamino)-3-oxodihydro-2H-furo[3,2-b]pyrrol-4(5H,6H,6aH)-yl)-3,3-di-methyl-1-oxobutan-2-yl)benzamide N—((S)-1-cyclopentyl-2-((3aS,6S,6aR)-6-(methylamino)-3-oxodihydro-2H-furo[3,2-b]pyrrol-4(5H,6H,6aH)-yl)-2-oxoethyl)-4-(4-propylpiperazin-1-yl)benzamide N—((S)-1-cyclopentyl-2-((3aS,6S,6aR)-6-(methylamino)-3-oxodihydro-2H-furo[3,2-b]pyrrol-4(5H,6H,6aH)-yl)-2-oxoethyl)-4-cyclopropylpiperazin-1-yl)benzamide 4-(4-cyclobutylpiperazin-1-yl)-N—((S)-1-cyclopentyl-2-((3aS,6S,6aR)-6-(methylamino)-3-oxodihydro-2H-furo[3,2-b]pyrrol-4(5H,6H,6aH)-yl)-2-oxoethyl)benzamide N—((S)-1-cyclopentyl-2-((3aS,6S,6aR)-6-(methylamino)-3-oxodihydro-2H-furo[3,2-b]pyrrol-4(5H,6H,6aH)-yl)-2-oxoethyl)-4-(1-propylpiperidin-4-yl)benzamide N—((S)-1-cyclopentyl-2-((3aS,6S,6aR)-6-(methylamino)-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclopentyl-2-((3aS,6S,6aR)-6-(methylamino)-3-oxodihydro-2H-furo[3,2-b]pyrrol-4(5H,6H,6aH)-yl)-2-oxoethyl)benzamide N—((S)-1-cyclohexyl-2-((3aS,6S,6aR)-6-(methylamino)-3-oxodihydro-2H-furo[3,2-b]pyrrol-4(5H,6H,6aH)-yl)-2-oxoethyl)-4-(4-ethylpiperazin-1-yl)benzamide N—((S)-1-cyclohexyl-2-((3aS,6S,6aR)-6-(methylamino)-3-oxodihydro-2H-furo[3,2-b]pyrrol-4(5H,6H,6aH)-yl)-2-oxoethyl)-4-(4-propylpiperazin-1-yl)benzamide N—((S)-1-cyclohexyl-2-((3aS,6S,6aR)-6-(methylamino)-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclohexyl-2-((3aS,6S,6aR)-6-(methylamino)-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclohexyl-2-((3aS,6S,6aR)-6-(methylamino)-3-oxodihydro-2H-furo[3,2-b]pyrrol-4(5H,6H,6aH)-yl)-2-oxoethyl)benzamide N—((S)-1-cyclohexyl-2-((3aS,6S,6aR)-6-(methylamino)-3-oxodihydro-2H-furo[3,2-b]pyrrol-4(5H,6H,6aH)-yl)-2-oxoethyl)-4-(1-propylpiperidin-4-yl)benzamide N—((S)-1-cyclohexyl-2-((3aS,6S,6aR)-6-(methylamino)-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclohexyl-2-((3aS,6S,6aR)-6-(methylamino)-3-oxodihydro-2H-furo[3,2-b]pyrrol-4(5H,6H,6aH)-yl)-2-oxoethyl)benzamide 4-(4-methylpiperazin-1-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide 4-(4-ethylpiperazin-1-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide 4-(4-isopropylpiperazin-1-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide 4-(4-(2-methoxyethyl)piperazin-1-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide 4-(4-cyclopropylpiperazin-1-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide 4-(4-cyclobutylpiperazin-1-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide 4-(1-ethylpiperidin-4-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)-4-(1-propylpiperidin-4-yl)benzamide 4-(1-isopropylpiperidin-4-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide 4-(1-(2-methoxyethyl)piperidin-4-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide 4-(1-cyclopropylpiperidin-4-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide 4-(1-cyclobutylpiperidin-4-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide 4-(4-methylpiperazin-1-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide 4-(4-ethylpiperazin-1-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)-4-(4-propylpiperazin-1-yl)benzamide 4-(4-isopropylpiperazin-1-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide 4-(4-(2-methoxyethyl)piperazin-1-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide 4-(4-cyclopropylpiperazin-1-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide 4-(4-cyclobutylpiperazin-1-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)-4-(1-propylpiperidin-4-yl)benzamide 4-(1-isopropylpiperidin-4-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide 4-(1-cyclopropylpiperidin-4-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide 4-(1-cyclobutylpiperidin-4-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide 4-(4-methylpiperazin-1-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(4-ethylpiperazin-1-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)-4-(4-propylpiperazin-1-yl)benzamide 4-(4-isopropylpiperazin-1-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(4-(2-methoxyethyl)piperazin-1-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(4-cyclopropylpiperazin-1-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(4-cyclobutylpiperazin-1-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(1-methylpiperidin-4-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(1-ethylpiperidin-4-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)-4-(1-propylpiperidin-4-yl)benzamide 4-(1-isopropylpiperidin-4-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(1-(2-methoxyethyl)piperidin-4-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(1-cyclopropylpiperidin-4-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(1-cyclobutylpiperidin-4-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(4-methylpiperazin-1-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide 4-(4-ethylpiperazin-1-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide 4-(4-isopropylpiperazin-1-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide 4-(4-(2-methoxyethyl)piperazin-1-yl)-N—((S)-1-((3aS,6S,6aS)-6-(methylthio)-3-oxodihydro-2H-furo[3,2-b]pyrrol-4(5H,6H,6aH)-yl)-3,3-di-methyl-1-oxobutan-2-yl)benzamide 4-(4-cyclopropylpiperazin-1-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide 4-(4-cyclobutylpiperazin-1-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide 4-(1-ethylpiperidin-4-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)-4-(1-propylpiperidin-4-yl)benzamide 4-(1-isopropylpiperidin-4-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide 4-(1-cyclopropylpiperidin-4-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide 4-(1-cyclobutylpiperidin-4-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(4-methylpiperazin-1-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(4-ethylpiperazin-1-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(4-propylpiperazin-1-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(1-methylpiperidin-4-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(1-ethylpiperidin-4-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(1-propylpiperidin-4-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(1-(2-methoxyethyl)piperidin-4-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(4-methylpiperazin-1-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(4-ethylpiperazin-1-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(4-propylpiperazin-1-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(1-methylpiperidin-4-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(1-ethylpiperidin-4-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(1-propylpiperidin-4-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(1-(2-methoxyethyl)piperidin-4-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)benzamide N—(S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(4-methylpiperazin-1-yl)benzamide N—(S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(4-ethylpiperazin-1-yl)benzamide N—(S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide N—(S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(4-isopropylpiperazin-1-yl)benzamide N—(S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(4-(2-methoxyethyl)piperazin-1-yl)benzamide N—(S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(4-cyclopropylpiperazin-1-yl)benzamide N—(S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(4-cyclobutylpiperazin-1-yl)benzamide N—(S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(1-propylpiperidin-4-yl)benzamide N—(S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(1-isopropylpiperidin-4-yl)benzamide N—(S)-1-((3aS,6S,6aS)-6-azido-3-oxodihydro-2H-furo[3,2-b]pyrrol-4(5H,6aH)-yl)-4,4-dimethyl-1-oxopentan-2-yl)-4-(1-(2-methoxyethyl)piperidin-4-yl)benzamide N—(S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(1-cyclopropylpiperidin-4-yl)benzamide N—(S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(1-cyclobutylpiperidin-4-yl)benzamide N—(S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(4-methylpiperazin-1-yl)benzamide N—(S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(4-ethylpiperazin-1-yl)benzamide N—(S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(4-propylpiperazin-1-yl)benzamide N—(S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(4-isopropylpiperazin-1-yl)benzamide N—(S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(4-(2-methoxyethyl)piperazin-1-yl)benzamide N—((S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(4-cyclopropylpiperazin-1-yl)benzamide N—((S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(4-cyclobutylpiperazin-1-yl)benzamide N—((S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(1-propylpiperidin-4-yl)benzamide N—((S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(1-cyclopropylpiperidin-4-yl)benzamide N—((S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(1-cyclobutylpiperidin-4-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(4-methylpiperazin-1-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(4-ethylpiperazin-1-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(4-propylpiperazin-1-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(4-isopropylpiperazin-1-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(4-(2-methoxyethyl)piperazin-1-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(4-cyclopropylpiperazin-1-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(4-cyclobutylpiperazin-1-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(1-methylpiperidin-4-yl)benzamide N-((2S,3S)-1-((3aS,6S,6aS)-6-azido-3-oxodihydro-2H-furo[3,2-b]pyrrol-4(5H,6aH)-yl)-3-methyl-1-oxopentan-2-yl)-4-(1-ethylpiperidin-4-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(1-propylpiperidin-4-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(1-isopropylpiperidin-4-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(1-(2-methoxyethyl)piperidin-4-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(1-cyclopropylpiperidin-4-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(1-cyclobutylpiperidin-4-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(4-methylpiperazin-1-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(4-ethylpiperazin-1-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(4-isopropylpiperazin-1-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(4-(2-methoxyethyl)piperazin-1-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(4-cyclopropylpiperazin-1-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(4-cyclobutylpiperazin-1-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(1-propylpiperidin-4-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(1-cyclopropylpiperidin-4-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(1-cyclobutylpiperidin-4-yl)benzamide N—((S)-1-cyclopentyl-2-((3aS,6S,6aS)-6-azido-3-oxodihydro-2H-furo[3,2-b]pyrrol-4(5H,6H,6aH)-yl)-2-oxoethyl)-4-(4-methylpiperazin-1-yl)benzamide N—((S)-1-cyclopentyl-2-((3aS,6S,6aS)-6-azido-3-oxodihydro-2H-furo[3,2-b]pyrrol-4(5H,6H,6aH)-yl)-2-oxoethyl)-4-(4-ethylpiperazin-1-yl)benzamide N—((S)-1-cyclopentyl-2-((3aS,6S,6aS)-6-azido-3-oxodihydro-2H-furo[3,2-b]pyrrol-4(5H,6H,6aH)-yl)-2-oxoethyl)-4-(4-propylpiperazin-1-yl)benzamide N—((S)-1-cyclopentyl-2-((3aS,6S,6aS)-6-azido-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclopentyl-2-((3aS,6S,6aS)-6-azido-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclopentyl-2-((3aS,6S,6aS)-6-azido-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclopentyl-2-((3aS,6S,6aS)-6-azido-3-oxodihydro-2H-furo[3,2-b]pyrrol-4(5H,6H,6aH)-yl)-2-oxoethyl)benzamide N—((S)-1-cyclopentyl-2-((3aS,6S,6aS)-6-azido-3-oxodihydro-2H-furo[3,2-b]pyrrol-4(5H,6H,6aH)-yl)-2-oxoethyl)-4-(1-propylpiperidin-4-yl)benzamide N—((S)-1-cyclopentyl-2-((3aS,6S,6aS)-6-azido-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclopentyl-2-((3aS,6S,6aS)-6-azido-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(4-methylpiperazin-1-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(4-ethylpiperazin-1-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(4-propylpiperazin-1-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclohexyl-2-((3aS,6S,6aS)-6-azido-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(1-methylpiperidin-4-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(1-ethylpiperidin-4-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(1-propylpiperidin-4-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(1-(2-methoxyethyl)piperidin-4-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclohexyl-2-((3aS,6S,6aS)-6-azido-3-oxodihydro-2H-furo[3,2-b]pyrrol-4(5H,6H,6aH)-yl)-2-oxoethyl)benzamide N—((S)-1-((3aS,6R,6aS)-6-hydroxy-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide N—((S)-1-((3aS,6R,6aS)-6-hydroxy-3-oxodihydro-2H-furo[3,2-b]pyrrol-4(5H,6H,6aH)-yl)-4,4-dimethyl-1-oxopentan-2-yl)-4-(4-isopropylpiperazin-1-yl)benzamide 4-(4-cyclopropylpiperazin-1-yl)-N—((S)-1-((3aS,6R,6aS)-6-hydroxy-3-oxodihydro-2H-furo[3,2-b]pyrrol-4(5H,6H,6aH)-yl)-4,4-dimethyl-1-oxopentan-2-yl)benzamide 4-(4-cyclobutylpiperazin-1-yl)-N—((S)-1-((3aS,6R,6aS)-6-hydroxy-3-oxodihydro-2H-furo[3,2-b]pyrrol-4(5H,6H,6aH)-yl)-4,4-dimethyl-1-oxopentan-2-yl)benzamide 4-(1-cyclopropylpiperidin-4-yl)-N—((S)-1-((3aS,6R,6aS)-6-hydroxy-3-oxodihydro-2H-furo[3,2-b]pyrrol-4(5H,6H,6aH)-yl)-4,4-dimethyl-1-oxopentan-2-yl)benzamide 4-(1-cyclobutylpiperidin-4-yl)-N—((S)-1-((3aS,6R,6aS)-6-hydroxy-3-oxodihydro-2H-furo[3,2-b]pyrrol-4(5H,6H,6aH)-yl)-4,4-dimethyl-1-oxopentan-2-yl)benzamide N—((S)-1-((3aS,6R,6aS)-6-hydroxy-3-oxodihydro-2H-furo[3,2-b]pyrrol-4(5H,6H,6aH)-yl)-4-methyl-1-oxopentan-2-yl)-4-(4-propylpiperazin-1-yl)benzamide N—((S)-1-((3aS,6R,6aS)-6-hydroxy-3-oxodihydro-2H-furo[3,2-b]pyrrol-4(5H,6H,6aH)-yl)-4-methyl-1-oxopentan-2-yl)-4-(4-isopropylpiperazin-1-yl)benzamide 4-(4-cyclopropylpiperazin-1-yl)-N—((S)-1-((3aS,6R,6aS)-6-hydroxy-3-oxodihydro-2H-furo[3,2-b]pyrrol-4(5H,6H,6aH)-yl)-4-methyl-1-oxopentan-2-yl)benzamide 4-(4-cyclobutylpiperazin-1-yl)-N—((S)-1-((3aS,6R,6aS)-6-hydroxy-3-oxodihydro-2H-furo[3,2-b]pyrrol-4(5H,6H,6aH)-yl)-4-methyl-1-oxopentan-2-yl)benzamide 4-(1-cyclopropylpiperidin-4-yl)-N—((S)-1-((3aS,6R,6aS)-6-hydroxy-3-oxodihydro-2H-furo[3,2-b]pyrrol-4(5H,6H,6aH)-yl)-4-methyl-1-oxopentan-2-yl)benzamide 4-(1-cyclobutylpiperidin-4-yl)-N—((S)-1-((3aS,6R,6aS)-6-hydroxy-3-oxodihydro-2H-furo[3,2-b]pyrrol-4(5H,6H,6aH)-yl)-4-methyl-1-oxopentan-2-yl)benzamide 4-(4-ethylpiperazin-1-yl)-N-((2S,3S)-1-((3aS,6R,6aS)-6-hydroxy-3-oxodihydro-2H-furo[3,2-b]pyrrol-4(5H,6H,6aH)-yl)-3-methyl-1-oxopentan-2-yl)benzamide N-((2S,3S)-1-((3aS,6R,6aS)-6-hydroxy-3-oxodihydro-2H-furo[3,2-b]pyrrol-4(5H,6H,6aH)-yl)-3-methyl-1-oxopentan-2-yl)-4-(4-propylpiperazin-1-yl)benzamide N-((2S,3S)-1-((3aS,6R,6aS)-6-hydroxy-3-oxodihydro-2H-furo[3,2-b]pyrrol-4(5H,6H,6aH)-yl)-3-methyl-1-oxopentan-2-yl)-4-(4-isopropylpiperazin-1-yl)benzamide 4-(4-cyclopropylpiperazin-1-yl)-N-((2S,3S)-1-((3aS,6R,6aS)-6-hydroxy-3-oxodihydro-2H-furo[3,2-b]pyrrol-4(5H,6H,6aH)-yl)-3-methyl-1-oxopentan-2-yl)benzamide 4-(4-cyclobutylpiperazin-1-yl)-N-((2S,3S)-1-((3aS,6R,6aS)-6-hydroxy-3-oxodihydro-2H-furo[3,2-b]pyrrol-4(5H,6H,6aH)-yl)-3-methyl-1-oxopentan-2-yl)benzamide 4-(1-cyclopropylpiperidin-4-yl)-N-((2S,3S)-1-((3aS,6R,6aS)-6-hydroxy-3-oxodihydro-2H-furo[3,2-b]pyrrol-4(5H,6H,6aH)-yl)-3-methyl-1-oxopentan-2-yl)benzamide 4-(1-cyclobutylpiperidin-4-yl)-N-((2S,3S)-1-((3aS,6R,6aS)-6-hydroxy-3-oxodihydro-2H-furo[3,2-b]pyrrol-4(5H,6H,6aH)-yl)-3-methyl-1-oxopentan-2-yl)benzamide 4-(4-ethylpiperazin-1-yl)-N—((S)-1-((3aS,6R,6aS)-6-hydroxy-3-oxodihydro-2H-furo[3,2-b]pyrrol-4(5H,6H,6aH)-yl)-3,3-dimethyl-1-oxobutan-2-yl)benzamide ((S)-1-((3aS,6R,6aS)-6-hydroxy-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide N—((S)-1-((3aS,6R,6aS)-6-hydroxy-3-oxodihydro-2H-furo[3,2-b]pyrrol-4(5H,6H,6aH)-yl)-3,3-dimethyl-1-oxobutan-2-yl)-4-(4-isopropylpiperazin-1-yl)benzamide 4-(4-cyclopropylpiperazin-1-yl)-N—((S)-1-((3aS,6R,6aS)-6-hydroxy-3-oxodihydro-2H-furo[3,2-b]pyrrol-4(5H,6H,6aH)-yl)-3,3-dimethyl-1-oxobutan-2-yl)benzamide 4-(4-cyclobutylpiperazin-1-yl)-N—((S)-1-((3aS,6R,6aS)-6-hydroxy-3-oxodihydro-2H-furo[3,2-b]pyrrol-4(5H,6H,6aH)-yl)-3,3-dimethyl-1-oxobutan-2-yl)benzamide 4-(1-cyclopropylpiperidin-4-yl)-N—((S)-1-((3aS,6R,6aS)-6-hydroxy-3-oxodihydro-2H-furo[3,2-b]pyrrol-4(5H,6H,6aH)-yl)-3,3-dimethyl-1-oxobutan-2-yl)benzamide 4-(1-cyclobutylpiperidin-4-yl)-N—((S)-1-((3aS,6R,6aS)-6-hydroxy-3-oxodihydro-2H-furo[3,2-b]pyrrol-4(5H,6H,6aH)-yl)-3,3-dimethyl-1-oxobutan-2-yl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)benzamide N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)-4-(4-methylpiperazin-1-yl)benzamide 4-(4-ethylpiperazin-1-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide 4-(4-isopropylpiperazin-1-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide 4-(4-(2-methoxyethyl)piperazin-1-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide 4-(4-cyclopropylpiperazin-1-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide 4-(4-cyclobutylpiperazin-1-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide 4-(1-cyclopropylpiperidin-4-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide 4-(1-cyclobutylpiperidin-4-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide 4-(4-ethylpiperazin-1-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)-4-(4-propylpiperazin-1-yl)benzamide 4-(4-isopropylpiperazin-1-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide 4-(4-(2-methoxyethyl)piperazin-1-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide 4-(4-cyclopropylpiperazin-1-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide 4-(4-cyclobutylpiperazin-1-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide 4-(1-cyclopropylpiperidin-4-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide 4-(1-cyclobutylpiperidin-4-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)-4-(4-methylpiperazin-1-yl)benzamide 4-(4-ethylpiperazin-1-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)-4-(4-propylpiperazin-1-yl)benzamide 4-(4-isopropylpiperazin-1-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide 4-(4-(2-methoxyethyl)piperazin-1-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide 4-(4-cyclopropylpiperazin-1-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide 4-(4-cyclobutylpiperazin-1-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide 4-(1-ethylpiperidin-4-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)-4-(1-propylpiperidin-4-yl)benzamide 4-(1-isopropylpiperidin-4-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide 4-(1-cyclopropylpiperidin-4-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide 4-(1-cyclobutylpiperidin-4-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)-4-(4-methylpiperazin-1-yl)benzamide 4-(4-ethylpiperazin-1-yl)-N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)benzamide N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide 4-(4-isopropylpiperazin-1-yl)-N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)benzamide N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)-4-(4-(2-methoxyethyl)piperazin-1-yl)benzamide 4-(4-cyclopropylpiperazin-1-yl)-N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)benzamide 4-(4-cyclobutylpiperazin-1-yl)-N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)benzamide 4-(1-cyclopropylpiperidin-4-yl)-N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)benzamide 4-(1-cyclobutylpiperidin-4-yl)-N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)benzamide N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)benzamide N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(1-ethylpiperidin-4-yl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)benzamide N—((S)-1-((3aS,6R,6aR)-6-amino-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide N—((S)-1-((3aS,6R,6aR)-6-amino-3-oxodihydro-2H-furo[3,2-b]pyrrol-4(5H,6H,6aH)-yl)-4,4-dimethyl-1-oxopentan-2-yl)-4-(4-cyclopropylpiperazin-1-yl)benzamide N—((S)-1-((3aS,6R,6aR)-6-amino-3-oxodihydro-2H-furo[3,2-b]pyrrol-4(5H,6H,6aH)-yl)-4,4-dimethyl-1-oxopentan-2-yl)-4-(4-cyclobutylpiperazin-1-yl)benzamide N-((2S,3S)-1-((3aS,6R,6aR)-6-amino-3-oxodihydro-2H-furo[3,2-b]pyrrol-4(5H,6H,6aH)-yl)-3-methyl-1-oxopentan-2-yl)-4-(4-ethylpiperazin-1-yl)benzamide N-((2S,3S)-1-((3aS,6R,6aR)-6-amino-3-oxodihydro-2H-furo[3,2-b]pyrrol-4(5H,6H,6aH)-yl)-3-methyl-1-oxopentan-2-yl)-4-(4-propylpiperazin-1-yl)benzamide N-((2S,3S)-1-((3aS,6R,6aR)-6-amino-3-oxodihydro-2H-furo[3,2-b]pyrrol-4(5H,6H,6aH)-yl)-3-methyl-1-oxopentan-2-yl)-4-(4-isopropylpiperazin-1-yl)benzamide N-((2S,3S)-1-((3aS,6R,6aR)-6-amino-3-oxodihydro-2H-furo[3,2-b]pyrrol-4(5H,6H,6aH)-yl)-3-methyl-1-oxopentan-2-yl)-4-(4-cyclopropylpiperazin-1-yl)benzamide N-((2S,3S)-1-((3aS,6R,6aR)-6-amino-3-oxodihydro-2H-furo[3,2-b]pyrrol-4(5H,6H,6aH)-yl)-3-methyl-1-oxopentan-2-yl)-4-(4-cyclobutylpiperazin-1-yl)benzamide N—((S)-1-((3aS,6R,6aR)-6-amino-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide N—((S)-1-((3aS,6R,6aR)-6-amino-3-oxodihydro-2H-furo[3,2-b]pyrrol-4(5H,6H,6aH)-yl)-3,3-dimethyl-1-oxobutan-2-yl)-4-(4-cyclopropylpiperazin-1-yl)benzamide N—((S)-1-((3aS,6R,6aR)-6-amino-3-oxodihydro-2H-furo[3,2-b]pyrrol-4(5H,6H,6aH)-yl)-3,3-dimethyl-1-oxobutan-2-yl)-4-(4-cyclobutylpiperazin-1-yl)benzamide N—((S)-2-((3aS,6R,6aR)-6-amino-3-oxodihydro-2H-furo[3,2-b]pyrrol-4(5H,6H,6aH)-yl)-1-cyclopentyl-2-oxoethyl)-4-(4-propylpiperazin-1-yl)benzamide N—((S)-2-((3aS,6R,6aR)-6-amino-3-oxodihydro-2H-furo[3,2-b]pyrrol-4(5H,6H,6aH)-yl)-1-cyclopentyl-2-oxoethyl)-4-(4-cyclopropylpiperazin-1-yl)benzamide N—((S)-2-((3aS,6R,6aR)-6-amino-3-oxodihydro-2H-furo[3,2-b]pyrrol-4(5H,6H,6aH)-yl)-1-cyclopentyl-2-oxoethyl)-4-(4-cyclobutylpiperazin-1-yl)benzamide N—((S)-2-((3aS,6R,6aR)-6-amino-3-oxodihydro-2H-furo[3,2-b]pyrrol-4(5H,6H,6aH)-yl)-1-cyclohexyl-2-oxoethyl)-4-(4-ethylpiperazin-1-yl)benzamide N—((S)-2-((3aS,6R,6aR)-6-amino-3-oxodihydro-2H-furo[3,2-b]pyrrol-4(5H,6H,6aH)-yl)-1-cyclohexyl-2-oxoethyl)-4-(4-propylpiperazin-1-yl)benzamide N—((S)-2-((3aS,6R,6aR)-6-amino-3-oxodihydro-2H-furo[3,2-b]pyrrol-4(5H,6H,6aH)-yl)-1-cyclohexyl-2-oxoethyl)-4-(4-isopropylpiperazin-1-yl)benzamide
N—((S)-2-((3aS,6R,6aR)-6-amino-3-oxodihydro-2H-furo[3,2-b]pyrrol-4(5H,6H,6aH)-yl)-1-cyclohexyl-2-oxoethyl)-4-(4-cyclopropylpiperazin-1-yl)benzamide
N—((S)-2-((3aS,6R,6aR)-6-amino-3-oxodihydro-2H-furo[3,2-b]pyrrol-4(5H,6H,6aH)-yl)-1-cyclohexyl-2-oxoethyl)-4-(4-cyclobutylpiperazin-1-yl)benzamide
N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(4-methylpiperazin-1-yl)benzamide
N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(4-ethylpiperazin-1-yl)benzamide
N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide
N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(4-isopropylpiperazin-1-yl)benzamide
N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(4-(2-methoxyethyl)piperazin-1-yl)benzamide
N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(4-cyclopropylpiperazin-1-yl)benzamide
N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(4-cyclobutylpiperazin-1-yl)benzamide
N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(1-propylpiperidin-4-yl)benzamide
N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(1-isopropylpiperidin-4-yl)benzamide
N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(1-(2-methoxyethyl)piperidin-4-yl)benzamide
N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(1-cyclopropylpiperidin-4-yl)benzamide
N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(1-cyclobutylpiperidin-4-yl)benzamide
N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(4-methylpiperazin-1-yl)benzamide
N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(4-ethylpiperazin-1-yl)benzamide
N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(4-propylpiperazin-1-yl)benzamide
N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(4-isopropylpiperazin-1-yl)benzamide
N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(4-(2-methoxyethyl)piperazin-1-yl)benzamide
N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(4-cyclopropylpiperazin-1-yl)benzamide
N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(4-cyclobutylpiperazin-1-yl)benzamide
N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(1-propylpiperidin-4-yl)benzamide
N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(1-cyclopropylpiperidin-4-yl)benzamide
N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(1-cyclobutylpiperidin-4-yl)benzamide
N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(4-methylpiperazin-1-yl)benzamide
N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(4-ethylpiperazin-1-yl)benzamide
N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(4-propylpiperazin-1-yl)benzamide
N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(4-isopropylpiperazin-1-yl)benzamide
N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(4-(2-methoxyethyl)piperazin-1-yl)benzamide
N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(4-cyclopropylpiperazin-1-yl)benzamide
N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(4-cyclobutylpiperazin-1-yl)benzamide
N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(1-methylpiperidin-4-yl)benzamide
N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(1-ethylpiperidin-4-yl)benzamide
N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(1-propylpiperidin-4-yl)benzamide
N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(1-isopropylpiperidin-4-yl)benzamide
N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(1-(2-methoxyethyl)piperidin-4-yl)benzamide
N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(1-cyclopropylpiperidin-4-yl)benzamide
N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(1-cyclobutylpiperidin-4-yl)benzamide
N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(4-methylpiperazin-1-yl)benzamide
N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(4-ethylpiperazin-1-yl)benzamide
N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide
N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(4-isopropylpiperazin-1-yl)benzamide
N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(4-(2-methoxyethyl)piperazin-1-yl)benzamide N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(4-cyclopropylpiperazin-1-yl)benzamide N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(4-cyclobutylpiperazin-1-yl)benzamide N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(1-propylpiperidin-4-yl)benzamide N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(1-cyclopropylpiperidin-4-yl)benzamide N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(1-cyclobutylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(4-methylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(4-ethylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(4-propylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(4-isopropylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(4-(2-methoxyethyl)piperazin-1-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(4-cyclopropylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(4-cyclobutylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(1-propylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(1-cyclopropylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(1-cyclobutylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(4-methylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(4-ethylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(4-propylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(4-isopropylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(4-(2-methoxyethyl)piperazin-1-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(4-cyclopropylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(4-cyclobutylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(1-methylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(1-ethylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(1-propylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(1-isopropylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(1-(2-methoxyethyl)piperidin-4-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(1-cyclopropylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(1-cyclobutylpiperidin-4-yl)benzamide In one highly preferred embodiment, the compound of the invention is selected from EXAMPLES 1, 2, 4, 5, 6, 7, 8, 13, 14, 15, 16, 22, 27 and 38 as described in the accompanying Examples section.

In an even more highly preferred embodiment, the compound of the invention is selected from EXAMPLES 2, 14 and 22 as described in the accompanying Examples section.

In a yet even more highly preferred embodiment, the compound of the invention is selected from EXAMPLES 60, 61 and 75 as described in the accompanying Examples section.

Pharmaceutical Compositions

A further aspect of the invention relates to a pharmaceutical composition comprising a compound of the invention admixed with one or more pharmaceutically acceptable diluents, excipients or carriers. Other active materials may also be present, as may be considered appropriate or advisable for the disease or condition being treated or prevented.

Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, 2$^{nd}$ Edition, (1994), Edited by A Wade and P J Weller. The carrier, or, if more than one be present, each of the carriers, must be acceptable in the sense of being compatible with the other ingredients of the formulation and not deleterious to the recipient.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically or veterinarily acceptable carrier or vehicle.

Salts/Esters

The compounds of the invention can be present as salts or esters, in particular pharmaceutically and veterinarily acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with amino acids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with amino acids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art.

Enantiomers are characterised by the absolute configuration of their chiral centres and described by the R- and S-sequencing rules of Cahn, Ingold and Prelog. Such conventions are well known in the art (e.g. see 'Advanced Organic Chemistry', $3^{rd}$ edition, ed. March, J., John Wiley and Sons, New York, 1985).

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3$H or $^{14}$C is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. For example, the invention includes compounds of general formula (I) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Prodrugs

The invention further includes the compounds of the present invention in prodrug form, i.e. covalently bonded compounds which release the active parent drug according to general formula (I) in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

A prodrug may for example constitute a ketal or hemiketal derivative of the exocyclic ketone functionality present in the tetrahydro-furo[3,2-b]pyrrol-3-one scaffold.

Solvates

The present invention also includes solvate forms of the compounds of the present invention. The terms used in the claims encompass these forms.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Assays

Another aspect of the invention relates to the use of a compound of the invention as defined hereinabove in an assay for identifying further candidate compounds that influence the activity of one or cysteine proteinases.

Preferably, the assay is capable of identifying candidate compounds that are capable of inhibiting one or more CAC1 cysteine proteinases.

More preferably, the assay is a competitive binding assay.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Preferably, the competitive binding assay comprises contacting a compound of the invention with a cysteine proteinase in the presence of a known substrate of said enzyme and detecting any change in the interaction between said cysteine proteinase and said known substrate.

A further aspect of the invention provides a method of detecting the binding of a ligand to a cysteine proteinase, said method comprising the steps of:

(i) contacting a ligand with cysteine proteinase in the presence of a known substrate of said enzyme;

(ii) detecting any change in the interaction between said enzyme and said known substrate; and wherein said ligand is a compound of the invention.

One aspect of the invention relates to a process comprising the steps of:

(a) performing an assay method described hereinabove;

(b) identifying one or more ligands capable of binding to a ligand binding domain; and (c) preparing a quantity of said one or more ligands.

Another aspect of the invention provides a process comprising the steps of:

(a) performing an assay method described hereinabove;

(b) identifying one or more ligands capable of binding to a ligand binding domain; and (c) preparing a pharmaceutical composition comprising said one or more ligands.

Another aspect of the invention provides a process comprising the steps of:

(a) performing an assay method described hereinabove;

(b) identifying one or more ligands capable of binding to a ligand binding domain;

(c) modifying said one or more ligands capable of binding to a ligand binding domain;

(d) performing the assay method described hereinabove;

(e) optionally preparing a pharmaceutical composition comprising said one or more ligands.

The invention also relates to a ligand identified by the method described hereinabove.

Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of one or more disorders selected from osteoporosis, Paget's disease, Chagas's disease, malaria, gingival disease such as gingivitis or periodontitis, hypercalaemia, metabolic bone disease and diseases involving matrix or cartilage degradation, such as osteoarthritis, rheumatoid arthritis and neoplastic diseases.

The above methods may be used to screen for a ligand useful as an inhibitor of one or more cysteine proteinases.

Compounds of general formula (I) are useful both as laboratory tools and as therapeutic agents. In the laboratory certain compounds of the invention are useful in establishing whether a known or newly discovered cysteine proteinase contributes a critical or at least significant biochemical function during the establishment or progression of a disease state, a process commonly referred to as 'target validation'.

According to a further aspect of the invention, there is provided a method of validating a known or putative cysteine proteinase as a therapeutic target, the method comprising:

(a) assessing the in vitro binding of a compound as described above to an isolated known or putative cysteine proteinase, providing a measure of potency; and optionally, one or more of the steps of:

(b) assessing the binding of the compound to closely related homologous proteinases of the target and general housekeeping proteinases (e.g. trypsin) to provide a measure of selectivity;

(c) monitoring a cell-based functional marker of a particular cysteine proteinase activity, in the presence of the compound; and (d) monitoring an animal model-based functional marker of a particular cysteine proteinase activity in the presence of the compound.

The invention therefore provides a method of validating a known or putative cysteine proteinase as a therapeutic target. Differing approaches and levels of complexity are appropriate to the effective inhibition and 'validation' of a particular target. In the first instance, the method comprises assessing the in vitro binding of a compound of general formula (I) to an isolated known or putative cysteine proteinase, providing a measure of 'potency'. An additional assessment of the binding of a compound of general formula (I) to closely related homologous proteinases of the target and general housekeeping proteinases (e.g. trypsin) provides a measure of 'selectivity'. A second level of complexity may be assessed by monitoring a cell-based functional marker of a particular cysteine proteinase activity, in the presence of a compound of general formula (I). For example, an 'osteoclast resorption assay' has been utilised as a cell-based secondary in vitro testing system for monitoring the activity of cathepsin K and the biochemical effect of proteinase inhibitors (e.g. see WO-A-9850533). An 'MHC-II processing—T-cell activation assay' has been utilised as a cell-based secondary in vitro testing system for monitoring the activity of cathepsin S and the biochemical effect of proteinase inhibitors (Shi, G-P., et al, *Immunity,* 10, 197-206, 1999). When investigating viral or bacterial infections such a marker could simply be a functional assessment of viral (e.g. count of mRNA copies) or bacterial loading and assessing the biochemical effect of proteinase inhibitors. A third level of complexity may be assessed by monitoring an animal model-based functional marker of a particular cysteine proteinase activity, in the presence of a compound of general formula (I). For example, murine models of *Leishmania* infection, *P. vinckei* infection, malaria (inhibition of falcipain) and *T. cruzi* infection (cruzipain), indicate that inhibition of cysteine proteinases that play a key role in pathogen propagation is effective in arresting disease symptoms, 'validating' said targets.

The invention therefore extends to the use of a compound of general formula (I) in the validation of a known or putative cysteine proteinase as a therapeutic target.

Biological Activity

The compounds of the present invention are structurally distinct from the prior art (e.g. WO-A-02057270; Quibell, M. et. al., Bioorg. Med. Chem. 13, 609-625, 2005; Quibell M, et al Bioorg. Med. Chem, 12, 5689-5710, 2004) in that a wide range of 6-substituents and an alkylpiperazine or alkylpiperidine are an intrinsic feature. Advantageously, compounds of the present invention that contain this combination of structural features exhibit surprisingly high efficacies for human cathepsin K together with high stability in human plasma (see table 1). Indeed, all of the compounds prepared to date exhibit potent in vitro inhibition versus human cathepsin K with Ki<50 nM. In contrast, the majority of the eighty-two prior art compounds detailed in WO-A-02057270 were significantly less potent against human cathepsin K (2-35 fold less potent) than the compounds of the present invention and in the majority of examples greater than 1000-fold less potent (for example see table 2).

Preferably, the compounds exhibit in vitro inhibition versus human cathepsin K with Ki<40 nM, more preferably <30 nM, even more preferably <20 nM, more preferably still <10 nM, and even more preferably <5 nM. The compounds of the invention exhibit high selectivity against other mammalian cathepsins displaying little or no inhibitory activity for cathepsins S, L, B and V at 1 □M compound.

The presently claimed compounds also exhibit desirable pharmacokinetic properties. Without wishing to be bound by theory, it is believed that the presence of a piperazine or piperidine ring moiety confers compounds of formula (I) with one or more of the following: favourable human liver microsome (HLM) stability, improved plasma stability and/or improved solubility, compared with other cathepsin K inhibitors known in the art (for example, those disclosed in WO 02/057270 and prior art compound 23/10 detailed in Quibell, M. et. al., Bioorg. Med. Chem. 13, 609-625, 2005; Quibell M, et al Bioorg. Med. Chem., 12, 5689-5710, 2004). In particular, results have shown that compounds of formula (I) as described herein exhibit surprisingly good stability in human plasma (see table 1, stability at 1 h, 37° C.).

In addition, presently claimed compounds exhibit inhibitory activity versus human osteoclast cells. A highly preferred sub-group of presently claimed compounds exhibit potent osteoclast activity versus human cells and surprisingly an intrinsic feature of the highly preferred sub-group is an experimentally determined Log D ($pH_{7.4}$) greater than 0.8. LogD is an experimentally determined characteristic of a compound that is considered to reflect the propensity of a compound to transfer across the lipid core of a membrane. LogD is defined as the logarithm of the distribution coefficient (D) at a selected pH, usually assumed to be measured in octanol/water. Without wishing to be bound by theory, it is believed that human osteoclast potency and experimentally determined Log D ($pH_{7.4}$) can be used as a means of further distinguishing highly preferred inhibitors of cathepsin K. For example, EXAMPLES 3, 23, 24, 25, 26 and 28 which exhibit in vitro potency versus human cathepsin K of 3.5 to 15.1 nM and human osteoclast inhibitory potency of 25 to 54% also exhibit Log D ($pH_{7.4}$) of 0.01 to 0.76. In contrast, EXAMPLES 1, 2, 4, 5, 6, 7, 8, 13, 14, 15, 16, 22, 27 and 38 which exhibit similar in vitro potency versus human cathepsin K of 3.7 to 16.3 nM, but all exhibit Log D ($pH_{7.4}$) greater than 0.8, show surprisingly improved human osteoclast inhibitory potency of 63 to 88%.

Therapeutic Use

Compounds of general formula (I) are useful for the in vivo treatment or prevention of diseases in which participation of a cysteine proteinase is implicated.

In particular, compounds of general formula I are inhibitors of a wide range of CAC1 cysteinyl proteinases for example cathepsin K, cathepsin S, cathepsin L, cathepsin F, cathepsin B, cathepsin V, cruzipains, falcipains and *leismania mexicana* CPB proteinase.

Preferably, the compound of general formula I is selective for cathepsin K. As used herein, the term "selective for cathepsin K" means that the inhibitor is selective for cathepsin K over one or more other mammalian CAC1 cysteinyl proteinases for example cathepsin S, cathepsin L, cathepsin F, cathepsin B and cathepsin V. Preferably, the inhibitor exhibits a selectivity ratio for cathepsin K over other mammalian CAC1 cysteinyl proteinases of greater than 2-fold, more preferably greater than 5-fold, more preferably greater than 10-fold, even more preferably greater than 25-fold, more preferably still, greater than 50-fold or 100-fold.

According to a further aspect of the invention, there is provided a compound of general formula (I) for use in medicine, especially for preventing or treating diseases in which the disease pathology may be modified by inhibiting a cysteine proteinase.

According to a further aspect of the invention, there is provided the use of a compound of general formula (I) in the preparation of a medicament for preventing or treating diseases in which the disease pathology may be modified by inhibiting a cysteine proteinase.

Certain cysteine proteinases function in the normal physiological process of protein degradation in animals, including humans, e.g. in the degradation of connective tissue. However, elevated levels of these enzymes in the body can result in pathological conditions leading to disease. Thus, cysteine proteinases have been implicated in various disease states, including but not limited to, infections by *Pneumocystis carinii, Trypsanoma cruzi, Trypsanoma brucei brucei* and *Crithidia fusiculata*; as well as in osteoporosis, osteoarthritis, rheumatoid arthritis, multiple sclerosis, chronic pain, autoimmunity, schistosomiasis, malaria, tumour metastasis, metachromatic leukodystrophy, muscular dystrophy, amytrophy, and the like (see WO-A-9404172 and EP-A-0603873 and references cited therein). Additionally, a secreted bacterial cysteine proteinase from *S. Aureus* called staphylopain has been implicated as a bacterial virulence factor (Potempa, J., et al. J. Biol. Chem., 262(6), 2664-2667, 1998).

The invention is useful in the prevention and/or treatment of each of the disease states mentioned or implied above. The present invention also is useful in a methods of treatment or prevention of diseases caused by pathological levels of cysteine proteinases, particularly cysteine proteinases of the papain superfamily, which methods comprise administering to an animal, particularly a mammal, most particularly a human, in need thereof a compound of the present invention. The present invention particularly provides methods for treating diseases in which cysteine proteinases are implicated, including infections by *Pneumocystis carinii, Trypsanoma cruzi, Trypsanoma brucei, Leishmania mexicana, Clostridium histolyticum, Staphylococcus aureus*, foot-and-mouth disease virus and *Crithidia fusiculata*; as well as in osteoporosis, osteoarthritis, rheumatoid arthritis, multiple sclerosis, chronic pain, autoimmunity, schistosomiasis, malaria, tumour metastasis, metachromatic leukodystrophy, muscular dystrophy, amytrophy.

Inhibitors of cathepsin K, particularly cathepsin K-specific compounds, are useful for the treatment of osteoporosis, Paget's disease, gingival diseases such as gingivitis and periodontitis, hypercalaemia of malignancy, metabolic bone disease, diseases involving matrix or cartilage degradation, in particular osteoarthritis and rheumatoid arthritis and neoplastic diseases.

Preferred features for each aspect of the invention are as for each other aspect mutatis mutandis.

Administration

The pharmaceutical compositions of the present invention may be adapted for rectal, nasal, intrabronchial, topical (including buccal and sublingual), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

In accordance with this invention, an effective amount of a compound of general formula (I) may be administered to inhibit the proteinase implicated with a particular condition or disease. Of course, this dosage amount will further be modified according to the type of administration of the compound. For example, to achieve an "effective amount" for acute therapy, parenteral administration of a compound of general formula (I) is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit a cysteine proteinase. The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect. Prodrugs of compounds of the present invention may be prepared by any suitable method. For those compounds in which the prodrug moiety is a ketone functionality, specifically ketals and/or hemiketals, the conversion may be effected in accordance with conventional methods.

The compounds of this invention may also be administered orally to the patient, in a manner such that the concentration of drug is sufficient to inhibit bone resorption or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Combinations

In a particularly preferred embodiment, the one or more compounds of the invention are administered in combination with one or more other active agents, for example, existing drugs available on the market. In such cases, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance.

Beneficial combinations may be suggested by studying the inhibitory activity of the test compounds with agents known or suspected of being valuable in the treatment of a particular disorder. This procedure can also be used to determine the order of administration of the agents, i.e. before, simultaneously, or after delivery. Such scheduling may be a feature of all the active agents identified herein.

Synthesis

Synthesis of 5,5-Bicyclic Core

One aspect of the invention relates to a process of preparing a compound of formula (I) as defined above, said process comprising converting a compound of formula (II), where $R^5$ is a protecting group, into a compound of formula (I)

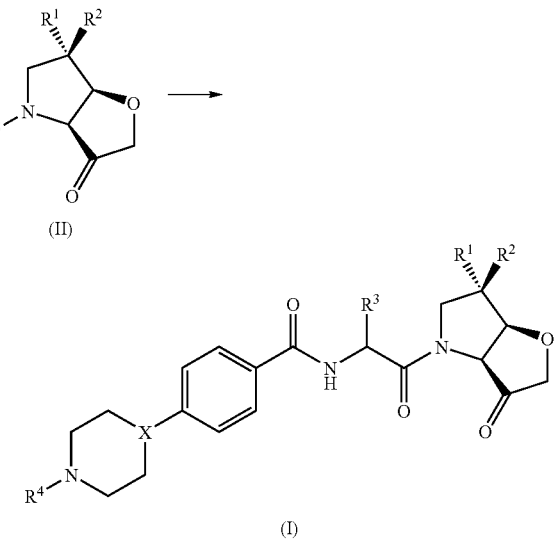

In one preferred embodiment, protecting group $R^5$ is selected from benzyloxycarbonyl, tert-butoxycarbonyl, fluoren-9-ylmethoxycarbonyl, 1-(biphenyl-4-yl)-1-methylethoxycarbonyl, α,α-dimethyl-3,5-dimethoxylbenzyloxycarbonyl, p-methoxybenzyloxycarbonyl, p-nitrobenzyloxycarbonyl, allyloxycarbonyl and trichloroethoxycarbonyl.

In one particularly highly preferred embodiment of the invention, $R^5$ is benzyloxycarbonyl, tert-butoxycarbonyl (Boc) or flouren-9-ylmethoxycarbonyl (Fmoc).

In one preferred embodiment, the process of the invention comprises the step of converting a compound of formula (III) into a compound of formula (II)

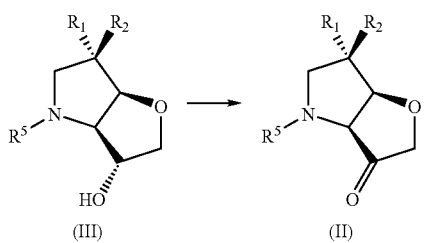

Any suitable oxidising agent may be used to convert the secondary alcohol group of (III) into the corresponding ketone (II). Suitable oxidising agents will be familiar to the skilled artisan. By way of example, the oxidation may be carried out via a Dess-Martin periodinane reaction [Dess, D. B. et al, J. Org. Chem. 1983, 48, 4155; Dess, D. B. et al, J. Am. Chem. Soc. 1991, 113, 7277], or via a Swern oxidation [Mancuso, A. J. et al, J. Org. Chem. 1978, 43, 2480]. Alternatively, the oxidation can be carried out using $SO_3$/pyridine/$Et_3N$/DMSO [Parith, J. R. et al, J. Am. Chem. Soc. 1967, 5505; U.S. Pat. No. 3,444,216, Parith, J. R. et al], $P_2O_5$/DMSO or $P_2O_5$/$Ac_2O$ [Christensen, S. M. et al, Organic Process Research and Development, 2004, 8, 777]. Other alternative oxidation reagents include activated dimethyl sulphoxide [Mancuso, A. J., Swern, D. J., Synthesis, 1981, 165], pyridinium chlorochromate [Pianeatelli, G. et al, Synthesis, 1982, 245] and Jones' reagent [Vogel, A, I., Textbook of Organic Chemistry, $6^{th}$ Edition].

More preferably, the process comprises treating a compound of formula (III) with Dess-Martin periodinane. Preferably, the reaction is carried out using dichloromethane as solvent.

In a more preferred embodiment the process of the invention comprises the step of converting a compound of formula (IV) into a compound of formula (III)

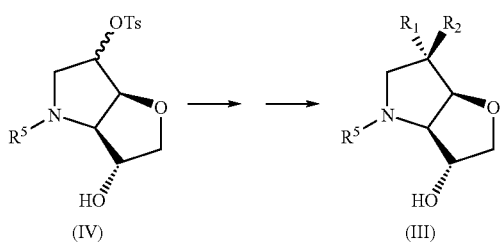

In an even more preferred embodiment the process of the invention comprises the step of converting a compound of formula (IVa) into a compound of formula (IIIa) or a compound of formula (IVb) into a compound of formula (IIIb)

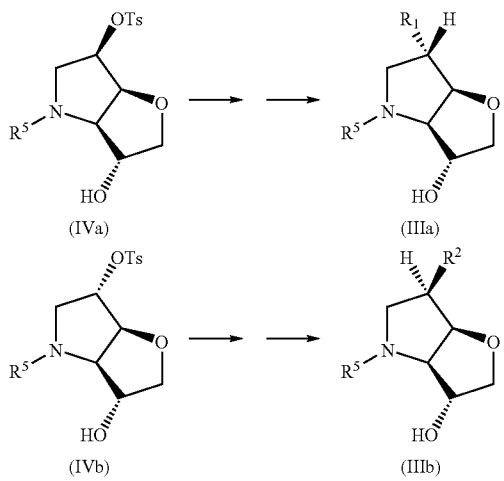

For compounds of formulae (IIIa) and (IIIb) wherein $R^1$ or $R^2$ are azide, it is preferred the $R^5$ protecting group is benzyloxycarbonyl (Cbz) and the displacement of tosylate is typically performed with sodium azide in DMF at elevated temperature, typically greater than 100° C. The azido analogues provide access to 6-amino analogues (e.g. see Scheme 13).

For compounds of formulae (IIIa) and (IIIb) wherein $R^1$ or $R^2$ are thiomethyl, it is preferred that the $R^5$ protecting group is tert-butoxycarbonyl (Boc) and the displacement of tosylate is typically performed with sodium thiomethoxide [CAS 5188-07-8] in DMF at elevated temperature, typically greater than 90° C. One skilled in the art will appreciate that use of alternative thioalkyl reagents provides access to other 6-alkylsulphide analogues (formulae III, $R^1$ or $R^2$ is $SR^6$ wherein $R^6$ is as previously defined).

Oxidation of the 6-alkylsulphide analogues of formulae (IIIa) and (IIIb) may provide access to the 6-alkylsulphoxides (formulae III, $R^1$ or $R^2$ is $SOR^8$ wherein $R^8$ is as previously defined) and 6-alkylsulphones (formulae III, $R^1$ or $R^2$ is $SO_2R^8$ wherein $R^8$ is as previously defined).

For compounds of formulae (IIIa) and (IIIb) wherein $R^1$ or $R^2$ are methylamino, it is preferred the $R^5$ protecting group is benzyloxycarbonyl (Cbz) and the displacement of tosylate is typically performed with methylamine in ethanol with heat. One skilled in the art will appreciate that use of alternative alkylamine reagents provides access to other 6-alkylamino analogues (formulae III, $R^1$ or $R^2$ is $NR^6R^7$ wherein $R^6$ and $R^7$ are as previously defined). Also, within $NR^6R^7$ when either $R^6$ or $R^7$ are hydrogen, it is preferred that the secondary amino function is further protected, for example with the tert-butoxycarbonyl group, providing compounds of formulae (IIIa) or (IIIb) wherein $R^5$ is Cbz and $R^1$ or $R^2$ are $BocNR^6$.

Compounds of formulae (IIIa) and (IIIb) wherein $R^1$ or $R^2$ are alkoxy ($OR^6$) can be prepared by direct synthesis (e.g. see scheme 11). Alternatively, for example the $R^1$=ethoxy analogue can be prepared by displacement of tosylate of formula (IVa) where it is preferred that the $R^5$ protecting group is tert-butoxycarbonyl (Boc). Displacement is typically performed with sodium ethoxide in ethanol with heat. One skilled in the art will appreciate that use of alternative alkoxy reagents provides access to other 6-alkoxy analogues (formulae III, $R^1$ or $R^2$ is $OR^6$ wherein $R^6$ is as previously defined).

In one preferred embodiment the process of the invention comprises the step of converting a compound of formula (V) into a compound of formula (IV)

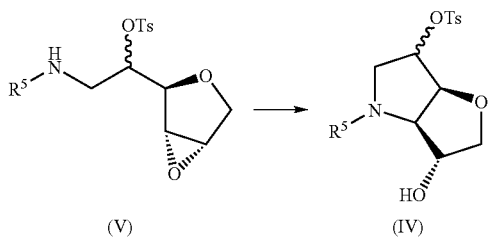

(V)  (IV)

More preferably, the process comprises treating a compound of formula (V) with sodium hydride. Preferably, the reaction is carried out in THF.

In an alternative preferred embodiment of the invention, the intra-molecular cyclisation of compound (V) is induced by removal of the protecting group $R^5$. Preferably, for this embodiment, $R^5$ is benzyloxycarbonyl (Cbz), and the process comprises hydrogenating a compound of formula (V) in the presence of a palladium catalyst.

In one preferred embodiment the process of the invention comprises the step of converting a compound of formula (VI) into a compound of formula (V)

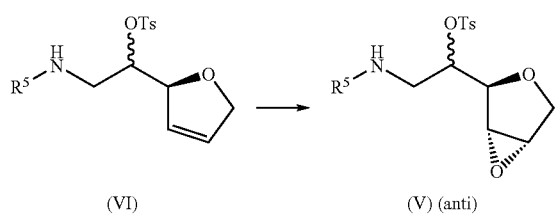

(VI)  (V) (anti)

In one preferred embodiment, the oxidising agent is mCPBA.

In another preferred embodiment, the oxidising agent is a dioxirane.

The use of dioxiranes as oxidising agents is well documented in the literature [see (a) Hodgson, D. M. et al, Synlett, 310 (2002); (b) Adam, W. et al, Acc. Chem. Res. 22, 205, (1989); (c) Yang, D. et al, J. Org. Chem., 60, 3887, (1995); (d) Mello, R. et al, J. Org. Chem., 53, 3890, (1988); (e) Curci, R. et al, Pure & Appl. Chem., 67(5), 811 (1995); (f) Emmons, W. D. et al, J. Amer. Chem. Soc. 89, (1955)].

Preferably, the dioxirane is generated in situ by the reaction of $KHSO_5$ with a ketone. However, the oxidation step can also be carried out using an isolated dioxirane, for example a stock solution of the dioxirane formed from acetone.

More preferably, the dioxirane is generated in situ using Oxone®, which is a commercially available oxidising agent containing $KHSO_5$ as the active ingredient.

Thus, in one preferred embodiment, the claimed process involves the in situ epoxidation of a compound of formula (VI) using Oxone® ($2KHSO_5.KHSO_4.K_2SO_4$) and a ketone co-reactant.

As mentioned above, the active ingredient of Oxone® is potassium peroxymonosulfate, $KHSO_5$ [CAS-RN 10058-23-8], commonly known as potassium monopersulfate, which is present as a component of a triple salt with the formula $2KHSO_5.KHSO_4.K_2SO_4$ [potassium hydrogen peroxymonosulfate sulfate (5:3:2:2), CAS-RN 70693-62-8; commercially available from DuPont]. The oxidation potential of Oxone® is derived from its peracid chemistry; it is the first neutralization salt of peroxymonosulfuric acid $H_2SO_5$ (also known as Caro's acid).

$$K^+\!-\!O\!-\!S(=\!O)_2(-\!OOH)$$

Potassium Monopersulfate

Under slightly basic conditions (pH 7.5-8.0), persulfate reacts with the ketone co-reactant to form a three membered cyclic peroxide (a dioxirane) in which both oxygens are bonded to the carbonyl carbon of the ketone. The cyclic peroxide so formed then epoxidises the compound of formula VI by syn specific oxygen transfer to the alkene bond.

Preferably, the ketone is of formula (XIX)

(XIX)

wherein $R^a$ and $R^b$ are each independently alkyl, aryl, haloalkyl or haloaryl.

Where $R^a$ and/or $R^b$ are alkyl, the alkyl group may be a straight chain or branched alkyl group. Preferably, the alkyl group is a $C_{1-20}$ alkyl group, more preferably a $C_{1-15}$, more preferably still a $C_{1-12}$ alkyl group, more preferably still, a $C_{1-8}$ or $C_{1-6}$ alkyl group, more preferably a $C_{1-4}$ alkyl group. Particularly preferred alkyl groups include, for example, methyl, ethyl, propyl, isopropyl, butyl, isobutyl, tert-butyl, pentyl and hexyl.

As used herein, the term "haloalkyl" refers to an alkyl group as described above in which one or more hydrogens are replaced by halo.

Where $R^a$ and/or $R^b$ are aryl, the aryl group is typically a $C_{6-12}$ aromatic group. Preferred examples include phenyl and naphthyl etc.

As used herein, the term "haloaryl" refers to an aryl group as described above in which one or more hydrogens are replaced by halo.

By way of example, the reaction of $KHSO_5$ (Oxone®) with a ketone of formula XVI would form a dioxirane of formula:

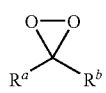

wherein $R^a$ and $R^b$ are as defined above.

More preferably, $R^a$ and $R^b$ are each independently alkyl or haloalkyl.

In a highly preferred embodiment, at least one of $R^a$ and $R^b$ is a haloalkyl, more preferably, $CF_3$ or $CF_2CF_3$.

In one preferred embodiment, $R^a$ and $R^b$ are each independently methyl or trifluoromethyl.

In one preferred embodiment of the invention, the ketone is selected from acetone and a 1,1,1-trifluoroalkyl ketone.

In a more preferred embodiment of the invention, the trifluoroalkyl ketone is 1,1,1-trifluoroacetone or 1,1,1-trifluoro-2-butanone, more preferably 1,1,1-trifluoro-2-butanone.

In one preferred embodiment the process of the invention comprises the step of converting a compound of formula (VII) into a compound of formula (VI)

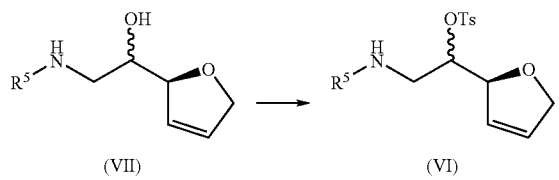

(VII) → (VI)

Preferably the process comprises treating a compound of formula (VII) with tosyl chloride in pyridine. Alternatively the process comprises treating a compound of formula (VII) with tosyl chloride in dichloromethane and triethylamine.

In one preferred embodiment the process of the invention comprises the step of converting a compound of formula (VIII) into a compound of formula (VII)

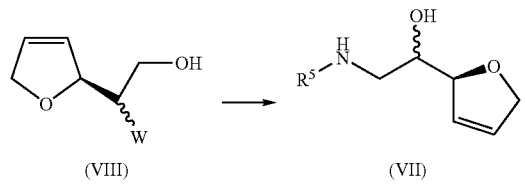

(VIII) → (VII)

where W is halogen or tosyl.

Preferably, this step comprises the steps of:
(a) reacting a compound of formula (VIII), where W is halogen or OTs, with aqueous ammonia and alcohol; and
(b) converting the product formed in step (a) to a compound of formula (VII).

Preferably, steps (a) and (b) of the above process are a one-pot process.

In one particularly preferred embodiment, $R^5$ is benzyloxycarbonyl, and step (b) comprises treating the mixture formed in step (a) with benzyloxycarbonyl chloride.

Preferably, W is I, Br or OTs, more preferably, Br or OTs, even more preferably OTs.

Preferably, the alcohol is isopropyl alcohol or ethanol.

In one preferred embodiment of the invention, said compound of formula VIII is prepared from a compound of formula IX

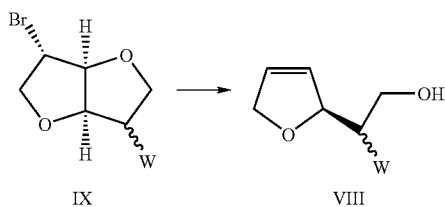

IX → VIII

Preferably, the above process comprises treating said compound of formula IX with methyl lithium.

More preferably, compound of formula IX is compound 47 and compound of formula VIII is compound 14; or compound of formula IX is compound 46 and compound of formula VIII is compound 13. Treatment of monobromotosylates 46 or 47 with zinc dust at room temperature in organic/aqueous mixtures (most preferably an isopropanol, tetrahydrofuran, water, ammonium chloride mixture) provides alcohols 13 and 14 respectively in high yield. Additionally, completion of the one-pot conversion gives alcohols VIIa and VIIb with defined stereochemistry and in high yield.

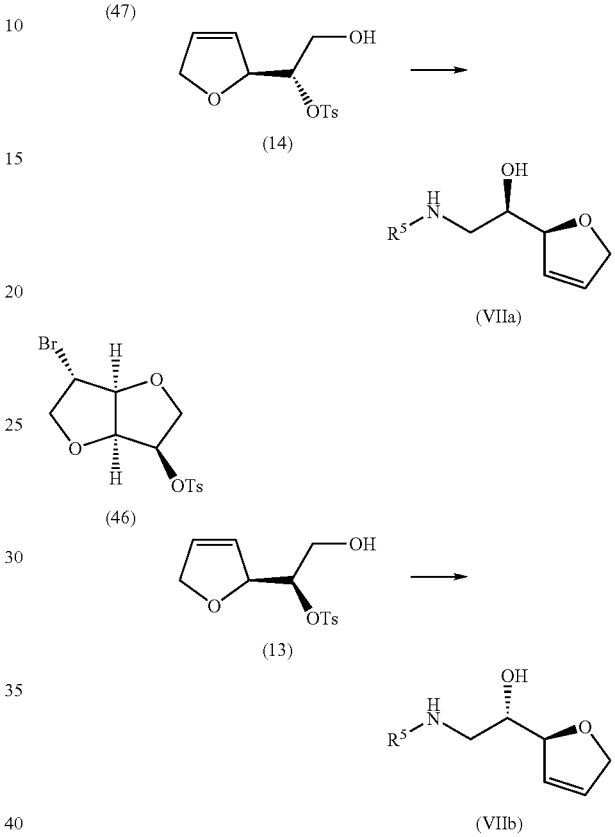

Commencing from the commercially available sugars isomannide and isosorbide, the present invention also provides facile preparation of monobromotosylates 46 and 47 One highly preferred preparation is shown below in Scheme 15

Scheme 15:

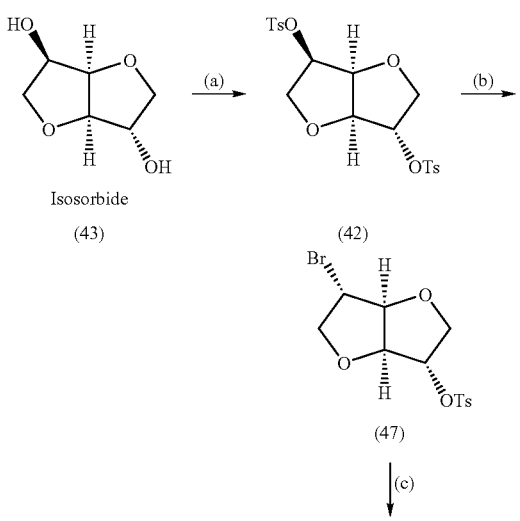

-continued

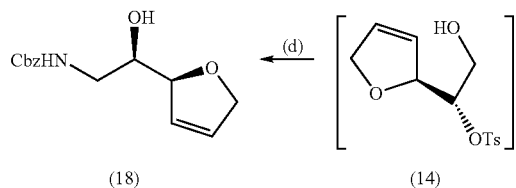

(18) (14)

(a) TsCl, triethylamine, DCM, 25° C. ⟶ 50° C., 20 h under Ar;
(b) LiBr, DMSO, 110° C. ⟶ 120° C., 10 h under Ar;
(c) Zn, $^i$PrOH, THF, H$_2$O, NH$_4$Cl, RT, 16 h;
(d) (i) NH$_4$OH, NH$_3$ in $^i$PrOH, 75° C., 16 h;
  (ii) Cbz-Cl, Na$_2$CO$_3$, dioxane, water.

Isosorbide (43) is converted to the di-tosylate (42) which is obtained following recrystallisation from methanol in 97% yield. Mono-bromination is effected by 2.5 eq lithium bromide in DMSO (or DMF) with temperature control 110° C.→120° C. The product bromide is isolated following extractive work-up and purification either by column chromatography (74%) or attractive for large scale by recrystallisation from methanol giving a first crop of 55% plus mother liquors containing good quality material that may be pooled from batch runs and purified later. Thus, preparation of monobromotosylate (47) with defined stereochemistry by methods in Scheme 15 is attractive for large scale applications. Treatment of monobromotosylate (47) with zinc dust at room temperature in organic/aqueous mixtures (most preferably an isopropanol, tetrahydrofuran, water, ammonium chloride mixture) provides alcohol (14) which is derivatised as the Cbz compound (18) through one pot conversion.

Scheme 16:

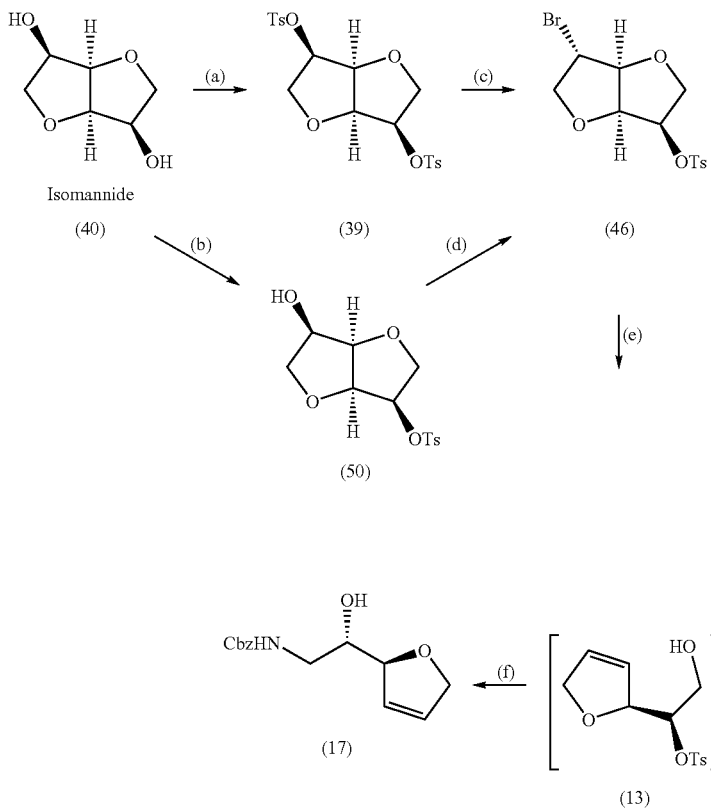

(a) 2.2 eq TsCl, KOH(aq), DCM, CCl$_4$, 0° C., 24 h under Ar;
(b) (i) 0.5 eq TsCl, KOH(aq), DCM, CCl$_4$, 0° C., 7 h under Ar or
  (ii) 1.0 eq TsCl, pyridine, 0° C. ⟶ RT, 1 h;
(c) LiBr, DMF, 100° C., 27 h;
(d) CBr$_4$, Ph$_3$P, pyridine, 65° C., 2 h under Ar;
(e) Zn, $^i$PrOH, THF, H$_2$O, NH$_4$Cl, RT, 16 h;
(f) (i) NH$_4$OH, NH$_3$ in $^i$PrOH, 75° C., 16 h;
  (ii) Cbz-Cl, Na$_2$CO$_3$, dioxane, water.

Treatment of isomannide (40) (Scheme 16) with tosylchloride (2.2 eq) in a bi-phasic potassium hydroxide/dichloromethane/carbon tetrachloride mixture at 0° C. gives ditosylate (39) in 48% yield following simple filtration and trituration with methanol. Alternatively, treatment of isomannide (40) with tosylchloride (0.5 eq) in a bi-phasic potassium hydroxide/dichloromethane/carbon tetrachloride mixture at 0° C. gives monotosylate in 38% yield following simple extraction and re-crystallisation from carbon tetrachloride (conditions as described in U.S. Pat. No. 6,858,632). Although the monotosylate can be obtained in higher yield by treatment of isomannide (40) with tosylchloride in pyridine, purification currently requires column chromatography which may becomes undesirable at large scale. Monobromotosylate (46) may then be prepared by treatment of ditosylate (39) with lithium bromide in DMF (29% yield following chromatography) or by treatment of monotosylate under Mitsunobu conditions with carbon tetrabromide (63% yield following chromatography). Treatment of monobromotosylate (46) with zinc dust at room temperature in organic/aqueous mixtures (most preferably an isopropanol, tetrahydrofuran, water, ammonium chloride mixture) provides alcohol (13) which is derivatised as the Cbz compound (17) through one pot conversion.

In one highly preferred embodiment of the invention, the 5,5-bicylic core is prepared in accordance with the steps set forth in Scheme 1 below:

The alcohol functionality of (18) may be derivatised as the para-toluene sulphonate (Ts) giving (R)-2-(benzyloxycarbonylamino)-1-((S)-2,5-dihydrofuran-2-yl)ethyl 4-methylbenzenesulfonate (32b) which proceeds through the anti-epoxide (R)-2-(benzyloxycarbonylamino)-1-((1S,2S,5S)-3,6-dioxabicyclo[3.1.0]hexan-2-yl)ethyl 4-methylbenzenesulphonate (33b). Hydrogenation of tosylate (33b) provides free amine that undergoes intramolecular cyclisation. Urethane protection of the secondary amine of the bicyclic intermediate gives (3R,3aR,6R,6aS)-benzyl 3-hydroxy-6-(tosyloxy)tetrahydro-2H-furo[3,2-b]pyrrole-4(5H)-carboxylate (34b) or (3R,3aR,6R,6aS)-tert-butyl 3-hydroxy-6-(tosyloxy)tetrahydro-2H-furo[3,2-b]pyrrole-4(5H)-carboxylate (35b).

Advantageously, the epoxidation to give the desired anti-epoxide is directed by the presence of the tosylate group whilst only modest stereoselectivity can be achieved for the corresponding saturated alkene. Thus, the stereoselectivity of the epoxidation is controlled to allow much higher yields of the desired anti-epoxide.

Scheme 1:

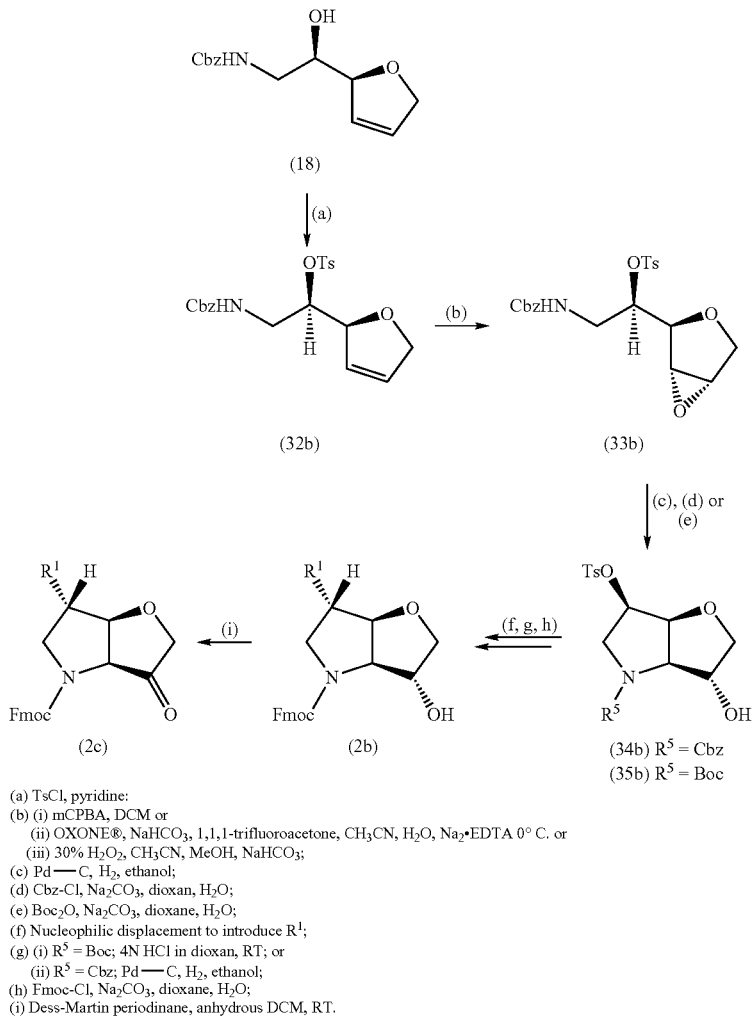

(a) TsCl, pyridine:
(b) (i) mCPBA, DCM or
    (ii) OXONE®, NaHCO$_3$, 1,1,1-trifluoroacetone, CH$_3$CN, H$_2$O, Na$_2$•EDTA 0° C. or
    (iii) 30% H$_2$O$_2$, CH$_3$CN, MeOH, NaHCO$_3$;
(c) Pd—C, H$_2$, ethanol;
(d) Cbz-Cl, Na$_2$CO$_3$, dioxan, H$_2$O;
(e) Boc$_2$O, Na$_2$CO$_3$, dioxane, H$_2$O;
(f) Nucleophilic displacement to introduce R$^1$;
(g) (i) R$^5$ = Boc; 4N HCl in dioxan, RT; or
    (ii) R$^5$ = Cbz; Pd—C, H$_2$, ethanol;
(h) Fmoc-Cl, Na$_2$CO$_3$, dioxane, H$_2$O;
(i) Dess-Martin periodinane, anhydrous DCM, RT.

An analogous reaction scheme can be applied to the enantiomer of (18), namely, benzyl (S)-2-((S)-2,5-dihydrofuran-2-yl)-2-hydroxyethyl carbamate (17), proceeding through the analogous anti-epoxide (S)-2-(benzyloxycarbonylamino)-1-((1S,2S,5S)-3,6-dioxabicyclo[3.1.0]hexan-2-yl)ethyl 4-methylbenzenesulphonate (32) (Scheme 2).

Scheme 2:

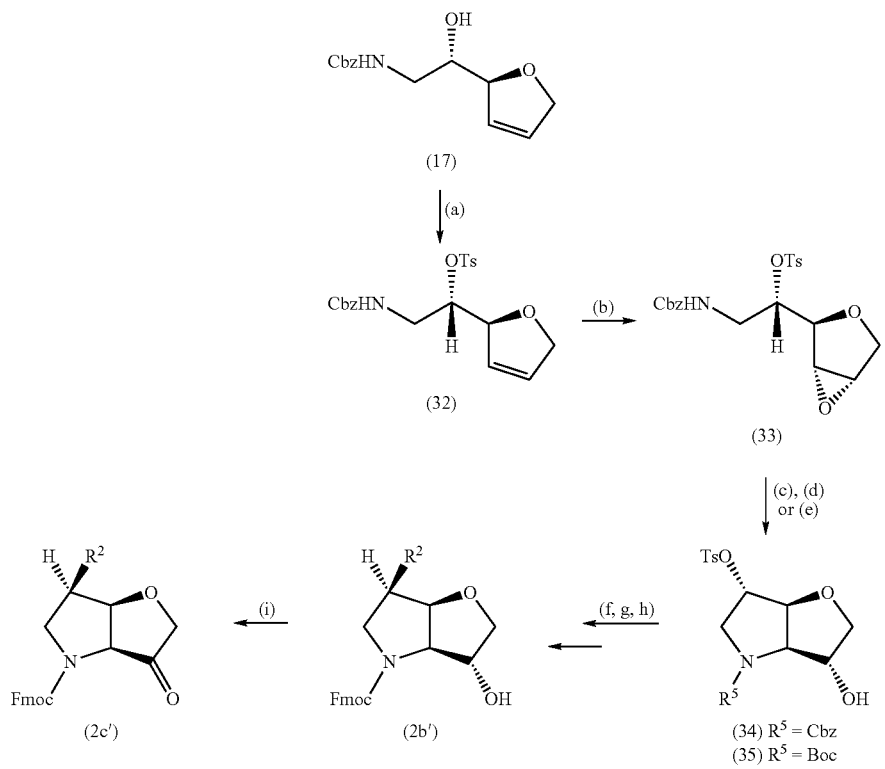

(a) TsCl, pyridine:
(b) (i) mCPBA, DCM or (ii) OXONE®, NaHCO$_3$, 1,1,1-trifluoroacetone, CH$_3$CN, H$_2$O, Na$_2$·EDTA 0° C. or (iii) 30% H$_2$O$_2$, CH$_3$CN, MeOH, NaHCO$_3$;
(c) Pd—C, H$_2$, ethanol; (d) Cbz-Cl, Na$_2$CO$_3$, dioxane, H$_2$O; (e) Boc$_2$O, Na$_2$CO$_3$, dioxane, H$_2$O;
(f) Nucleophilic displacement to introduce R$^2$; (g) (i) R$^5$ = Boc; 4N HCl in dioxan, RT; or (ii) R$^5$ = Cbz; Pd—C, H$_2$, ethanol; (h) Fmoc-Cl, Na$_2$CO$_3$, dioxan, H$_2$O; (i) Dess-Martin periodinane, anhydrous DCM, RT.

The tosyl group of bicyclic intermediates (34), (34b), (35), (35b) can act as a leaving group by employing a suitable nucleophile to provide access to the corresponding 6-substituted analogues.

For example, treatment of tosylate (34b) with sodium azide in dimethylformamide with heating provides 6-azido analogue (3R,3aR,6S,6aS)-benzyl 6-azido-3-hydroxytetrahydro-2H-furo[3,2-b]pyrrole-4(5H)-carboxylate (36b) Scheme 13. Reduction of azide to amine e.g. with triphenylphosphine/water (e.g. see Mandville, G. et al, J. Org. Chem., 61, 1122, 1996) provides the 6-amino intermediate which is Boc-protected under standard Schotten-Baumann conditions providing (37b). Conversion of Cbz to Fmoc-protection and oxidation then provides building blocks (8b) and (8c) that can be utilised in a solid phase method to prepare 6-amino analogues of general formula I (R$^1$=NH$_2$). An analogous reaction sequence may be applied to tosylate (34) to provide the opposite 6-amino epimers (7b) and (7c) used to prepare 6-amino analogues of general formula I (R$^2$=NH$_2$). One skilled in the art will appreciate that tosylates (34), (34b), (35), (35b) are exceptionally versatile analogues that open-up synthetic routes to a wide range of 6-substituted compounds.

Scheme 13:

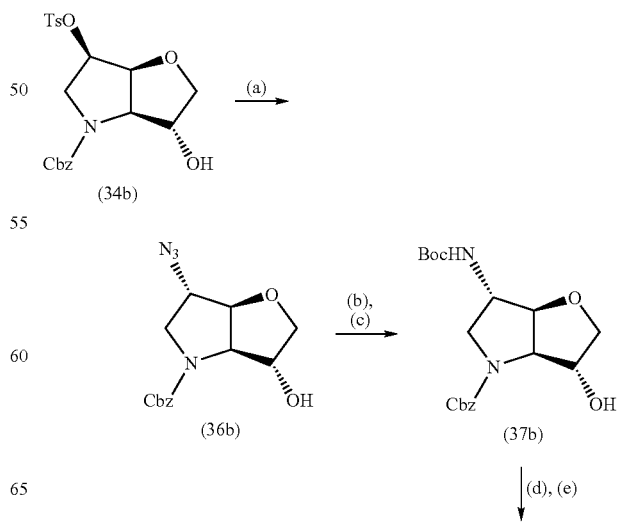

-continued

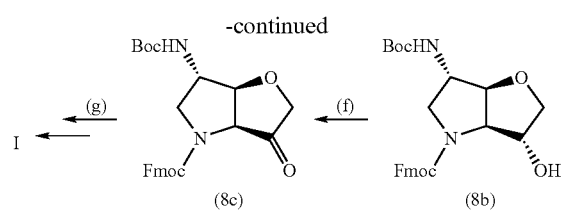

(a) 2.0 eq. Sodium azide, DMF, 135° C., overnight
(b) 1.5 eq. Triphenylphosphine, 10 eq. water, THF, 45° C., overnight;
(c) 1.5 eq. tert-butylcarbonate, 2.1 eq Na$_2$CO$_3$, dioxan, H$_2$O;
(d) Pd——C, H$_2$, ethanol or methanol;
(e) 1.05 eq Fmoc-Cl, 2.1 eq Na$_2$CO$_3$, dioxan, H$_2$O;
(f) Dess-Martin periodinane, anhydrous DCM, RT;
(g) Standard linker-construct and
    'Solid-Phase' e.g. see WO02057270 pg 105-106, 124-127, 135-136.

In an alternative embodiment, the alcohol functionality of (17) may be protected e.g. as the acid labile tert-butyl ether and utilised as detailed in Scheme 10 below, wherein benzyl (S)-2-((S)-2,5-dihydrofuran-2-yl)-2-hydroxyethyl carbamate (17) proceeds through the anti-epoxide benzyl (S)-2-((1S, 2R,5S)-3,6-dioxabicyclo[3.1.0]hexan-2-yl)-2-tert-butoxyethyl carbamate (28). An analogous reaction scheme can be applied to benzyl (R)-2-((S)-2,5-dihydrofuran-2-yl)-2-hydroxyethyl carbamate (18) proceeding through the analogous anti-epoxide benzyl (R)-2-((1S,2R,5S)-3,6-dioxabicyclo [3.1.0]hexan-2-yl)-2-tert-butoxyethyl carbamate (28b). Preparation of tert-butyl ethers is typically performed through reaction of alcohol with 2-methylpropene in a solvent such as dichloromethane with acid catalysis (e.g. see Wunsch, E. and Jentsch, J. *Chem. Ber.,* 97, 2490, 1964).

As a further alternative, the alcohol functionality of (17) may be derivatised as the methyl ether (30) and utilised as detailed in Scheme 11, wherein benzyl (S)-2-((S)-2,5-dihydrofuran-2-yl)-2-hydroxyethyl carbamate (17) proceeds through the anti-epoxide benzyl (S)-2-((1S,2R,5S)-3,6-dioxabicyclo[3.1.0]hexan-2-yl)-2-methoxyethyl carbamate (31). An analogous reaction scheme can be applied to benzyl (R)-2-((S)-2,5-dihydrofuran-2-yl)-2-hydroxyethyl carbamate (18) proceeding through the analogous anti-epoxide benzyl (R)-2-((1S,2R,5S)-3,6-dioxabicyclo[3.1.0]hexan-2-yl)-2-methoxyethyl carbamate (31b). Preparation of methyl ethers is typically performed through reaction of alcohol with methyl iodide in a solvent such as acetonitrile with silver (I) oxide catalysis (e.g. see Finch, N. et al, *J. Org. Chem.*, 40, 206, 1975 and refs. cited therein). Alternatively, methyl ethers (30) and (30b) are prepared from alcohols (17) and (18) by reaction with trimethyloxonium fluoroborate, proton sponge [1,8-bis(dimethylamino)naphthalene] and molecular sieves in dichloromethane.

Scheme 11:

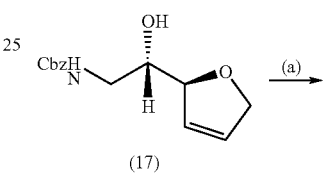

Scheme 10:

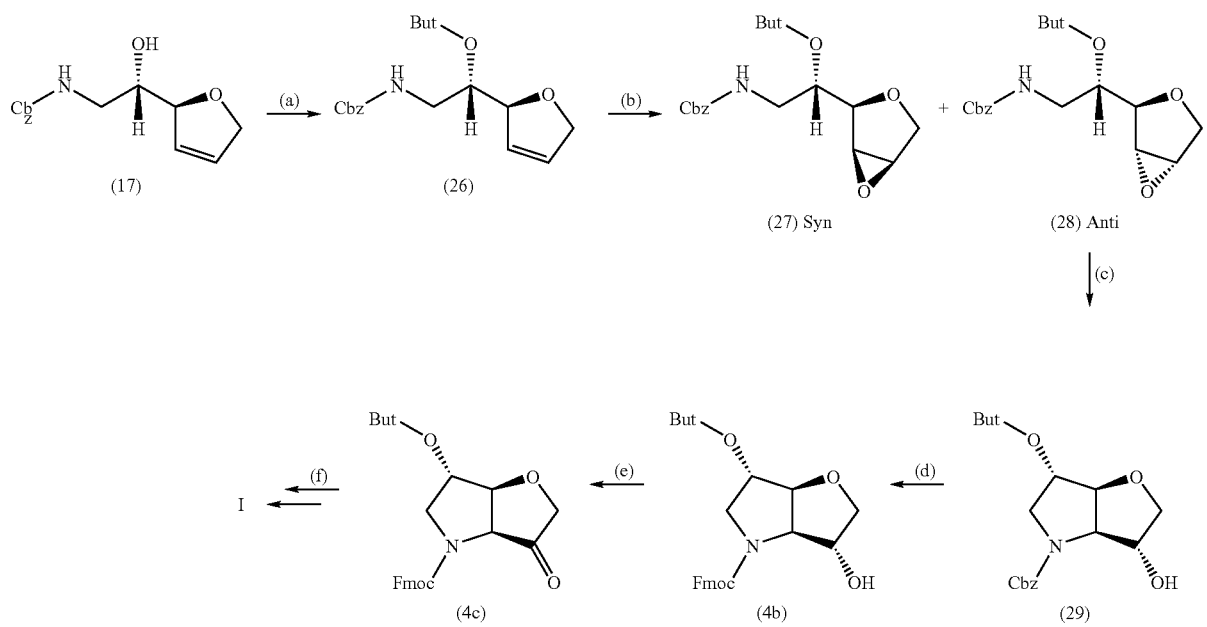

(a) 2-methylpropene(g), DCM, cat. conc. H$_2$SO$_4$, -78° C.;
(b) (i) 10 eq mCPBA, DCM, RT or (ii) OXONE®, NaHCO$_3$, 1,1,1-trifluoroacetone, CH$_3$CN, H$_2$O, Na$_2$·EDTA;
(c) NaH, anhydrous THF;
(d) (i) Pd——C, H$_2$ ethanol or methanol (ii) 1.05 eq Fmoc-Cl, 2.1 eq Na$_2$CO$_3$, dioxan, H$_2$O;
(e) Dess-Martin periodinane, anhydrous DCM, RT;
(f) Standard linker-construct and 'Solid-Phase' e.g. see WO 02/057270 pg 105-106, 124-127, 135-136.

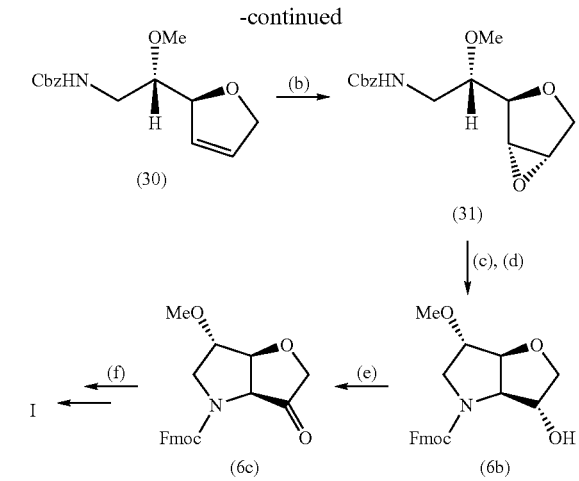

(a) MeI, Ag₂O, CH₃CN, 75–80° C.; or Me₃OBF₄, 4 Å sieves, Proton Sponge, DCM;
(b) OXONE®, NaHCO₃, 1,1,1-trifluoroacetone, CH₃CN, H₂O, Na₂·EDTA, 0° C.;
(c) Pd—C, H₂, ethanol;
(d) Fmoc-Cl, Na₂CO₃, dioxane, H₂O;
(e) Dess-Martin periodinane, DCM.
(f) Standard linker-construct and 'Solid-Phase' e.g. see WO02057270 pg 105-106, 124-127, 135-136.

Furthermore, the processes of the invention provide compounds of formula I and intermediates such as compounds of formulae III that contain a substituent in the 6-position either by direct synthesis (e.g. —OH, 6-OMe etc) or by nucleophilic substitution of the 6-tosylates (e.g. compounds 34/35) or 6-mesylates. By way of example, nucleophilic substitution of the tosyl analogue (compound 34b) with azide provides the 6-N₃ analogue ($R^1=N_3$); one skilled in the art will appreciate that protection of the alcohol (e.g. with trimethylsilyl) functionality within this analogue followed by reduction of the 6-azido to 6-amino functionality (e.g. as detailed in scheme 13) provides a primary that may be N-alkylated (e.g. displacement of an alkyl halide [$R^6$-halogen] or reductive amination [with aldehydes such as $R^7$CHO or ketones such as $R^9R^7C=O$]) providing compounds wherein $R^1=NR^6R^7$. Alternatively, nucleophilic substitution of the tosyl analogue (compound 34b) with methylamine provides an additional route towards N-alkylated compounds wherein $R^1=NHMe$. One skilled in the art will appreciate that use of alternative alkylamine reagents provides access to other 6-alkylamino analogues (formulae III, $R^1$ or $R^2$ is $NR^6R^7$ wherein $R^6$ and $R^7$ are as previously defined). Also, within $NR^6R^7$ when either $R^6$ or $R^7$ are hydrogen, it is preferred that the secondary amino function is further protected, for example with the tert-butoxycarbonyl group, providing compounds of formulae (IIIa) or (IIIb) wherein $R^5$ is Cbz and $R^1$ or $R^2$ is BocNR⁶. Alternatively, nucleophilic substitution of the tosyl analogue (compounds 34 or 35) with sodium thiomethoxide [CAS 5188-07-8] in dimethylacetamide at 90° C. provides the 6-SMe functionalised analogue; one skilled in the art will appreciate that use of alternative thioalkyl reagents provides access to other 6-alkylsulphide analogues (formulae III, $R^1$ or $R^2$ is $SR^6$ wherein $R^6$ is as previously defined); additionally one skilled in the art will appreciate that oxidation of the 6-alkylsulphide analogues of formulae (IIIa) and (IIIb) may provide access to the 6-alkylsulphoxides (formulae III, $R^1$ or $R^2$ is $SOR^8$ wherein $R^8$ is as previously defined) and 6-alkylsulphones (formulae III, $R^1$ or $R^2$ is $SO_2R^8$ wherein $R^8$ is as previously defined). Compounds of formulae (IIIa) and (IIIb) wherein $R^1$ or $R^2$ are alkoxy ($OR^6$) can be prepared by direct synthesis (e.g. as generally detailed in scheme 11). Alternatively, for example the $R^1$=ethoxy analogue can be prepared by displacement of tosylate of formula (IVa) where it is preferred that the $R^5$ protecting group is tert-butoxycarbonyl (Boc). Displacement is typically performed with sodium ethoxide in ethanol with heat. One skilled in the art will appreciate that use of alternative alkoxy reagents provides access to other 6-alkoxy analogues (formulae III, $R^1$ or $R^2$ is $OR^6$ wherein $R^6$ is as previously defined).

Other displacement reagents may be suitable for access to other 6-functionalised analogues, e.g. alkylmetal reagents such as methyllithium (e.g. see Hanessian, S. et al, J. Am. Chem. Soc., 1990, 112(13), 5276-5290) towards the 6-Me analogue; trifluoromethylating reagents such as trifluoromethyl trimethylsilane (e.g. see Sevenard. D. V. et al, Syn. Lett., 2001, 3, 379-381) or trifluoromethyl magnesium iodide towards the 6-CF₃ analogue. Thus, these tosyl analogues not only direct the stereofacial preference of the epoxidation step, but also provide versatile intermediates to access a host of 6-substituted bicyclic species.

Synthesis of Compounds of Formula (I)

To those skilled in the practices of organic chemistry, compounds of general formula (I) may be readily synthesised by a number of chemical strategies, performed either in solution or on the solid phase (see Atherton, E. and Sheppard, R. C. In 'Solid Phase Peptide Synthesis: A Practical Approach', Oxford University Press, Oxford, U.K. 1989, for a general review of solid phase synthesis principles), or a combination thereof.

Compounds of general formula (I) may be conveniently considered as a combination of three building blocks (P1, P2 and P3) that respectively occupy the S1, S2 and S3 binding sites of the protease (see Berger, A and Schechter, I., Philos. Trans. R. Soc. Lond. [Biol.], 257, 249-264, 1970 for a description of the designation of enzyme S-subsites and substrate P-subsites within enzyme-substrate or enzyme-inhibitor complexes). The notional concepts of P1, P2 and P3 are used herein for convenience only and the above-mentioned compounds are intended to be within the scope of the invention regardless of binding mode.

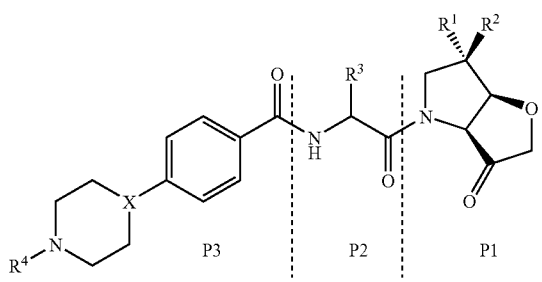

A suitably protected and/or activated building block may then be prepared and subsequently chemically bonded (coupled) together with other building blocks to provide compounds of general formula (I).

Compounds of formula (I) may be prepared: (1) by the stepwise addition of P3 and P2 to the bicyclic tetrahydrofuro[3,2-b]pyrrol-3-one core; or (2) by reaction of the bicyclic tetrahydrofuro[3,2-b]pyrrol-3-one core with a P3-P2 prescursor molecule; or (3) by introducing the P3-P2 group prior to formation of the bicyclic tetrahydrofuro[3,2-b]pyrrol-3-one core, i.e. prior to the oxidation step or prior to the intramolecular cyclisation step.

Thus, alternative orders of coupling of the building blocks are possible, for example P2+P1→P2-P1 then addition of P3→P3-P2-P1 or P3+P2→P3-P2 then addition to P1→P3-P2-P1. Within each of these combinations each of the P1, P2 or P3 building blocks may contain additional alternative functionalities that are further transformed following coupling to give the final compound. For example the ketone functionality of the P1 building block may be protected as a ketal during coupling of building blocks and transformed to the final ketone by hydrolysis following completion of the coupling reactions. Alternatively, the ketone functionality of the P1 building block may be initially introduced via a lower oxidation state such as the corresponding alcohol and following completion of the coupling reactions be re-introduced by oxidation of the alcohol. Alternatively, the ketone functionality of the P1 building block may be protected through a semi-carbazone suitable for solid phase synthesis (e.g. see WO 02/057270 and references cited therein) and following completion of the coupling reactions released from the solid phase by acidolytic reaction.

The chemical bond formed by coupling of the building blocks is a secondary amide (P3-P2) or a tertiary amide (P2-P1) that are formed through reaction of an activated carboxylic acid with a primary and secondary amine respectively. Many methods are available for activation of a carboxylic acid prior to coupling to an amine and in principle, any of these methods may be used herein. Typical carboxylic acid activation methods are exemplified but not restricted to the azide method, mixed anhydride method (e.g. via isobutylchloroformate), carbodiimide methods (e.g. via dicyclohexylcarbodiimide, diisopropylcarbodiimide, 1-ethyl-3-(3'-dimethylamino propyl)carbodiimide), active ester method (e.g. via p-nitrophenyl ester, N-hydroxysuccinic imido ester, pentafluorophenyl ester), uronium method (e.g. via addition of HBTU, PyBop, BOP), carbonyldiimidazole method or via pre-formation of acyl fluorides or acyl chlorides. In some instances the coupling reaction may be enhanced by the addition of a further activation catalyst such as 1-hydroxybenzotriazole, or 4-dimethylaminopyridine. A general description of carboxylic acid activation techniques and the use of activation additives may be found in Bodanszky, M. 'Principles of Peptide Synthesis', $2^{nd}$ rev. ed., Springer-Verlag, Berlin, 1993 and references cited therein.

The α-amino group of the P2 amino acid building block is usually protected during coupling reactions to the P1 building block to avoid the formation of undesired self-condensation products. The art of α-amino protection is well known in peptide chemistry (e.g. see Bodanszky, M. 'Principles of Peptide Synthesis', $2^{nd}$ rev. ed., Springer-Verlag, Berlin, 1993 and references cited therein) and example protection groups include, but are not limited to, 9-fluorenylmethoxycarbonyl (Fmoc), tert-butoxycarbonyl (Boc), benzyloxycarbonyl (Cbz), allyloxycarbonyl (Alloc) and trichloroethoxycarbonyl (Treoc). The Fmoc group is particularly well suited for solid phase syntheses (e.g. see Atherton, E.; Sheppard, R. C. in 'Solid Phase Peptide Synthesis A Practical Approach', IRL Press, Oxford, U.K., 1989) typically being removed by treatment with 20% v/v piperidine in dimethylformamide or 1% v/v 1,8-diazabicyclo[5.4.0]undec-7-ene in dimethylformamide. The Boc group is particularly well suited to solution phase syntheses typically being removed by treatment with trifluoroacetic acid based mixtures or HCl in dioxane or ethyl acetate. The Cbz group is also particularly well suited for solution phase syntheses typically being removed by catalytic hydrogenation with hydrogen and palladium catalysis or by treatment with HBr in acetic acid. Once the coupling sequence is complete, any protecting groups are removed in whatever manner is dictated by the choice of protecting groups (for a general description of protecting groups and their respective stabilities and methods of removal see Greene, T. W. and Wuts, P. G. M. 'Protective Groups in Organic Synthesis' John Wiley and Sons, New York, 1991 and references therein).

In the simplest example, the entire left hand portion of a compound of general formula (I) (i.e. P3-P2) as the carboxylic acid can be prepared in solution by traditional organic chemistry methods and coupled to ketone, alcohol or ketal intermediates such as compounds (IIb), (IIc) and (IId). Then oxidation of the alcohol intermediate (e.g. Dess-Martin periodinane in DCM) or acidolytic cleavage of the ketal intermediate provides compounds of general formula (I). The alcohol oxidation route is particularly useful when the compound of general formula (I) contains a substituent that is labile to trifluoroacetic acid, this being the final reagent used in each of the solid phase syntheses.

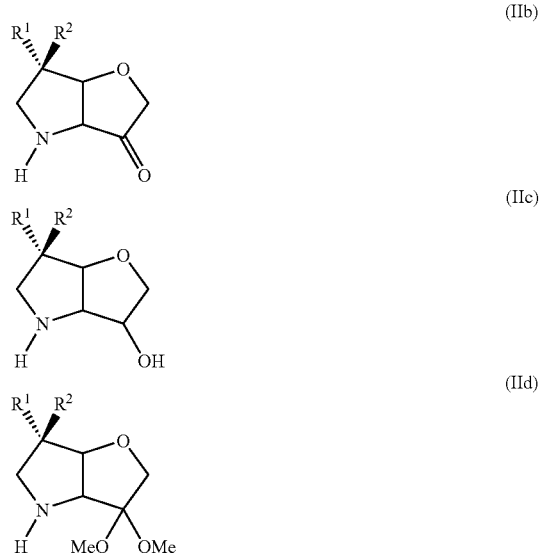

Examples of these different coupling tactics have been detailed previously (see (i) Quibell, M. et. al., *Bioorg. Med. Chem.* 13, 609-625, 2005. (ii) Wang, Y. et. al., *Bioorg. Med. Chem Lett.* 15, 1327-1331, 2005) and the optimum synthetic route is dependant upon the specific substituent combinations of the target compound of general formula (I).

In more detail, one preferred strategy for the synthesis of compounds of general formula (I) comprises:—

(a) Preparation of an appropriately functionalised and protected bicyclic ketone or bicyclic alcohol building block in solution;

(b) Attachment of the building block (a) to the solid phase through a linker that is stable to the conditions of synthesis, but readily labile to cleavage at the end of a synthesis (see James, I. W., *Tetrahedron,* 55(Report N° 489), 4855-4946, 1999, for examples of the 'linker' function as applied to solid phase synthesis);

(c) Solid phase organic chemistry (see Brown, R. D. *J Chem. Soc., Perkin Trans.* 1, 19, 3293-3320, 1998), to construct the remainder of the molecule;

(d) Compound cleavage from the solid phase into solution; and (e) Cleavage work-up and compound analysis.

A second strategy for the synthesis of compounds of general formula (I) comprises:—

(a) Preparation of an appropriately functionalised and protected bicyclic intermediate building block in solution. Preferred protecting groups for solution phase chemistry are the 9-fluorenylmethoxycarbonyl (Fmoc), Nα-tert-butoxycarbonyl (Boc), Nα-benzyloxycarbonyl (Cbz) and Nα-allyloxycarbonyl group (Alloc).

(b) Standard organic chemistry methods for the conversion of building block obtained in step (a) towards compounds of general formula (I).

As mentioned above, in one preferred embodiment of the invention, compounds of formula (I) may be prepared using conventional solution phase chemistry, for example, as described in Quibell, M et al, Bioorg. Med. Chem., 13, 609-625, 2005 (see in particular, Schemes 3 and 4). The solution phase strategy is attractive in being able to generate larger quantities of preferred analogues, typically on a multi-gram to multi-kilogram scale.

The synthetic strategy is based on reversible anchorage of the ketone functionality via a hydrazide linker bond using general multipin techniques previously described in the art (Watts J. et al, Bioorg. Med. Chem. 12(11), 2903, 2004; Quibell M., et al, Bioorg. Med. Chem. 5689-5710, 2004; Grabowksa U. et al, J. Comb. Chem. 2000, 2(5), 475).

Compounds of formula (II) may be utilised in a solid phase synthesis of inhibitor molecules (1). The solid phase linkage of an aldehyde or ketone, has previously been described by a variety of methods (e.g. see (a) James, I. W., 1999, (b) Lee, A., Huang, L., Ellman, J. A., J. Am. Chem. Soc, 121(43), 9907-9914, 1999, (c) Murphy, A. M., et al, J. Am. Chem. Soc, 114, 3156-3157, 1992). A suitable method amenable to the reversible linkage of an alkyl ketone functionality is through a combination of the previously described chemistries. The semicarbazide, 4-[[(hydrazinocarbonyl)amino]methyl]cyclohexane carboxylic acid. trifluoroacetate (Murphy, A. M., et al, J. Am. Chem. Soc, 114, 3156-3157, 1992), may be utilised as illustrated in Scheme 3, exemplified by linkage of the tetrahydrofuro[3,2-b]pyrrol-3-one (II; $R^5$=Fmoc).

Scheme 3:

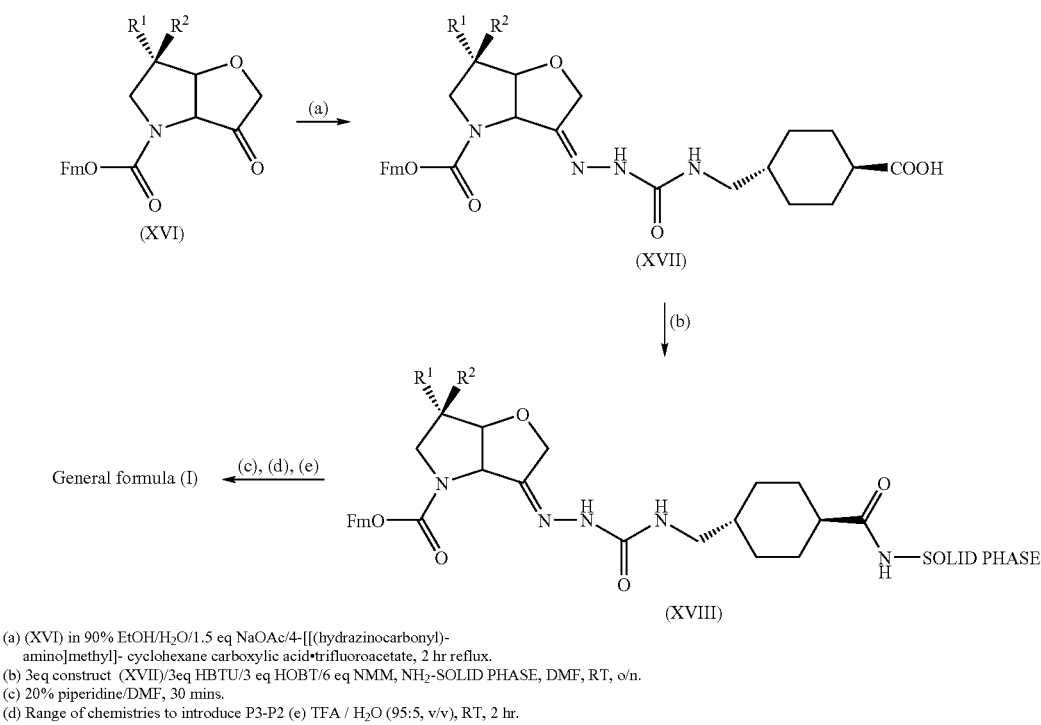

(a) (XVI) in 90% EtOH/H₂O/1.5 eq NaOAc/4-[[(hydrazinocarbonyl)-amino]methyl]- cyclohexane carboxylic acid•trifluoroacetate, 2 hr reflux.
(b) 3eq construct (XVII)/3eq HBTU/3 eq HOBT/6 eq NMM, NH₂-SOLID PHASE, DMF, RT, o/n.
(c) 20% piperidine/DMF, 30 mins.
(d) Range of chemistries to introduce P3-P2 (e) TFA / H₂O (95:5, v/v), RT, 2 hr.

In an alternative preferred embodiment of the invention, compounds of formula (I) may be prepared using conventional solid phase chemistry, for example, as described in Quibell M, et al Bioorg. Med. Chem, 12, 5689-5710, 2004, see in particular, Scheme 3 and Section 3.2, and references cited therein; and Bioorg. Med. Chem, 13, 609-625, 2005, see Scheme 5 and Section 2.2, and references cited therein). The solid phase strategy is attractive in being able to generate many thousands of analogues, typically on a 5-100 mg scale, through established parallel synthesis methodologies (e.g. see (a) Bastos, M.; Maeji, N. J.; Abeles, R. H. Proc. Natl. Acad. Sci. USA, 92, 6738-6742, 1995).

Construct (XVII) is prepared through reaction of the linker molecule and the tetrahydrofuro[3,2-b]pyrrol-3-one II ($R^5$=Fmoc) by refluxing in aqueous ethanol/sodium acetate. Standard solid phase techniques (e.g. see Atherton, E. and Sheppard, R. C., 1989) are used to anchor the construct to an amino-functionalised solid phase through the free carboxylic acid functionality of (XVII), providing the loaded construct (XVIII). Loaded construct (XVIII) be reacted with a wide range of carboxylic acids available commercially or in the literature, to introduce the left-hand portion 'P3-P2'.

The present invention is further described by way of example.

EXAMPLES

General Procedures

Solvents were purchased from ROMIL Ltd, U.K. at SpS or Hi-Dry grade unless otherwise stated. $^1$H NMR and $^{13}$C NMR were obtained on a Bruker DPX400 (400 MHz $^1$H frequency and 100 MHz $^{13}$C frequency; QXI probe) or Bruker Avance 500 MHz (TXI probe with ATM) in the solvents indicated. Chemical shifts are expressed in parts per million (δ) and are referenced to residual signals of the solvent. Coupling constants (J) are expressed in Hz. All analytical HPLC were obtained on Phenomenex Jupiter $C_4$, 5μ, 300 Å, 250×4.6 mm, using mixtures of solvent A (0.1% aq trifluoroacetic acid (TFA)) and solvent B (90% acetonitrile/10% solvent A) on automated Agilent systems with 215 and/or 254 nm UV detection. Unless otherwise stated a gradient of 10 to 90% B in A over 25 min at 1.5 mL/min was performed for full analytical HPLC. HPLC-MS analysis was performed on an Agilent 1100 series LC/MSD, using automated Agilent HPLC systems, with a gradient of 10 to 90% B in A over 10 min on Phenomenex Luna $C_8$, 5μ, 300 Å, 50×2.0 mm at 0.6 mL/min. Semi-preparative HPLC purification was performed on Phenomenex Jupiter $C_4$, 5μ, 300 Å, 250×10 mm, using a gradient of 10 to 90% B in A over 25 min at 4 mL/min on automated Agilent systems with 215 and/or 254 nm UV detection. Flash column purification was performed on silica gel 60 (Merck 9385) or using isolute SPE flash silica columns (Biotage, Hengoed, UK).

Preparation of Benzyl (S)-2-((S)-2,5-dihydrofuran-2-yl)-2-hydroxyethyl Carbamate (17)

(i) Preparation of (3R,3aS,6R,6aS)-Hexahydrofuro[3,2-b]furan-3,6-diyl bis(4-methylbenzenesulfonate) (39)

Isomannide (40) (50 g, 342.5 mmol) and p-toluenesulphonyl chloride (143.6 g, 753.2 mmol) were dissolved in a mixture of carbon tetrachloride (300 mL), dichloromethane (30 mL) and water (250 mL). The flask was cooled to 0° C. and a solution of potassium hydroxide (42.0 g, 750.0 mmol) in water (42 mL) added dropwise over 2 hours with stirring under argon. The resulting biphasic mixture was stirred vigorously at 0° C. for 24 hours. The resulting off-white precipitate, comprising a mixture of mono- and bistosylates (approximately 1:1), was collected by filtration in vacuo. The filter cake was washed with water then triturated with methanol (500 mL). The solid was isolated by filtration in vacuo to obtain ditosylate (39) as an off-white powder (75 g, 48%). $[\alpha]_D^{18}$ +96.7° (c=10.5, CHCl$_3$).

(ii) Preparation of (3R,3aS,6S,6aS)-6-Bromohexahydrofuro[3,2-b]furan-3-yl 4-methylbenzenesulfonate (46)

A stirred mixture of ditosylate (39) (16.9 g, 37.22 mmol) and lithium bromide (4.85 g, 55.84 mmol) in N,N-dimethylformamide (100 mL) was heated at 100° C. for 27 hours. The mixture was allowed to cool then water (150 mL) added before extracting with tert-butyl methyl ether (1×100 mL then 5×50 mL). The organic phase was dried (MgSO$_4$), filtered and reduced in vacuo to give a colourless oil which solidified on standing. Flash chromatography over silica, eluting with ethyl acetate:heptane mixtures 0:100 to 80:20 gave bromotosylate (46) as a white solid (2.86 g, 29%). TLC (R$_f$=0.45 diethyl ether heptane, 1:1), analytical HPLC: R$_t$=16.768 min; HPLC-MS: 363.1/365.0 [M+H]$^+$, 380.1/382.1, 749.0/751.0 [2M+Na]$^+$; $[\alpha]_D^{18}$ +64.7° (c=8.5, CHCl$_3$); δ$_H$ (500 MHz, CDCl$_3$) 2.45 (3H, s, CH$_3$), 3.74 (1H, dd, 7.05 Hz, CH$_2$), 3.95 (1H, dd, 6.47 Hz, CH$_2$), 4.14-4.22 (2H, m, CH$_2$), 4.29 (1H, d, J=3.03 Hz, CHBr), 4.68 (1H, d, J=4.03 Hz, CHCH), 4.76 (1H, t, J=4.48 Hz, CHOTs), 4.87 (1H, m, CHCH), 7.36 (2H, brd, J=7.97 Hz, aromatic CH$_3$CCH), 7.83 (2H, brd, J=8.33 Hz, aromatic OSO$_2$CCH). δ$_C$ (125 MHz, CDCl$_3$) 21.69 (CH$_3$), 50.06 (CHBr), 70.26 (CH$_2$CHOTs), 76.54 (CH$_2$CHBr), 78.27 (CHOTs), 80.17 and 88.80 (CHCHCHOTs), 127.98 and 129.94 (aromatic CH), 133.01 (CHOSO$_2$C quaternary), 145.28 (CH$_3$C quaternary).

(iii) Preparation of (3R,3aS,6R,6aR)-6-Hydroxyhexahydrofuro[3,2-b]furan-3-yl 4-methylbenzenesulfonate (50)

Isomannide (40) (10 g, 68.49 mmol) and p-toluenesulphonyl chloride (6.53 g, 34.25 mmol) were dissolved in a mixture of carbon tetrachloride (50 mL), dichloromethane (5 mL) and water (40 mL). The flask was cooled to 0° C. and a solution of potassium hydroxide (1.92 g, 34.25 mmol) in water (5 mL) added dropwise over 30 minutes with stirring. The resulting biphasic mixture was stirred at 0° C. for 7 hours. Then off-white precipitate was collected by filtration in vacuo then partitioned between dichloromethane (30 mL) and water (10 mL). The organic phase was washed with brine (2×10 mL) then dried (Na$_2$SO$_4$), filtered and reduced in vacuo to leave a colourless solid. Recrystallisation from carbon tetrachloride gave monotosylate (50) as colourless granules (3.92 g, 38%). TLC (R$_f$=0.11, EtOAc:heptane 1:1); analytical HPLC main peak, R$_t$=10.692 min; HPLC-MS 318.2, 323.1 [M+Na]$^+$, 623.2 [2M+Na]$^+$; $[\alpha]_D^{18}$ +72.2° (c=5.4, CHCl$_3$); δ$_H$ (500 MHz, CDCl$_3$) 2.44 (3H, s, CH$_3$), 3.54 (1H, dd, 7.23 Hz, OCH$_2$CHOH), 3.78 (1H, dd, 7.59 Hz, OCH$_2$CHOTs), 3.95 (1H, dd, 6.45 Hz, OCH$_2$CHOH), 4.01 (1H, dd, J=9.33 and 6.64 Hz, OCH$_2$CHOTs), 4.26 (1H, m, CHOH), 4.42 and 4.48 (each 1H, brt, J=5.03 and 5.00 Hz respectively, CHCHCHOH and CHCHCHOTs), 4.90 (1H, dd, 6.84 Hz, CHOTs), 7.37 (2H, d, J=8.13 Hz, aromatic CH$_3$CCH), 7.82 (2H, d, J=8.20 Hz, aromatic OSO$_2$CCH); δ$_C$ (125 MHz, CDCl$_3$) 21.69 (CH$_3$), 70.03 (CH$_2$CHOTs), 72.29 (CHOTs), 74.02 (CH$_2$CHOH), 80.00 (CH$_2$CHOH), 81.36 (CHCHOTs), 81.76 (CHCHOH), 128.00 and 129.89 (aromatic CH), 133.04 (CHOSO$_2$C quaternary), 145.26 (CH$_3$C quaternary).

(iv) Alternative preparation of (3R,3aS,6R,6aR)-6-Hydroxyhexahydrofuro[3,2-b]furan-3-yl 4-methylbenzenesulfonate (50)

A solution of p-toluenesulfonyl chloride (24.8 g, 130 mmol) in pyridine (150 mL) was added to a stirred solution of isomannide (40) (19.0 g, 130 mmol) in pyridine (150 mL) over 1 hour at 0° C. then stirred at ambient temperature for 1 hour. The mixture was poured onto iced-water (1 L) then extracted with dichloromethane (3×300 mL). The organic phase washed with brine (300 mL), dried (MgSO$_4$), filtered and reduced in vacuo to leave a residue. Flash chromatography over silica, eluting with ethyl acetate:heptane mixtures 0:100 to 50:50 gave monotosylate (50) (23.4 g, 60%) as a white solid.

(v) Alternative Preparation of (3R,3aS,6S,6aS)-6-Bromohexahydrofuro[3,2-b]furan-3-yl 4-methylbenzenesulfonate (46)

A solution of carbon tetrabromide (18.12 g, 54.63 mmol) in pyridine (100 mL) was added to a solution of monotosylate

(50) (14.9 g, 49.66 mmol) and triphenylphosphine (26.1 g, 99.32 mmol) in pyridine (150 mL) over 30 minutes, then the mixture heated at 65° C. for 1.5 hours under an atmosphere of argon. Water (200 mL) was added then the aqueous phase extracted with dichloromethane (5×100 mL). The organic phase was washed with brine (50 mL), then dried (MgSO$_4$), filtered and reduced in vacuo to leave a residue which was azeotroped with toluene (5×50 mL). Flash chromatography over silica, eluting with diethyl ether:heptane mixtures 0:100 to 100:0 gave bromotosylate (46) (7.70 g, 43%) as a white solid. $[\Box]_D^{17}$+68.6° (c=0.51, CHCl$_3$).

(vi) Preparation of (R)-1-((S)-2,5-Dihydrofuran-2-yl)-2-hydroxyethyl 4-methyl Benzenesulfonate (13)

A solution of ammonium chloride (100 mg, 1.87 mmol) in water (1.25 mL) then zinc dust (100 mg, 1.54 mmol) were added to a solution of bromotosylate (46) (0.5 g, 1.38 mmol) in tetrahydrofuran (5 mL) and propan-2-ol (2.5 mL) under argon. The mixture was stirred for 16 hours before filtering the suspension through celite in vacuo. The filter cake was washed with diethyl ether (20 mL). Hydrochloric acid (1M, 20 mL) was added to the filtrate then the organic phase separated. The aqueous layer was extracted with diethyl ether (20 mL) then the combined organic phase was washed with brine (20 mL), then dried (MgSO$_4$), filtered and reduced in vacuo to leave a residue. Flash chromatography over silica, eluting with ethyl acetate:heptane mixtures 20:80 to 50:50 gave alcohol (13) (292 mg, 75%) as a white solid. $[\Box]_D^{15}$−64.8° (c=9.8, CHCl$_3$).

(vii) Preparation of Benzyl (S)-2-((S)-2,5-dihydrofuran-2-yl)-2-hydroxyethylcarbamate (17); Zinc and 'One-Pot' Procedure A solution of ammonium chloride (560 mg, 10.5 mmol) in water (7 mL) was added to a solution of bromotosylate (46) (2.86 g, 7.88 mmol) in propan-2-ol (14 mL) under argon. Zinc dust (560 mg, 8.67 mmol) was then added in portions over 4 minutes then the suspension stirred for 16 hours before filtering through celite in vacuo. The filter cake was washed with diethyl ether (60 mL). Hydrochloric acid (1M, 60 mL) was added to the filtrate then the organic phase separated. The aqueous layer was extracted with diethyl ether (60 mL) then the combined organic phase was washed with brine (60 mL), then dried (MgSO$_4$), filtered and reduced in vacuo. The residue was dissolved in ammonium hydroxide (18 mL) and a solution of ammonia in propan-2-ol (12 mL, 2.0M, 24 mmol) then divided into three equal portions and heated in sealed tubes at 75° C. for 16 hours. The mixtures were combined using methanol then the solvents were removed in vacuo. The residue was azeotroped with diethyl ether (3×10 mL) to obtain (S)-2-amino-1-((S)-2,5-dihydrofuran-2-yl)ethanol which was used without further purification.

A solution of sodium carbonate (1.75 g, 16.6 mmol) in water (16 mL) was added whilst stirring to a solution of (S)-2-amino-1-((S)-2,5-dihydrofuran-2-yl)ethanol (assumed to be 7.88 mmol) in 1,4-dioxane (20 mL). The mixture was cooled to 0° C. then benzylchloroformate (1.69 mL, 11.82 mmol) was added dropwise over 10 minutes. The mixture was stirred at 0° C. for 85 minutes, then dichloromethane (75 mL) and water (100 mL) added. The organic phase was separated and the aqueous extracted with dichloromethane (2×50 mL). The organic layer was washed with brine (50 mL), then dried (Na$_2$SO$_4$), filtered and reduced in vacuo to leave a residue (3.1 g). Flash chromatography over silica, eluting with ethyl acetate:heptane mixtures 20:80 to 70:30 gave alcohol (17) (1.10 g, 53%). $[\Box]_D^{18}$−83.1° (c=9.9, CHCl$_3$).

Preparation of Benzyl (R)-2-((S)-2,5-dihydrofuran-2-yl)-2-hydroxyethyl Carbamate (18)

(i) Preparation of (3R,3aS,6S,6 as)-Hexahydrofuro[3,2-b]furan-3,6-diyl bis(4-methylbenzenesulfonate) (42)

A stirred solution of p-toluenesulfonyl chloride (57.4 g, 301 mmol) and isosorbide (43) (20 g, 137 mmol) in pyridine (315 mL) was heated at 95° C. for 4.5 hours under an atmosphere of argon then stood at ambient temperature for 16 hours before being poured onto iced-water (1 L). The aqueous was extracted with dichloromethane (2×500 mL), then the combined organic layers were washed with water (2×500 mL), then dried (Na$_2$SO$_4$), filtered then reduced in vacuo to leave a viscous oil (65.22 g). The oil was crystallized from hot methanol (350 mL). The white solid was collected by filtration in vacuo, then washed with methanol (100 mL) and dried in vacuo to obtain ditosylate (42) as a white solid (45.87 g, 74%). TLC (R$_f$=0.30, EtOAc:heptane 2:3), analytical HPLC single main peak, R$_t$=20.219 min., HPLC-MS 455.1 [M+H]$^+$, 931.2 [2M+Na]$^+$, $[\Box]_D^{20}$+57.2° (c=10.2, CHCl$_3$); $\delta_H$ (500 MHz, CDCl$_3$) 2.44 (6H, s, CH$_3$), 3.68 (1H, dd, 6.46 Hz, CH$_2$), 3.82-3.87 (2H, m, CH$_2$), 3.94 (1H, d, J=11.28 Hz, CH$_2$), 4.46 (1H, d, J=4.44 Hz, CHCHOTs), 4.58 (1H, t, J=4.74 Hz, CHCHOTs), 4.82-4.86 (2H, m, CHOTs), 7.32-7.36 (4H, m, aromatic CH$_3$CCH), 7.74-7.80 (4H, m, aromatic OSO$_2$CCH).

(ii) Alternative Preparation of (3R,3aS,6S,6aS)-Hexahydrofuro[3,2-b]furan-3,6-diyl bis(4-methyl-benzenesulfonate) (42)

Triethylamine (123.2 mL, 876 mmol) was added dropwise to a stirred solution of p-toluenesulfonyl chloride (156.6 g, 822 mmol) and isosorbide (43) (40 g, 274 mmol) in dichloromethane (600 mL) over 15 minutes. The mixture was stirred at 25° C. for 16 hours then at 50° C. for 4 hours before diluting with dichloromethane (1 L). The organic layer was washed with water (2×1 L), then dried (Na$_2$SO$_4$), filtered then reduced in vacuo to leave a viscous oil. The oil was crystallized from hot methanol (600 mL) to obtain ditosylate (42) as a white solid (120.1 g, 97%). $[\Box]_D^{15}$+56.3° (c=11.2, CHCl$_3$).

(iii) Preparation of (3S,3aS,6S,6aS)-6-Bromo-hexahydrofuro[3,2-b]furan-3-yl 4-methylbenzenesulfonate (47)

Lithium bromide (9.6 g, 110.1 mmol) was added to a stirred solution of ditosylate (42) (20.0 g, 44.05 mmol) in dimethylformamide (100 mL) under an atmosphere of argon. The mixture was heated at 110° C. for 5 hours then stood at ambient temperature for 3 days, then heated at 90° C. for 3.5 hours. The mixture was diluted with water (250 mL) extracted with tert-butyl methyl ether (4×125 mL) then the organic phase washed with water (3×125 mL), brine (125 mL), dried (MgSO$_4$), filtered and reduced in vacuo to leave a brown oil (16.8 g). Flash chromatography over silica, eluting with ethyl acetate:heptane mixtures 0:100 to 30:70 gave bromotosylate (47) (11.88 g, 74%) as a pale yellow solid. TLC (R$_f$=0.20, EtOAc:heptane 1:3); analytical HPLC main peak, R$_t$=18.050 min; HPLC-MS 381.0/383.0 [M+H$_2$O+H]$^+$, 385.0/387.0 [M+Na]$^+$; $[\Box]_D^{18}$+51.0° (c=5.0, CHCl$_3$); $\delta_H$ (500 MHz, CDCl$_3$) 2.45 (3H, s, CH$_3$), 3.84 (1H, dd, 3.51 Hz, CH$_2$), 4.05-4.15 (3H, m, CH$_2$), 4.28 (1H, d, J=3.40 Hz, CHBr), 4.78 (1H, d, J=3.37 Hz, CHCH), 4.84 (1H, d, J=3.42 Hz, CHOTs), 4.90 (1H, d, J=3.37 Hz, CHCH), 7.36 (2H, brd, J=7.98 Hz, aromatic CH$_3$CCH), 7.79 (2H, brd, J=8.32 Hz, aromatic OSO$_2$CCH).

(iv) Alternative Preparation of (3S,3aS,6S,6aS)-6-Bromohexahydrofuro[3,2-b]furan-3-yl 4-methylbenzenesulfonate (47)

Lithium bromide (19.2 g, 220.2 mmol) was added to a stirred solution of ditosylate (42) (40.0 g, 88.1 mmol) in dimethyl sulfoxide (200 mL) under an atmosphere of argon. The mixture was heated at 110° C. for 8 hours then at 120° C. for 1.75 hours. The mixture was diluted with water (500 mL) then extracted with tert-butyl methyl ether (4×250 mL). The organic phase was washed with water (3×250 mL) then brine (250 mL), dried (MgSO$_4$), filtered and reduced in vacuo to leave an orange solid. Recrystallisation from methanol (100 mL) gave bromotosylate (47) (17.47 g, 55%) as a pale yellow solid. $[□]_D^{15}$ +49.5° (c=11.7, CHCl$_3$).

(v) Preparation of (S)-1-((S)-2,5-Dihydrofuran-2-yl)-2-hydroxyethyl 4-methyl Benzenesulfonate (14)

Ammonium chloride (20 mg, 0.37 mmol) then zinc dust (20 mg, 0.31 mmol) were added to a solution of bromotosylate (47) (100 mg, 0.28 mmol) in ethanol (1.5 mL) under argon. The mixture was stirred for 16 hours before filtering the suspension through celite in vacuo. The filter cake was washed with ethanol (20 mL) then the filtrate reduced in vacuo to leave a residue (111 mg). Flash chromatography over silica, eluting with ethyl acetate heptane mixtures 20:80 to 40:60 gave alcohol (14) (53 mg, 68%) as a white solid. TLC (R$_f$=0.15, EtOAc:heptane 1:2); analytical HPLC main peak, R$_t$=12.543 min; HPLC-MS 285.1 [M+H]$^+$, 302.1, 591.2 [2M+Na]$^+$; $[□]_D^{15}$ −86.8° (c=5.3, CHCl$_3$); δ$_H$ (500 MHz, CDCl$_3$) 2.12 (1H, brs, OH), 2.44 (3H, s, aryl-CH$_3$), 3.77 (2H, d, J=4.85 Hz, CH$_2$OH), 4.54-4.58 (3H, m, CH$_2$OCH), 4.94-4.98 (1H, m, CHOTs), 5.64-5.67 and 5.97-6.00 (2H total, m, CH$_2$CH=CH), 7.33 (2H, brd, J=8.23 Hz, aromatic CH$_3$CCH), 7.79 (2H, brd, J=8.31 Hz, aromatic OSO$_2$CCH); δ$_C$ (125 MHz, CDCl$_3$) 21.660 (CH$_3$), 62.303 (CH$_2$OH), 75.940 (OCH$_2$CH=CH), 82.720 and 85.221 (OCHCHOTs), 124.792, 127.977, 129.479 and 129.749 (OCH$_2$CH=CH and aromatic CH), 133.496 (CHOSO$_2$C quaternary), 144.973 (CH$_3$C quaternary).

(vi) Alternative Preparation of (S)-1-((S)-2,5-Dihydrofuran-2-yl)-2-hydroxyethyl 4-methyl Benzenesulfonate (14)

A solution of ammonium chloride (200 mg, 3.7 mmol) in water (2.5 mL) then zinc dust (200 mg, 3.1 mmol) were added to a solution of bromotosylate (47) (1 g, 2.75 mmol) in tetrahydrofuran (10 mL) and propan-2-ol (5 mL) under argon. The mixture was stirred for 16 hours before filtering the suspension through celite in vacuo. The filter cake was washed with diethyl ether (20 mL). Hydrochloric acid (1M, 20 mL) was added to the filtrate then the organic phase separated. The aqueous layer was extracted with diethyl ether (20 mL) then the combined organic phase was washed with brine (20 mL), then dried (MgSO$_4$), filtered and reduced in vacuo to leave a residue (1.06 g). Flash chromatography over silica, eluting with ethyl acetate:heptane mixtures 20:80 to 50:50 gave alcohol (14) (528 mg, 68%) as a white solid. $[□]_D^{16}$ −82.7° (c=11.3, CHCl$_3$).

(vii) Preparation of Benzyl (R)-2-((S)-2,5-dihydrofuran-2-yl)-2-hydroxyethylcarbamate (18). Zinc and 'One-Pot' Procedure A solution of ammonium chloride (600 mg, 11.2 mmol) in water (7.5 mL) was added to a solution of bromotosylate (47) (3.0 g, 8.26 mmol) in propan-2-ol (15 mL) under argon. Zinc dust (600 mg, 9.2 mmol) was then added in portions over 4 minutes and the mixture was stirred for 16 hours before filtering the suspension through celite in vacuo. The filter cake was washed with diethyl ether (60 mL). Hydrochloric acid (1M, 60 mL) was added to the filtrate then the organic phase separated. The aqueous layer was extracted with diethyl ether (60 mL) then the combined organic phase was washed with brine (60 mL), then dried (MgSO$_4$), filtered and reduced in vacuo. The residue was dissolved in ammonium hydroxide (18 mL) and a solution of ammonia in propan-2-ol (12 mL, 2.0M, 24 mmol), then divided into two equal portions and heated in sealed tubes at 75° C. for 16 hours. The mixtures were combined using methanol then the solvents were removed in vacuo. The residue was azeotroped with diethyl ether (3×10 mL) to obtain (R)-2-amino-1-((S)-2,5-dihydrofuran-2-yl)ethanol which was used without further purification.

A solution of sodium carbonate (1.84 g, 17.4 mmol) in water (16 mL) was added whilst stirring to a suspension of (R)-2-amino-1-((S)-2,5-dihydrofuran-2-yl)ethanol (assumed to be 8.26 mmol) in 1,4-dioxane (20 mL). The mixture was cooled to 0° C. then benzylchloroformate (1.77 mL, 12.4 mmol) was added dropwise over 5 minutes. The mixture was stirred at 0° C. for 55 minutes then dichloromethane (75 mL) and water (100 mL) added. The organic phase was separated and the aqueous extracted with dichloromethane (2×50 mL). The organic phase was washed with brine (50 mL), then dried (Na$_2$SO$_4$), filtered and reduced in vacuo to leave a residue (3.7 g). Flash chromatography over silica, eluting with ethyl acetate:heptane mixtures 20:80 to 70:30 gave alcohol (18) (1.26 g, 58%). $[□]_D^{16}$ −62.0° (c=5.0, CHCl$_3$).

Preparation of (S)-2-(Benzyloxycarbonylamino)-1-((S)-2,5-dihydrofuran-2-yl)ethyl 4-methylbenzenesulfonate (32)

A solution of p-toluenesulfonyl chloride (252 mg, 1.32 mmol) in pyridine (7.0 mL), alcohol (17) (290 mg, 1.10 mmol) was stirred at 24° C. for 2 days then diluted with water (15 mL). The product was extracted into tert-butyl methyl ether (3×20 mL) then dried (MgSO$_4$), filtered and reduced in vacuo. Flash chromatography over silica, eluting with ethyl acetate:heptane mixtures 7:93 to 20:80 gave tosylate (32) (282 mg, 61%) as a colourless oil. TLC (R$_f$=0.35, EtOAc:heptane 1:1), analytical HPLC single main peak, R$_t$=19.02 min., HPLC-MS 418.2 [M+H]$^+$, 857.3 [2M+Na]$^+$; $[□]_D^{11}$ −86.1° (c=1.103, CHCl$_3$; δ$_H$ (500 MHz, CDCl$_3$) 2.37 (3H, s, aryl-CH$_3$), 3.29-3.37 and 3.50-3.56 (2H total, m, CH$_2$NH), 4.53-4.56 (2H total, m, OCH$_2$CH=CH), 4.62-4.66 (1H, m, OCHCH=CH), 4.85-4.90 (1H, m, CHOTs), 5.02-5.08 (2H, m, OCH$_2$Ph), 5.02 (1H, brs, NH), 5.65-5.70 and 5.94-5.98 (2H total, m, CH$_2$CH=CH), 7.27 (2H, d, J=8.12 Hz, aromatic CH$_3$CCH), 7.29-7.37 (5H, m, phenyl CH), 7.76 (2H, d, J=8.23 Hz, aromatic OSO$_2$CCH); δ$_C$ (125 MHz, CDCl$_3$) 21.609 (aryl-CH$_3$), 41.749 (CH$_2$NHCbz), 66.833 (CH$_2$Ph), 75.939 (OCH$_2$CH=CH), 81.235 (CHOTs), 85.203 (OCHCH=CH), 124.702, 127.887, 128.026, 128.128, 128.504, 129.687 and 129.757 (OCH$_2$CH=CH and aromatic CH), 133.591 (CHOSO$_2$C quaternary), 136.368 (Cbz quaternary), 144.906 (CH$_3$C quaternary), 156.271 (Cbz C=O).

Alternative Preparation of (S)-2-(Benzyloxycarbonylamino)-1-((S)-2,5-dihydro furan-2-yl)ethyl 4-methylbenzenesulfonate (32)

A solution of p-toluenesulfonyl chloride (760 mg, 3.99 mmol) in pyridine (10.0 mL), alcohol (17) (600 mg, 2.28 mmol) was stirred at 40° C. for a total of 6 hours and stood at 24° C. for 16 hours then diluted with water (20 mL). The product was extracted into tert-butyl methyl ether (2×50 mL) then dried (MgSO$_4$), filtered and reduced in vacuo. Flash chromatography over silica, eluting with ethyl acetate:heptane mixtures 10:90 to 30:70 gave tosylate (32) (789 mg, 83%) as a white solid.

Preparation of (R)-2-(Benzyloxycarbonylamino)-1-((S)-2,5-dihydrofuran-2-yl) ethyl 4-methyl Benzenesulfonate (32b)

A solution of p-toluenesulfonyl chloride (368 mg, 2.03 mmol) in pyridine (1.5 mL) was added to alcohol (18) (333 mg, 1.27 mmol). The mixture was stirred at 14° C. for 16 hours and at 24° C. for 3.5 hours then diluted with tert-butyl methyl ether (35 mL). The organic layer was washed with water (15 mL), brine (15 mL), then dried (MgSO$_4$), filtered and reduced in vacuo to leave a pale yellow oil (0.712 g). Flash chromatography over silica, eluting with ethyl acetate:heptane mixtures 15:85 to 30:70 gave tosylate (32b) (429 mg, 81%) as a white solid. TLC (R$_f$=0.75, EtOAc:heptane 3:1), analytical HPLC single main peak, R$_t$=18.93 min., HPLC-MS 374.2, 418.2 [M+H]$^+$, 857.3 [2M+Na]$^+$; [□]$_D^{18.5}$–30.2° (c=1.326, CHCl$_3$); δ$_H$ (500 MHz, CDCl$_3$) 2.39 (3H, s, aryl-CH$_3$), 3.29-3.37 and 3.53-3.62 (2H total, m, CH$_2$NH), 4.44-4.50 and 4.52-4.57 (2H total, m, OCH$_2$CH=CH), 4.59-4.65 (1H, m, OCHCH=CH), 4.87-4.92 (1H, m, CHOTs), 5.05 (2H, m, OCH$_2$Ph), 5.03 (1H, brs, NH), 5.69-5.73 and 5.94-5.98 (2H total, m, CH$_2$CH=CH), 7.28 (2H, d, J=8.10 Hz, aromatic CH$_3$CCH), 7.29-7.37 (5H, phenyl CH), 7.77 (2H, d, J=8.10 Hz, aromatic OSO$_2$CCH); δ$_C$ (125 MHz, CDCl$_3$) 21.627 (aryl-CH$_3$), 41.119 (CH$_2$NHCbz), 66.856 (CH$_2$Ph), 75.987 (OCH$_2$CH=CH), 82.352 (CHOTs), 85.622 (OCHCH=CH), 124.792, 127.825, 128.027, 128.126, 128.504, 129.357 and 129.537 (OCH$_2$CH=CH and aromatic CH), 133.674 (CHOSO$_2$C quaternary), 136.348 (Cbz quaternary), 144.941 (CH$_3$C quaternary), 156.273 (Cbz C=O).

Epoxidation Studies with (R)-2-(Benzyloxycarbonylamino)-1-((S)-2,5-dihydro furan-2-yl)ethyl 4-methylbenzenesulfonate (32b)

(a) 3-Chloroperbenzoic acid (97 mg, ≦77%, 0.43 mmol) was added to a stirred solution of alkene (32b) (36 mg, 0.086 mmol) in dichloromethane (1.5 mL). The mixture was stirred for 20 hours at ambient temperature then 3-chloroperbenzoic acid (97 mg, ≦77%, 0.43 mmol) was added and stirring continued for 1 day at 24° C. then diluted with dichloromethane (15 mL). The organic phase was washed with aqueous sodium hydroxide solution (5%, 10 mL), water (10 mL), then dried (Na$_2$SO$_4$), filtered and reduced in vacuo to leave a residue (0.038 mg). Flash chromatography over silica, eluting with ethyl acetate:heptane mixtures 10:90 to 50:50 gave (in order of elution) anti-(33b) (16 mg, 43%) as a colourless viscous oil and syn-epoxide (9 mg, 24%) as a white solid. Data for anti-(33b); TLC (R$_f$=0.50, EtOAc:heptane 1:1), analytical HPLC single main peak, R$_t$=17.999 min., HPLC-MS 434.1 [M+H]$^+$, 456.1 [M+Na]$^+$, 889.2 [2M+Na]$^+$; [□]$_D^{17}$+ 25.6° (c=2.54, CHCl$_3$); δ$_H$ (500 MHz, CDCl$_3$) 2.41 (3H, s, aryl-CH$_3$), 3.31-3.38 and 3.60-3.66 (2H total, m, CH$_2$NH), 3.67 (1H, d, J=10.46 Hz, OCH$_2$CH), 3.75 and 3.81 (each 1H, d, 2.75 Hz respectively, OCH$_2$CHCH), 3.94 (1H, d, J=10.57 Hz, OCH$_2$CH), 4.07 (1H, d, J=6.90 Hz, OCHCHOTs), 4.60-4.64 (1H, m, CHOTs), 4.97-5.01 (1H brt, NH), 5.08 (2H, brs, CH$_2$Ph), 7.29-7.37 (7H, aromatic CH$_3$CCH and phenyl CH), 7.78 (2H, d, J=8.18 Hz, aromatic OSO$_2$CCH); δ$_C$ (125 MHz, CDCl$_3$) 21.665 (aryl-CH$_3$), 42.054 (CH$_2$NHCbz), 56.175 and 57.048 (OCH$_2$CHCH), 67.031 (CH$_2$Ph), 67.672 (OCH$_2$CH), 76.732 (OCHCHOTs), 79.388 (CHOTs), 127.776, 128.108, 128.222, 128.544 and 130.043 (aromatic CH), 133.249 (CHOSO$_2$C quaternary), 136.192 (Cbz quaternary), 145.487 (CH$_3$C quaternary), 156.224 (Cbz C=O). Data for syn-epoxide; TLC (R$_f$=0.42, EtOAc:heptane 1:1), analytical HPLC single main peak, R$_t$=18.009 min., HPLC-MS 434.1 [M+H]$^+$, 889.2 [2M+Na]$^+$; δ$_H$ (500 MHz, CDCl$_3$) 2.40 (3H, s, aryl-CH$_3$), 3.40-3.47 and 3.58-3.63 (2H total, m, CH$_2$NH), 3.62 and 3.72 (each 1H, d and dd respectively, 3.01, 0.60 Hz respectively, OCH$_2$CHCH), 3.67 (1H, d, J=10.68 Hz, OCH$_2$CH), 3.92 (1H, d, J=7.07 Hz, OCHCHOTs), 3.97 (1H, d, J=10.67 Hz, OCH$_2$CH), 4.65-4.70 (1H, m, CHOTs), 5.00-5.04 (1H brt, NH), 5.05 (2H, brs, CH$_2$Ph), 7.29-7.37 (7H, aromatic CH$_3$CCH and phenyl CH), 7.83 (2H, d, J=8.11 Hz, aromatic OSO$_2$CCH); δ$_C$ (125 MHz, CDCl$_3$) 21.664 (aryl-CH$_3$), 41.958 (CH$_2$NHCbz), 55.948 and 56.425 (OCH$_2$CHCH), 66.823 (CH$_2$Ph), 68.008 (OCH$_2$CH), 76.498 (OCHCHOTs), 78.395 (CHOTs), 127.986, 128.072, 128.110, 128.493 and 129.928 (aromatic CH), 133.189 (CHOSO$_2$C quaternary), 136.383 (Cbz quaternary), 145.177 (CH$_3$C quaternary), 156.202 (Cbz C=O).

(b) To a solution of alkene (32b) (262 mg, 0.63 mmol) in acetonitrile (4 mL) and aqueous Na$_2$.EDTA (4 mL, 0.4 mmol solution) at 0° C. was added 1,1,1-trifluoroacetone (0.67 mL, 7.54 mmol) via a pre-cooled syringe. To this solution was added in portions a mixture of sodium bicarbonate (0.44 g, 5.28 mmol) and OXONE® (1.20 g, 1.95 mmol) over a period of 55 minutes. The mixture was stirred for 2.5 hours then diluted with water (25 mL) and the product extracted into dichloromethane (2×25 mL). The combined organic layers were washed with brine (12.5 mL) then dried (Na$_2$SO$_4$), filtered and reduced in vacuo to leave a residue (310 mg). Flash chromatography over silica, eluting with ethyl acetate:heptane mixtures 15:85 to 50:50 gave anti-(33b) as a viscous white oil (216 mg, 79%).

Epoxidation of (S)-2-(Benzyloxycarbonylamino)-1-((S)-2,5-dihydro furan-2-yl)ethyl 4-methylbenzenesulfonate (32)

(a) To a solution of alkene (32) (765 mg, 1.83 mmol) in acetonitrile (10 mL) and aqueous Na$_2$.EDTA (10 mL, 0.4 mmol solution) at 0° C. was added 1,1,1-trifluoroacetone (1.98 mL, 22.0 mmol). To this solution was added in portions a mixture of sodium bicarbonate (1.29 g, 15.4 mmol) and OXONE® (3.49 g, 5.68 mmol) over a period of 1.5 hours. The mixture was stirred for 1.5 hours then diluted with water (30 mL) and the product extracted into dichloromethane (3×30 mL). The combined organic layers were washed with brine (50 mL) then dried (MgSO$_4$), filtered and reduced in vacuo. Flash chromatography over silica, eluting with ethyl acetate:heptane mixtures 10:90 to 30:70 gave (in order of elution) anti-(33) as a white solid (597 mg, 75%) and syn-epoxide (35 mg, 4%) as a white solid. Data for anti-(33); TLC (R$_f$=0.50, EtOAc:heptane 1:1), analytical HPLC single main peak, R$_t$=17.989 min., HPLC-MS 434.2 [M+H]$^+$, 889.3 [2M+Na]$^+$; [□]$_D^{11.5}$–49.08° (c=1.630, CHCl$_3$); δ$_H$ (500 MHz, CDCl$_3$) 2.38 (3H, s, aryl-CH$_3$), 3.30-3.37 and 3.44-3.50 (2H, m, CH$_2$NH), 3.73 and 2.74 (2H, each d, 2.73 Hz respectively, OCH$_2$CHCH), 3.81 (1H, d, J=10.08 Hz, OCH$_2$CH), 3.91 (1H, d, J=10.12 Hz, OCH$_2$CH), 4.13 (1H, d, J=2.04 Hz, OCHCHOTs), 4.83-4.86 (1H, m, CHOTs), 4.89-5.00 (1H brt, J=5.39 Hz, NH), 5.02-5.09 (2H, m, CH$_2$Ph), 7.28 (2H, d, J=8.10 Hz, aromatic CH$_3$CCH), 7.31-7.38 (5H, phenyl CH), 7.76 (2H, d, J=8.22 Hz, aromatic OSO$_2$CCH); δ$_C$ (125 MHz, CDCl$_3$) 21.636 (aryl-CH$_3$), 42.085 (CH$_2$NHCbz), 56.414 and 57.217 (OCH$_2$CHCH), 66.977 (CH$_2$Ph), 68.582 (OCH$_2$CH), 76.846 (OCHCHOTs), 79.979 (CHOTs), 127.668, 128.073, 128.241, 128.551 and 130.001 (aromatic CH), 133.489 (CHOSO$_2$C quaternary), 136.172 (Cbz quaternary), 145.322 (CH$_3$C quaternary), 156.247 (Cbz C=O). Data for syn-epoxide; TLC (R$_f$=0.45, EtOAc:heptane 1:1), analytical HPLC main peak, R$_t$=17.902 min., HPLC-MS 434.2 [M+H]$^+$, 889.3 [2M+Na]$^+$; [□]$_D$$^{12.5}$–38.4° (c=2.277, CHCl$_3$); δ$_H$ (500 MHz, CDCl$_3$) 2.39 (3H, s, aryl-CH$_3$), 3.49-3.58 and 3.58-3.66 (2H total, m, CH$_2$NH), 3.62 (1H, d, J=10.27 Hz OCH$_2$CH), 3.71 (1H, d, J=3.01 Hz, epoxide CH), 3.88 (1H, brd, J=10.62 Hz, OCH$_2$CH), 3.88 (1H, brs, epoxide CH), 3.97 (1H, d, J=6.11 Hz, OCHCHOTs), 4.69-4.74 (1H, m, CHOTs), 5.02-5.11 (3H, m, NH and CH$_2$Ph), 7.28-7.38 (7H, aromatic CH$_3$CCH and phenyl CH), 7.80 (2H, brd, J=8.22 Hz, aromatic OSO$_2$CCH); δ$_C$ (125 MHz, CDCl$_3$) 21.634 (aryl-CH$_3$), 41.450 (CH$_2$NHCbz), 55.391 and 55.741 (OCH$_2$CHCH), 66.828 (CH$_2$Ph), 67.724 (OCH$_2$CH), 76.526 (OCHCHOTs), 79.632 (CHOTs), 127.805, 128.958, 128.102, 128.117, 128.504, 128.550, 128.596, 129.742, 130.002 and 130.177 (aromatic CH), 133.093 (CHOSO$_2$C quaternary), 136.330 (Cbz quaternary), 144.990 (CH$_3$C quaternary), 156.344 (Cbz C=O).

Preparation of (3R,3aR,6R,6aS)-tert-Butyl 3-hydroxy-6-(tosyloxy)tetrahydro-2H-furo[3,2-b]pyrrole-4(5H)-carboxylate (35b)

Ethanol (1.5 mL) was added dropwise to a mixture of 10% palladium on charcoal (20 mg) and anti-(33b) (100 mg, 0.25 mmol) under an atmosphere of argon. The argon was replaced by hydrogen then the suspension was stirred for 4.5 hours before filtering the mixture through celite in vacuo. The filter cake was washed with ethanol (10 mL) then the solvents removed in vacuo from the filtrate. The residue was azeotroped with toluene (2×3 mL) to obtain (3R,3aR,6R,6aS)-3-hydroxyhexahydro-2H-furo[3,2-b]pyrrol-6-yl 4-methylbenzenesulfonate which was used without further purification.

A solution of sodium carbonate (56 mg, 0.275 mmol) in water (0.75 mL) was added whilst stirring to a solution of (3R,3aR,6R,6aS)-3-hydroxyhexahydro-2H-furo[3,2-b]pyrrol-6-yl 4-methylbenzenesulfonate in 1,4-dioxane (0.75 mL). A solution of di-tert-butyl dicarbonate (60 mg, 0.275 mmol) in 1,4-dioxane (0.5 mL) was added dropwise over 5 minutes then the mixture stirred for 1 hour before adding an additional aliquot of di-tert-butyl dicarbonate (40 mg, 0.184 mmol) in 1,4-dioxane (0.25 mL) dropwise over 1 minute. The mixture was stirred for 70 minutes then water (5 mL) was added and the product extracted into dichloromethane (3×5 mL). The organic layer was washed with brine (5 mL), then dried (Na$_2$SO$_4$), filtered and reduced in vacuo to leave a residue (132 mg). Flash chromatography over silica, eluting with ethyl acetate:heptane mixtures 15:85 to 45:55 gave bicyclic alcohol (35b) (58.9 mg, 60%) as a white solid. TLC (R$_f$=0.30, EtOAc:heptane 1:1), analytical HPLC single main peak, R$_t$=16.54 min., HPLC-MS 344.1 [M+2H–$^t$Bu]$^+$, 821.3 [2M+Na]$^+$; [□]$_D$$^{18.5}$–30.3° (c=6.10, CHCl$_3$); δ$_H$ (500 MHz, CDCl$_3$) mixture of rotamers major:minor 2:1; 1.44 (6H, brs, (CH$_3$)$_3$C, major), 1.46 (3H, brs, (CH$_3$)$_3$C, minor), 1.98 (0.33H, d, J=4.00 Hz, OH minor), 2.44 (3H, s, aryl-CH$_3$), 2.69 (0.66H, d, J=2.88 Hz, OH major), 3.08-3.15 (0.33H, m, BocNCH$_2$ minor), 3.26-3.32 (0.66H, m, BocNCH$_2$ major), 3.75-3.87 (2H, m, 1×OCH$_2$CHOH and 1×BocNCH$_2$), 3.94-4.02 (1H, m, OCH$_2$CHOH), 4.07 (1H, brs, BocNCH), 4.35 (0.33H, brs, OCH$_2$CHOH minor), 4.41 (0.66H, brs, OCH$_2$CHOH major), 4.52 (0.66H, t, J=4.75 Hz, TsOCHCH major), 4.65 (0.33H, t, J=3.95 Hz, TsOCHCH minor), 4.72-4.78 (1H, m, TsOCHCH), 7.34 (2H, brd, J=7.82 Hz, aromatic CH$_3$CCH), 7.82 (2H, brd, J=8.01 Hz, aromatic OSO$_2$CCH); δ$_C$ (125 MHz, CDCl$_3$) 21.681 (aryl-CH$_3$), 28.294/28.386 ((CH$_3$)$_3$C), 46.810/48.177 (BocNCH$_2$), 68.153/68.484 (BocNCH), 75.484/75.697 (OCH$_2$CHOH), 76.228/76.980 (OCH$_2$CHOH), 76.269/76.585 (TsOCHCH), 79.391/80.233 (TsOCHCH), 81.079/81.139 ((CH$_3$)$_3$C quaternary), 127.973, 129.911, 129.966 and 130.125 (aromatic CH), 133.144 (CHOSO$_2$C quaternary), 145.247 (CH$_3$C quaternary), 153.161/154.244 (Boc C=O).

Preparation (3R,3aR,6S,6aS)-tert-Butyl 3-hydroxy-6-(tosyloxy)tetrahydro-2H-furo[3,2-b]pyrrole-4(5H)-carboxylate (35)

Ethanol (20 mL) was added dropwise to a mixture of 10% palladium on charcoal (50 mg) and anti-(33) (578 mg, 1.33 mmol) under an atmosphere of argon. The argon was replaced by hydrogen then the suspension was stirred for 1.5 hours before filtering the mixture through celite in vacuo. The filter cake was washed with ethanol then the solvents removed in vacuo from the filtrate to obtain (3R,3aR,6S,6aS)-3-hydroxyhexahydro-2H-furo[3,2-b]pyrrol-6-yl 4-methylbenzenesulfonate which was used without further purification.

A solution of sodium carbonate (297 mg, 2.80 mmol) in water (10 mL) was added whilst stirring to a solution of (3R,3aR,6S,6aS-3-hydroxyhexahydro-2H-furo[3,2-b]pyrrol-6-yl 4-methylbenzenesulfonate in 1,4-dioxane (7 mL). A solution of di-tert-butyl dicarbonate (320 mg, 1.47 mmol) in 1,4-dioxane (3 mL) was added then the mixture stirred for 2 hours then stored at 4° C. for 16 hours then water (30 mL) was added and the product extracted into dichloromethane (3×30 mL). The organic layer was washed with brine (30 mL), then dried (MgSO$_4$), filtered and reduced in vacuo to leave a residue. Flash chromatography over silica, eluting with ethyl acetate:heptane mixtures 20:80 to 40:60 gave bicyclic alcohol (35) (292 mg, 55%) as a white solid. TLC (R$_f$=0.38, EtOAc:heptane 3:2), analytical HPLC single main peak, R$_t$=16.80 min., HPLC-MS 344.1 [M+2H–$^t$Bu]$^+$, 821.3 [2M+Na]$^+$; [□]$_D$$^{15}$–36.5° (c=3.42, CHCl$_3$); δ$_H$ (500 MHz, CDCl$_3$) mixture of rotamers major:minor 2:1; 1.43 (6H, brs, (CH$_3$)$_3$C, major), 1.47 (3H, brs, (CH$_3$)$_3$C, minor), 2.19 (0.33H, d, J=4.06 Hz, OH minor), 2.80 (0.66H, d, J=3.10 Hz, OH major), 2.45 (3H, s, aryl-CH$_3$), 3.27 (0.33H, dd, J=13.48 and 3.65 Hz, BocNCH$_2$ minor), 3.35 (0.66H, dd, 3.83 Hz, BocNCH$_2$ major), 3.72-3.82 (3H, m, 2×OCH$_2$CHOH and 1×BocNCH$_2$), 4.21-4.24 (1H, brs, BocNCH), 4.37 (0.33H, brs, OCH$_2$CHOH minor), 4.44 (0.66H, brs, OCH$_2$CHOH major), 4.46 (0.66H, brd, J=4.62 Hz, TsOCHCH major), 4.64 (0.33H, brd, J=4.18 Hz, TsOCHCH minor), 4.74 (0.33H, brd, J=3.09 Hz, TsOCH minor), 4.77 (0.66H, brd, J=3.43 Hz, TsOCH major), 7.35 (2H, brd, J=7.95 Hz, aromatic CH$_3$CCH), 7.78 (2H, brd, J=8.24 Hz, aromatic OSO$_2$CCH); δ$_C$ (125 MHz, CDCl$_3$) 21.679 (aryl-CH$_3$), 28.308/28.434 ((CH$_3$)$_3$C), 50.487/51.186 (BocNCH$_2$), 68.000/68.553 (BocNCH), 74.330/74.458 (OCH$_2$CHOH), 75.499/76.335 (OCH$_2$CHOH), 80.187/80.914 (TsOCHCH), 80.849 ((CH$_3$)$_3$C quaternary), 83.599/84.662 (TsOCHCH), 127.816, 127.852 and 130.125 (aromatic CH), 133.081/133.268

(CHOSO₂C quaternary), 145.371 (CH₃C quaternary), 153.259/154.119 (Boc C=O).

Preparation of (3R,3aR,6S,6aS)— tert-Butyl 3-hydroxy-6-(methylsulfonyloxy)tetrahydro-2H-furo[3,2-b]pyrrole-4(5H)-carboxylate (53)

(i) Preparation of (S)-2-(Benzyloxycarbonylamino)-1-((S)-2,5-dihydrofuran-2-yl)ethyl Methane Sulfonate (51)

Triethylamine (0.594 mL, 4.25 mmol) then methanesulfonyl chloride (0.309 mL, 3.99 mmol) were added to a stirred solution of (alcohol (17) (700 mg, 2.66 mmol) in dichloromethane (15 mL). The mixture was stirred for 2 hours then diluted with water (20 mL). The product was extracted into dichloromethane (2×25 mL) then dried (MgSO₄), filtered and reduced in vacuo. Flash chromatography over silica, eluting with ethyl acetate:heptane mixtures 10:90 to 40:60 gave mesylate (51) (584 mg, 64%) as a white solid. TLC (R_f=0.35, EtOAc:heptane 1:1), analytical HPLC single main peak, R_t=14.21 min., HPLC-MS 342.1 [M+H]⁺, 364.1 [M+Na]⁺, 705.2 [2M+Na]⁺; [□]_D$^{12.5}$−67.0° (c=1.034, CHCl₃); δ_H (500 MHz, CDCl₃) 3.02 (3H, s, OSO2CH₃), 3.48 (1H, dt, 6.40 Hz, CH₂NH), 3.62 (1H, dt, 6.24 Hz, CH₂NH), 4.61-4.71 (3H, m, OCH₂CH=CH and OCHCH=CH), 4.93-4.97 (1H, m, CHOMs), 5.10 (2H, brs, OCH₂Ph), 5.26 (1H, brs, NH), 5.82-5.87 and 6.06-6.11 (2H total, m, CH₂CH=CH), 7.28-7.37 (5H, m, aromatic CH); δ_C (125 MHz, CDCl₃) 38.487 (OSO₂CH₃), 42.063 (CH₂NHCbz), 67.002 (CH₂Ph), 75.768 (OCH₂CH=CH), 81.235 (CHOMs), 85.485 (OCHCH=CH), 124.835, 128.096, 128.177, 128.519, and 130.104 (OCH₂CH=CH and aromatic CH), 136.275 (Cbz quaternary), 156.500 (Cbz C=O).

(ii) Preparation of (S)-2-(Benzyloxycarbonylamino)-1-((1S,2S,5S)-3,6-dioxabicyclo[3.1.0]hexan-2-yl) ethyl methanesulfonate anti-(52)

To a solution of mesylate (51) (439 mg, 1.29 mmol) in acetonitrile (7 mL) and aqueous Na₂.EDTA (7 mL, 0.4 mmol solution) at 0° C. was added 1,1,1-trifluoroacetone (1.38 mL, 15.4 mmol). To this solution was added in portions a mixture of sodium bicarbonate (0.907 g, 10.8 mmol) and OXONE® (2.45 g, 3.99 mmol) over a period of 80 minutes. The mixture was stirred for 30 minutes then diluted with water (10 mL) and the product extracted into dichloromethane (1×10 mL and 2×20 mL). The combined organic layers were washed with brine (30 mL) then dried (MgSO₄), filtered and reduced in vacuo. Flash chromatography over silica, eluting with ethyl acetate:heptane mixtures 10:90 to 50:50 gave (in order of elution) anti-(52) (271 mg, 59%) and syn-epoxide (71 mg, 15%) as colourless oils. Data for anti-(52); TLC (R_f=0.41, EtOAc:heptane 3:2), analytical HPLC single main peak, R_t=13.556 min., HPLC-MS 358.2 [M+H]⁺, 380.2 [M+Na]⁺, 737.3 [2M+Na]⁺; [□]_D$^{12.5}$−28.8° (c=1.910, CHCl₃); δ_H (500 MHz, CDCl₃) 2.99 (3H, s, OSO₂CH₃), 3.47 and 3.50 (1H total, each brt, J=6.24 Hz, CH₂NH), 3.60 and 3.63 (1H total, each brt, 5.63 respectively, CH₂NH), 3.86-3.90 (3H, m, OCH₂CHCH), 3.98 (1H, d, J=10.27 Hz, OCH₂CH), 4.17 (1H, d, J=2.70 Hz, OCHCHOMs), 4.83-4.87 (1H, m, CHOMs), 5.08-5.14 (2H m, CH₂Ph), 5.23 (1H, brs, NH), 7.30-7.36 (5H, m, aromatic CH); δ_C (125 MHz, CDCl₃) 38.570 (OSO₂CH₃), 42.217 (CH₂NHCbz), 56.231 and 57.062 (OCH₂CHCH), 67.176 (CH₂Ph), 68.353 (OCH₂CH), 77.063 (OCHCHOMs), 79.435 (CHOMs), 128.209, 128.343 and 128.587 (aromatic CH), 136.089 (Cbz quaternary), 156.528 (Cbz C=O). Data for syn-epoxide; TLC (R_f=0.29, EtOAc:heptane 3:2), analytical HPLC main peak, R_t=13.639 min., HPLC-MS 358.1 [M+H]⁺, 737.2 [2M+Na]⁺; [□]_D$^{12.5}$−9.2° (c=3.543, CHCl₃); δ_H (500 MHz, CDCl₃) 3.04 (3H, s, OSO₂CH₃), 3.60-3.80 (2H, m, CH₂NH), 3.72 (1H, d, J=10.54 Hz, OCH₂CHCH), 3.79 (1H, d, J=2.90 Hz, epoxide CH), 3.96 (1H, d, J=2.84 Hz, epoxide CH), 3.99 (1H, d, J=7.36 Hz, OCHCHOMs) 4.06 (1H, d, J=10.68 Hz, OCH₂CHCH), 4.78 (1H, dt, 4.25 Hz, CHOMs), 5.07-5.14 (2H, m, CH₂Ph), 5.29 (1H, brs, NH), 7.29-7.37 (5H, m, aromatic CH); δ_C (125 MHz, CDCl₃) 38.234 (OSO₂CH₃), 42.241 (CH₂NHCbz), 55.571 and 56.081 (OCH₂CHCH), 67.047 (CH₂Ph), 67.852 (OCH₂CH), 76.662 (OCHCHOMs), 80.615 (CHOMs), 128.023, 128.195 and 128.531 (aromatic CH), 136.212 (Cbz quaternary), 156.653 (Cbz C=O).

(iii) Ethanol (3 mL) was added dropwise to a mixture of 10% palladium on charcoal (5 mg) and anti-(52) (60 mg, 0.17 mmol) under an atmosphere of argon. The argon was replaced by hydrogen then the suspension was stirred for 1 hour before filtering the mixture through celite in vacuo. The filter cake was washed with ethanol then the solvents removed in vacuo from the filtrate to obtain (3R,3aR,6S,6aS)-3-hydroxyhexahydro-2H-furo[3,2-b]pyrrol-6-yl methanesulfonate which was used without further purification.

A solution of sodium carbonate (37 mg, 0.35 mmol) in water (2 mL) was added whilst stirring to a solution of (3R, 3aR,6S,6aS)-3-hydroxyhexahydro-2H-furo[3,2-b]pyrrol-6-yl methanesulfonate in 1,4-dioxane (1 mL). A solution of di-tert-butyl dicarbonate (40 mg, 0.18 mmol) in 1,4-dioxane (1 mL) was added then the mixture stirred for 3 hours before adding di-tert-butyl dicarbonate (40 mg, 0.18 mmol). The mixture was stirred for 16 hours then water (10 mL) was added and the product extracted into dichloromethane (1×10 mL and 2×15 mL). The organic layer was washed with brine (15 mL), then dried (MgSO₄), filtered and reduced in vacuo to leave a residue. Flash chromatography over silica, eluting with ethyl acetate:heptane mixtures 20:80 to 50:50 gave bicyclic alcohol (53) (27 mg, 49%) as a white solid. TLC (R_f=0.15, EtOAc:heptane 1:1), HPLC-MS 268.1 [M+2H−$^t$Bu]⁺, 346.1 [M+Na]⁺, 669.3 [2M+Na]⁺; [□]_D$^{12.5}$−46.1° (c=2.820, CHCl₃); δ_H (500 MHz, CDCl₃) mixture of rotamers major:minor 2:1; 1.45 (6H, brs, (CH₃)₃C major), 1.49 (3H, brs, (CH₃)₃C minor), 2.20 (1H, brs, OH), 3.05 (1H, s, OSO₂CH₃ minor), 3.06 (2H, s, OSO₂CH₃ major), 3.43 (0.33H, dd, 2.70 Hz, BocNCH₂ minor), 3.50 (0.66H, dd, 3.75 Hz, BocNCH₂ major), 3.82-3.87 (2H, m, 1.33×OCH₂CHOH and 0.66×BocNCH₂ major), 3.90 (0.66H, dd, J=9.46 and 2.77 Hz, OCH₂CHOH major), 3.96 (0.33H, brd, J=13.48 Hz, BocNCH₂ minor), 4.26 (0.33H, d, J=3.92 Hz, BocNCH minor), 4.30 (0.66H, d, J=3.58 Hz, BocNCH major), 4.42 (0.33H, brs, OCH₂CHOH minor), 4.50 (0.66H, brs, OCH₂CHOH major), 4.72 (0.66H, d, J=2.87 Hz, MsOCHCH major), 4.80 (0.33H, d, J=3.54 Hz, MsOCHCH minor), 5.00 (1H, brs, MSOCH); δ_C (125 MHz, CDCl₃) 28.352/28.446 ((CH₃)₃C quaternary), 38.644/38.711 (OSO₂CH₃), 50.675/51.401 (BocNCH₂), 68.078/68.631 (BocNCH), 74.505/74.590 (OCH₂CHOH), 75.662/76.402 (OCH₂CHOH), 79.776/80.274 (MsOCHCH), 81.013/81.181 (C(CH₃)₃ quaternary), 83.872/84.785 (MsOCHCH), 153.452/154.266 (Boc C=O).

Preparation of (3aS,6S,6aS)-(9H-fluoren-9-yl)methyl 6-tert-butoxy-3-oxotetrahydro-2H-furo[3,2-b]pyrrole-4(5H)-carboxylate (4c)

(i) Preparation of Benzyl (S)-2-tert-butoxy-2-((S)-2,5-dihydrofuran-2-yl)ethylcarbamate (26). Alcohol (17) (270 mg, 1.02 mmol) was dissolved in anhydrous dichloromethane (8 mL) in a 50 mL glass pressure tube and cooled to −78° C. Isobutene (~3 mL) was condensed into the solution and conc. H₂SO₄ (25 □L) added. The tube was sealed and stirred at ambient temperature overnight. The sealed tube was cooled to −78° C., N-methylmorpholine (60 □L, 1 eq. w.r.t. conc. H₂SO₄) added and allowed to warm to ambient temperature, unsealed, with stirring over 2 h. Dichloromethane (25 mL) was added and the organics washed with pH 3 HCl (25 mL), NaHCO₃ (25 mL) then brine (25 mL) and dried (Na₂SO₄). The solvents were removed in vacuo to give a tan oil. The crude oil was purified on a 5 g Flash silica cartridge eluting with a gradient of heptane:ethyl acetate 9:1→6:1. Desired fractions were combined and reduced in vacuo to provide ether (26) as a clear gum (222 mg, 68%). TLC (KMnO₄ stain, $R_f$=0.46, heptane:ethyl acetate 1:2), analytical HPLC $R_t$=17.10 min, HPLC-MS (single main UV peak with $R_t$=2.91 min, 264.1 [M+2H−Bu]⁺, 342.2 [M+Na]⁺, 661.3 [2M+Na]⁺); $[□]_D^{18}$−94.3° (c=1.962, CHCl₃).

(ii) Preparation of epoxide mixture Benzyl (S)-2-((1R,2R,5R)-3,6-dioxabicyclo[3.1.0]hexan-2-yl)-2-tert-butoxyethylcarbamate syn-(27) and Benzyl (S)-2-((1S,2R,5S)-3,6-dioxabicyclo[3.1.0]hexan-2-yl)-2-tert-butoxyethylcarbamate anti-(28). Method 1; meta-Chloroperbenzoic acid. Ether (26) (210 mg, 0.66 mmol) was dissolved in anhydrous dichloromethane (10 mL) with stirring and meta-chloroperoxybenzoic acid (1.48 g, 77% reagent, 6.6 mmol) added. The mixture was stirred at ambient temperature under argon for 16 h. Dichloromethane (20 mL) was added and the organic phase washed with 10% aqueous w/v solution of sodium hydroxide (2×20 mL), then dried (Na₂SO₄), filtered and reduced in vacuo to leave a clear gum (200 mg). The crude gum was purified on a 5 g Flash silica cartridge eluting with a gradient of heptane:ethyl acetate 9:1→7:1. Desired fractions containing the co-eluting epoxides were combined and reduced in vacuo to provide a viscous oil (183 mg, 82.7%). TLC ($R_f$=0.30 (figure of eight mixture of syn and anti epoxides), EtOAc:heptane 2:1), HPLC-MS 236.1, 280.1 [M+2H−Bu]⁺, 358.2 [M+Na]⁺, 693.2 [2M+Na]⁺.

(iii) Alternative preparation of epoxide mixture Benzyl (S)-2-((1R,2R,5R)-3,6-dioxabicyclo[3.1.0]hexan-2-yl)-2-tert-butoxyethylcarbamate syn-(27). and Benzyl (S)-2-((1S,2R,5S)-3,6-dioxabicyclo[3.1.0]hexan-2-yl)-2-tert-butoxyethylcarbamate anti-(28). Method 2; Oxone. To a solution of ether (26) (9.5 mg, 0.030 mmol) in acetonitrile (0.15 mL) and aqueous Na₂.EDTA (0.15 mL, 0.4 mmol solution) at 0° C. was added 1,1,1-trifluoroacetone (0.032 mL, 0.36 mmol). To this solution was added in portions a mixture of sodium bicarbonate (21 mg, 0.25 mmol) and OXONE® (57 mg, 0.092 mmol) over a period of 1 hour. The mixture was stirred for 50 minutes then diluted with water (5 mL) and the product extracted into dichloromethane (2×50 mL). The combined organic layers were washed with brine (5 mL) then dried (Na₂SO₄), filtered and reduced in vacuo. ¹H nmr analysis of the residue indicated a 10:1 mixture benzyl anti-(28) and syn-(27) respectively (6.7 mg).

(iv) Preparation of Benzyl (S)-2-((1R,2R,5R)-3,6-dioxabicyclo[3.1.0]hexan-2-yl)-2-tert-butoxyethylcarbamate syn-(27) and (3R,3aR,6S,6aS)-benzyl 6-tert-butoxy-3-hydroxytetrahydro-2H-furo[3,2-b]pyrrole-4(5H)-carboxylate (29). Epoxide mixture (27, 28) (175 mg, 0.52 mmol) was dissolved in anhydrous THF (3 mL), cooled to 0° C. and sodium hydride (60% dispersion in oil) (26.2 mg, 0.65 mmol) added. The mixture was stirred at ambient temperature for 3 h. Dichloromethane (25 mL) was added and the organic phase washed with brine (1×25 mL), then dried (Na₂SO₄), filtered and reduced in vacuo to leave an opaque gum (~150 mg). The crude gum was purified on a 5 g Flash silica cartridge eluting with a gradient of heptane:ethyl acetate 9:1→5:1 to provide two products:

(a) Syn-epoxide (27) as a viscous oil (39.2 mg, 0.12 mmol, 22.4%), TLC ($R_f$=0.37, EtOAc:heptane 1:1), analytical HPLC $R_t$=15.61 min, HPLC-MS 280.1 [M+2H−Bu]⁺, 358.2 [M+Na]⁺, 693.2 [2M+Na]⁺.

(b) Bicycle alcohol (29) as a viscous oil (80.4 mg, 0.24 mmol, 46%), TLC ($R_f$=0.31, EtOAc:heptane 1:1), analytical HPLC $R_t$=15.17 min, HPLC-MS 236.1, 280.1 [M+2H−Bu]⁺, 358.2 [M+Na]⁺, 693.2 [2M+Na]⁺; $[□]_D^{18}$−46.0° (c=8.04, CHCl₃); ¹H NMR (500 MHz, CDCl₃ at 300K): δ 1.18 (s, C(CH₃)₃, 9H), 1.98 (d, J=4.0 Hz, OH, 0.4H), 2.76 (d, J=2.6 Hz, OH, 0.6H), 3.36-3.44 (m, CbzNCH₂, 0.6H), 3.45-3.52 (m, CbzNCH₂, 1H), 3.62 (d, J=11.8 Hz, CbzNCH₂, 0.4H), 3.70-3.92 (m, OCH₂CHOH, 2H), 4.04 (b, CHOBuᵗ, 1H), 4.26 (b, NCHCHOH, 1H), 4.36 (b, OCH₂CHOH, 0.4H), 4.45 (d, J=4.6 Hz, BuᵗOCHCHO, 1H), 4.48 (b, OCH₂CHOH, 0.6H), 5.09-5.26 (m, OCH₂Ph, 2H), 7.34-7.37 (bm, 5H aromatic); ¹³C NMR (125 MHz, CDCl₃ at 300K): δ 28.08/28.12 (C(CH₃)₃), 53.48/53.71 (CbzNCH₂), 67.11/67.29 (OCH₂Ph), 68.31/69.27 (NCHCHOH), 72.51/73.29 (CHOBuᵗ), 73.88 (OCH₂CHOH), 74.72/74.78 (C(CH₃)₃), 75.80/76.62 (OCH₂CHOH), 86.89/87.52 (BuᵗOCHCHO), 127.81/127.93/128.06/128.23/128.50/128.68 (aromatic CH), 136.43 (aromatic quaternary), 154.51/155.26 (NHC(O)O).

(v) Preparation of (3R,3aR,6S,6aS)-(9H-fluoren-9-yl)methyl 6-tert-butoxy-3-hydroxytetrahydro-2H-furo[3,2-b]pyrrole-4(5H)-carboxylate (4b). Bicycle alcohol (29) (75 mg, 0.22 mmol) was dissolved in methanol (5 mL), cooled to 0° C. and 10% palladium on charcoal (20 mg) added. The mixture was stirred, then evacuated and flushed with hydrogen. The mixture was warmed to ambient temperature and after 1 h. filtered through celite. The filter cake was washed with ethanol (3×5 mL) and the combined filtrates reduced in vacuo to provide the crude amine (~45 mg). HPLC-MS 146.1 [M+2H−Bu]⁺, 202.1 [M+H]⁺, 425.2 [M+Na]⁺. The crude amine was dissolved in 1,4-dioxane (3.5 mL) with stirring, ice-cooled and a solution of sodium carbonate (50 mg, 0.47 mmol) in water (3.5 mL) was added. 9-Fluorenylmethyl chloroformate (61 mg, 0.234 mmol) in 1,4-dioxane (2.5 mL) was added dropwise over 30 minutes and the mixture stirred for a further 1 h. CHCl₃ (25 mL) was then added and the organic phase washed with 0.1N HCl (25 mL), sat. NaHCO₃ (25 mL), then brine (25 mL) and dried (Na₂SO₄). The organic layer was filtered and reduced in vacuo to leave a clear film (~100 mg). The crude film was purified on a 5 g Flash silica cartridge eluting with a gradient of heptane:ethyl acetate 8:1→2:1 to provide alcohol (4b) as a white solid (74.4 mg, 0.175 mmol, 78%). TLC ($R_f$=0.33, EtOAc:heptane 1:1), analytical HPLC $R_t$=18.78 min, HPLC-MS 368.1 [M+2H−Bu]⁺, 424.2 [M+H]⁺, 446.2 [M+Na]⁺, 869.4 [2M+Na]⁺; $[□]_D^{18}$−34.8° (c=6.9, CHCl₃).

(vi) Preparation of (3aS,6S,6aS)-(9H-fluoren-9-yl)methyl 6-tert-butoxy-3-oxotetrahydro-2H-furo[3,2-b]pyrrole-4(5H)-carboxylate (4c). Alcohol (4b) (70 mg, 0.165 mmol) was dissolved in anhydrous dichloromethane (5 mL) with stirring under argon. Dess-Martin periodinane (141 mg, 0.33 mmol) was added and the mixture stirred for 2 h. The mixture was diluted with DCM (20 mL) and washed with sat. NaHCO₃/0.25M Na₂S₂O₃, sat. NaHCO₃, brine (25 mL each) and dried (Na₂SO₄). The organic layer was filtered and reduced in vacuo to leave a clear film (~110 mg). The crude film was purified on a 5 g Flash silica cartridge eluting with a gradient of heptane:ethyl acetate 7:1→2:1 to provide ketone (4c) as a colourless gum (70.5 mg, 0.165 mmol, 99.8%). TLC ($R_f$=0.50, EtOAc:heptane 1:1), analytical HPLC broad peak with $R_t$=18.58-20.92 min, HPLC-MS 366.1 [M+2H−Bu]$^+$, 422.2 [M+H]$^+$, 444.2 [M+Na]$^+$, 865.4 [2M+Na]$^+$; $[\square]_D^{18}$−1000.8° (c=6.5, CHCl$_3$); $^1$H NMR (500 MHz, CDCl$_3$ at 300K): δ 1.22 (s, C(CH$_3$)$_3$, 9H), 3.55-3.67 (m, FmocNCH$_2$, 1.6H), 3.78-3.83 (m, FmocNCH$_2$, 0.4H), 3.90-3.96 (m, OCH$_2$C(O), 1H), 4.10-4.19 (m, OCH$_2$C(O)+CHOBu$^t$, 2H), 4.25-4.42 (m, 0.4+0.6 FmocCH+1×FmocCH$_2$+.NCHC(O), 3H), 4.50 (q, J=6.7, 3.7 Hz, FmocCH$_2$), 4.59/4.64 (b, Bu$^t$OCHCHO, 1H), 7.30 (d, J=6.65 Hz, Fmoc H-2 and H-7), 7.39 (t, J=7.5 Hz, Fmoc H-3 and H-6), 7.57 (d, J=7.2 Hz, 1.2 Fmoc H-1 and H-8), 7.66 (d, J=7.1 Hz, 0.8 Fmoc H-1 or H-8), 7.76 (d, J=7.55 Hz, Fmoc H-4 and H-5); $^{13}$C NMR (125 MHz, CDCl$_3$ at 300K): δ 28.10 (C(CH$_3$)$_3$), 47.13 (FmocCH), 53.40/53.84 (FmocNCH$_2$), 61.12/61.56 (NCHC(O)), 67.63/68.38 (FmocCH$_2$), 69.99 (OCH$_2$C(O)), 72.54/73.21 (CHOBu$^t$), 75.05/75.13 (C(CH$_3$)$_3$), 86.36/87.37 (Bu$^t$OCHCHO), 119.89/119.96 (Fmoc C-4 and C-5), 124.97/125.03/125.25/125.59 (Fmoc C-1 and C-8), 126.99/127.04 (Fmoc C-2 and C-7), 127.67 (Fmoc C-3 and C-6), 141.22/141.33/143.71/143.87/144.47 (Fmoc quaternary aromatics), 155.17 (FmOC(O)N), 208.02/208.31 (C=O).

Preparation of (3aS,6R,6aS)-(9H-fluoren-9-yl)methyl 6-tert-butoxy-3-oxotetrahydro-2H-furo[3,2-b]pyrrole-4(5H)-carboxylate (3c)

(i) Preparation of Benzyl (R)-2-tert-butoxy-2-((S)-2,5-dihydrofuran-2-yl)ethylcarbamate (26b). Alcohol (18) (400 mg, 1.52 mmol) was dissolved in anhydrous dichloromethane (8 mL) in a 50 mL glass pressure tube and cooled to −78° C. Isobutene (~4 mL) was condensed into the solution and conc. H$_2$SO$_4$ (35 $\square$L) added. The tube was sealed and stirred at ambient temperature for 6 h. The sealed tube was cooled to −78° C., N-methylmorpholine (75 $\square$L, 1 eq. w.r.t. conc. H$_2$SO$_4$) added and allowed to warm to ambient temperature, unsealed, with stirring over 2 h. Dichloromethane (20 mL) was added and the organics washed with pH 3 HCl (25 mL), NaHCO$_3$ (25 mL) then brine (25 mL) and dried (Na$_2$SO$_4$). The solvents were removed in vacuo to give an opaque gum (350 mg). The crude gum was purified on a 5 g Flash silica cartridge eluting with a gradient of heptane:ethyl acetate 7:1→2:1. Desired fractions were combined and reduced in vacuo to provide ether (26b) as a thick clear oil (204 mg, 42%) and recovered starting alcohol (108 mg, 27%). TLC (KMnO$_4$ stain, $R_f$=0.70, heptane:ethyl acetate 2:1), analytical HPLC $R_t$=16.85 min, HPLC-MS (single main UV peak with $R_t$=2.85 min, 264.1 [M+2H−Bu]$^+$, 342.2 [M+Na]$^+$, 661.3 [2M+Na]$^+$); $[\square]_D^{18}$−560.8° (c=2.068, CHCl$_3$).

(ii) Preparation of epoxide mixture Benzyl (R)-2-((1R,2R,5R)-3,6-dioxabicyclo[3.1.0]hexan-2-yl)-2-tert-butoxyethylcarbamate syn-(27b). and Benzyl (R)-2-((1S,2R,5S)-3,6-dioxabicyclo[3.1.0]hexan-2-yl)-2-tert-butoxyethylcarbamate anti-(28b). Method 1; meta-Chloroperbenzoic acid. Ether (26b) (175 mg, 0.55 mmol) was dissolved in anhydrous dichloromethane (7.5 mL) with stirring and meta-chloroperoxybenzoic acid (1.22 g, 77% reagent, 5.5 mmol) added. The mixture was stirred at ambient temperature under argon for 16 h. Dichloromethane (20 mL) was added and the organic phase washed with 10% aqueous w/v solution of sodium hydroxide (2×50 mL), then dried (Na$_2$SO$_4$), filtered and reduced in vacuo to leave a clear oil (180 mg). The crude oil was purified on a 5 g Flash silica cartridge eluting with a gradient of heptane:ethyl acetate 8:1→2:1. Desired fractions containing the co-eluting epoxides were combined and reduced in vacuo to provide a clear gum (171 mg, 92.7%). TLC ($R_f$=0.28 (mixture of syn and anti epoxides), EtOAc:heptane 1:2), HPLC-MS 236.1, 280.1 [M+2H−Bu]$^+$, 358.2 [M+Na]$^+$, 693.2 [2M+Na]$^+$.

(iii) Alternative preparation of epoxide mixture Benzyl (R)-2-((1R,2R,5R)-3,6-dioxabicyclo[3.1.0]hexan-2-yl)-2-tert-butoxyethylcarbamate syn-(27b). and Benzyl (R)-2-((1S,2R,5S)-3,6-dioxabicyclo[3.1.0]hexan-2-yl)-2-tert-butoxyethylcarbamate anti-(28b). Method 2; Oxone. To a solution of ether (26b) (9.5 mg, 0.030 mmol) in acetonitrile (0.15 mL) and aqueous Na$_2$.EDTA (0.15 mL, 0.4 mmol solution) at 0° C. was added 1,1,1-trifluoroacetone (0.032 mL, 0.36 mmol). To this solution was added in portions a mixture of sodium bicarbonate (21 mg, 0.25 mmol) and OXONE® (57 mg, 0.092 mmol) over a period of 1 hour. The mixture was stirred for 50 minutes then diluted with water (5 mL) and the product extracted into dichloromethane (2×50 mL). The combined organic layers were washed with brine (5 mL) then dried (Na$_2$SO$_4$), filtered and reduced in vacuo. $^1$H nmr analysis of the residue indicated a 10:1 mixture of anti-(28b) and syn-(27b) respectively (8.9 mg).

(iv) Preparation of Benzyl (R)-2-((1R,2R,5R)-3,6-dioxabicyclo[3.1.0]hexan-2-yl)-2-tert-butoxyethylcarbamate syn-(27b) and (3R,3aR,6R,6aS)-benzyl 6-tert-butoxy-3-hydroxytetrahydro-2H-furo[3,2-b]pyrrole-4(5H)-carboxylate (29b). Epoxide mixture (27b, 28b) (165 mg, 0.49 mmol) was dissolved in anhydrous THF (3 mL), cooled to 0° C. and sodium hydride (60% dispersion in oil) (24.6 mg, 0.615 mmol) added. The mixture was stirred at ambient temperature overnight. Dichloromethane (25 mL) was added and the organic phase washed with brine (1×25 mL), then dried (Na$_2$SO$_4$), filtered and reduced in vacuo to leave a colourless gum (~200 mg). The crude gum was purified on a 5 g Flash silica cartridge eluting with a gradient of heptane:ethyl acetate 6:1→1:2 to provide two products:

(c) Syn-epoxide (27b) as a viscous oil (88 mg, 0.26 mmol, 53.4%), TLC ($R_f$=0.42, EtOAc:heptane 1:1), analytical HPLC $R_t$=15.64 min, HPLC-MS 280.1 [M+2H−Bu]$^+$, 358.2 [M+Na]$^+$, 693.2 [2M+Na]$^+$; $[\square]_D^{18}$−36.9° (c=8.8, CHCl$_3$); $^1$H NMR (500 MHz, CDCl$_3$ at 300K): δ 1.25 (s, C(CH$_3$)$_3$, 9H), 3.20-3.25 (dq, CbzNHCH$_2$, 1H), 3.57-3.64 (m, CbzNHCH$_2$, 1H), 3.67-3.71 (b, CH$_2$OCHCHOBu$^t$+CH$_2$OCHCHOBu$^t$, 3H), 3.73-3.77 (m, CHOCH+CHOCH, 2H), 4.08 (d, J=10.70 Hz, CH$_2$OCHCHOBu$^t$, 1H), 5.03-5.14 (dd, J=12.2 Hz, OCH$_2$Ph, 2H), 5.22 (d, J=5.5 Hz, NH, 1H), 7.35 (bm, 5H aromatic); $^{13}$C NMR (125 MHz, CDCl$_3$ at 300K): δ 28.38 (C(CH$_3$)$_3$), 44.22 (CbzNHCH$_2$), 56.71/56.83 (CHOCH+CHOCH), 66.63 (OCH$_2$Ph), 68.03 (CH$_2$OCHCHOBu$^t$), 68.23 (CH$_2$OCHCHOBu$^t$), 75.30 (C(CH$_3$)$_3$), 78.71 (CH$_2$OCHCHOBu$^t$), 128.05/128.20/128.47 (aromatic CH), 136.67 (aromatic quaternary), 156.53 (NHC(O)O).

(d) Bicycle alcohol (29b) as a viscous oil (33 mg, 0.10 mmol, 20.0%), TLC ($R_f$=0.13, EtOAc:heptane 1:1), analytical HPLC $R_t$=13.66 min, HPLC-MS 236.1, 280.1 [M+2H−Bu]$^+$, 358.2 [M+Na]$^+$, 693.2 [2M+Na]$^+$; $[\square]_D^{18}$−22.7° (c=3.3, CHCl$_3$); $^1$H NMR (500 MHz, CDCl$_3$ at 300K): δ 1.23 (s, C(CH$_3$)$_3$, 9H), 1.91/2.56 (b, OH, 0.4/0.6H), 3.06-3.14 (m, CbzNCH$_2$, 1H), 3.68-3.75/3.81-3.86 (dq, J=7.7 Hz, CbzNCH$_2$, 0.6+0.4H), 3.75-3.80 (m, OCH$_2$CHOH, 1H), 4.00-4.06 (m, CHOBu$^t$+0.4 OCH$_2$CHOH, 1.4H), 4.09-4.14 (m, NCHCHOH+0.6 OCH$_2$CHOH, 1.6H), 4.35 (b, OCH$_2$CHOH, 0.4H), 4.45-4.48 (m, OCH$_2$CHOH, 0.6H), 4.48-4.51 (m, Bu$^t$OCHCHO, 1H), 5.08-5.20 (m, OCH$_2$Ph, 2H), 7.35 (bm, 5H aromatic); $^{13}$C NMR (125 MHz, CDCl$_3$ at 300K): δ 28.15 (C(CH$_3$)$_3$), 48.97/49.09 (CbzNCH$_2$), 67.23/67.39 (OCH$_2$Ph), 68.23/69.23 (NCHCHOH), 70.81/71.04 (CHOBu$^t$), 74.53/74.57 (C(CH$_3$)$_3$), 74.98/75.25 (OCH$_2$CHOH), 77.19/77.32 (OCH$_2$CHOH), 81.47/82.29 (Bu$^t$OCHCHO), 127.99/128.04/128.18/128.36/128.54/128.72 (aromatic CH), 136.28 (aromatic quaternary), 154.21/155.06 (NHC(O)O).

(v) Preparation of (3R,3aR,6R,6aS)-(9H-fluoren-9-yl)methyl 6-tert-butoxy-3-hydroxytetrahydro-2H-furo[3,2-b]pyrrole-4(5H)-carboxylate (3b). Alcohol (29b) (33 mg, 0.1 mmol) was dissolved in methanol (5 mL), cooled to 0° C. and 10% palladium on charcoal (15 mg) added. The mixture was stirred, then evacuated and flushed with hydrogen. The mixture was warmed to ambient temperature and after 1 h. filtered through celite. The filter cake was washed with ethanol (3×5 mL) and the combined filtrates reduced in vacuo to provide the crude amine (~15 mg). HPLC-MS 146.1 [M+2H-Bu]$^+$, 202.1 [M+H]$^+$, 425.2 [M+Na]$^+$. The crude amine was dissolved in 1,4-dioxane (2.5 mL) with stirring, ice-cooled and a solution of sodium carbonate (22 mg, 0.21 mmol) in water (2.5 mL) was added. 9-Fluorenylmethyl chloroformate (27 mg, 0.10 mmol) in 1,4-dioxane (2.5 mL) was added dropwise over 30 minutes and the mixture stirred for a further 1 h. CHCl$_3$ (25 mL) was then added and the organic phase washed with 0.1N HCl (25 mL), sat. NaHCO$_3$ (25 mL), then brine (25 mL) and dried (Na$_2$SO$_4$). The organic layer was filtered and reduced in vacuo to leave a clear film (~40 mg). The crude film was purified on a 5 g Flash silica cartridge eluting with a gradient of heptane:ethyl acetate 8:1→1:1 to provide alcohol (3b) as a white solid (27.3 mg, 0.065 mmol, 65.8%). TLC (R$_f$=0.16, EtOAc:heptane 1:1), analytical HPLC R$_t$=17.39 min, HPLC-MS 368.2 [M+2H-Bu]$^+$, 424.2 [M+H]$^+$, 446.2 [M+Na]$^+$, 869.4 [2M+Na]$^+$; [□]$_D^{18}$ −12.2° (c=2.45, CHCl$_3$).

(vi) Preparation of (3aS,6R,6aS)-(9H-fluoren-9-yl)methyl 6-tert-butoxy-3-oxotetrahydro-2H-furo[3,2-b]pyrrole-4(5H)-carboxylate (3c). Bicycle alcohol (3b) (25 mg, 0.06 mmol) was dissolved in anhydrous dichloromethane (3 mL) with stirring under argon. Dess-Martin periodinane (50 mg, 0.12 mmol) was added and the mixture stirred overnight. The mixture was diluted with DCM (20 mL) and washed with sat. NaHCO$_3$/0.25M Na$_2$S$_2$O$_3$, sat. NaHCO$_3$, brine (25 mL each) and dried (Na$_2$SO$_4$). The organic layer was filtered and reduced in vacuo to leave a tan gum (~40 mg). The crude gum was purified on a 5 g Flash silica cartridge eluting with a gradient of heptane:ethyl acetate 6:1→3:1 to provide ketone (3c) as a white solid (21.9 mg, 0.052 mmol, 88.1%). TLC (R$_f$=0.57, EtOAc:heptane 2:1), analytical HPLC broad peak with R$_t$=17.15-19.96 min, HPLC-MS 366.1 [M+2H-Bu]$^+$, 422.2 [M+H]$^+$, 444.2 [M+Na]$^+$, 865.4 [2M+Na]$^+$; [□]$_D^{18}$ −870.5° (c=1.6, CHCl$_3$); $^1$H NMR (500 MHz, CDCl$_3$ at 300K): δ 1.25 (s, C(CH$_3$)$_3$, 9H), 3.30-3.40 (m, FmocNCH$_2$, 1H), 3.61-3.66 (m, FmocNCH$_2$, 0.4H), 3.76-3.80 (m, FmocNCH$_2$, 0.6H), 4.01-4.17 (m, OCH$_2$C(O), 2H), 4.22-4.35 (m, NCHC(O)+CHOBu$^t$+FmocCH+0.6 FmocCH$_2$, 3.6H), 4.37-4.43 (bt, 0.4 FmocCH$_2$), 4.49-4.54/4.56-4.63 (m, 0.4 FmocCH$_2$+ 0.6 FmocCH$_2$), 4.69-4.72/4.72-4.77 (m, Bu$^t$OCHCHO, 1H), 7.29-7.33 (m, Fmoc H-2 and H-7), 7.38 (t, J=7.45 Hz, Fmoc H-3 and H-6), 7.56 (d, J=8.7 Hz, 1.0 Fmoc H-1 or H-8), 7.65 (d, J=7.3 Hz, 0.5 Fmoc H-1 or H-8), (d+m, J=7.55 Hz, Fmoc H-4 and H-5+0.5H-1 or H-8); $^{13}$C NMR (125 MHz, CDCl$_3$ at 300K): δ 28.11 (C(CH$_3$)$_3$), 47.19 (FmocCH), 50.48/50.94 (FmocNCH$_2$), 60.45/60.83 NCHC(O)), 67.64/68.23 (FmocCH$_2$), 71.32/71.45 (OCH$_2$C(O)), 71.50 (CHOBu$^t$), 75.22 (C(CH$_3$)$_3$), 80.78/81.49 (Bu$^t$OCHCHO), 119.88/119.95 (Fmoc C4 and C-5), 124.98/125.01/125.20/125.43 (Fmoc C-1 and C-8), 127.03 (Fmoc C-2 and C-7), 127.65/127.71 (Fmoc C-3 and C-6), 141.22/141.33/143.63/143.97/144.38 (Fmoc quaternary aromatics), 155.10 (CH$_2$OC(O)N), 208.56/208.66 (C=O).

Preparation of (3aS,6S,6aS)-(9H-Fluoren-9-yl)methyl 6-methoxy-3-oxotetrahydro-2H-furo[3,2-b]pyrrole-4(5H)-carboxylate (6c)

(i) Preparation of Benzyl (S)-2-((S)-2,5-dihydrofuran-2-yl)-2-methoxyethyl carbamate (30). Methyl iodide (1.18 mL, 19.0 mmol) was added to a stirred mixture of alcohol (17) (1.0 g, 3.80 mmol) and silver (I) oxide (1.32 g, 5.70 mmol) in acetonitrile (15 mL). The mixture was heated at 75° C. for 3 hours then at 80° C. for 3.5 hours. Silver (I) oxide (0.20 g, 0.86 mmol) and methyl iodide (0.25 mL, 4.0 mmol) were added and heating continued for 4 hours then allowed to cool to ambient temperature, filtered and reduced in vacuo. Flash chromatography over silica, eluting with ethyl acetate:heptane mixtures 10:90 to 30:70 gave methyl ether (30) (731 mg, 69%) as a colourless oil. TLC (R$_f$=0.40, EtOAc:heptane 1:1), analytical HPLC single main peak, R$_t$=13.107 min., HPLC-MS 278.1 [M+H]$^+$, 577.2 [2M+Na]$^+$; [□]$_D^{19}$ −100.4° (c=2.888, CHCl$_3$); δ$_H$ (500 MHz, CDCl$_3$) 3.20 (1H, dt, 5.67 Hz, CH$_2$N), 3.32-3.36 (1H, m, CHOCH$_3$), 3.44 (3H, s, CHOCH$_3$), 3.42-3.49 (1H, m, CH$_2$N), 4.57-4.71 (2H, m, OCH$_2$CH=CH), 4.88-4.92 (1H, m, OCHCH=CH), 5.09 (2H, s, OCH$_2$Ph), 5.16 (1H, brs, NH), 5.79-5.83 and 5.95-5.99 (2H total, m, CH$_2$CH=CH), 7.29-7.36 (5H, aromatic CH); δ$_C$ (125 MHz, CDCl$_3$) 0.952 (CH$_2$NHCbz), 58.752 (OCH$_3$), 66.705 (CH$_2$Ph), 75.589 (OCH$_2$CH=CH), 81.184 (CHOCH$_3$), 86.559 (OCHCH=CH), 126.033, 128.097 and 128.497 (OCH$_2$CH=CH and Cbz aromatic CH), 136.555 (Cbz quaternary), 156.441 (Cbz C=O).

(ii) Alternative preparation of Benzyl (R)-2-((S)-2,5-dihydrofuran-2-yl)-2-methoxyethylcarbamate (30). Trimethyloxonium fluoroborate (19.12 g, 129.3 mmol) was added to a stirred mixture of benzyl (S)-2-((S)-2,5-dihydrofuran-2-yl)-2-hydroxyethylcarbamate (17) (20.0 g, 76.0 mmol), 4 Å molecular sieves (66 g), 1,8-bis(dimethylamino)naphthalene (97.8 g, 456.2 mmol) and dichloromethane (500 mL) under an atmosphere of argon. The mixture was stirred for 2 hours then filtered through celite in vacuo. The filter cake was washed with dichloromethane (750 mL) then the solvents removed in vacuo from the filtrate. The residue was triturated with TBME (250 mL) then the granular solid removed by filtration in vacuo. The solid was washed with TBME (3×100 mL) then the combined filtrates washed with hydrochloric acid (2.5M, 1×100 mL then 2×50 mL), brine (50 mL) then dried (Na$_2$SO$_4$), filtered and reduced in vacuo to leave a pale yellow oil. Flash chromatography over silica, eluting with ethyl acetate:heptane mixtures 10:90 to 50:50 gave methylether (30) as a colourless oil (17.2 g, 82%).

(iii) Preparation of Benzyl (S)-2-((1S,2R,5S)-3,6-dioxabicyclo[3.1.0]hexan-2-yl)-2-methoxyethyl carbamate anti-(31). To a solution of methyl ether (30) (731 mg, 2.64 mmol) in acetonitrile (15 mL) and aqueous Na$_2$.EDTA (15 mL, 0.4 mmol solution) at 0° C. was added 1,1,1-trifluoroacetone (2.84 mL, 31.7 mmol). To this solution was added in portions a mixture of sodium bicarbonate (1.87 g, 22.2 mmol) and OXONE® (5.04 g, 8.19 mmol) over a period of 1.5 hours. The mixture was stirred for 15 minutes then diluted with water (50 mL) and the product extracted into dichloromethane (3×50 mL). The combined organic layers were washed with brine (75 mL) then dried (MgSO$_4$), filtered and reduced in vacuo. Flash chromatography over silica, eluting with ethyl acetate: heptane mixtures 10:90 to 30:70 gave anti-(31) (323 mg, 42%) as a colourless oil. TLC (R$_f$=0.25, EtOAc:heptane 1:1), analytical HPLC single main peak, $R_t$=10.901 min., HPLC-MS 294.2 [M+H]$^+$, 609.3 [2M+Na]$^+$; $[\square]_D^{15}$+12.1° (c=2.890, CHCl$_3$); $\delta_H$ (500 MHz, CDCl$_3$) 3.27-3.55 (6H, m, CH$_2$NH, CHOCH$_3$), 3.72 and 3.78 (2H, each d, 2.49 Hz respectively, OCH$_2$CHCH), 3.84 (1H, d, J=9.98 Hz, OCH$_2$CH), 3.94 (1H, d, J=10.02 Hz, OCH$_2$CH), 4.12 (1H, d, J=2.76 Hz, OCHCHOCH$_3$), 5.10 (2H, s, CH$_2$Ph), 5.27 (1H, brs, NH), 7.28-7.37 (5H, m, phenyl CH); $\delta_C$ (125 MHz, CDCl$_3$) 40.819 (CH$_2$NHCbz), 56.769 and 57.700 (OCH$_2$CHCH), 58.442 (OCH$_3$), 66.784 (CH$_2$Ph), 68.446 (OCH$_2$CH), 78.631 (OCHCHOCH$_3$), 79.264 (CHOCH$_3$), 128.079, 128.160 and 128.521 (aromatic CH), 136.451 (Cbz quaternary), 156.532 (Cbz C=O).

(iv) (3R,3aR,6S,6aS)-(9H-Fluoren-9-yl)methyl 3-hydroxy-6-methoxytetrahydro-2H-furo[3,2-b]pyrrole-4(5H)-carboxylate (6b). Ethanol (15 mL) was added dropwise to a mixture of 10% palladium on charcoal (30 mg) and anti-(31) (315 mg, 1.07 mmol) under an atmosphere of argon. The argon was replaced by hydrogen then the suspension was stirred for 1.5 hours then 10% palladium on charcoal (30 mg) was added. The mixture was stirred for 2 hours then 10% palladium on charcoal (50 mg) was added. The mixture was stirred for 4.5 hours then filtered through celite in vacuo. The filter cake was washed with ethanol then the solvents removed in vacuo from the filtrate to obtain the crude (3R,3aR,6S,6aS)-6-methoxyhexahydro-2H-furo[3,2-b]pyrrol-3-ol which was used without further purification.

A solution of sodium carbonate (239 mg, 2.26 mmol) in water (10 mL) was added whilst stirring to a solution of (3R,3aR,6S,6aS)-6-methoxyhexahydro-2H-furo[3,2-b]pyrrol-3-ol in 1,4-dioxane (7 mL). A solution of 9-fluorenylmethoxycarbonyl chloride (319 mg, 1.23 mmol) in 1,4-dioxane (3 mL) was added then the mixture stirred for 40 minutes then water (30 mL) was added and the product extracted into dichloromethane (1×40 mL then 2×30 mL). The organic layer was washed with brine (50 mL), then dried (MgSO$_4$), filtered and reduced in vacuo to leave a residue. Flash chromatography over silica, eluting with ethyl acetate:heptane mixtures 7:93 to 45:55 gave bicyclic alcohol (6b) (270 mg, 66%) as a white solid. TLC ($R_f$=0.34, EtOAc:heptane 3:2), analytical HPLC single main peak, $R_t$=15.990 min., HPLC-MS 382.1 [M+H]$^+$, 404.1 [M+Na]$^+$, 785.3 [2M+Na]$^+$; $[\square]_D^{18.5}$−35.4° (c=2.758, CHCl$_3$); $\delta_H$ (500 MHz, CDCl$_3$) mixture of rotamers major:minor 3:2; 1.02 (0.6H, d, J=3.55 Hz, OH major), 2.59 (0.40H, d, J=3.19 Hz, OH minor), 3.10 (0.6H, dd, 3.89 Hz, FmocNCH$_2$ major), 3.26 (1.8H, s, OCH$_3$ major), 3.30 (0.4H, dd, 4.19 Hz, FmocNCH$_2$ minor), 3.35 (1.2H, s, OCH$_3$ minor), 3.49 (0.6H, m, OCH$_2$CHOH major), 3.52 (0.6H, dd, 1.81 Hz, OCH$_2$CHOH major), 3.55-3.59 (1.2H, m, OCH$_2$CHOH major and FmocNCH major), 3.64 (0.6H, d, J=3.69 Hz, CHOCH$_3$ major), 3.65-3.70 (1H, m, FmocNCH$_2$), 3.75-3.79 (0.8H, m, OCH$_2$CHOH minor and CHOCH$_3$ minor), 3.85 (0.4H, dd, J=9.85 and 4.46 Hz, OCH$_2$CHOH minor), 4.22-4.26 (1.4H, m, FmocNCH minor and Fmoc CH), 4.37 (0.6H, d, J=4.64 Hz, OCHCHOCH$_3$ major), 4.40-4.44 (1.2H, m, Fmoc CH$_2$ minor and OCH$_2$CHOH minor), 4.60 (0.4H, d, J=4.94 Hz, OCHCHOCH$_3$ minor), 4.70 (0.6H, dd, J=10.80 and 3.96 Hz, Fmoc CH$_2$ major), 4.82 (0.6H, dd, 4.25 Hz, Fmoc CH$_2$ major), 7.29-7.80 (8H, Fmoc aromatic CH); $\delta_C$ (125 MHz, CDCl$_3$) 47.248/47.378 (Fmoc CH), 49.754/50.177 (FmocNCH$_2$), 56.868/56.996 (OCH$_3$), 65.736/67.270 (Fmoc CH$_2$), 68.262/69.085 (FmocNCH), 73.760/74.008 (OCH$_2$CHOH), 75.812/76.183 (OCHCHOH), 81.509/82.286 (OCHCHOCH$_3$), 83.496/84.166 (OCHCHOCH$_3$), 119.805, 119.982, 120.003, 124.494, 124.576, 124.958, 124.975, 127.019, 127.034, 127.404, 127.488, 127.637, 127.726, 127.754 and 127.865 (Fmoc aromatic CH), 143.633, 143.909, 143.943 and 144.037 (Fmoc quaternary), 154.255/155.025 (Fmoc C=O).

(v) (3aS,6S,6aS)-(9H-Fluoren-9-yl)methyl 6-methoxy-3-oxotetrahydro-2H-furo[3,2-b]pyrrole-4(5H)-carboxylate (6c). Dess-Martin periodinane (600 mg, 1.42 mmol) was added to a stirred solution of bicyclic alcohol (6b) (270, 0.71 mmol) in dichloromethane (10 mL) at 0° C. under an atmosphere of argon. The mixture was allowed to warm to ambient temperature over 2 hours then Dess-Martin periodinane (300 mg, 0.71 mmol) added. The mixture was stirred for 4 hours then diluted with dichloromethane (20 mL). The organic phase was washed with a mixture of saturated aqueous sodium bicarbonate and 0.25M sodium thiosulphate solution (1:1, 15 mL), then saturated aqueous sodium bicarbonate (10 mL), then brine (10 mL), then dried (MgSO$_4$), filtered and reduced in vacuo. Flash chromatography over silica, eluting with ethyl acetate:heptane mixtures 15:85 to 40:60 gave bicyclic ketone (6c) (200 mg, 74%) as a white solid. TLC ($R_f$=0.45, EtOAc:heptane 7:3), analytical HPLC broad main peak, $R_t$=15.676-16.668 min., HPLC-MS 380.2 [M+H]$^+$, 781.3 [2M+Na]$^+$; $[\square]_D^{17}$−105.6° (c=9.468, CHCl$_3$); $\delta_H$ (500 MHz, CDCl$_3$) mixture of rotamers approx. 1:1; 3.33 (1.5H, s, OCH$_3$), 3.38 (1.5H, s, OCH$_3$), 3.42-3.49 (1H, m, FmocNCH$_2$), 3.82 (0.5H, d, J=12.07 Hz, FmocNCH$_2$), 3.89-4.01 (2H, m, OCHCHOMe and OCH$_2$C=O), 4.05-4.19 (1.5H, m, OCH$_2$C=O and FmocNCH$_2$), 4.21-4.34 (1.5H, m, Fmoc-CH$_2$ and Fmoc-CH), 4.37-4.40 (1H, m, FmocNCH), 4.42-4.56 (1.5H, m, Fmoc-CH$_2$), 4.74 (0.5H, d, J=4.33 Hz, OCHCHOCH$_3$), 4.79 (1H, d, J=4.14 Hz, OCHCHOCH$_3$), 7.28-7.76 (8H, Fmoc aromatic CH); $\delta_C$ (125 MHz, CDCl$_3$); 47.104/47.156 (Fmoc-CH), 49.957 (FmocNCH$_2$), 56.975/57.031 (OCH$_3$), 60.853/61.278 (FmocNCH), 67.649/68.476 (Fmoc-CH$_2$), 70.078 (OCH$_2$C=O), 81.701/82.335 (OCHCHOCH$_3$), 83.549/84.751 (OCHCHOCH$_3$), 119.894, 119.962, 124.963, 125.226, 125.524, 127.029, 127.065 and 127.695 (Fmoc aromatic CH), 141.238, 141.309, 143.654, 143.811 and 144.354 (Fmoc quaternary), 155.065/155.203 (Fmoc C=O), 207.830/207.992 (ketone C=O).

Preparation of (3R,3aR,6S,6aS)-Benzyl 3-hydroxy-6-methoxytetrahydro-2H-furo[3,2-b]pyrrole-4(5H)-carboxylate (72)

Sodium hydride (60% dispersion in oil, 800 mg, 19.95 mmol) was added over 1 minute to a stirred solution consisting of a 4:1 mixture of anti-epoxide benzyl (S)-2-((1S,2R,5S)-3,6-dioxabicyclo[3.1.0]hexan-2-yl)-2-methoxyethyl carbamate (31) and syn-epoxide benzyl (S)-2-((1R,2R,5R)-3,6-dioxabicyclo[3.1.0]hexan-2-yl)-2-methoxyethyl carbamate (4.5 mg, 15.35 mmol total) in tetrahydrofuran (15 mL) at 0° C. under an atmosphere of argon. The mixture was stirred at 0° C. for 30 minutes then at ambient temperature overnight then dichloromethane (150 mL) added. The organic layer was washed with brine (75 mL), then dried (Na$_2$SO$_4$), filtered and reduced in vacuo to leave a residue (5.8 g). The residue was treated 4N HCl in dioxin (18 mL, 75 mmol) for 1 h then reduced in vacuo. Flash chromatography over silica, eluting with ethyl acetate:heptane mixtures 25:75 to 50:50 gave (3R,3aR,6S,6aS)-benzyl 3-hydroxy-6-methoxytetrahydro-2H-furo[3,2-b]pyrrole-4(5H)-carboxylate (72) as a straw coloured oil (2.20 g, 7.5 mmol). TLC ($R_f$=0.30, EtOAc:heptane 3:2), analytical HPLC single main peak, $R_t$=9.50 min.; HPLC-MS 294.1 [M+H]$^+$, 609.2 [2M+Na]$^+$; $[\square]_D^{22.0}$−49.6° (c=2.52, CHCl$_3$).

(vii) Alternative Preparation of (3R,3aR,6S,6aS)-Benzyl 3-hydroxy-6-methoxytetrahydro-2H-furo[3,2-b]pyrrole-4(5H)-carboxylate (72). Ethanol (100 mL) was added dropwise to a mixture of 10% palladium on charcoal (400 mg) and benzyl (S)-2-((1S,2R,5S)-3,6-dioxabicyclo[3.1.0]hexan-2-yl)-2-methoxyethyl carbamate (31) (4.0 g, 13.65 mmol) under an atmosphere of argon. The argon was replaced by hydrogen then the suspension was stirred for 15 hours then filtered through celite in vacuo. The filter cake was washed with ethanol then the solvents removed in vacuo from the filtrate to obtain the crude (3R,3aR,6S,6aS)-6-methoxyhexahydro-2H-furo[3,2-b]pyrrol-3-ol which was used without further purification.

A solution of sodium carbonate (3.04 g, 28.7 mmol) in water (20 mL) was added whilst stirring to a solution of (3R,3aR,6S,6aS)-6-methoxyhexahydro-2H-furo[3,2-b]pyrrol-3-ol (prepared as above, assumed to be 13.65 mmol) in 1,4-dioxane (50 mL). Benzyl chloroformate (2.88 mL, 20.48 mmol) was added dropwise then the mixture stirred for 6 hours, then water (200 mL) was added and the product extracted into dichloromethane (3×75 mL). The organic layer was dried ($Na_2SO_4$), filtered and reduced in vacuo to leave a colourless oil (4.95 g). Flash chromatography over silica, eluting with ethyl acetate:heptane mixtures 15:85 to 75:25 gave (3R,3aR,6S,6aS)-benzyl 3-hydroxy-6-methoxytetrahydro-2H-furo[3,2-b]pyrrole-4(5H)-carboxylate (72) (2.98 g, 74%) as a colourless oil. TLC ($R_f$=0.47, EtOAc:heptane 2:1), analytical HPLC single main peak, $R_t$=9.78 min., HPLC-MS 294.1 $[M+H]^+$, 316.1 $[M+Na]^+$, 609.2 $[2M+Na]^+$; $\delta_H$ (500 MHz, $CDCl_3$) mixture of rotamers major:minor 3:2; 3.29 (0.4H, dd, 3.87 Hz, 1×$CbzNCH_2$ minor), 3.34 (3H, s, $OCH_3$), 3.34-3.38 (0.6H, m, 1×$CbzNCH_2$ major), 3.69-3.97 (4H, m, 1×$CbzNCH_2$, $OCH_2CHOH$ and CHOMe), 4.26 (1H, brt, J=5.55 Hz, $OCHCHOCH_3$), 4.37 (0.4H, brs, $OCH_2CHOH$ minor), 4.49 (0.6H, brs, $OCH_2CHOH$ major), 4.61 (1H, d, J=4.89 Hz, CbzNCH), 5.09-5.24 (2H, m, $CH_2Ph$), 7.30-7.40 (5H, m, aromatic CH); $\delta_C$ (125 MHz, $CDCl_3$) 50.14/50.41 ($CbzNCH_2$), 56.97/57.03 ($OCH_3$), 67.26/67.38 ($CH_2Ph$), 68.15/69.14 (CbzNCH), 74.05/74.34 ($OCH_2CHOH$), 75.79/76.59 ($OCH_2CHOH$), 81.64/82.34 ($OCHCHOCH_3$), 83.47/84.59 ($OCHCHOCH_3$), 127.91, 127.96, 128.13/128.26/128.52/128.56/128.67 and 128.80 (aromatic CH), 136.26/136.32 (aromatic quaternary), 154.50/155.13 (Cbz C=O).

Preparation of (3aS,6R,6aS)-(9H-Fluoren-9-yl)methyl 6-methoxy-3-oxotetrahydro-2H-furo[3,2-b]pyrrole-4(5H)-carboxylate (5c)

(i) Preparation of Benzyl (R)-2-((S)-2,5-dihydrofuran-2-yl)-2-methoxyethyl carbamate (30b). Methyl iodide (1.89 mL, 30.4 mmol) was added to a stirred mixture of alcohol (18) (2.0 g, 7.59 mmol) and silver (I) oxide (2.64 g, 11.4 mmol) in acetonitrile (32 mL). The mixture was heated at 72° C. for 3 hours then stood at ambient temperature for 16 hours. Heating was continued for 1.5 hours at 72° C. then the mixture allowed to cool to ambient temperature, filtered and reduced in vacuo. Flash chromatography over silica, eluting with an ethyl acetate:heptane mixture 1:1 to give methyl ether (30b) (1.05 g, 50%) with an estimated purity of 93%, as a colourless oil together with recovered alcohol (18) (694 mg, 35%). Data for methyl ether (30b); TLC ($R_f$=0.35, EtOAc:heptane 1:1), analytical HPLC main peak, $R_t$=13.082 min., HPLC-MS 278.1 $[M+H]^+$, 577.2 $[2M+Na]^+$; $[\square]_D^{18}$ −54.5° (c=3.487, $CHCl_3$); $\delta_H$ (500 MHz, $CDCl_3$) 3.22-3.27, (2H, m, $CH_2N$ and $CHOCH_3$), 3.42 (3H, s, $CHOCH_3$), 3.44-3.53 (1H, m, $CH_2N$), 4.58-4.67 (2H, m, $OCH_2CH$=CH), 4.88 (1H, m, OCHCH=CH), 5.09 (2H, s, $OCH_2Ph$), 5.18 (1H, brs, NH), 5.80-5.84 and 5.97-6.00 (2H total, m, $CH_2CH$=CH), 7.29-7.36 (5H, m, aromatic CH); $\delta_C$ (125 MHz, $CDCl_3$) 40.634 ($CH_2NHCbz$), 58.141 ($OCH_3$), 66.697 ($CH_2Ph$), 75.621 ($OCH_2CH$=CH), 81.912 ($CHOCH_3$), 86.193 (OCHCH=CH), 126.506, 128.084, 128.100, 128.328, and 128.491 ($OCH_2CH$=CH and Cbz aromatic CH), 136.563 (Cbz quaternary), 156.481 (Cbz C=O).

(ii) Alternative preparation of Benzyl (R)-2-((S)-2,5-dihydrofuran-2-yl)-2-methoxyethylcarbamate (30b). Trimethyloxonium fluoroborate (2.16 g, 14.61 mmol) was added to a stirred mixture of benzyl (R)-2-((S)-2,5-dihydrofuran-2-yl)-2-hydroxyethylcarbamate (18) (2.26 g, 8.59 mmol), 4 Å molecular sieves (7.1 g), 1,8-bis(dimethylamino)naphthalene (11.0 g, 51.6 mmol) and dichloromethane (55 mL) under an atmosphere of argon. The mixture was stirred for 2 hours then filtered through celite in vacuo. The filter cake was washed with dichloromethane (300 mL) then the solvents removed in vacuo from the filtrate. The residue was triturated with diethyl ether (100 mL) then the yellow solid removed by filtration in vacuo. The solid was washed with diethyl ether (100 mL) then the combined filtrates washed with hydrochloric acid (2.5M, 1×50 mL then 2×25 mL), brine (50 mL) then dried ($Na_2SO_4$), filtered and reduced in vacuo to leave a pale yellow oil (1.93 g). Flash chromatography over silica, eluting with ethyl acetate:heptane mixtures 5:95 to 50:50 gave methylether (30b) as a colourless oil (1.42 g, 60%).

(iii) Preparation of Benzyl (R)-2-((1S,2R,5S)-3,6-dioxabicyclo[3.1.0]hexan-2-yl)-2-methoxyethyl carbamate anti-(31b). To a solution of methyl ether (30b) (1.0 g, 3.61 mmol) in acetonitrile (20 mL) and aqueous $Na_2$.EDTA (20 mL, 0.4 mmol solution) at 0° C. was added 1,1,1-trifluoroacetone (3.87 mL, 43.3 mmol). To this solution was added in portions a mixture of sodium bicarbonate (2.54 g, 30.3 mmol) and OXONE® (6.87 g, 11.2 mmol) over a period of 1.5 hours. The mixture was stirred for 30 minutes then diluted with water (50 mL) and the product extracted into dichloromethane (3×50 mL). The combined organic layers were washed with brine (60 mL) then dried ($Na_2SO_4$), filtered and reduced in vacuo. Flash chromatography over silica, eluting with ethyl acetate:heptane mixtures 7:93 to 50:50 gave a 3:1 mixture of anti-(31b) and syn-epoxide benzyl (R)-2-((1R,2R,5R)-3,6-dioxabicyclo[3.1.0]hexan-2-yl)-2-methoxyethyl carbamate respectively (611 mg, 58%) as a colourless oil. TLC ($R_f$=0.25, EtOAc:heptane 1:1), analytical HPLC two main peaks, $R_t$=11.792 and 12.132 min. (approx. 3:1 respectively). HPLC-MS 294.2 $[M+H]^+$, 316.1 $[M+Na]^+$, 609.3 $[2M+Na]^+$.

(iv) (3R,3aR,6R,6aS)— (9H-Fluoren-9-yl)methyl 3-hydroxy-6-methoxytetrahydro-2H-furo[3,2-b]pyrrole-4(5H)-carboxylate (5b). Ethanol (30 mL) was added dropwise to a mixture of 10% palladium on charcoal (200 mg) and syn-/anti-epoxides respectively (605 mg, 2.06 mmol) under an atmosphere of argon. The argon was replaced by hydrogen then the suspension was stirred for 2.5 hours then filtered through celite in vacuo. The filter cake was washed with ethanol then the solvents removed in vacuo from the filtrate to obtain the crude (3R,3aR,6R,6aS)-6-methoxyhexahydro-2H-furo[3,2-b]pyrrol-3-ol which was used without further purification.

A solution of sodium carbonate (459 mg, 4.33 mmol) in water (20 mL) was added whilst stirring to a solution of (3R,3aR,6R,6aS)-6-methoxyhexahydro-2H-furo[3,2-b]pyrrol-3-ol in 1,4-dioxane (20 mL). A solution of 9-fluorenylmethoxycarbonyl chloride (614 mg, 2.37 mmol) in 1,4-dioxane (3 mL) was added then the mixture stirred for 1.5 hours then water (30 mL) was added and the product extracted into dichloromethane (3×50 mL). The organic layer was washed with brine (70 mL), then dried ($Na_2SO_4$), filtered and reduced in vacuo to leave a residue. Flash chromatography over silica, eluting with ethyl acetate:heptane mixtures 10:90 to 80:20 gave (in order of elution) syn-epoxide (9H-fluoren-9-yl)methyl (R)-2-((1R,2R,5R)-3,6-dioxabicyclo[3.1.0]hexan-2-yl)-2-methoxyethyl carbamate (111 mg, 14%) as a colourless oil and bicyclic alcohol (5b) (453 mg, 58%) as a white solid. Data for syn-epoxide; TLC ($R_f$=0.22, EtOAc:heptane 1:1), analytical HPLC single main peak, $R_t$=17.108 min.; HPLC-MS 382.2 [M+H]$^+$, 404.2 [2M+Na]$^+$; $[\square]_D^{19}$–24.5° (c=6.120, CHCl$_3$); $\delta_H$ (500 MHz, CDCl$_3$) 3.37-3.56 (3H, m, CHOCH$_3$ and CH$_2$NH), 3.49 (3H, s, OCH$_3$ major), 3.71 (1H, d, J=10.63 Hz, OCH$_2$CH), 3.75 (1H, d, J=7.48 Hz, OCHCHOCH$_3$), 3.79-3.84 (2H, m, OCH$_2$CHCH), 4.04 (1H, d, J=10.67 Hz, OCH$_2$CH), 4.23 (1H, t, J=6.97 Hz, Fmoc CH), 4.38 (2H, d, J=7.12 Hz, Fmoc CH$_2$), 5.16 (1H brs, NH), 7.29-7.76 (8H, Fmoc aromatic CH); $\delta_C$ (125 MHz, CDCl$_3$), 40.837 (CH$_2$NHFmoc), 47.259 (Fmoc CH), 56.424/56.648 (OCH$_2$CHCH), 58.047 (OCH$_3$), 66.688 (Fmoc CH$_2$), 67.700 (OCH$_2$CH), 77.573 (OCHCHOCH$_3$), 78.238 (CHOCH$_3$), 119.932, 125.088, 126.998 and 127.617 (Fmoc aromatic CH), 141.277, 143.021 and 144.021 (Fmoc quaternary), 156.521 (Cbz C=O). Data for bicyclic alcohol (5b); TLC ($R_f$=0.05, EtOAc:heptane 1:1), analytical HPLC single main peak, $R_t$=15.004 min., HPLC-MS 382.2 [M+H]$^+$, 404.2 [M+Na]$^+$, 785.3 [2M+Na]$^+$; $[\square]_D^{16}$–10.0° (c=4.016, CHCl$_3$); $\delta_H$ (500 MHz, CDCl$_3$) mixture of rotamers major: minor 4:3; 0.96 (0.57H, d, J=3.54 Hz, OH major), 2.51 (0.43H, d, J=3.50 Hz, OH minor), 2.93 (0.57H, t, J=10.12 Hz, FmocNCH$_2$ major), 3.07-3.15 (0.43H, m, FmocNCH$_2$ minor), 3.36 (1.71H, s, OCH$_3$ major), 3.41 (1H, brd, J=4.63 Hz, FmocNCH major), 3.46 (1.29H, s, OCH$_3$ minor), 3.48-3.52 (0.57H, m, OCH$_2$CHOH major), 3.56-3.64 (1.14H, m, CHOCH$_3$ major and OCH$_2$CHOH major), 3.73-3.86 (2.43H, m, OCH$_2$CHOH, FmocNCH$_2$ and CHOCH$_3$ minor), 4.00 (0.43H, dd, 9.90 Hz, OCH$_2$CHOH minor), 4.16 (1H, dd, 1.09 Hz, FmocNCH minor), 4.20-4.25 (1H, m, Fmoc CH), 4.38-4.43 (0.86H, m, OCHOH minor and 1×Fmoc CH$_2$ minor), 4.45 (0.57H, t, J=4.29 Hz, CHCHOCH$_3$ major), 4.49 (0.43H, dd, 6.82 Hz, Fmoc CH$_2$ minor), 4.69-4.73 (0.43H, m, OCHCHOCH$_3$ minor), 4.75 (0.57H, dd, 3.74 Hz, Fmoc CH$_2$ major), 4.81 (0.57H, dd, 4.01 Hz, Fmoc CH$_2$ major), 7.28-7.81 (8H, Fmoc aromatic CH); $\delta_C$ (125 MHz, CDCl$_3$) 47.276/47.369 (Fmoc CH), 47.504/47.898 (FmocNCH$_2$), 57.788/57.839 (OCH$_3$), 65.761/67.333 (Fmoc CH$_2$), 68.812/69.338 (FmocNCH), 74.940/75.145 (OCH$_2$CHOH), 76.276/76.746 (OCH$_2$CHOH), 78.834/79.335 (OCHCHOCH$_3$), 78.994/79.507 (OCHCHOCH$_3$), 119.859, 119.895, 120.036, 124.389, 124.442, 124.877, 124.960, 127.035, 127.059, 127.451, 127.494, 127.803, 127.89 and 127.941 (Fmoc aromatic CH), 141.348, 141.373, 141.434, 143.585, 143.585, 143.729, 143.911 and 143.947 (Fmoc quaternary), 153.937/154.896 (Fmoc C=O).

(v) (3aS,6R,6aS)-(9H-Fluoren-9-yl)methyl 6-methoxy-3-oxotetrahydro-2H-furo[3,2-b]pyrrole-4(5H)-carboxylate (5c). Dess-Martin periodinane (985 mg, 2.32 mmol) was added to a stirred solution of bicyclic alcohol (5b) (443 mg, 1.16 mmol) in dichloromethane (17 mL) at 0° C. under an atmosphere of argon. The mixture was stirred for 2 hours then allowed to warm to ambient temperature then stirred for 2 hours, then diluted with dichloromethane (30 mL). The organic phase was washed with a mixture of saturated aqueous sodium bicarbonate and 0.5M sodium thiosulphate solution (1:1, 30 mL), then saturated aqueous sodium bicarbonate (20 mL), then brine (20 mL), then dried (Na$_2$SO$_4$), filtered and reduced in vacuo. Flash chromatography over silica, eluting with ethyl acetate:heptane mixtures 20:80 to 40:60 gave bicyclic ketone (5c) (305 mg, 69%) as a white solid. TLC ($R_f$=0.50, EtOAc:heptane 3:1), analytical HPLC broad main peak, $R_t$=14.547-17.583 min., HPLC-MS 380.2 [M+H]$^+$, 781.3 [2M+Na]$^+$; $[\square]_D^{16.5}$–95.5° (c=2.565, CHCl$_3$); $\delta_H$ (500 MHz, CDCl$_3$) mixture of rotamers approx. 1:1; 3.46 (3H, s, OCH$_3$), 3.42-3.53 (1H, m, FmocNCH$_2$), 3.64-3.70 (0.5H, m, FmocNCH$_2$), 3.75-3.81 (0.5H, m, FmocNCH$_2$), 3.90-3.95 (1H, m, OCHCHOMe), 4.09-4.15 (1H, m, OCH$_2$C=O), 4.20-4.35 (3H, m, 1×Fmoc CH, 1×OCH$_2$C=O, 0.5×Fmoc-NCH, and 0.5×Fmoc CH$_2$), 4.38-4.44 (1H, m, FmocNCH and Fmoc CH$_2$), 4.50-4.61 (1H, m, Fmoc CH$_2$), 4.88-4.91 (1H, m, OCHCHOCH$_3$), 7.28-7.77 (8H, Fmoc aromatic CH); $\delta_C$ (125 MHz, CDCl$_3$); 46.944/47.188 (Fmoc CH), 48.972/49.088 (FmocNCH$_2$), 58.036 (OCH$_3$), 60.295/60.704 (FmocNCH), 67.746/68.277 (Fmoc CH$_2$), 71.427 (OCH$_2$C=O), 79.339/80.093 (OCHCHOCH$_3$), 79.424/80.241 (OCHCHOCH$_3$), 119.904, 119.993, 120.191, 124.990, 125.190, 125.380, 127.053, 127.094, 127.734, 127.848 and 128.038 (Fmoc aromatic CH), 141.302, 143.604, 143.910 and 144.285 (Fmoc quaternary), 155.141 (Fmoc C=O), 208.397/208.594 (ketone C=O).

Preparation of (3R,3aR,6R,6aS)-Benzyl 3-hydroxy-6-methoxytetrahydro-2H-furo[3,2-b]pyrrole-4(5H)-carboxylate (73)

Sodium hydride (60% dispersion in oil, 164 mg, 4.11 mmol) was added over 1 minute to a stirred solution consisting of an ~4:1 mixture of anti-epoxide benzyl (R)-2-((1S,2R,5S)-3,6-dioxabicyclo[3.1.0]hexan-2-yl)-2-methoxyethyl carbamate (31b) and syn-epoxide benzyl (R)-2-((1R,2R,5R)-3,6-dioxabicyclo[3.1.0]hexan-2-yl)-2-methoxyethyl carbamate (963 mg, 3.29 mmol total) in tetrahydrofuran (10 mL) at 0° C. under an atmosphere of argon. The mixture was stirred at 0° C. for 30 minutes then at ambient temperature for 2.75 hours then dichloromethane (150 mL) added. The organic layer was washed with brine (75 mL), then dried (Na$_2$SO$_4$), filtered and reduced in vacuo to leave a residue (1.0 g). Flash chromatography over silica, eluting with ethyl acetate:heptane mixtures 30:70 to 90:10 gave (3R,3aR,6R,6aS)-benzyl 3-hydroxy-6-methoxytetrahydro-2H-furo[3,2-b]pyrrole-4(5H)-carboxylate (73) as a colourless oil (657 mg, 85% based on anti-epoxide). TLC ($R_f$=0.30, EtOAc:heptane 2:1), analytical HPLC single main peak, $R_t$=8.70 min.; HPLC-MS 294.1 [M+H]$^+$, 609.2 [2M+Na]$^+$; $[\square]_D^{23.0}$–29.4° (c=2.38, CHCl$_3$); $\delta_C$ (125 MHz, CDCl$_3$) 47.93/48.02 (CbzNCH$_2$), 57.87/57.90 (OCH$_3$), 67.39/67.46 (CH$_2$Ph), 68.43/69.40 (CbzNCH), 75.24/75.41 (OCH$_2$CHOH), 76.07 (OCH$_2$CHOH), 78.88/79.22/79.56/79.72 (OCHCHOCH$_3$)+(OCHCHOCH$_3$), 127.96/128.03/128.17/128.24/128.35/128.55/128.69 (aromatic CH), 136.06/136.18 (aromatic quaternary), 154.19/155.02 (Cbz C=O).

Preparation of (3aS,6S,6aR)-(9H-fluoren-9-yl)methyl 6-(tert-butoxycarbonylamino)-3-oxotetrahydro-2H-furo[3,2-b]pyrrole-4(5H)-carboxylate (8c)

(i) Preparation of (3R,3aR,6R,6aS)— Benzyl 3-hydroxy-6-(tosyloxy)tetrahydro-2H-furo[3,2-b]pyrrole-4(5H)-carboxylate (34b). Ethanol (1.5 mL) was added dropwise to a mixture of 10% palladium on charcoal (10 mg) and anti-(33b) (12.0 mg, 0.028 mmol) under an atmosphere of argon. The argon was replaced by hydrogen then the suspension was stirred for 1.75 hours before filtering the mixture through celite in vacuo. The filter cake was washed with ethanol (7.5 mL) then the solvents removed in vacuo from the filtrate. The residue was azeotroped with toluene (2 mL) to obtain (3R,3aR,6R,6aS)-3-hydroxyhexahydro-2H-furo[3,2-b]pyrrol-6-yl 4-methylbenzenesulfonate (7.6 mg, 89%) as a pale yellow oil which was used without further purification. TLC ($R_f$=0.01, EtOAc:heptane 1:1), HPLC-MS 300.1 [M+H]$^+$, 621.2 [2M+Na]$^+$.

A solution of sodium carbonate (6.2 mg, 0.058 mmol) in water (0.15 mL) was added whilst stirring to a solution of (3R,3aR,6R,6aS)-3-hydroxyhexahydro-2H-furo[3,2-b]pyrrol-6-yl 4-methylbenzenesulfonate in 1,4-dioxane (0.3 mL). Benzylchloroformate (5.9 μL, 0.042 mmol) was added then the mixture stirred for 2 hours. Water (5 mL) was added and the product extracted into dichloromethane (2×5 mL). The organic layer was washed with brine (5 mL), then dried ($Na_2SO_4$), filtered and reduced in vacuo to leave a residue (10.6 mg). Flash chromatography over silica, eluting with ethyl acetate:heptane mixtures 20:80 to 50:50 gave bicyclic alcohol (34b) (6.6 mg, 54%) as a white solid. TLC ($R_f$=0.20, EtOAc:heptane 1:1), analytical HPLC single main peak, $R_t$=17.32 min., HPLC-MS 434.1 $[M+H]^+$, 889.2 $[2M+Na]^+$; $[\square]_D^{23.0}$ −25.7° (c=2.53, $CHCl_3$); $\delta_H$ (500 MHz, $CDCl_3$) mixture of rotamers major:minor 2:1; 2.01 (0.33H, brs, OH minor), 2.43 (3H, s, aryl-$CH_3$), 2.77 (0.66H, brs, OH major), 3.18-3.24 (0.33H, m, $CbzNCH_2$ minor), 3.33-3.38 (0.66H, m, $CbzNCH_2$ major), 3.79-3.85 (1H, m, $OCH_2CHOH$), 3.86-3.91 (1H, m, $CbzNCH_2$), 3.92-3.96 (0.33H, m, $OCH_2CHOH$ minor), 3.96-4.01 (0.66H, m, $OCH_2CHOH$ major), 4.13-4.16 (1H, m, CbzNCH), 4.35 (0.33H, m, $OCH_2CHOH$ minor), 4.45 (0.66H, m, $OCH_2CHOH$ major), 4.56 (0.33H, t, J=4.64 Hz, TsOCHCH, minor), 4.64 (0.66H, t, J=4.36 Hz, TsOCHCH, major), 4.71-4.78 (1H, m, TsOCHCH), 5.06-5.17 (2H, m, $CH_2Ph$), 7.31-7.38 (7H, m, phenyl CH and aromatic $CH_3CCH$), 7.80 (2H, d, J=8.33 Hz, aromatic $OSO_2CCH$); $\delta_C$ (125 MHz, $CDCl_3$) 21.683 (aryl-$CH_3$), 47.384/47.855 ($CbzNCH_2$), 67.636/67.717 ($CH_2Ph$), 68.042/68.817 (CbzNCH), 75.525/75.967 ($OCH_2CHOH$), 75.967/76.836 ($OCH_2CHOH$), 76.068/76.401 (TsOCHCH), 79.342/80.208 (TsOCHCH), 127.965, 128.107, 128.382, 128.510, 128.605, 128.753, 129.940 and 129.997 (aromatic CH), 132.991 ($CHOSO_2C$ quaternary), 135.779/135.869 (Cbz quaternary), 145.319 ($CH_3C$ quaternary), 153.862/154.751 (Cbz C=O).

(ii) Preparation of (3R,3aR,6S,6aS)-benzyl 6-azido-3-hydroxytetrahydro-2H-furo[3,2-b]pyrrole-4(5H)-carboxylate (36b). Sodium azide (15 mg, 0.231 mmol) was added to a stirred solution of bicyclic alcohol (34b) (50 mg, 0.115 mmol) in dimethylformamide (1 mL) under an atmosphere of argon. The mixture was heated at 70° C. for 18 hours then sodium azide (10 mg, 0.154 mmol) was added and heating continued at 105° C. for 21 hours. Water (6 mL) was added and the product extracted into tert-butyl methyl ether (3×3 mL). The organic layer was washed with brine (9 mL), then dried ($Na_2SO_4$), filtered and reduced in vacuo to leave a residue (56 mg). Flash chromatography over silica, eluting with ethyl acetate:pentane mixtures 1:2 gave bicyclic azidoalcohol (36b) (28 mg, 80%) as a (viscous) colourless oil. TLC ($R_f$=0.25, EtOAc:heptane 1:1), analytical HPLC single main peak, $R_t$=13.43 min., HPLC-MS 277.2 $[M-N_2+H]^+$, 327.2 $[M+Na]^+$, 631.3 $[2M+Na]^+$; $[\square]_D^{17}$ −22.4° (c=1.56, $CHCl_3$); $\delta_H$ (500 MHz, $CDCl_3$) mixture of rotamers major:minor 2:1; 1.9 and 3.2 (approx. 1H total, each brs, OH), 3.39-3.45 (1H, m, $CbzNCH_2$), 3.74 (0.66H, d, J=12.37 Hz, $CbzNCH_2$, major), 3.78-3.91 (2H, m, $OCH_2CHOH$), 3.87 (0.33H, J=12.24 Hz, $CbzNCH_2$, minor), 4.02 (1H, d, J=4.21 Hz, $CHN_3$), 4.28 (0.33H, d, J=4.45 Hz, CbzNCH minor), 4.30 (0.66H, d, J=4.58 Hz, CbzNCH major), 4.39 (0.33H, brs, $OCH_2CHOH$ minor), 4.50 (0.66H, brs, $OCH_2CHOH$ major), 4.61 (1H, d, J=4.56 Hz, $CHCHN_3$), 5.13 (0.33H, d, J=12.08 Hz, $CH_2Ph$ minor), 5.13 (1.322H, s, $CH_2Ph$ major), 5.23 (0.33H, d, J=12.27 Hz, $CH_2Ph$ minor), 7.30-7.38 (5H, m, phenyl CH); $\delta_C$ (125 MHz, $CDCl_3$) 50.000/50.282 ($CbzNCH_2$), 62.823/63.317 ($CHN_3$), 67.601 ($CH_2Ph$), 68.013/68.998 (CbzNCH), 74.633/74.660 ($OCH_2CHOH$), 75.378/76.251 ($OCH_2CHOH$), 84.223/85.159 ($CHCHN_3$), 127.959, 127.976, 128.292, 128.368, 128.587 and 128.715 (aromatic CH), 135.933/136.109 (Cbz quaternary), 154.172/154.808 (Cbz C=O).

(iii) Preparation of (3R,3aR,6S,6aS)-benzyl 6-(tert-butoxycarbonylamino)-3-hydroxytetrahydro-2H-furo[3,2-b]pyrrole-4(5H)-carboxylate (37b).

(a) Reduction of azide. Azide (36b) (54 mg, 0.177 mmol) was dissolved in THF (6 mL) with stirring and water (32 □L, 1.77 mmol) added followed by triphenylphosphine (70 mg, 0.266 mmol). The mixture was heated at 45° C. under nitrogen overnight. The mixture was reduced in vacuo to a syrup used directly in the next step. HPLC-MS 279.1 $[M+H]^+$, 301.1 $[M+Na]^+$, 557.2, 579.3 $[2M+Na]^+$.

(b) Amine protection. Crude amine (~0.18 mmol) was dissolved in 1,4-dioxan (2.5 mL) with stirring and ice-cooled and a solution of sodium carbonate (42 mg, 0.37 mmol) in water (2.5 mL) was added. Di-tert-butylcarbonate (46 mg, 0.27 mmol) in 1,4-dioxane (1.0 mL) was added dropwise over 30 minutes and the mixture stirred overnight at ambient temperature. DCM (20 mL) was then added and the organic phase washed with 0.1N HCl (20 mL), sat. $NaHCO_3$ (20 mL), then brine (20 mL) and dried ($Na_2SO_4$). The organic layer was filtered and reduced in vacuo to leave a clear gum. The crude gum was purified on a 5 g Flash silica cartridge eluting with a gradient of heptane:ethyl acetate 5:1→1:2 to provide alcohol (37b) as a white foam (65.5 mg) contaminated with triphenylphosphine oxide. TLC ($R_f$=0.43, EtOAc:heptane 2:1), analytical HPLC $R_t$=15.05 min (product 8.25% by UV) and 15.39 min (triphenylphosphine oxide 91.25% by V), HPLC-MS 279.1 $[M+H-Boc]^+$, 323.1 $[M+2H-Bu]^+$, 401.1 $[M+Na]^+$, 557.2, 779.3 $[2M+Na]^+$.

(iv) Preparation of (3R,3aR,6S,6aR)-(9H-fluoren-9-yl) methyl 6-(tert-butoxycarbonylamino)-3-hydroxytetrahydro-2H-furo[3,2-b]pyrrole-4(5H)-carboxylate (8b). Bicycle alcohol (37b) (60 mg, ~0.16 mmol) was dissolved in methanol (5 mL), cooled to 0° C. and 10% palladium on charcoal (15 mg) added. The mixture was stirred, then evacuated and flushed with hydrogen. The mixture was warmed to ambient temperature and after 2 h. filtered through celite. The filter cake was washed with ethanol (3×5 mL) and the combined filtrates reduced in vacuo to provide the crude amine (~16 mg). HPLC-MS 245.2 $[M+H]^+$, 279.1, 511.3 $[M+Na]^+$, 557.2. The crude amine was dissolved in 1,4-dioxane (2.5 mL) with stirring, ice-cooled and a solution of sodium carbonate (35.5 mg, 0.333 mmol) in water (2.5 mL) was added. 9-Fluorenylmethyl chloroformate (43 mg, 0.166 mmol) in 1,4-dioxane (1.0 mL) was added dropwise over 30 minutes and the mixture stirred for a further 1 h. EtOAc (25 mL) was then added and the organic phase washed with 0.1N HCl (25 mL), sat. $NaHCO_3$ (25 mL), then brine (25 mL) and dried ($Na_2SO_4$). The organic layer was filtered and reduced in vacuo to leave a clear film (72.5 mg). The crude film was purified on a 5 g Flash silica cartridge eluting with a gradient of heptane:ethyl acetate 6:1→3:1 to provide alcohol (8b) as a white solid (40.0 mg) with triphenylphosphine oxide. TLC ($R_f$=0.23, EtOAc:heptane 1:1), analytical HPLC 15.39 min (triphenylphosphine oxide 63.8% by UV) and $R_t$=18.30 min (product 33.8% by UV), HPLC-MS 411.2 $[M+2H-Bu]^+$, 489.2 $[M+Na]^+$, 955.4 $[2M+Na]^+$ and 279.1, 557.2.

(v) Preparation of (3aS,6S,6aR)-(9H-fluoren-9-yl)methyl 6-(tert-butoxycarbonylamino)-3-oxotetrahydro-2H-furo[3, 2-b]pyrrole-4(5H)-carboxylate (8c). Bicycle alcohol (8b) (40 mg, ~0.08 mmol) was dissolved in anhydrous dichloromethane (3 mL) with stirring under argon. Dess-Martin periodinane (68 mg, 0.16 mmol) was added and the mixture stirred overnight. The mixture was diluted with DCM (20 mL) and washed with sat. NaHCO$_3$/0.25M Na$_2$S$_2$O$_3$, sat. NaHCO$_3$, brine (20 mL each) and dried (Na$_2$SO$_4$). The organic layer was filtered and reduced in vacuo to leave a colourless gum (~41 mg). The crude gum was purified on a 5 g Flash silica cartridge eluting with a gradient of heptane: ethyl acetate 5:1→2:1 to provide ketone (8c) as a white solid (17.3 mg, 0.037 mmol). TLC (R$_f$=0.36, EtOAc:heptane 1:1), analytical HPLC broad peak with R$_t$=18.14-20.32 min, HPLC-MS 409.2 [M+2H−Bu]$^+$, 465.2 [M+H]$^+$, 487.2 [M+Na]$^+$, 951.4 [2M+Na]$^+$; [□]$_D^{22}$−67.6° (c=0.74, CHCl$_3$).

Preparation of (3aS,6R,6aR)-(9H-fluoren-9-yl)methyl 6-(tert-butoxycarbonylamino)-3-oxotetrahydro-2H-furo[3,2-b]pyrrole-4(5H)-carboxylate (7c)

(i) Preparation of (3R,3aR,6S,6aS)-Benzyl 3-hydroxy-6-(tosyloxy)tetrahydro-2H-furo[3,2-b]pyrrole-4(5H)-carboxylate (34). Ethanol (6 mL) was added dropwise to a mixture of 10% palladium on charcoal (50 mg) and anti-(33) (547 mg, 1.26 mmol) under an atmosphere of argon. The argon was replaced by hydrogen then the suspension was stirred at 20° C. for 3.75 hours before filtering the mixture through celite in vacuo. The filter cake was washed with ethanol (40 mL) then the solvents removed in vacuo from the filtrate to obtain (3R,3aR,6S,6aS)-3-hydroxyhexahydro-2H-furo[3,2-b]pyrrol-6-yl 4-methylbenzenesulfonate which was used without further purification.

A solution of sodium carbonate (281 mg, 2.65 mmol) in water (5 mL) was added whilst stirring to a solution of (3R,3aR,6S,6aS)-3-hydroxyhexahydro-2H-furo[3,2-b]pyrrol-6-yl 4-methylbenzenesulfonate in 1,4-dioxane (5 mL). A solution of benzyl chloroformate (0.225 mL, 1.96 mmol) in 1,4-dioxane (2.5 mL) was added over 20 minutes then the mixture stirred for 35 minutes, then water (50 mL) was added and the product extracted into dichloromethane (2×50 mL). The organic layer was washed with brine (50 mL), then dried (Na$_2$SO$_4$), filtered and reduced in vacuo to leave a residue. Flash chromatography over silica, eluting with ethyl acetate:heptane mixtures 25:75 to 50:50 gave bicyclic alcohol (34) (518 mg, 95%) as a white solid. TLC (R$_f$=0.25, EtOAc:heptane 3:2), analytical HPLC single main peak, R$_t$=17.86 min., HPLC-MS 434.2 [M+H]$^+$, 456.1 [M+Na]$^+$, 889.3 [2M+Na]$^+$; [□]$_D^{16.5}$−23.1° (c=1.190, CHCl$_3$); δ$_H$ (500 MHz, CDCl$_3$) mixture of rotamers major:minor 3:2; 1.96 (0.4H, d, J=4.11 Hz, OH minor), 2.43 (1.8H, s, aryl-CH$_3$ major), 2.44 (1.2H, s, aryl-CH$_3$ minor), 2.59 (0.6H, d, J=3.42 Hz, OH major), 3.35 (0.4H, dd, 3.71 Hz, CbzNCH$_2$ minor), 3.41 (0.6H, dd, 3.80 Hz, CbzNCH$_2$ major), 3.74-3.88 (3H, m, 2×OCH$_2$CHOH and 1×CbzNCH$_2$), 4.29 (0.4H, s, CbzNCH minor), 4.31 (0.6H, s, CbzNHCH major), 4.37 (0.4H, brs, OCH$_2$CHOH minor), 4.49 (0.6H, brs, OCH$_2$CHOH major), 4.51 (0.6H, d, J=4.59 Hz, TsOCHCH major), 4.64 (0.4H, brd, J=4.44 Hz, TsOCHCH minor), 4.77 (0.4H, d, J=3.43 Hz, TsOCHCH minor), 4.79 (0.6H, d, J=3.53 Hz, TsOCHCH major), 5.06-5.13 (1.6H, m, CH$_2$Ph), 5.21 (0.4H, d, J=12.22 Hz, CH$_2$Ph minor), 7.30 (7H, m, aromatic-CH and CH$_3$CCH), 7.75-7.79 (2H, m, aromatic OSO$_2$CCH); δ$_C$ (125 MHz, CDCl$_3$) 21.658 (aryl-CH$_3$), 51.015/51.082 (CbzNCH$_2$), 67.511/67.622 (CH$_2$Ph), 67.953/68.902 (CbzNCH), 74.375/74.420 (OCH$_2$CHOH), 75.322/76.156 (OCH$_2$CHOH), 79.944/80.600 (TsOCHCH), 83.537/84.651 (TsOCHCH), 127.791, 127.837, 127.942, 128.011, 128.382, 128.485, 128.558, 128.703 and 130.102 (aromatic CH), 133.021/133.087 (CHOSO$_2$C quaternary), 135.895/136.018 (Cbz quaternary), 145.441 (CH$_3$C quaternary), 153.976/154.591 (Cbz C=O).

(ii) Preparation of (3R,3aR,6R,6aS)-benzyl 6-azido-3-hydroxytetrahydro-2H-furo[3,2-b]pyrrole-4(5H)-carboxylate (36). Bicycle alcohol (34) (400 mg, 0.93 mmol) was dissolved in dimethylformamide (2 mL) in a glass pressure tube and sodium azide (120 mg, 1.85 mmol) added. The mixture was sealed and heated at 135° C. with stirring overnight. The viscous dark mixture was reduced in vacuo and the residue partitioned between DCM (25 mL) and brine (25 mL). The organic phase was washed with sat. NaHCO$_3$ (25 mL), brine (25 mL) and dried (Na$_2$SO$_4$). The organic layer was filtered and reduced in vacuo to leave a dark gum (105 mg). The crude gum was partially purified on a 5 g Flash silica cartridge eluting with a gradient of heptane:ethyl acetate 8:1→3:1 to provide azidoalcohol (36) as a thick tan oil (77 mg). TLC (R$_f$=0.50, EtOAc:heptane 2:1) plus an unidentified by-product (R$_f$=0.40, EtOAc:heptane 2:1), HPLC-MS277.1 [M+H−N$_2$]$^+$, 305.1 [M+H]$^+$, 327.1 [M+Na]$^+$, 631.2 [2M+Na]$^+$.

(iii) Preparation of (3R,3aR,6R,6aR)-benzyl 6-(tert-butoxycarbonylamino)-3-hydroxytetrahydro-2H-furo[3,2-b]pyrrole-4(5H)-carboxylate (37).

(a) Reduction of azide. Azide (36) (77 mg, ~0.25 mmol) was dissolved in THF (8.5 mL) with stirring and water (46 □L, 2.53 mmol) added followed by triphenylphosphine (99 mg, 0.38 mmol). The mixture was heated at 45° C. under nitrogen overnight. The mixture was reduced in vacuo, the residue dissolved in DCM (10 mL) and washed with 0.1N HCl (2×5 mL). The aqueous layer was then adjusted to pH 11 with sat. NaCO$_3$ and back extracted with DCM (4×10 mL). The combined DCM back extracts were dried (Na$_2$SO$_4$), filtered and reduced in vacuo to leave a yellow oil (29.8 mg) used directly in the next step. HPLC-MS 279.1 [M+H]$^+$, 301.1 [M+Na]$^+$, 579.3 [2M+Na]$^+$.

(b) Amine protection. Crude amine (29.8 mg, ~0.11 mmol) was dissolved in 1,4-dioxan (1.5 mL) with stirring and ice-cooled and a solution of sodium carbonate (26 mg, 0.24 mmol) in water (1.5 mL) was added. Di-tert-butylcarbonate (28 mg, 0.16 mmol) in 1,4-dioxane (1.0 mL) was added dropwise over 30 minutes and the mixture stirred for a further 1 h at ambient temperature. DCM (20 mL) was then added and the organic phase washed with 0.1N HCl (20 mL), sat. NaHCO$_3$ (20 mL), then brine (20 mL) and dried (Na$_2$SO$_4$). The organic layer was filtered and reduced in vacuo to leave a clear gum (~44 mg). The crude gum was purified on a 5 g Flash silica cartridge eluting with a gradient of heptane:ethyl acetate 6:1→1:1 to provide alcohol (37) as a clear gum (30.0 mg, 0.08 mmol, 32% from azide). TLC (R$_f$=0.40, EtOAc:heptane 2:1), analytical HPLC R$_t$=15.25 min, HPLC-MS 279.1 [M+H−Boc]$^+$, 323.1 [M+2H−Bu]$^+$, 401.1 [M+Na]$^+$, 779.3 [2M+Na]$^+$.

(iv) Preparation of (3R,3aR,6R,6aR)-(9H-fluoren-9-yl)methyl 6-(tert-butoxycarbonylamino)-3-hydroxytetrahydro-2H-furo[3,2-b]pyrrole-4(5H)-carboxylate (7b). Bicycle alcohol (37) (30 mg, 0.08 mmol) was dissolved in methanol (3 mL), cooled to 0° C. and 10% palladium on charcoal (10 mg) added. The mixture was stirred, then evacuated and flushed with hydrogen. The mixture was warmed to ambient temperature and after 5 h. filtered through celite. The filter cake was washed with ethanol (3×5 mL) and the combined filtrates reduced in vacuo to provide the crude amine (~16 mg). HPLC-MS 245.2 [M+H]$^+$, 511.3 [M+Na]$^+$. The crude amine was dissolved in 1,4-dioxane (2.5 mL) with stirring, ice-cooled and a solution of sodium carbonate (18 mg, 0.165 mmol) in water (2.5 mL) was added. 9-Fluorenylmethyl chloroformate (22 mg, 0.084 mmol) in 1,4-dioxane (1.0 mL) was added dropwise over 30 minutes and the mixture stirred for a further 1 h. DCM (25 mL) was then added and the organic phase washed with 0.1N HCl (25 mL), sat. NaHCO$_3$ (25 mL), then brine (25 mL) and dried (Na$_2$SO$_4$). The organic layer was filtered and reduced in vacuo to leave a clear film. The crude film was purified on a 5 g Flash silica cartridge eluting with a gradient of heptane:ethyl acetate 6:1→1:1 to provide alcohol (7b) as a white solid (23.4 mg, 0.05 mmol, 63%). TLC ($R_f$=0.46, EtOAc:heptane 2:1), analytical HPLC $R_t$=18.52 min, HPLC-MS 367.2 [M+H−Boc]$^+$, 411.2 [M+2H−Bu]$^+$, 489.2 [M+Na]$^+$, 955.4 [2M+Na]$^+$; $[\square]_D^{18}$−17.1° (c=2.34, CHCl$_3$).

(v) Preparation of (3aS,6R,6aR)-(9H-fluoren-9-yl)methyl 6-(tert-butoxycarbonylamino)-3-oxotetrahydro-2H-furo[3,2-b]pyrrole-4(5H)-carboxylate (7c). Bicycle alcohol (7b) (23 mg, 0.05 mmol) was dissolved in anhydrous dichloromethane (3 mL) with stirring under argon. Dess-Martin periodinane (42 mg, 0.10 mmol) was added and the mixture stirred overnight. Additional Dess-Martin periodinane (21 mg, 0.05 mmol) was added and the mixture stirred for a further 2 h. The mixture was diluted with DCM (20 mL) and washed with sat. NaHCO$_3$/0.25M Na$_2$S$_2$O$_3$, sat. NaHCO$_3$, brine (25 mL each) and dried (Na$_2$SO$_4$). The organic layer was filtered and reduced in vacuo to leave a colourless film (~26 mg). The crude film was purified on a 5 g Flash silica cartridge eluting with a gradient of heptane:ethyl acetate 6:1→2:1 to provide ketone (7c) as a white solid (17.2 mg, 0.037 mmol, 74%). TLC ($R_f$=0.34, EtOAc:heptane 1:1), analytical HPLC broad peak with $R_t$=17.94-20.0 min, HPLC-MS 365.1 [M+H−Boc]$^+$, 409.1 [M+2H−Bu]$^+$, 465.2 [M+H]$^+$, 487.2 [M+Na]$^+$, 505.2 [M+18+Na]$^+$, 951.3 [2M+Na]$^+$; $[\square]_D^{18}$−84.3° (c=1.72, CHCl$_3$); $^1$H NMR (500 MHz, CDCl$_3$ at 300K): δ 1.45 (s, C(CH$_3$)$_3$, 9H), 3.05 (t, J=10.40 Hz, FmocNCH$_2$, 1H), 4.01 (d, J=16.90 Hz, OCH$_2$C(O), 1H), 4.03-4.08 (b, Fmoc-NCH$_2$, 0.4H), 4.15-4.65 (bm, FmocNCH$_2$+FmocCH+OCH$_2$C(O)+NCHC(O)+FmocCH$_2$, 5.6H), 4.75 (b, BocNH-CHCHO, 1H), 5.07 (b, BocNHCH, 1H), 7.32 (dt, J=0.95, 8.4 Hz, Fmoc H-2 and H-7), 7.39 (t, J=7.50 Hz, Fmoc H-3 and H-6), 7.56 (bd, J=6.2 Hz, 1.0 Fmoc H-1 or H-8), 7.65 (bd, J=6.6 Hz, 0.25 Fmoc H-1 or H-8), 7.73-7.77 (d+m, J=7.40 Hz, Fmoc H-4 and H-5+0.75H-1 or H-8); $^{13}$C NMR (125 MHz, CDCl$_3$ at 300K): δ 28.30 (C(CH$_3$)$_3$), 47.17 (FmoccCH$_2$), 48.21/48.36 (FmocNCH$_2$), 51.83/52.35 (CHNHBoc), 60.95/61.31 (NCHC(O)), 68.00/68.33 (FmocCH$_2$), 70.66 (OCH$_2$C(O)), 80.32/81.12 (BocNHCH-CHO), 119.91/120.02 (Fmoc C-4 and C-5), 124.95/125.01/125.13/125.36 (Fmoc C-1 and C-8), 127.10 (Fmoc C-2 and C-7), 127.75 (Fmoc C-3 and C-6), 141.27/141.33/143.52/143.69/144.30 (Fmoc quaternary aromatics), 154.37/154.66/155.10 (FmOC(O)N+Bu$^t$OC(O)NH), 207.31/207.45 (C=O).

Preparation of (3R,3aR,6S,6aS)-tert-butyl 3-hydroxy-6-(methylthio)tetrahydro-2H-furo[3,2-b]pyrrole-4(5H)-carboxylate (54)

A stirred solution of tosylate (35b) (250 mg, 0.63 mmol) and sodium thiomethoxide [CAS 5188-07-8] (88 mg, 1.25 mmol) in 3 ml of DMA was heated under an atmosphere of argon in a sealed pressure vessel at 90° C. for 2 hours. The mixture was then allowed to cool to ambient temperature then an aqueous saturated solution of ammonium chloride (10 mL) was added. The aqueous phase was extracted with tert-butyl methyl ether (3×7 ml). The organic phase was dried (MgSO$_4$), filtered and reduced in vacuo to leave an oil. Flash chromatography over silica, eluting with diethyl ether:pentane 2:1 gave thiomethylether (54) as colourless oil (0.152 g, 88%). TLC ($R_f$=0.29, Et$_2$O:pentane 2:1), HPLC-MS 220.1 [M+2H−$^t$Bu]$^+$, 573.2 [2M+H]$^+$; $δ_H$ (500 MHz, CDCl$_3$) mixture of rotamers 1:1; 1.46 (4.5H, s, CCH$_3$), 1.49 (4.5H, s, CCH$_3$), 2.16 (3H, s, SCH$_3$), 3.20 (1H, brs, BocNCH$_2$), 3.47-4.05 (4H, m, OCH$_2$CHOH, BocNCH$_2$ and CHSCH$_3$), 4.24-4.45 (2H, m, BocNCH and OCH$_2$CHOH), 4.63 (1H, s, OCHCHSCH$_3$).

Preparation of (3R,3aR,6S,6aS)-(9H-fluoren-9-yl) methyl 3-hydroxy-6-(methylthio)tetrahydro-2H-furo[3,2-b]pyrrole-4(5H)-carboxylate (55)

A solution of HCl in 1,4-dioxane (4M, 5.5 mL) was added to thiomethylether (54) (152 mg, 0.55 mmol). The mixture stirred for 1 hour then the solvents removed in vacuo. The residue was azeotroped with CH$_3$CN (5 mL) to obtain (3R,3aR,6S,6aS)-6-(methylthio)hexahydro-2H-furo[3,2-b]pyrrol-3-ol which was used without further purification.

A solution of (3R,3aR,6S,6aS)-6-(methylthio)hexahydro-2H-furo[3,2-b]pyrrol-3-ol in 1,4-dioxane (5 mL) was added whilst stirring to a solution of sodium carbonate (123 mg, 1.16 mmol) in water (1.5 mL) at 0° C. A solution of 9-fluorenylmethoxycarbonyl chloride (150 mg, 0.58 mmol) in 1,4-dioxane (1.5 mL) was added dropwise over 5 minutes then the mixture allowed to warm to ambient temperature over 2 hours. Water (20 mL) was added and the product extracted into dichloromethane (3×10 mL). The organic layer was dried (Na$_2$SO$_4$), filtered and reduced in vacuo to leave a residue. Flash chromatography over silica, eluting with diethyl ether: pentane mixtures 2:1 gave alcohol (55) as a white solid (130 mg, 60%). TLC ($R_f$=0.19, Et$_2$O:pentane 2:1); HPLC-MS 398.2 [M+H]$^+$, 420.1 [M+Na]$^+$, 817.3 [2M+H]$^+$; analytical HPLC single main peak, $R_t$=16.096 min., $[\square]_D^{17}$−59.4° (c=2.78, CHCl$_3$); $δ_H$ (500 MHz, CDCl$_3$) mixture of rotamers major:minor 4:3; 1.06 (0.57H, d, J=3.63 Hz, OH major), 2.04 (1.71H, s, SCH$_3$ major), 2.14 (1.29H, s, SCH$_3$ minor), 2.57 (0.43H, d, J=2.83 Hz, OH minor), 3.10 (0.57H, d, J=5.40 Hz, FmocNCH$_2$ major), 3.21-3.24 (0.43H, m, FmocNCH$_2$ minor), 3.41 (0.57H, dd, 5.57 Hz, OCH$_2$CHOH major), 3.52-3.82 (4.43H, m, FmocNCH, CHSCH$_3$ OCH$_2$CHOH minor, 1×FmocNCH$_2$ and 1×OCH$_2$CHOH), 3.92 (0.43H, dd, 4.41 Hz, OCH$_2$CHOH minor), 4.23-4.84 (4.57H, m, Fmoc CH, OCHCHSCH$_3$, Fmoc CH$_2$ minor and 1×OCH$_2$CHOH major), 7.28-7.80 (8H, Fmoc aromatic CH); $δ_C$ (125 MHz, CDCl$_3$) 14.574/14.768 (SCH$_3$), 47.234, 47.445, 48.069 and 48.826 (Fmoc CH and CHSCH$_3$), 50.417/50.633 (FmocNCH$_2$), 65.752/67.282 (Fmoc CH$_2$), 68.555/69.282 (FmocNCH), 74.361/74.600 (OCH$_2$CHOH), 75.774/76.148 (OCH$_2$CHOH), 85.505/86.026 (OCHCHOCH$_3$), 119.848, 120.003, 120.029, 124.512, 124.593, 124.946, 127.030, 127.063, 127.427, 127.507, 127.755, 127.771 and 127.892 (Fmoc aromatic CH), 141.196, 141.320, 141.378, 141.428, 143.581, 143.818, 143.890 and 143.964 (Fmoc quaternary), 154.115/154.849 (Fmoc C=O).

Preparation of (3aS,6S,6aS)-(9H-Fluoren-9-yl)methyl 6-(methylthio)-3-oxotetrahydro-2H-furo[3,2-b] pyrrole-4(5H)-carboxylate (56)

Dess-Martin periodinane (130 mg, 0.65 mmol) was added to a stirred solution of alcohol (55) (278 mg, 0.33 mmol) in dichloromethane (10 mL) under an atmosphere of argon. The mixture was stirred for 1 hour then diluted with dichloromethane (25 mL). The organic phase was washed with a mixture of saturated aqueous sodium bicarbonate and 10% aqueous sodium thiosulphate solution (1:1, 20 mL), then dried (Na$_2$SO$_4$), filtered and reduced in vacuo. Flash chromatography over silica, eluting with diethyl ether:pentane mixtures 60:40 to 65:35 gave ketone (56) (113 mg, 87%) as a white solid. TLC ($R_f$=0.24, Et$_2$O:pentane 2:1); analytical HPLC two main peaks, $R_t$=15.71 and 15.91 min.; HPLC-MS 396.1 [M+H]$^+$, 414.1 [M+H$_2$O+Na]$^+$, 813.2 [2M+H]$^+$;

$[\square]_D^{18}$ −137.3° (c=2.33, CHCl$_3$). $\delta_H$ (500 MHz, CDCl$_3$) mixture of rotamers approx. 1:1; 2.15 (1.5H, s, SCH$_3$), 2.19 (1.5H, s, SCH$_3$), 3.30-3.38 (1H, m, CHSMe), 3.68-3.80 (1.5H, m, FmocNCH$_2$), 3.93-4.05 (1.5H, m, 0.5×FmocNCH$_2$ and OCH$_2$C=O), 4.10-4.35 (2.5H, m, OCH$_2$C=O, Fmoc-CH, and 0.5×Fmoc-CH$_2$), 4.40-4.54 (2.5H, m 1.5×Fmoc-CH$_2$ and FmocNCH), 4.74-4.84 (1H, m, OCHCHSCH$_3$), 7.28-7.77 (8H, Fmoc aromatic CH); $\delta_C$ (125 MHz, CDCl$_3$); 14.662 (SCH$_3$), 47.133 (Fmoc-CH), 48.449/48.954 (CHSCH$_3$), 50.539/53.419 (FmocNCH$_2$), 61.005/61.420 (FmocNCH), 67.710/68.437 (Fmoc-CH$_2$), 70.733 (OCH$_2$C=O), 85.174/86.042 (OCHCHSCH$_3$), 119.916, 119.987, 124.917, 124.964, 125.240, 125.448, 127.069, 127.712 and 127.969 (Fmoc aromatic CH), 141.255/141.317, 143.627, 143.778 and 144.264 (Fmoc quaternary), 154.942/ 155.049 (Fmoc C=O), 207.818/207.973 (ketone C=O).

Preparation of (3R,3aR,6S,6aR)-benzyl 3-hydroxy-6-(methylamino)tetrahydro-2H-furo[3,2-b]pyrrole-4 (5H)-carboxylate (57)

A stirred solution of tosylate (34b) (200 mg, 0.46 mmol) and methylamine in ethanol (33% wt, 6 mL) was heated in a sealed pressure vessel at 150° C. for 72 hours. The mixture was then allowed to cool to ambient temperature then solvents removed in vacuo. The residue was dissolved in dichloromethane (20 mL), washed with water (15 mL) then dried (Na$_2$SO$_4$), filtered and reduced in vacuo. Flash chromatography over silica, eluting with dichloromethane:methanol mixtures 97:3 to 95:5 gave methylaminoalcohol (57) as a pale yellow solid (47 mg, 35%). TLC (R$_f$=0.22, DCM:MeOH 93:7), HPLC-MS 293.1 [M+H]$^+$, 315.2 [M+Na]$^+$, 607.3 [2M+Na]$^+$; $\delta_H$ (500 MHz, CDCl$_3$) mixture of rotamers major: minor 3:2; 2.42 (1.8H, s, NHCH$_3$ major), 2.3 (1.2H, s, NHCH$_3$ minor), 3.14-3.16 (1H, m, CHNHCH$_3$), 3.35-4.48 (7H, m, OCH$_2$CHOH, CHCHCHCH$_2$NCbz), 5.06 and 5.22 (0.8H total, each d, J=12.22 Hz, Cbz minor), 5.12 (1.2H, s, Cbz major), 7.27-7.37 (5H, m, aromatic CH).

Preparation of (3R,3aR,6S,6aR)-benzyl 6-(tert-butoxycarbonyl(methyl)amino)-3-hydroxytetrahydro-2H-furo[3,2-b]pyrrole-4(5H)-carboxylate (58)

A solution of di-tert-butyl dicarbonate (48 mg, 0.22 mmol) and diisopropyl ethyl amine (30 mg, 0.23 mmol) in dichloromethane (1.5 mL) was added dropwise over 5 minutes to a solution of methylaminoalcohol (57) (47 mg, 0.161 mmol) dichloromethane (1.5 mL). The mixture was stirred for 16 hours then diluted with dichloromethane (10 mL), then washed with hydrochloric acid (1M, 5 mL), reduced in vacuo to leave Boc alcohol (58) as a yellow oil (72 mg). TLC (R$_f$=0.41, Et$_2$O), HPLC-MS 293.1 [M−Boc+H]$^+$, 337.1 [M+2H−$^t$Bu]$^+$, 415.2 [M+Na]$^+$, 807.3 [2M+Na]$^+$.

Preparation of (3R,3aR,6S,6aS)-tert-butyl 6-ethoxy-3-hydroxytetrahydro-2H-furo[3,2-b]pyrrole-4(5H)-carboxylate (59)

A stirred mixture of tosylate (35b) (20 mg, 0.05 mmol), ethanol (1 mL) and sodium ethoxide solution in ethanol (21% wt, 94 µL, 0.25 mmol) was heated under an atmosphere of argon at 80° C. for 16 hours. The mixture was diluted with aqueous saturated sodium hydrogen carbonate solution (10 mL) then extracted with tert-butyl methyl ether (3×5 mL). The organic phase was dried (MgSO$_4$), filtered and reduced in vacuo to leave an oil. Flash chromatography over silica, eluting with diethyl ether:pentane mixtures 65:35 to 83:17 gave ethoxyalcohol (59) as a pale yellow solid (1 mg, 7%). TLC (R$_f$=0.50, Et$_2$O); analytical HPLC main peak, R$_t$=15.35 min., HPLC-MS 218.1 [M+2H−$^t$Bu]$^+$, 296.1 [M+Na]$^+$, 569.3 [2M+Na]$^+$.

Preparation of 4-(4-cyclobutylpiperazin-1-yl)benzoic Acid (64)

(i) Methyl 4-(piperazin-1-yl)benzoate (CAS 163210-97-7, 500 mg, 2.27 mmol) was dissolved in THF (10 mL) and water (0.2 mL) with stirring. Cyclobutanone (0.238 g, 3.4 mmol) was added followed by acetic acid (0.5 mL) and sodium cyanoborohydride (0.211 g, 3.4 mmol). The mixture was refluxed for 6 h, cooled and reduced in vacuo. The residue was dissolved in 1N HCl (3 mL) and water (12 mL) then washed with ethyl acetate (2×10 mL). The aqueous layer was adjusted to pH 10 with potassium carbonate and extracted with ethyl acetate (3×10 mL). The combined organics were dried (MgSO$_4$), filtered and reduced in vacuo to give crude methyl ester (0.56 g).

(ii) Methyl ester (0.51 g, assume 1.85 mmol) was suspended in 10% NaOH (3 mL) and water (3 mL) added. The mixture was heated at 80° C. for 2 h, then cooled to 0° C. The mixture was acidified to pH 2 with 6N HCl, then cooled for 2 h at −5° C. A tan solid was filtered and washed thoroughly with hexane and dried in vacuo to give acid (64) (yield 0.25 g). HPLC-MS 261 [M+H]$^+$.

Preparation of 4-(1-ethylpiperidin-4-yl)benzoic Acid (65)

(i) Methyl 4-(piperidin-4-yl)benzoate (CAS 281235-04-9, 1.0 g, 4.6 mmol), DIPEA (0.653 g, 5.07 mmol) and ethyl bromide (0.516 mL, 6.9 mmol) were dissolved in 1,2-dimethoxyethane (18 mL) and refluxed at 78° C. overnight. The mixture was cooled, reduced in vacuo and the residue was partitioned between ethyl acetate and aq. sodium carbonate. The aqueous phase was extracted twice with ethyl acetate and the combined organics were dried (MgSO$_4$), filtered and reduced in vacuo to give crude methyl ester. The crude ester was purified over silica gel eluting with CHCl$_3$:MeOH (97.5: 2.5 v/v).

(ii) Methyl ester (0.51 g, assume 2.05 mmol) was suspended in 10% NaOH (3 mL) and water (3 mL) added. The mixture was heated at 80° C. for 2 h, then cooled to 0° C. The mixture was acidified to pH 2 with 6N HCl, then cooled for 2 h at −5° C. A solid was filtered and washed thoroughly with hexane and dried in vacuo to give acid (65) (yield 0.25 g).

Preparation of 4-(1-cyclopropylpiperidin-4-yl)benzoic Acid (66)

(i) Methyl 4-(piperidin-4-yl)benzoate (CAS 281235-04-9, 0.5 g, 2.27 mmol) was dissolved in a mixture of THF (10 mL) and MeOH (10 mL). Acetic acid (1.38 g, 22.7 mmol) and [(1-ethoxycyclopropyl)oxy]trimethylsilane (0.8 g, 4.6 mmol) were added followed by sodium cyanoborohydride (0.433 g, 6.9 mmol). The mixture was stirred for 7 h then reduced in vacuo. The residue was dissolved in 1N HCl (3 mL) and water (12 mL) then washed with ethyl acetate (2×10 mL). The aqueous layer was adjusted to pH 10 with potassium carbonate and extracted with ethyl acetate (3×10 mL). The combined organics were washed with brine then dried (MgSO$_4$), filtered and reduced in vacuo to give crude methyl ester (0.35 g). The crude ester was purified over silica gel eluting with hexane:ethyl acetate (85:15 v/v).

(ii) Methyl ester (0.20 g, assume 0.77 mmol) was suspended in 10% NaOH (2.5 mL) and water (2.5 mL) added. The mixture was heated at 80° C. for 2 h, then cooled to 0° C. The mixture was acidified to pH 2 with 6N HCl, then cooled for 2 h at −5° C. A solid was filtered and washed thoroughly with hexane and dried in vacuo to give acid (66) (yield 0.04 g).

Preparation of 4-(1-cyclobutylpiperidin-4-yl)benzoic Acid (67)

(i) Methyl 4-(piperidin-4-yl)benzoate (CAS 281235-04-9, 0.25 g, 1.13 mmol) was dissolved in a mixture of THF (6 mL) and water (0.1 mL). Acetic acid (0.25 mL) and cyclobutanone (0.119 g, 1.7 mmol) were added followed by sodium cyanoborohydride (0.15 g, 2.4 mmol). The mixture was refluxed for 5 h then cooled and reduced in vacuo. The residue was dissolved in 1N HCl (4 mL) and water (15 mL) then washed with ethyl acetate (2×10 mL). The aqueous layer was adjusted to pH 10 with potassium carbonate and extracted with ethyl acetate (3×10 mL). The combined organics were washed with brine then dried (MgSO$_4$), filtered and reduced in vacuo to give crude methyl ester (0.23 g).

(ii) Methyl ester (0.23 g, assume 0.84 mmol) was suspended in 10% NaOH (2.5 mL) and water (2.5 mL) added. The mixture was heated at 80° C. for 2 h, then cooled to 0° C. The mixture was acidified to pH 2 with 6N HCl, then cooled for 2 h at −5° C. A solid was filtered and washed thoroughly with hexane and dried in vacuo to give acid (67) (yield 0.1 g).

Solid Phase Chemistry

Fmoc-ketone building blocks (3c-8c, 56) were utilised in a solid phase synthesis of example inhibitors (1-79) of general formula I. The methods used were directly analogous to those described in detail in WO02057270, utilising the 4-{[(Hydrazinocarbonyl)amino]methyl}cyclohexane carboxylic acid trifluoroacetate based linker, solid phase lanterns (ex Mimotopes), standard Fmoc chemistries and acidolytic cleavage followed by semi-preparative HPLC purification (see WO02057270 pg 124-127 for full generic details). Alternative EXAMPLES of the invention can readily be prepared by the general methods detailed in WO02057270 through use of the appropriately derivatised 4-(4-alkylpiperazin-1-yl) benzoic acid or 4-(1-alkylpiperidin-4-yl)benzoic acid building block (general synthetic details for preparation are given in WO0158886) such as 4-(4-methylpiperazin-1-yl)benzoic acid (CAS 354813-15-3), 4-(4-ethylpiperazin-1-yl)benzoic acid (CAS 354813-18-6), 4-(4-propylpiperazin-1-yl)benzoic acid (CAS 354813-21-1), 4-(4-isopropylpiperazin-1-yl)benzoic acid (CAS 354813-24-4), 4-(4-(2-methoxyethyl)piperazin-1-yl)benzoic acid (CAS 354813-30-2), 4-(4-cyclopropylpiperazin-1-yl)benzoic acid (CAS 883743-83-7), 4-(1-methylpiperidin-4-yl)benzoic acid (CAS 35481349-3), 4-(1-propylpiperidin-4-yl)benzoic acid (CAS 354813-33-5), 4-(1-isopropylpiperidin-4-yl)benzoic acid (CAS 35481342-6), 4-(1-(2-methoxyethyl)piperidin-4-yl)benzoic acid (CAS 354813-38-0). Additional novel preferred carboxylic acids are prepared by simple adaptation of the general methods detailed in WO01058886.

Example 1

N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)-4-(4-methylpiperazin-1-yl)benzamide

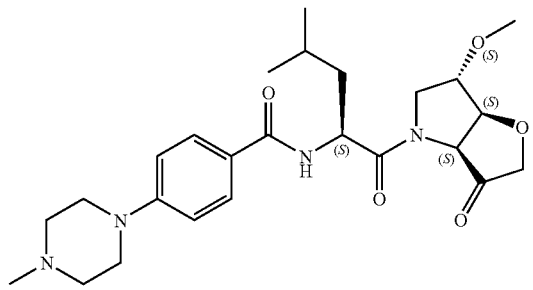

HPLC-MS $R_t$=2.96 min, 473.3 [M+H]$^+$, 491.3 [M+H+18]$^+$.

Example 2

N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)-4-(4-methylpiperazin-1-yl)benzamide

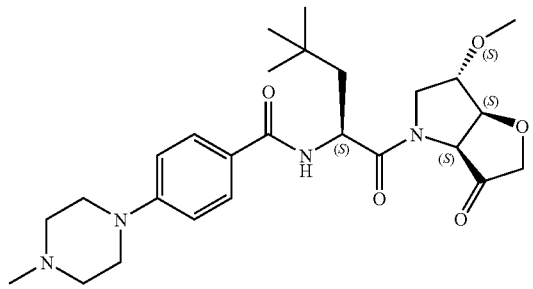

HPLC-MS $R_t$=3.26 min, 487.3 [M+H]$^+$, 505.3 [M+H+18]$^+$.

Example 3

N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)-4-(4-methylpiperazin-1-yl)benzamide

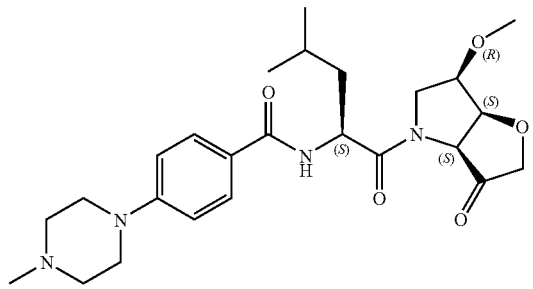

HPLC-MS $R_t$=2.83 min, 473.2 [M+H]$^+$, 491.2 [M+H+18]$^+$.

Example 4

N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)-4-(4-methylpiperazin-1-yl)benzamide

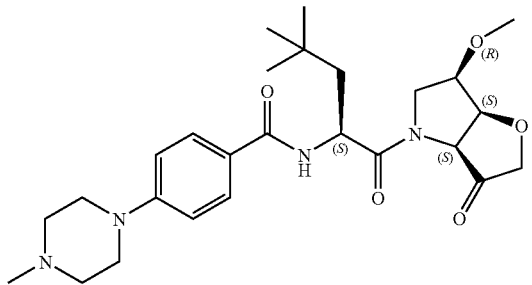

HPLC-MS $R_t$=3.05 min, 487.3 [M+H]$^+$, 505.3 [M+H+18]$^+$.

Example 5

4-(4-ethylpiperazin-1-yl)-N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)benzamide

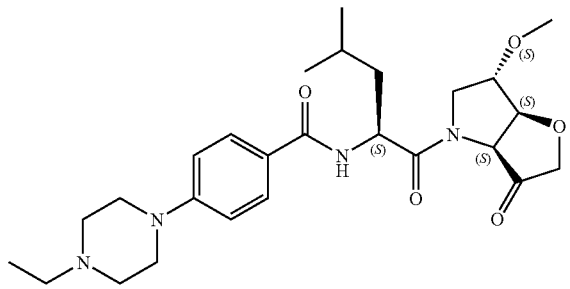

HPLC-MS $R_t$=3.06 min, 487.3 [M+H]$^+$, 505.3 [M+H+18]$^+$.

Example 6

4-(4-ethylpiperazin-1-yl)-N—((S)-1-((3aS,6S,6aS)-6-methoxy-3-oxodihydro-2H-furo[3,2-b]pyrrol-4(5H,6H,6aH)-yl)-4,4dimethyl-1-oxopentan-2-yl)benzamide

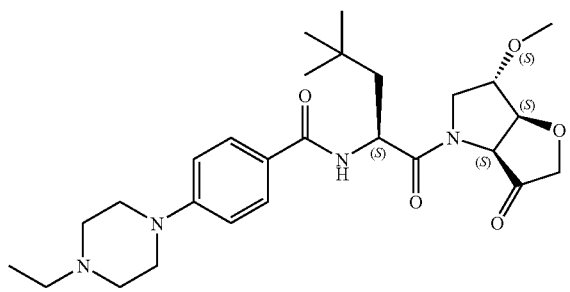

HPLC-MS $R_t$=3.36 min, 501.3 [M+H]$^+$, 519.3 [M+H+18]$^+$.

Example 7

4-(4-ethylpiperazin-1-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide

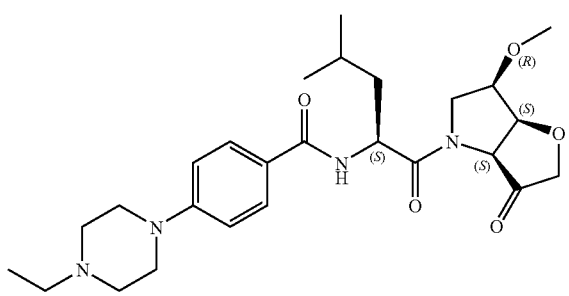

HPLC-MS $R_t$=2.85 min, 487.3 [M+H]$^+$, 505.3 [M+H+18]$^+$.

Example 8

4-(4-ethylpiperazin-1-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide

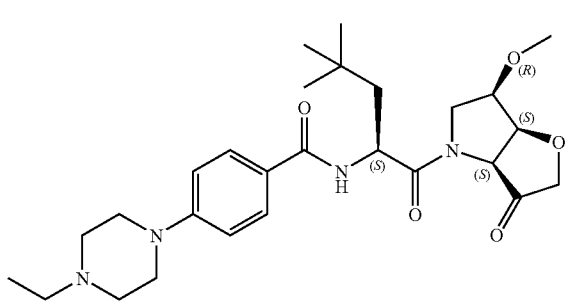

HPLC-MS $R_t$=3.18 min, 501.3 [M+H]$^+$, 519.3 [M+H+18]$^+$.

Example 9

N—((S)-1-((3aS,6S,6aR)-6-amino-3-oxodihydro-2H-furo[3,2-b]pyrrol-4(5H,6H,6aH)-yl)-4-methyl-1-oxopentan-2-yl)-4-(4-propylpiperazin-1-yl)benzamide

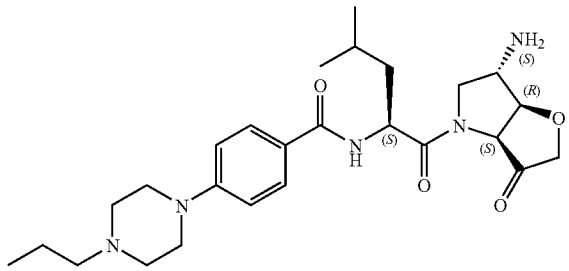

HPLC-MS $R_t$=2.37 min, 486.4 [M+H]$^+$, 504.4 [M+H+18]$^+$.

Example 10

N—((S)-1-((3aS,6R,6aR)-6-amino-3-oxodihydro-2H-furo[3,2-b]pyrrol-4(5H,6H,6aH)-yl)-4-methyl-1-oxopentan-2-yl)-4-(4-propylpiperazin-1-yl)benzamide

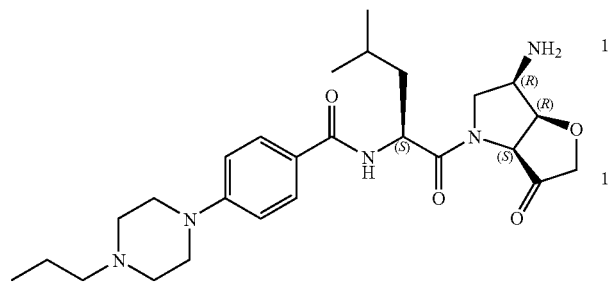

HPLC-MS $R_t$=2.37 min, 486.4 [M+H]$^+$.

Example 11

N—((S)-1-((3aS,6S,6aS)-6-hydroxy-3-oxodihydro-2H-furo[3,2-b]pyrrol-4(5H,6H,6aH)-yl)-4-methyl-1-oxopentan-2-yl)-4-(4-propylpiperazin-1-yl)benzamide

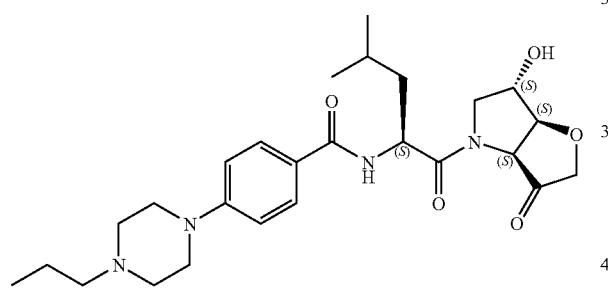

HPLC-MS $R_t$=2.85 min, 487.3 [M+H]$^+$, 505.3 [M+H+18]$^+$.

Example 12

N—((S)-1-((3aS,6R,6aS)-6-hydroxy-3-oxodihydro-2H-furo[3,2-b]pyrrol-4(5H,6H,6aH)-yl)-4-methyl-1-oxopentan-2-yl)-4-(4-propylpiperazin-1-yl)benzamide

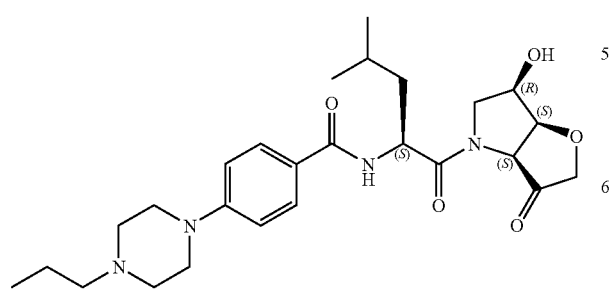

HPLC-MS $R_t$=2.71 min, 487.4 [M+H]$^+$, 505.4 [M+H+18]$^+$.

Example 13

N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)-4-(4-propylpiperazin-1-yl)benzamide

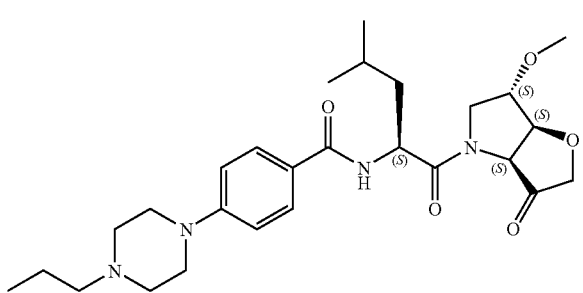

HPLC-MS $R_t$=3.27 min, 501.3 [M+H]$^+$, 519.3 [M+H+18]$^+$.

Example 14

N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide

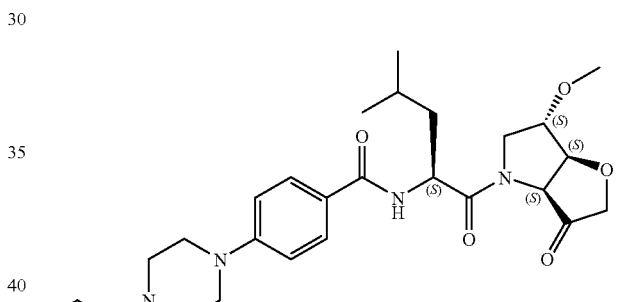

HPLC-MS $R_t$=3.58 min, 515.3 [M+H]$^+$, 533.3 [M+H+18]$^+$.

Example 15

N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)-4-(4-propylpiperazin-1-yl)benzamide

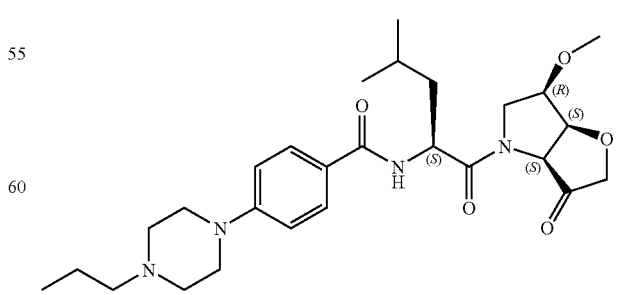

HPLC-MS $R_t$=3.24 min, 501.3 [M+H]$^+$, 519.3 [M+H+18]$^+$.

Example 16

N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide

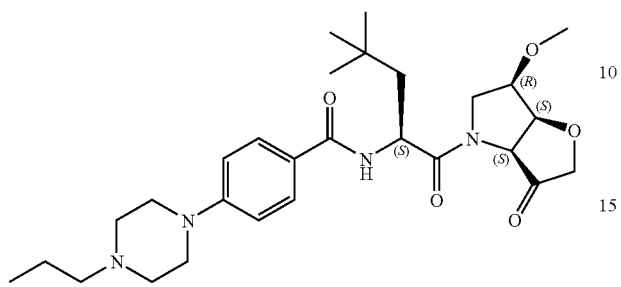

HPLC-MS $R_t$=3.39 min, 515.3 [M+H]$^+$, 533.3 [M+H+18]$^+$.

Example 17

4-(4-isopropylpiperazin-1-yl)-N—((S)-1-((3aS,6S,6aR)-6-amino-3-oxodihydro-2H-furo[3,2-b]pyrrol-4(5H,6H,6aH)-yl)-4,4-dimethyl-1-oxopentan-2-yl)benzamide

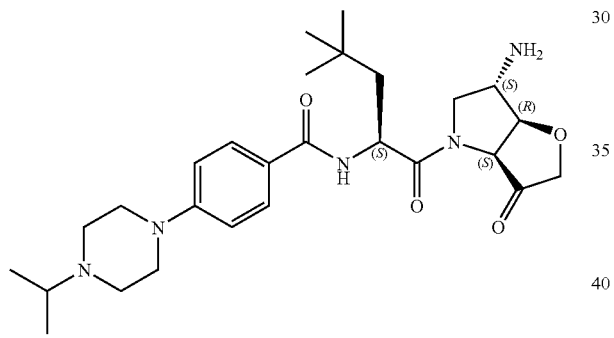

HPLC-MS $R_t$=2.61 min, 500.4 [M+H]$^+$, 518.4 [M+H+18]$^+$.

Example 18

4-(4-isopropylpiperazin-1-yl)-N—((S)-1-((3aS,6R,6aR)-6-amino-3-oxodihydro-2H-furo[3,2-b]pyrrol-4(5H,6H,6aH)-yl)-4,4-dimethyl-1-oxopentan-2-yl)benzamide

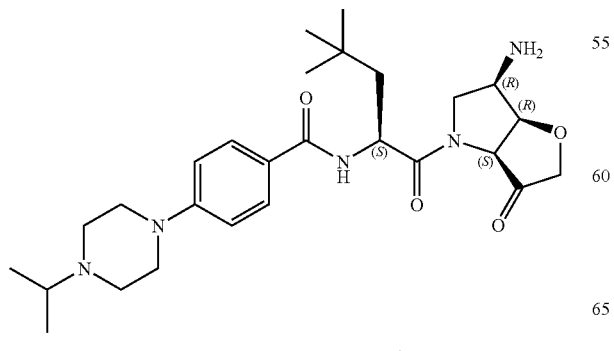

HPLC-MS $R_t$=2.64 min, 500.4 [M+H]$^+$

Example 19

4-(4-isopropylpiperazin-1-yl)-N—((S)-1-((3aS,6S,6aS)-6-hydroxy-3-oxodihydro-2H-furo[3,2-b]pyrrol-4(5H,6H,6aH)-yl)-4,4-dimethyl-1-oxopentan-2-yl)benzamide

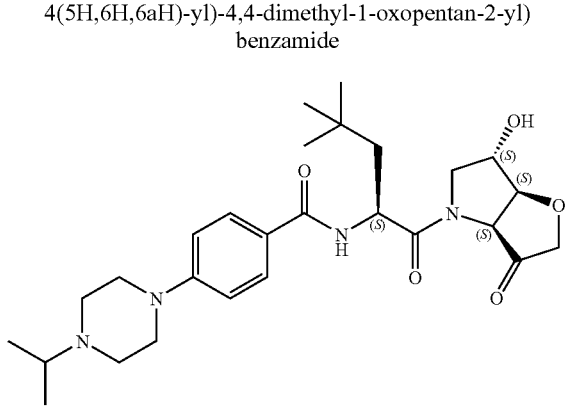

HPLC-MS $R_t$=3.05 min, 501.4 [M+H]$^+$, 519.4 [M+H+18]$^+$.

Example 20

4-(4-isopropylpiperazin-1-yl)-N—((S)-1-((3aS,6R,6aS)-6-hydroxy-3-oxodihydro-2H-furo[3,2-b]pyrrol-4(5H,6H,6aH)-yl)-4,4-dimethyl-1-oxopentan-2-yl)benzamide

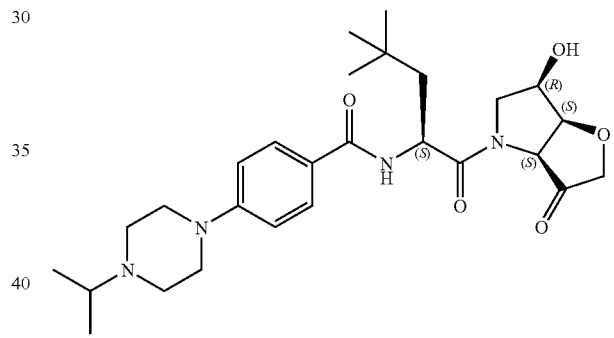

HPLC-MS $R_t$=2.98 min, 501.4 [M+H]$^+$, 519.4 [M+H+18]$^+$.

Example 21

4-(4-isopropylpiperazin-1-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide

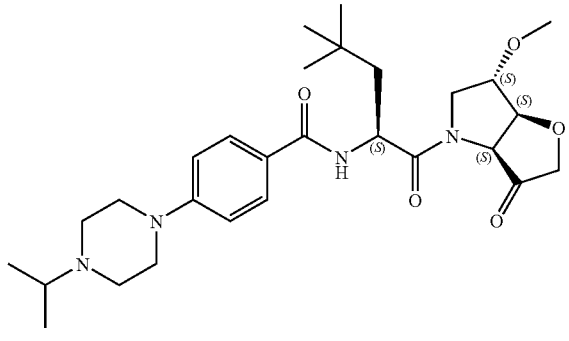

HPLC-MS $R_t$=3.53 min, 515.4 [M+H]$^+$, 533.4 [M+H+18]$^+$.

Example 22

4-(4-isopropylpiperazin-1-yl)-N—((S)-1-((3aS,6R, 6aS)-6-methoxy-3-oxodihydro-2H-furo[3,2-b]pyrrol-4(5H,6H,6aH)-yl)-4,4-dimethyl-1-oxopentan-2-yl)benzamide

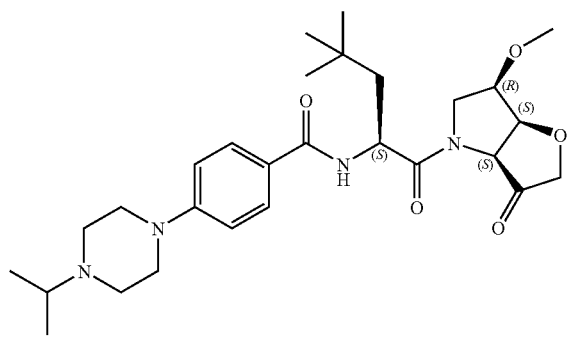

HPLC-MS $R_t$=3.32 min, 515.3 [M+H]$^+$, 533.3 [M+H+18]$^+$.

Example 23

N—((S)-1-((3aS,6S,6aR)-6-amino-3-oxodihydro-2H-furo[3,2-b]pyrrol-4(5H,6H,6aH)-yl)-4-methyl-1-oxopentan-2-yl)-4-(4-(2-methoxyethyl)piperazin-1-yl)benzamide

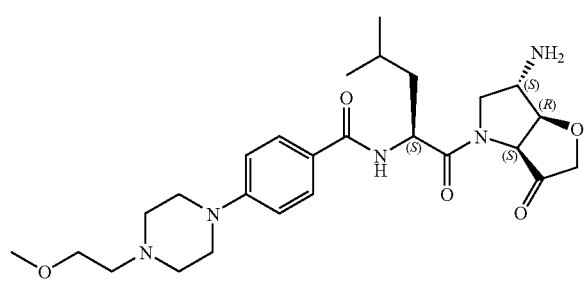

HPLC-MS $R_t$=2.14 min, 502.3 [M+H]$^+$, 520.3 [M+H+18]$^+$.

Example 24

N—((S)-1-((3aS,6R,6aR)-6-amino-3-oxodihydro-2H-furo[3,2-b]pyrrol-4(5H,6H,6aH)-yl)-4-methyl-1-oxopentan-2-yl)-4-(4-(2-methoxyethyl)piperazin-1-yl)benzamide

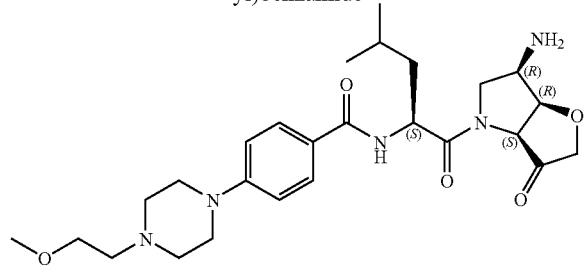

HPLC-MS $R_t$=2.12 min, 502.3 [M+H]$^+$.

Example 25

N—((S)-1-((3aS,6S,6aS)-6-hydroxy-3-oxodihydro-2H-furo[3,2-b]pyrrol-4(5H,6H,6aH)-yl)-4-methyl-1-oxopentan-2-yl)-4-(4-(2-methoxyethyl)piperazin-1-yl)benzamide

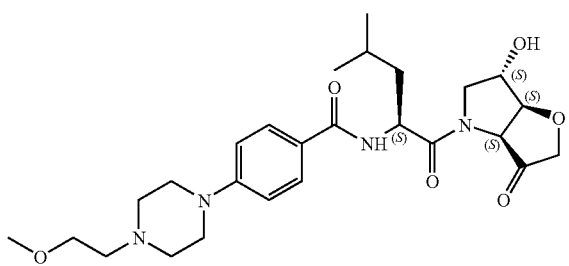

HPLC-MS $R_t$=2.83 min, 503.3 [M+H]$^+$, 521.3 [M+H+18]$^+$.

Example 26

N—((S)-1-((3aS,6R,6aS)-6-hydroxy-3-oxodihydro-2H-furo[3,2-b]pyrrol-4(5H,6H,6aH)-yl)-4-methyl-1-oxopentan-2-yl)-4-(4-(2-methoxyethyl)piperazin-1-yl)benzamide

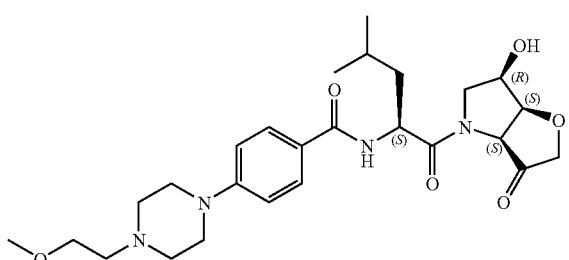

HPLC-MS $R_t$=2.59 min, 503.3 [M+H]$^+$, 521.3 [M+H+18]$^+$.

Example 27

N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)-4-(4-(2-methoxyethyl)piperazin-1-yl)benzamide

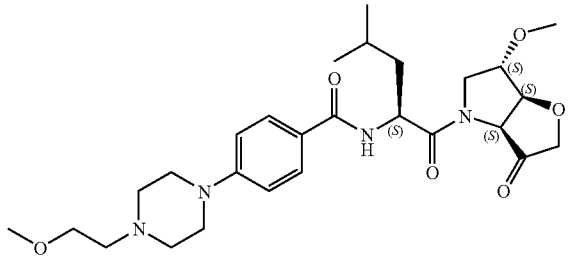

HPLC-MS $R_t$=3.16 min, 517.3 [M+H]$^+$, 535.3 [M+H+18]$^+$.

Example 28

N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)-4-(4-(2-methoxyethyl)piperazin-1-yl)benzamide

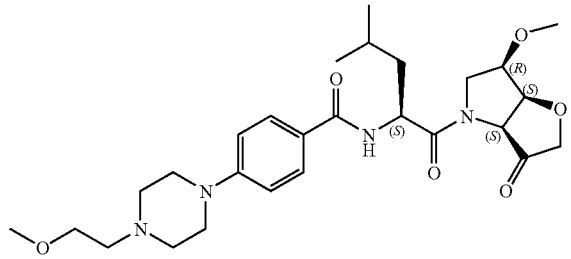

HPLC-MS $R_t$=2.96 min, 517.3 [M+H]$^+$, 535.3 [M+H+18]$^+$.

Example 29

4-(4-cyclopropylpiperazin-1-yl)-N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)benzamide

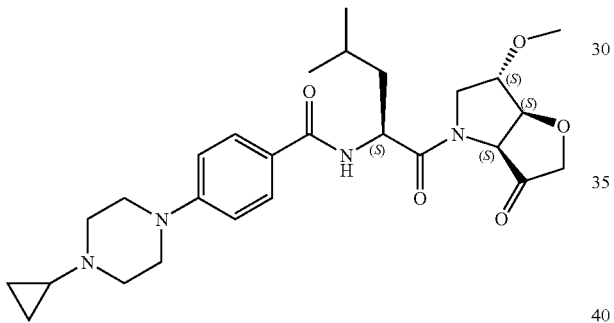

HPLC-MS $R_t$=3.19 min, 499.4 [M+H]$^+$, 517.4 [M+H+18]$^+$.

Example 30

4-(4-cyclopropylpiperazin-1-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide

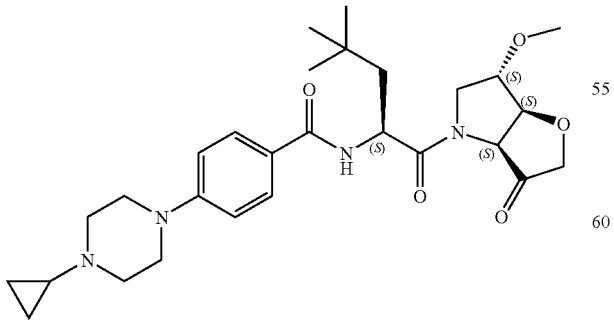

HPLC-MS $R_t$=3.50 min, 513.4 [M+H]$^+$, 531.4 [M+H+18]$^+$.

Example 31

4-(4-cyclopropylpiperazin-1-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide

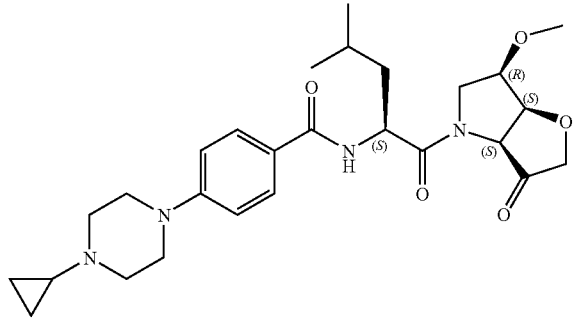

HPLC-MS $R_t$=2.95 min, 499.4 [M+H]$^+$, 517.4 [M+H+18]$^+$.

Example 32

4-(4-cyclopropylpiperazin-1-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide

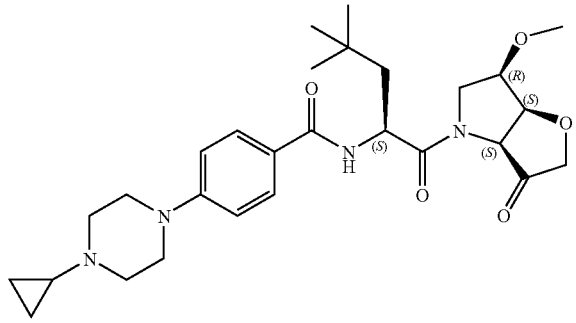

HPLC-MS $R_t$=3.31 min, 513.4 [M+H]$^+$, 531.4 [M+H+18]$^+$.

Example 33

N—((S)-1-((3aS,6S,6aR)-6-amino-3-oxodihydro-2H-furo[3,2-b]pyrrol-4(5H,6H,6aH)-yl)-4,4-dimethyl-1-oxopentan-2-yl)-4-(1-propylpiperidin-4-yl)benzamide

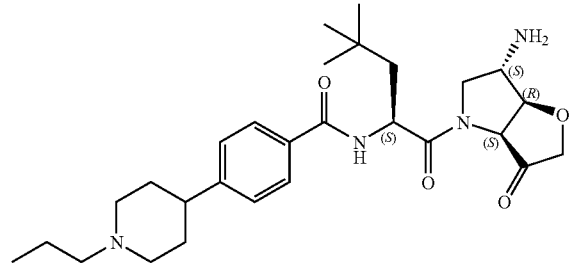

HPLC-MS $R_t$=2.87 min, 499.4 [M+H]$^+$, 517.4 [M+H+18]$^+$.

Example 34

N—((S)-1-((3aS,6R,6aR)-6-amino-3-oxodihydro-2H-furo[3,2-b]pyrrol-4(5H,6H,6aH)-yl)-4,4-dimethyl-1-oxopentan-2-yl)-4-(1-propylpiperidin-4-yl)benzamide

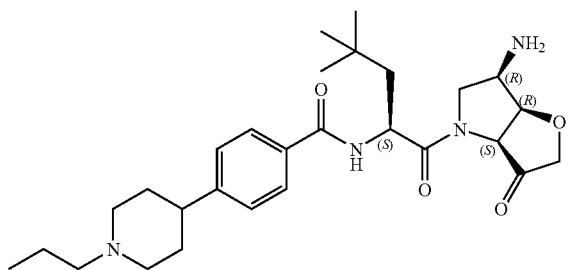

HPLC-MS R$_t$=2.91 min, 499.4 [M+H]$^+$, 517.4 [M+H+18]$^+$.

Example 35

N—((S)-1-((3aS,6S,6aS)-6-hydroxy-3-oxodihydro-2H-furo[3,2-b]pyrrol-4(5H,6H,6aH)-yl)-4,4-dimethyl-1-oxopentan-2-yl)-4-(1-propylpiperidin-4-yl)benzamide

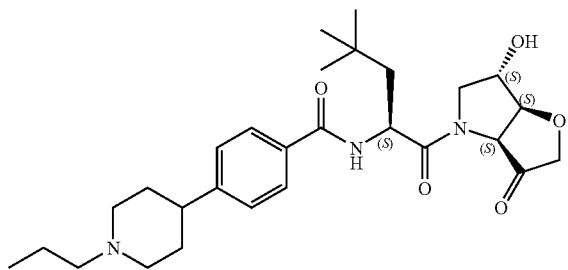

HPLC-MS R$_t$=3.32 min, 500.4 [M+H]$^+$, 518.4 [M+H+18]$^+$.

Example 36

N—((S)-1-((3aS,6R,6aS)-6-hydroxy-3-oxodihydro-2H-furo[3,2-b]pyrrol-4(5H,6H,6aH)-yl)-4,4-dimethyl-1-oxopentan-2-yl)-4-(1-propylpiperidin-4-yl)benzamide

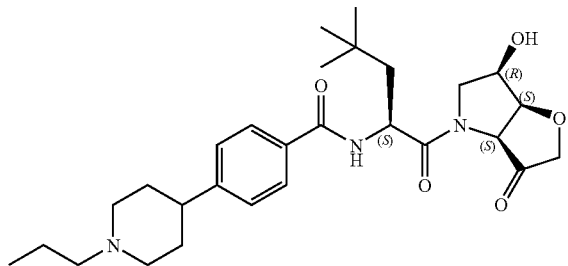

HPLC-MS R$_t$=3.25 min, 500.4 [M+H]$^+$, 518.4 [M+H+18]$^+$.

Example 37

N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)-4-(1-propylpiperidin-4-yl)benzamide

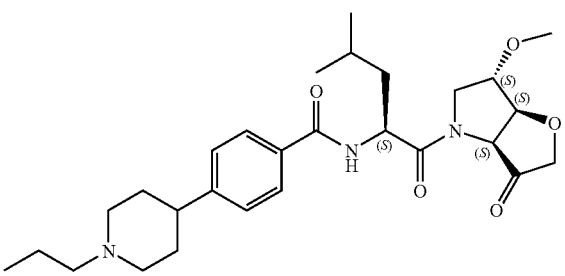

HPLC-MS R$_t$=3.48 min, 500.3 [M+H]$^+$, 518.3 [M+H+18]$^+$.

Example 38

N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)-4-(1-propylpiperidin-4-yl)benzamide

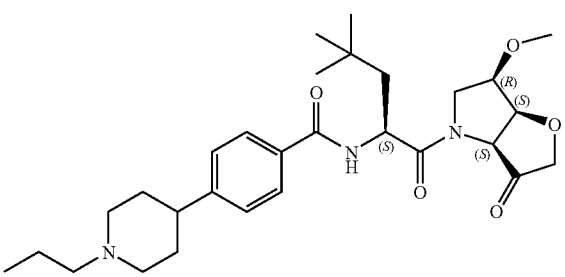

HPLC-MS R$_t$=3.58 min, 514.3 [M+H]$^+$, 532.3 [M+H+18]$^+$.

Example 39

N—((S)-1-((3aS,6S,6aR)-6-amino-3-oxodihydro-2H-furo[3,2-b]pyrrol-4(5H,6H,6aH)-yl)-4-methyl-1-oxopentan-2-yl)-4-(1-(2-methoxyethyl)piperidin-4-yl)benzamide

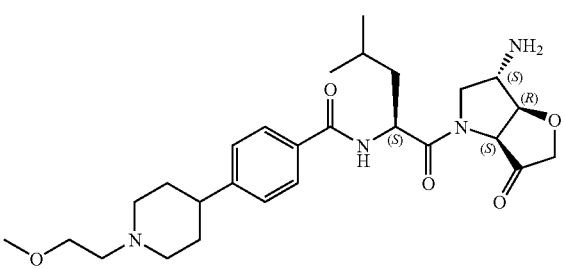

HPLC-MS R$_t$=2.44 min, 501.4 [M+H]$^+$, 519.4 [M+H+18]$^+$.

Example 40

N—((S)-1-((3aS,6R,6aR)-6-amino-3-oxodihydro-2H-furo[3,2-b]pyrrol-4(5H,6H,6aH)-yl)-4-methyl-1-oxopentan-2-yl)-4-(1-(2-methoxyethyl)piperidin-4-yl)benzamide

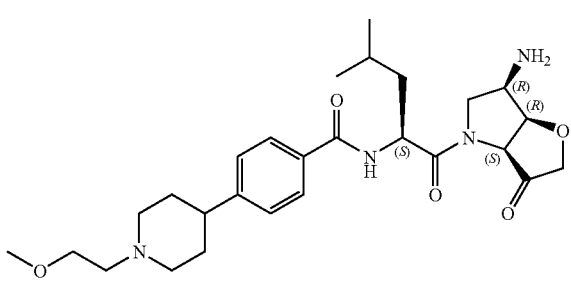

HPLC-MS $R_t$=2.45 min, 501.4 [M+H]$^+$, 519.4 [M+H+18]$^+$.

Example 41

N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)-4-(1-propylpiperidin-4-yl)benzamide

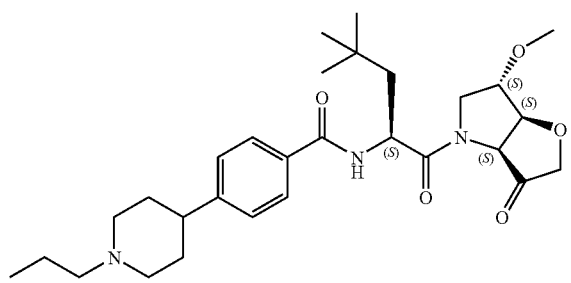

HPLC-MS $R_t$=3.82 min, 514.3 [M+H]$^+$, 532.3 [M+H+18]$^+$.

Example 42

N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)-4-(1-propylpiperidin-4-yl)benzamide

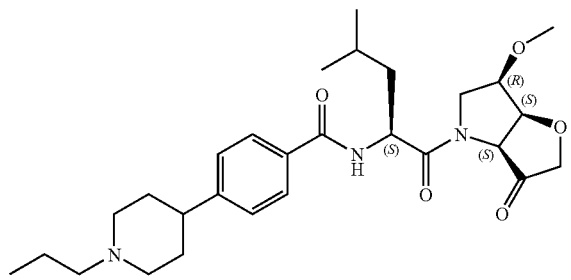

HPLC-MS $R_t$=3.27 min, 500.3 [M+H]$^+$, 518.3 [M+H+18]$^+$.

Example 43

N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)-4-(1-(2-methoxyethyl)piperidin-4-yl)benzamide

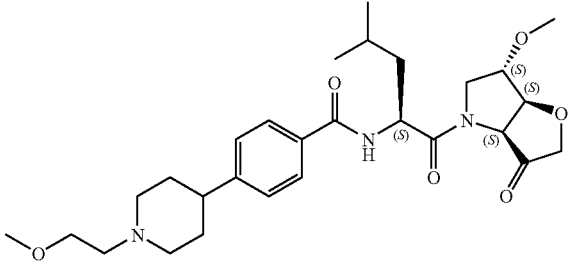

HPLC-MS $R_t$=2.86 min, 516.4 [M+H]$^+$, 534.4 [M+H+18]$^+$.

Example 44

N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)-4-(1-(2-methoxyethyl)piperidin-4-yl)benzamide

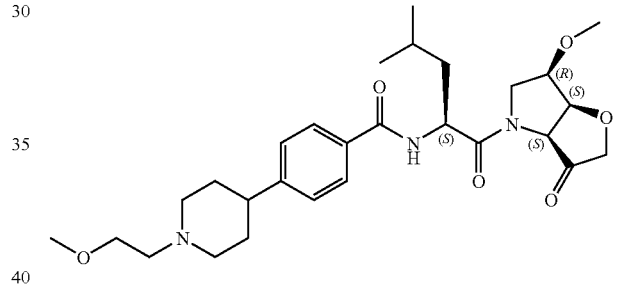

HPLC-MS $R_t$=2.77 min, 516.4 [M+H]$^+$, 534.4 [M+H+18]$^+$.

Example 45

4-(1-cyclopropylpiperidin-4-yl)-N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)benzamide

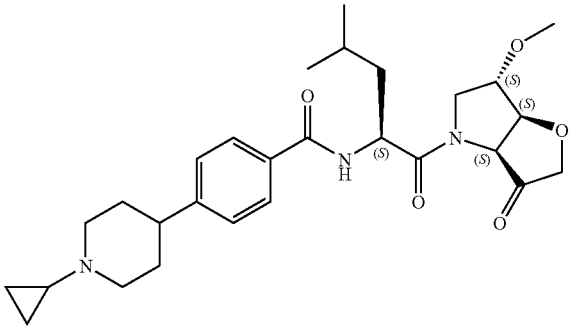

HPLC-MS $R_t$=3.40 min, 498.4 [M+H]$^+$, 516.4 [M+H+18]$^+$.

Example 46

4-(1-cyclopropylpiperidin-4-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide

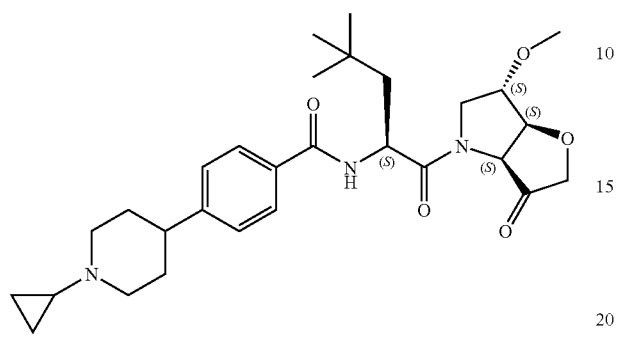

HPLC-MS $R_t$=3.76 min, 512.4 [M+H]$^+$, 530.4 [M+H+18]$^+$.

Example 47

N—((S)-1-((3aS,6S,6aS)-6-hydroxy-3-oxodihydro-2H-furo[3,2-b]pyrrol-4(5H,6H,6aH)-yl)-4-methyl-1-oxopentan-2-yl)-4-(1-(2-methoxyethyl)piperidin-4-yl)benzamide

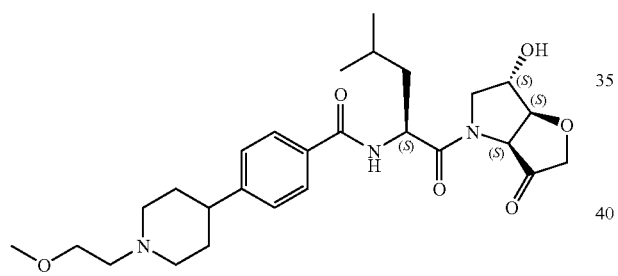

HPLC-MS $R_t$=3.28 min, 502.4 [M+H]$^+$, 520.4 [M+H+18]$^+$.

Example 48

N—((S)-1-((3aS,6R,6aS)-6-hydroxy-3-oxodihydro-2H-furo[3,2-b]pyrrol-4(5H,6H,6aH)-yl)-4-methyl-1-oxopentan-2-yl)-4-(1-(2-methoxyethyl)piperidin-4-yl)benzamide

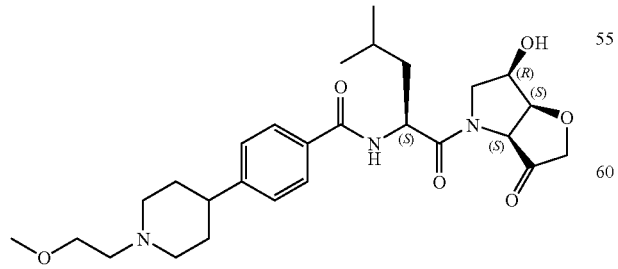

HPLC-MS $R_t$=3.14 min, 502.4 [M+H]$^+$, 520.4 [M+H+18]$^+$.

Example 49

4-(1-cyclopropylpiperidin-4-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide

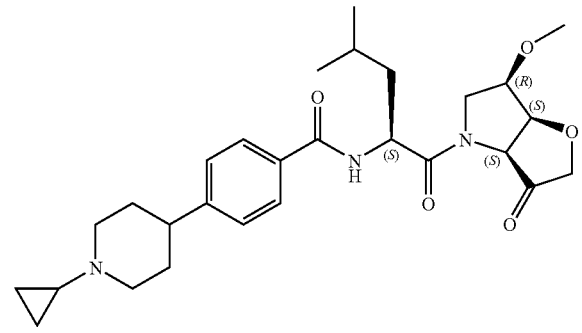

HPLC-MS $R_t$=3.17 min, 498.4 [M+H]$^+$, 516.4 [M+H+18]$^+$.

Example 50

4-(1-cyclopropylpiperidin-4-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide

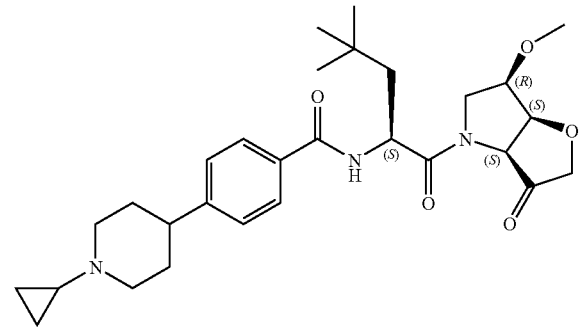

HPLC-MS $R_t$=3.49 min, 512.4 [M+H]$^+$, 530.4 [M+H+18]$^+$.

Example 51

N—((S)-1-((3aS,6S,6aS)-6-hydroxy-3-oxodihydro-2H-furo[3,2-b]pyrrol-4(5H,6H,6aH)-yl)-3,3-dimethyl-1-oxobutan-2-yl)-4-(4-methylpiperazin-1-yl)benzamide

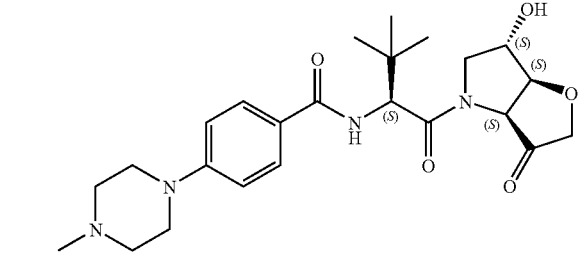

HPLC-MS $R_t$=2.52 min, 459.2 [M+H]$^+$, 477.2 [M+H+18]$^+$.

Example 52

N-((2S,3S)-1-((3aS,6S,6aS)-6-hydroxy-3-oxodihydro-2H-furo[3,2-b]pyrrol-4(5H,6H,6aH)-yl)-3-methyl-1-oxopentan-2-yl)-4-(4-methylpiperazin-1-yl)benzamide

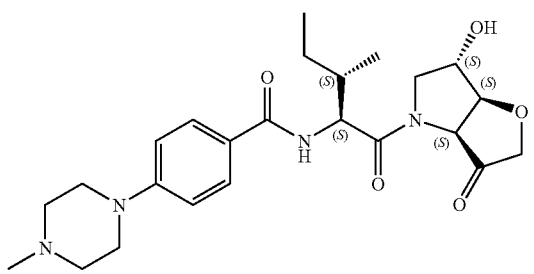

HPLC-MS $R_t$=2.62 min, 459.2 [M+H]$^+$, 477.2 [M+H+18]$^+$.

Example 53

N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(4-methylpiperazin-1-yl)benzamide

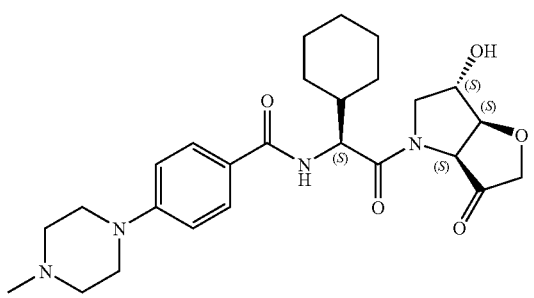

HPLC-MS $R_t$=3.12 min, 485.2 [M+H]$^+$, 503.3 [M+H+18]$^+$, 991.4 [2M+Na]$^+$.

Example 54

N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(4-methylpiperazin-1-yl)benzamide

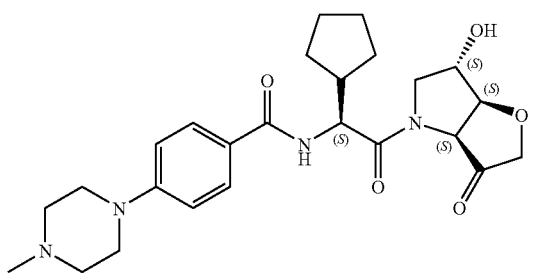

HPLC-MS $R_t$=2.77 min, 471.2 [M+H]$^+$, 489.2 [M+H+18]$^+$.

Example 55

N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(4-propylpiperazin-1-yl)benzamide

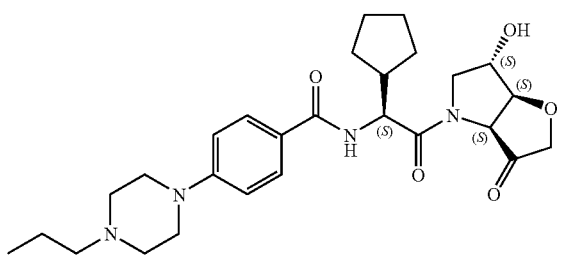

HPLC-MS $R_t$=3.08 min, [499.3 M+H]$^+$, 517.3 [M+H+18]$^+$.

Example 56

N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(1-propylpiperidin-4-yl)benzamide

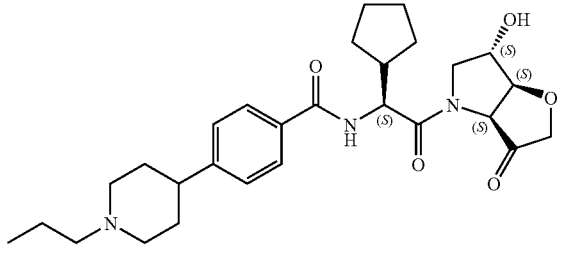

HPLC-MS $R_t$=3.27 min, 498.3 [M+H]$^+$, 516.3 [M+H+18]$^+$.

Example 57

N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)-4-(4-methylpiperazin-1-yl)benzamide

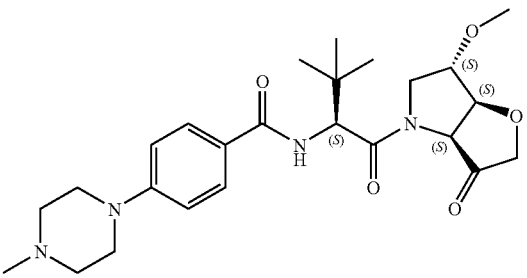

HPLC-MS $R_t$=2.83 min, 473.2 [M+H]$^+$, 491.2 [M+H+18]$^+$.

Example 58

N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)-4-(4-methylpiperazin-1-yl)benzamide

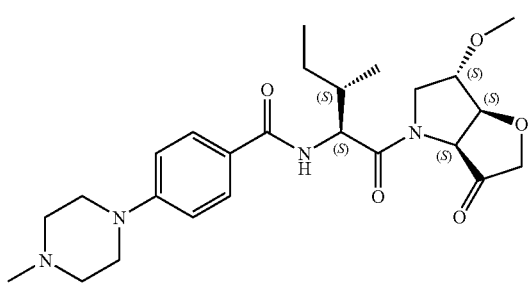

HPLC-MS R$_t$=2.93 min, 473.2 [M+H]$^+$, 491.3 [M+H+18]$^+$, 967.5 [2M+Na]$^+$.

Example 59

N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(4-methylpiperazin-1-yl)benzamide

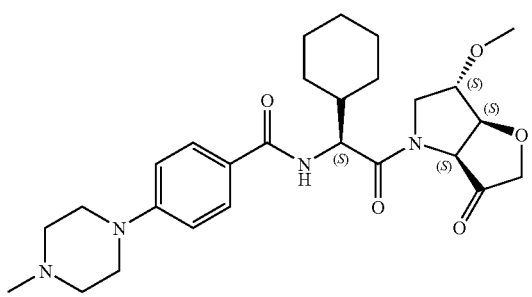

HPLC-MS R$_t$=3.40 min, 499.3 [M+H]$^+$, 517.3 [M+H+18]$^+$, 1019.4 [2M+Na]$^+$.

Example 60

N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-methylpiperazin-1-yl)benzamide

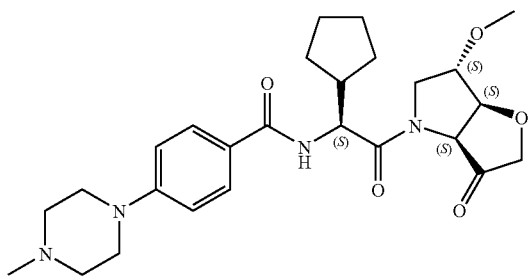

HPLC-MS R$_t$=3.08 min, 485.3 [M+H]$^+$, 503.3 [M+H+18]$^+$, 991.5 [2M+Na]$^+$.

Example 61

N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-ethylpiperazin-1-yl)benzamide

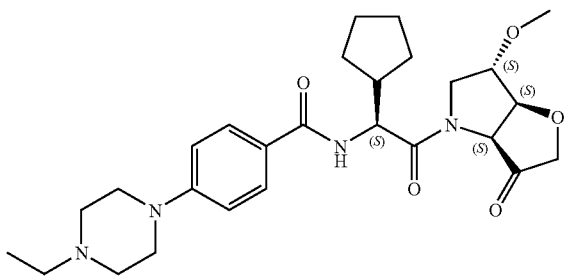

HPLC-MS R$_t$=3.17 min, [499.3 M+H]$^+$, 517.3 [M+H+18]$^+$.

Example 62

N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-propylpiperazin-1-yl)benzamide

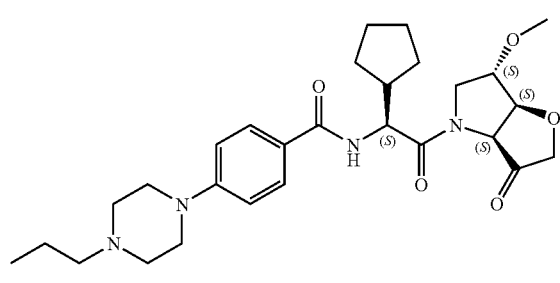

HPLC-MS R$_t$=3.38 min, 513.3 [M+H]$^+$, 531.3 [M+H+18]$^+$, 1047.4 [2M+Na]$^+$.

Example 63

N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-isopropylpiperazin-1-yl)benzamide

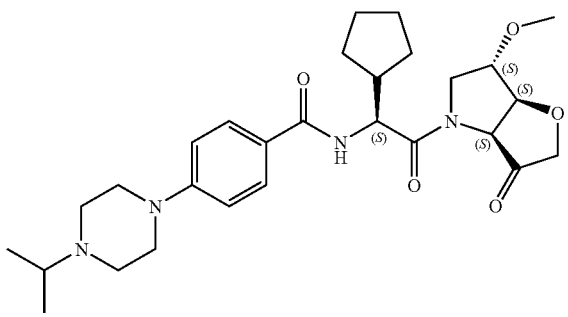

HPLC-MS R$_t$=3.31 min, 513.3 [M+H]$^+$, 531.3 [M+H+18]$^+$, 1047.4 [2M+Na]$^+$.

Example 64

N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-(2-methoxyethyl)piperazin-1-yl)benzamide

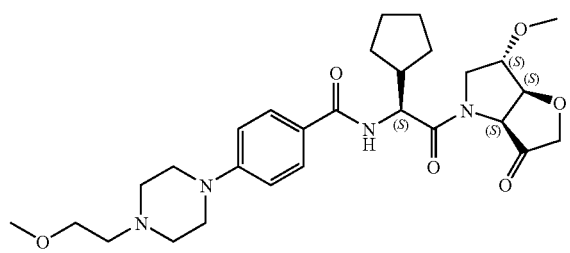

HPLC-MS $R_t$=3.26 min, 529.3 [M+H]$^+$, 547.3 [M+H+18]$^+$, 1079.4 [2M+Na]$^+$.

Example 65

N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-cyclopropylpiperazin-1-yl)benzamide

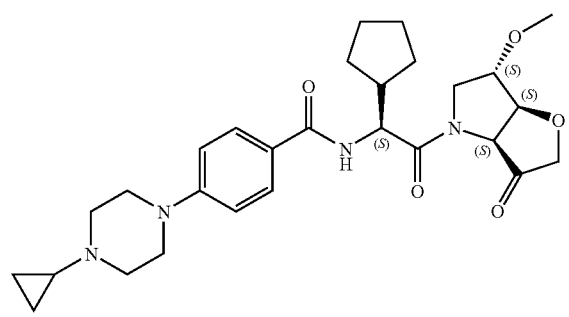

HPLC-MS $R_t$=3.25 min, 511.3 [M+H]$^+$, 529.3 [M+H+18]$^+$.

Example 66

4-(4-cyclobutylpiperazin-1-yl)-N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)benzamide

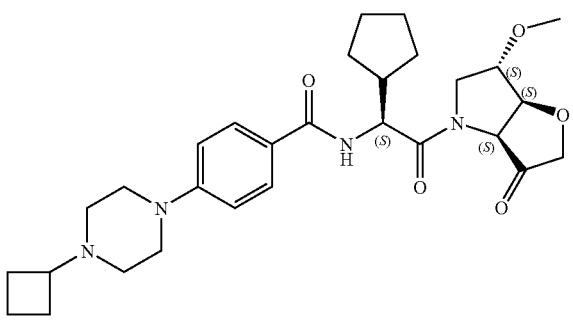

HPLC-MS $R_t$=3.41 min, 525.3 [M+H]$^+$, 543.3 [M+H+18]$^+$, 1071.5 [2M+Na]$^+$.

Example 67

N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-ethylpiperidin-1-yl)benzamide

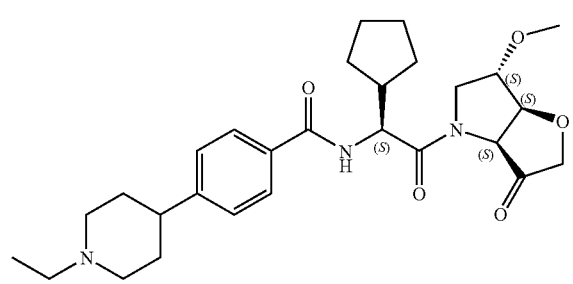

HPLC-MS $R_t$=3.34 min, 498.3 [M+H]$^+$, 516.3 [M+H+18]$^+$.

Example 68

N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-propylpiperidin-1-yl)benzamide

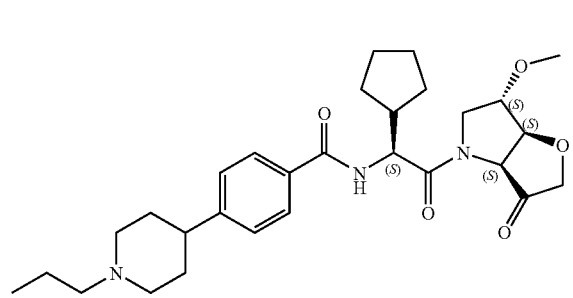

HPLC-MS $R_t$=3.57 min, 512.3 [M+H]$^+$, 530.3 [M+H+18]$^+$, 1045.5 [2M+Na]$^+$.

Example 69

N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-isopropylpiperidin-1-yl)benzamide

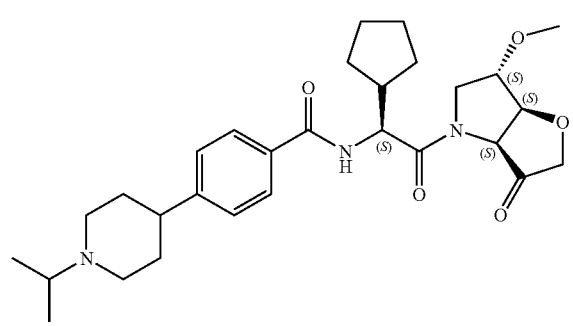

HPLC-MS $R_t$=3.51 min, 512.3 [M+H]$^+$, 530.3 [M+H+18]$^+$.

Example 70

N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(1-(2-methoxyethyl)piperidin-4-yl)benzamide

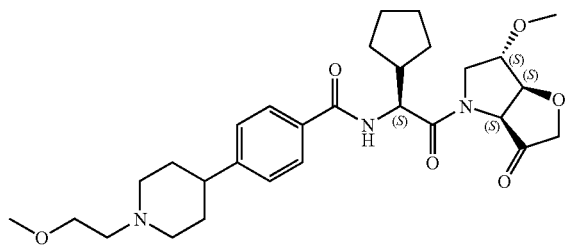

HPLC-MS $R_t$=3.45 min, 528.3 [M+H]$^+$, 546.3 [M+H+18]$^+$.

Example 71

N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(1-cyclopropylpiperidin-4-yl)benzamide

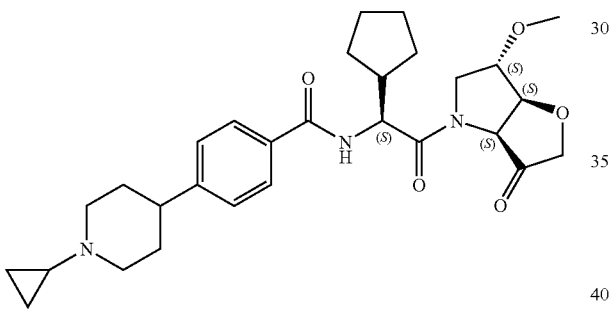

HPLC-MS $R_t$=3.47 min, 510.3 [M+H]$^+$, 528.3 [M+H+18]$^+$, 1041.5 [2M+Na]$^+$.

Example 72

4-(1-cyclobutylpiperidin-4-yl)-N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)benzamide

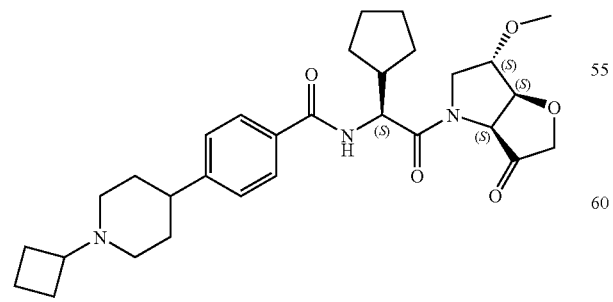

HPLC-MS $R_t$=3.62 min, 524.3 [M+H]$^+$, 542.3 [M+H+18]$^+$, 1069.5 [2M+Na]$^+$.

Example 73

N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)-4-(4-methylpiperazin-1-yl)benzamide

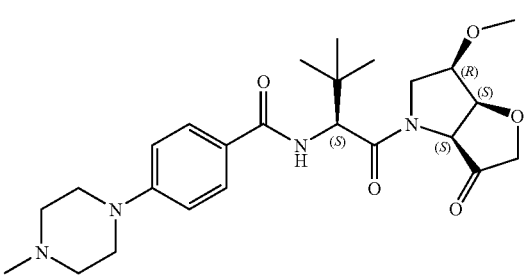

HPLC-MS $R_t$=2.70 min, 473.2 [M+H]$^+$, 491.2 [M+H+18]$^+$.

Example 74

N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)-4-(4-methylpiperazin-1-yl)benzamide

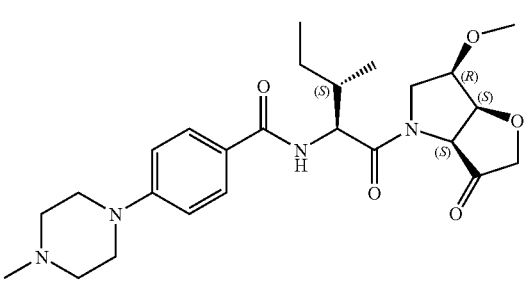

HPLC-MS $R_t$=2.72 min, 473.2 [M+H]$^+$, 491.2 [M+H+18]$^+$.

Example 75

N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(4-ethylpiperazin-1-yl)benzamide

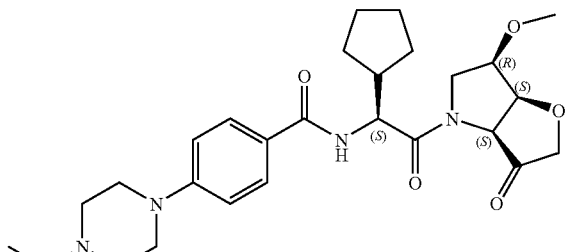

HPLC-MS $R_t$=2.96 min, 499.3 [M+H]$^+$, 517.3 [M+H+18]$^+$.

Example 76

N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(4-(2-methoxyethyl)piperazin-1-yl)benzamide

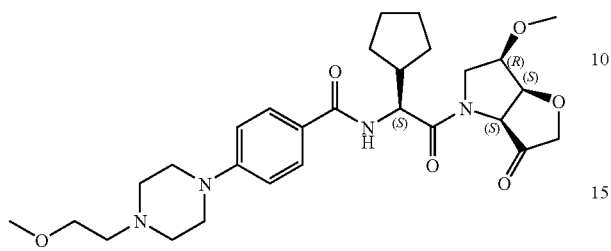

HPLC-MS $R_t$=3.05 min, 529.3 [M+H]$^+$, 547.3 [M+H+18]$^+$.

Example 77

N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(4-methylpiperazin-1-yl)benzamide

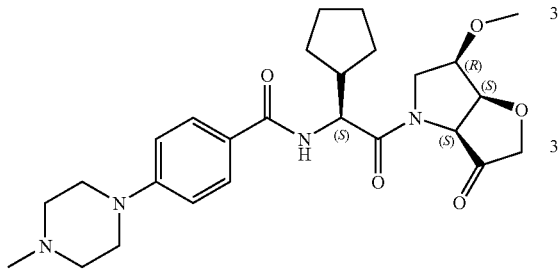

HPLC-MS $R_t$=2.76 min, 485.3 [M+H]$^+$, 503.3 [M+H+18]$^+$.

Example 78

N—((S)-1-cyclopentyl-2-((3aS,6S,6aS)-6-methylthio-3-oxodihydro-2H-furo[3,2-b]pyrrol-4(5H,6H,6aH)-yl)-2-oxoethyl)-4-(4-methylpiperazin-1-yl)benzamide (93)

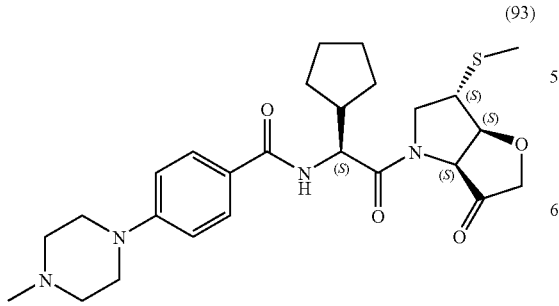

HPLC-MS $R_t$=3.50 min, 501.1 [M+H]$^+$, 519.2 [M+H+18]$^+$.

Example 79

N—((S)-1-cyclopentyl-2-((3aS,6S,6aS)-6-methylsulfinyl-3-oxodihydro-2H-furo[3,2-b]pyrrol-4(5H,6H,6aH)-yl)-2-oxoethyl)-4-(4-methylpiperazin-1-yl)benzamide (94)

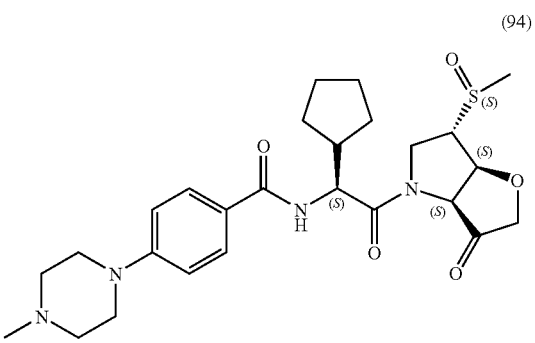

Prepared from (EXAMPLE 78) with oxidation whilst on solid phase using Dess Martin periodinane in DCM overnight;

HPLC-MS $R_t$=2.23 min, 517.2 [M+H]$^+$, 535.2 [M+H+18]$^+$.

Solution Phase Syntheses.

Alternatively, examples of the invention may be prepared by traditional solution phase organic chemistry techniques commencing from building blocks such as (3R,3aR,6S,6aS)-6-methoxyhexahydro-2H-furo[3,2-b]pyrrol-3-ol or (3R,3aR,6R,6aS)-6-methoxyhexahydro-2H-furo[3,2-b]pyrrol-3-ol for example.

Alternative Preparation of 4-(4-isopropylpiperazin-1-yl)-N—((S)-1-((3aS,6R,6aS-6-methoxy-3-oxodihydro-2H-furo[3,2-b]pyrrol-4(5H,6H,6aH)-yl)-4,4-dimethyl-1-oxopentan-2-yl)benzamide Example 22

(i) Preparation of tert-Butyl (S)-1-((3R,3aR,6R,6aS)-3-hydroxy-6-methoxydihydro-2H-furo[3,2-b]pyrrol-4(5H,6H,6aH)-yl)-4,4-dimethyl-1-oxopentan-2-ylcarbamate Palladium on charcoal (10%, 285 mg) was added to a solution containing a 3:1 mixture of benzyl (R)-2-((1S,2R,5S)-3,6-dioxabicyclo[3.1.0]hexan-2-yl)-2-methoxyethyl carbamate (31) and benzyl (R)-2-((1R,2R,5R)-3,6-dioxabicyclo[3.1.0]hexan-2-yl)-2-methoxyethyl carbamate (31b) respectively (2.85 g, 9.73 mmol) in ethanol (130 mL) under an atmosphere of argon. The argon was replaced by hydrogen then the suspension was stirred for 80 minutes then filtered through celite in vacuo. The filter cake was washed with ethanol then the solvents removed in vacuo from the filtrate. The residue was azeotroped with toluene to obtain the crude (3R,3aR,6R,6aS)-6-methoxyhexahydro-2H-furo[3,2-b]pyrrol-3-ol which was used without further purification.

A solution of (S)-tert-butyl 1-fluoro-4,4-dimethyl-1-oxopentan-2-ylcarbamate (2.64 g, 10.7 mmol) in dimethylformamide (25 mL) was added under argon to a solution of (3R,3aR,6aR)-hexahydro-2H-furo[3,2-b]pyrrol-3-ol hydrochloride (assumed to be 9.73 mmol) in dimethylformamide (25 mL). The mixture was stirred for 1 hour then (S)-tert-butyl 1-fluoro-4,4-dimethyl-1-oxopentan-2-ylcarbamate (0.59 g, 2.4 mmol) was added. The mixture was stirred for 2 hours then the solvents removed in vacuo. The residue was diluted with brine (250 mL) then extracted with dichloromethane (3×100 mL). The combined organic layers were dried (Na$_2$SO$_4$), filtered and reduced in vacuo. Flash chromatography over silica, eluting with ethyl acetate:heptane mixtures 50:50 to 100:0 gave tert-butyl (S)-1-((3R,3aR,6R,6aS)-3-hydroxy-6-methoxydihydro-2H-furo[3,2-b]pyrrol-4(5H,6H,6aH)-yl)-4,4-dimethyl-1-oxopentan-2-ylcarbamate as a yellow solid (1.73 g, 61% calculated from amount of benzyl (R)-2-((1S,2R,5S)-3,6-dioxabicyclo[3.1.0]hexan-2-yl)-2-methoxyethyl carbamate present in the starting material). TLC (R$_f$=0.10, EtOAc:heptane 2:1), analytical HPLC main peak, R$_t$=13.445 min., HPLC-MS 331.2 [M+2H−$^t$Bu]$^+$, 387.2 [M+H]$^+$, 409.2 [M+Na]$^+$, 795.4 [2M+Na]$^+$; [α]$_D^{20}$+ 14.03° (c=1.96, CHCl$_3$); δ$_H$ (500 MHz, CDCl$_3$) mixture of rotamers major:minor 4:3; 0.95 (9H, s, CH$_2$C(CH$_3$)$_3$), 1.40 (9H, s, OC(CH$_3$)$_3$), 1.38-1.55 (1.57H, m, CH$_2$C(CH$_3$)$_3$), 1.58 (0.43H, dd, 9.24 Hz, CH$_2$C(CH$_3$)$_3$ minor), 3.18 (0.43H, dd, J=11.56 and 9.58 Hz, NCH$_2$CHOCH$_3$ minor), 3.31 (0.57H, t, J=9.42 Hz, NCH$_2$CHOCH$_3$ major), 3.38 (0.43H, brs, OH minor), 3.45 (1.29H, s, OCH$_3$ minor), 3.47 (1.71H, s, OCH$_3$ major), 3.62 (0.43H, dd, 6.23 Hz, OCH$_2$CHOH minor), 3.71-3.76 (0.43H, m, CHOCH$_3$ minor), 3.78 (0.57H, dd, 4.23 Hz, OCH$_2$CHOH major), 3.88-3.93 (0.53H, m, CHOCH$_3$ major), 4.00-4.06 (1H, m, OCH$_2$CHOH major and NCH$_2$CHOCH$_3$ minor), 4.11 (0.53H, dd, 7.36 Hz, NCH$_2$CHOCH$_3$ major), 4.24-4.34 (2.43H, m, OCH$_2$CHOHCH and OCH$_2$CHOH minor), 4.45-4.51 (0.43H, m, CHCH$_2$C(CH$_3$)$_3$ minor), 4.67-4.73 (1.57H, m, CHCHOCH$_3$ and CHCH$_2$C(CH$_3$)$_3$ major), 5.14 (0.43H, d, J=9.35 Hz, NH minor), 5.27 (0.57H, d, J=10.03 Hz, NH major), 5.54 (0.57H, d, J=5.30 Hz, OH major); δ$_C$ (125 MHz, CDCl$_3$) 28.27/28.36 (OC(CH$_3$)$_3$), 29.71/29.85 (CH$_2$C(CH$_3$)$_3$), 30.55/30.65 (CH$_2$C(CH$_3$)$_3$), 46.14/46.96 (CH$_2$C(CH$_3$)$_3$), 46.56/48.56 (NCH$_2$CHOCH$_3$), 48.72/49.46 (CHCH$_2$C(CH$_3$)$_3$), 58.02/58.10 (OCH$_3$), 69.96/70.33 (OCH$_2$CHOHCH), 74.08/74.98 (OCH$_2$CHOH), 76.37/79.71 (CHOH), 77.96/79.42 (CHOCH$_3$), 78.44/80.45 (OCHCHOCH$_3$), 79.82/80.45 (OC(CH$_3$)$_3$), 155.31/156.06 (Boc C=O), 172.64/173.24 (CH$_2$NC=O).

(ii) Preparation of (S)-2-Amino-1-((3R,3aR,6R,6aS)-3-hydroxy-6-methoxydihydro-2H-furo[3,2-b]pyrrol-4(5H,6H,6aH)-yl)-4,4-dimethylpentan-1-one hydrochloride A solution of HCl in 1,4-dioxane (4.0M, 25 mL, 100 mmol) was added to tert-butyl (S)-1-((3R,3aR,6R,6aS)-3-hydroxy-6-methoxydihydro-2H-furo[3,2-b]pyrrol-4(5H,6H,6aH)-yl)-4,4-dimethyl-1-oxopentan-2-ylcarbamate (1.73 g, 4.48 mmol). The solution was stirred for 2 hours then the solvents were removed in vacuo and the residue azeotroped with toluene (1×50 mL then 1×25 mL) to leave (S)-2-amino-1-((3R,3aR,6R,6aS)-3-hydroxy-6-methoxydihydro-2H-furo[3,2-b]pyrrol-4(5H,6H,6aH)-yl)-4,4-dimethylpentan-1-one hydrochloride as an off-white solid which was used without further purification. TLC (R$_f$=0.0, EtOAc:heptane 2:1), analytical HPLC main peak, R$_t$=4.047 min., HPLC-MS 287.2 [M+H]$^+$, 595.3 [2M+Na]$^+$; δ$_C$ (125 MHz, CD$_3$OH) 29.66 (C(CH$_3$)$_3$), 30.45 (C(CH$_3$)$_3$), 44.51/49.24 (NCH$_2$CHOCH$_3$ and CH$_2$C(CH$_3$)$_3$), 50.03 (CHCH$_2$C(CH$_3$)$_3$), 57.85 (OCH$_3$), 70.64 (CHCHOH), 74.83 (CHCHOH), 75.56 (CH$_2$CHOH), 78.13 and 79.11 (CHCHOCH$_3$), 169.80/169.98 (NC=O).

(iii) Preparation of N—((S)-1-((3R,3aR,6R,6aS)-3-Hydroxy-6-methoxydihydro-2H-furo[3,2-b]pyrrol-4(5H,6H,6aH)-yl)-4,4-dimethyl-1-oxopentan-2-yl)-4-(4-isopropylpiperazin-1-yl)benzamide 4-Methylmorpholine (0.98 mL, 8.9 mmol) was added to a suspension of 2-(1H-benzotriazole-1-yl)-1,1,3,3-tetramethyluronium hexafluorophosphate (HBTU, 1.69 g, 4.45 mmol), 1-hydroxybenzotriazole monohydrate (0.68 g, 4.45 mmol) and 4-(4-isopropylpiperazin-1-yl)benzoic acid (82% wt., 1.41 g, 4.66 mmol) in dimethylformamide (8 mL). The suspension was sonicated for 3 minutes then added to (S)-2-amino-1-((3R,3aR,6R,6aS)-3-hydroxy-6-methoxydihydro-2H-furo[3,2-b]pyrrol-4(5H,6H,6aH)-yl)-4,4-dimethylpentan-1-one hydrochloride (prepared as above, assume 4.24 mmol). After 2.5 hours saturated sodium hydrogen carbonate solution (50 mL) was added then the aqueous phase was extracted with dichloromethane (3×20 mL). The combined organic layers were washed with brine (50 mL), then dried (Na$_2$SO$_4$), filtered and reduced in vacuo. Flash chromatography over silica, eluting with methanol:dichloromethane mixtures 0:100 to 10:90 gave N—((S)-1-((3R,3aR,6R,6aS)-3-hydroxy-6-methoxydihydro-2H-furo[3,2-b]pyrrol-4(5H,6H,6aH)-yl)-4,4-dimethyl-1-oxopentan-2-yl)-4-(4-isopropylpiperazin-1yl)benzamide as a pale yellow solid (1.77 g, 81%). TLC (R$_f$=0.10-0.15 double spot, MeOH:CH$_2$Cl$_2$ 5:95), analytical HPLC main peak, R$_t$=10.16 min., HPLC-MS 517.4 [M+H]$^+$, 1033.7 [2M+Na]$^+$; [α]$_D^{19}$+ 28.85° (c=3.64, CHCl$_3$); δ$_H$ (500 MHz, CDCl$_3$) mixture of rotamers major:minor 5:3; 0.98 (9H, s, C(CH$_3$)$_3$), 1.08 (3.78H, d, J=6.53 Hz, NCH(CH$_3$)$_2$ major), 1.09 (2.22H, d, J=6.52 Hz, NCH(CH$_3$)$_2$ minor), 1.58-1.67 (1.37H, m, CH$_2$C(CH$_3$)$_3$), 1.76 (0.63H, dd, 9.43 Hz, CH$_2$C(CH$_3$)$_3$ major), 2.64-2.69 (4H, m, CH$_2$CH$_2$NCH(CH$_3$)$_2$), 2.69-2.76 (1H, m, NCH(CH$_3$)$_2$), 3.18 (0.63H, dd, 9.63 Hz, NCH$_2$CHOCH$_3$ major), 3.27-3.33 (4H, m, CH$_2$CH$_2$NCH$_3$), 3.37 (0.37H, brt, J=9.45 Hz, NCH$_2$CHOCH$_3$ minor), 3.46 (1.89H, s, OCH$_3$ major), 3.48 (1.11H, s, OCH$_3$ minor), 3.63 (0.63H, dd, 6.40 Hz, OCH$_2$CHOH major), 3.74-3.78 (0.63H, m, CHOCH$_3$ major), 3.79 (0.37H, dd, 4.09 Hz, OCH$_2$CHOH minor), 3.92-3.96 (0.37H, m, CHOCH$_3$ minor), 4.03-4.09 (1H, m, NCH$_2$CHOCH$_3$), 4.28-4.38 (3H, m, OCH$_2$CHOHCH and 1×OCH$_2$CHOH), 4.67 (0.37H, brt, J=4.59 Hz, OCH-CHOCH$_3$ minor), 4.72 (0.63H, brt, J=5.04 Hz, OCH-CHOCH$_3$ major), 4.97-5.03 (0.37H, m, CHCH$_2$C(CH$_3$)$_3$ minor), 5.24-5.29 (0.63H, m, CHCH$_2$C(CH$_3$)$_3$ major), 5.96 (0.63H, brs, OH major), 6.62 (0.37H, d, J=8.39 Hz, NH minor), 6.71 (0.63H, d, J=9.83 Hz, NH major), 6.82-6.87 (2H, m, aromatic CH), 7.66-7.70 (2H, m, aromatic CH); δ$_C$ (125 MHz, CDCl$_3$) 18.50 (CH(CH$_3$)$_2$, 29.79/29.91 (C(CH$_3$)$_3$), 30.71/30.75 (C(CH$_3$)$_3$), 46.18/47.10 (CH$_2$C(CH$_3$)$_3$), 46.56 (NCH$_2$CHOCH$_3$), 47.82/48.30 (CHCH$_2$C(CH$_3$)$_3$), 47.87/49.01 (NCH$_2$CH$_2$NCH(CH$_3$)$_2$), 48.40/48.44 (NCH$_2$CH$_2$NCH(CH$_3$)$_2$), 54.56/54.60 (NCH(CH$_3$)$_2$), 58.06/58.03 (OCH$_3$), 69.93/70.56 (OCH$_2$CHOHCH), 74.01/75.01 (OCH$_2$CHOH), 76.35/79.85 (CHOH), 77.94/79.41 (CHOCH$_3$), 78.54/80.45 (OCHCHOCH$_3$), 113.92/114.06/128.52 and 128.73 (aromatic CH), 122.18/123.16 (aromatic quaternary), 153.53/153.80 (aromatic quaternary), 166.57/167.19 (NHC=O), 172.37/173.13 (CH$_2$NC=O).

(iv) Oxidation to Example 22

Dess-Martin periodinane (2.82 g, 6.66 mmol) was added to a stirred solution of N—((S)-1-((3R,3aR,6R,6aS)-3-hydroxy-6-methoxydihydro-2H-furo[3,2-b]pyrrol-4(5H,6H,6aH)-yl)-4,4-dimethyl-1-oxopentan-2-yl)-4-(4-isopropylpiperazin-1yl)benzamide (1.72 g, 3.33 mmol) in dichloromethane (65 mL) under an atmosphere of argon. The mixture was stirred for 18 hours then diluted with dichloromethane (300 mL). The organic phase was washed with aqueous sodium hydroxide solution (1M, 100 mL) then the aqueous extracted with dichloromethane (150 mL). The organic layer was washed with aqueous sodium hydroxide solution (1M, 100 mL) then brine (150 mL), then dried (Na$_2$SO$_4$), filtered and reduced in vacuo to give 4-(4-isopropylpiperazin-1-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide a pale yellow solid (1.408 g, 82%). TLC (R$_f$=0.45, MeOH:CH$_2$Cl$_2$ 1:19), analytical HPLC main peak, R$_t$=10.39 min., HPLC-MS 515.3 [M+H]$^+$, 533.3 [M+H$_2$O+H]$^+$, 1051.6 [2M+Na]$^+$; [☐]$_D^{22}$- 31.08° (c=3.7, CHCl$_3$); δ$_H$ (500 MHz, CDCl$_3$) 0.99 (9H, s, C(CH$_3$)$_3$), 1.08 (6H, d, J=6.52 Hz, NCH(CH$_3$)$_2$), 1.68-1.74 (2H, m, CH$_2$C(CH$_3$)$_3$), 2.65 (4H, brt, J=5.04 Hz, CH$_2$NCH (CH$_3$)$_2$), 2.67-2.73 (1H, m, NCH(CH$_3$)$_2$), 3.29 (4H, brt, J=5.05 Hz, CH$_2$CH$_2$NCH(CH$_3$)$_2$), 3.49 (3H, s, OCH$_3$), 3.61 (1H, dd, 5.35 Hz, NCH$_2$CHOCH$_3$), 4.00-4.04 (1H, m, CHOCH$_3$), 4.09 (1H, d, J=16.89 Hz, OCH$_2$C=O), 4.20 (1H, d, J=16.93 Hz, OCH$_2$C=O), 4.27 (1H, dd, 5.88 Hz, NCH$_2$CHOCH$_3$), 4.74 (1H, d, J=6.86 Hz, OCH$_2$(C=O)CH), 4.91 (1H, dd, 4.28 Hz, OCHCHOCH$_3$), 4.94-5.00 (1H, m, CHCH$_2$C(CH$_3$)$_3$), 6.61 (1H, d, J=8.69 Hz, NH), 6.84 (2H, brd, J=8.95 Hz, aromatic CH), 7.65 (2H, brd, J=8.91 Hz, aromatic CH); δ$_C$ (125 MHz, CDCl$_3$) 18.53 (NCH(CH$_3$)$_2$), 29.75/29.80 (C(CH$_3$)$_3$), 30.75/30.77 (C(CH$_3$)$_3$), 46.53 (CH$_2$C(CH$_3$)$_3$), 47.02 (NCH$_2$CH$_2$NCH(CH$_3$)$_2$), 48.24 (CHCH$_2$C(CH$_3$)$_3$), 48.43 (NCH$_2$CH$_2$NCH(CH$_3$)$_2$), 49.76 (NCH$_2$CHOCH$_3$), 54.49 (NCH(CH$_3$)$_2$), 58.23 (OCH$_3$), 60.49 (OCH$_2$C(=O)CH), 71.45 (OCH$_2$C=O), 78.84 (CHOCH$_3$), 80.25 (OCHCHOCH$_3$), 114.01/114.10/128.49 and 129.83 (aromatic CH), 123.08 (aromatic quaternary), 153.55 (aromatic quaternary), 166.69 (NHC=O), 173.53 (CH$_2$NC=O), 207.93 (ketone C=O).

Formation of Example. Hydrochloride Salt.

EXAMPLE ketone (free base) (1 mmol) was dissolved in acetonitrile (16.7 mL) and standardised 0.1N HCl (1.5 eq, 15.0 mL) was added. The mixture was frozen and lyophilised to leave the EXAMPLE hydrochloride salt as a solid.

Example A

Assays for Cysteine Protease Activity

The compounds of this invention may be tested in one of a number of literature based biochemical assays that are designed to elucidate the characteristics of compound inhibition. The data from these types of assays enables compound potency and the rates of reaction to be measured and quantified. This information, either alone or in combination with other information, would allow the amount of compound required to produce a given pharmacological effect to be determined.

In Vitro Cathepsin Ki Inhibition Measurements

Stock solutions of substrate or inhibitor were made up to 10 mM in 100% dimethylsulfoxide (DMSO) (Rathburns, Glasgow, U.K.) and diluted as appropriately required. In all cases the DMSO concentration in the assays was maintained at less than 1% (vol./vol.). The equilibrium inhibition constants ($K_i^{SS}$) for each compound were measured under steady-state conditions monitoring enzyme activity as a function of inhibitor concentration. The values were calculated on the assumption of pure competitive behaviour (Cornish-Bowden, A. *Fundamentals of enzyme kinetics* Portland Press; 1995, 93-128). Human recombinant cathepsin K (0.25 nM final; B. Turk, Josef, Stefan Institute, Ljubljana, Slovenia), was routinely assayed in 100 mM sodium acetate; pH 5.5 containing 1 mM EDTA, 10 mM L-cysteine and 1.8 µM Z-Leu-Arg-AMC ([S]=K$_M$).

Measurement of the Apparent Macroscopic Binding (Michaelis) Constants (K$_M^{app}$) for Substrates The apparent macroscopic binding constant (K$_M^{app}$) for each substrate was calculated, from the dependence of enzyme activity as a function of substrate concentration. The observed rates were plotted on the ordinate against the related substrate concentration on the abscissa and the data fitted by direct regression analysis (Prism v 3.02; GraphPad, San Diego, USA) using Equation 1 (Cornish-Bowden, A. *Fundamentals of enzyme kinetics* Portland Press; 1995, 93-128).

$$v_i = \frac{V_{max}^{app} \cdot [S_o]}{[S_o] + K_M^{app}} \quad (1)$$

In Equation 1 '$v_i$' is the observed initial rate, '$V_{max}^{app}$' is the observed maximum activity at saturating substrate concentration, '$K_M^{app}$' is the apparent macroscopic binding (Michaelis) constant for the substrate, '$[S_o]$' is the initial substrate concentration.

Measurement of the Inhibition Constants

The apparent inhibition constant (K$_i$) for each compound was determined on the basis that inhibition was reversible and occurred by a pure-competitive mechanism. The K$_i$ values were calculated, from the dependence of enzyme activity as a function of inhibitor concentration, by direct regression analysis (Prism v 3.02) using Equation 2 (Cornish-Bowden, A., 1995).

$$v_i = \frac{V_{max}^{app} \cdot [S]}{[S] + \{K_M^{app} \cdot ([I]/K_i)\}} \quad (2)$$

In Equation 2 '$v_i$' is the observed residual activity, '$V_{max}^{app}$' is the observed maximum activity (i.e. in the absence of inhibitor), '$K_M^{app}$' is the apparent macroscopic binding (Michaelis) constant for the substrate, '[S]' is the initial substrate concentration, '$K_i$' is the apparent dissociation constant and '[I]' is the inhibitor concentration.

In situations where the apparent dissociation constant ($K_i^{app}$) approached the enzyme concentrations, the $K_i^{app}$ values were calculated using a quadratic solution in the form described by Equation 3 (Morrison, J. F. *Trends Biochem. Sci.*, 7, 102-105, 1982; Morrison, J. F. *Biochim. Biophys. Acta*, 185, 269-286, 1969; Stone, S. R. and Hofsteenge, J. *Biochemistry*, 25, 4622-4628, 1986).

$$v_i = \frac{F\left\{E_o - I_o - K_i^{app} + \sqrt{(E_o - I_o - K_i^{app})^2 + 4 \cdot K_i^{app} \cdot E_o}\right\}}{2} \quad (3)$$

$$K_i^{app} = K_i(1 + [S_o]/K_M^{app}) \quad (4)$$

In Equation 3 '$v_i$' is the observed residual activity, 'F' is the difference between the maximum activity (i.e. in the absence of inhibitor) and minimum enzyme activity, '$E_o$' is the total enzyme concentration, '$K_i^{app}$' is the apparent dissociation constant and '$I_o$' is the inhibitor concentration. Curves were fitted by non-linear regression analysis (Prism) using a fixed value for the enzyme concentration. Equation 4 was used to account for the substrate kinetics, where '$K_i$' is the inhibition constant, '$[S_o]$' is the initial substrate concentration and '$K_M^{app}$' is the apparent macroscopic binding (Michaelis) constant for the substrate (Morrison, 1982).

The Second-Order Rate of Reaction of Inhibitor with Enzyme

Where applicable, the concentration dependence of the observed rate of reaction ($k_{obs}$) of each compound with enzyme was analysed by determining the rate of enzyme inactivation under pseudo-first order conditions in the presence of substrate (Morrison, J. F., *TIBS*, 102-105, 1982; Tian, W. X. and Tsou, C. L., *Biochemistry*, 21, 1028-1032, 1982; Morrison, J. F. and Walsh, C. T., from Meister (Ed.), *Advances in Enzymol.*, 61, 201-301, 1988; Tsou, C. L., from Meister (Ed.), *Advances in Enzymol.*, 61, 381436, 1988). Assays were carried out by addition of various concentrations of inhibitor to assay buffer containing substrate. Assays were initiated by the addition of enzyme to the reaction mixture and the change in fluorescence monitored over time. During the course of the assay less than 10% of the substrate was consumed.

$$F = v_s t + \frac{(v_o - v_s)[1 - e^{(k_{obs} \cdot t)}]}{k_{obs}} + D \quad (5)$$

The activity fluorescence progress curves were fitted by non-linear regression analysis (Prism) using Eq. 5 (Morrison, 1969; Morrison, 1982); where 'F' is the fluorescence response, 't' is time, '$v_o$' is the initial velocity, '$v_s$' is the equilibrium steady-state velocity, '$k_{obs}$' is the observed pseudo first-order rate constant and 'D' is the intercept at time zero (i.e. the ordinate displacement of the curve). The second order rate constant was obtained from the slope of the line of a plot of $k_{obs}$ versus the inhibitor concentration (i.e. $k_{obs}/[I]$). To correct for substrate kinetics, Eq. 6 was used, where '$[S_o]$' is the initial substrate concentration and '$K_M^{app}$' is the apparent macroscopic binding (Michaelis) constant for the substrate.

$$k_{inact} = \frac{k_{obs}(1 + [S_o]/K_M^{app})}{[I]} \quad (6)$$

Compounds of the invention were tested by the above described assays and observed to exhibit cathepsin K inhibitory activity with an in vitro Ki inhibitory constant of less than or equal to 100 nM.

Liver Microsomal Incubations:

Human and rat liver microsomes were purchased from BD Gentest (Woburn, Mass., USA) and β-nicotinamide adenine dinucleotide 2'-phosphate reduced tetrasodium salt (NADPH) was purchased from Sigma-Aldrich (Poole, Dorset, UK). All liver microsome incubations were carried out in 50 mM potassium phosphate buffer at pH 7.4, with a final microsomal protein concentration of 0.5 mg/mL. Compounds were taken from 5 mM DMSO stock solutions and diluted in incubation buffer to give a final concentration of 25 μM, with a final DMSO concentration of 0.5% v/v. In brief, compounds were added to the incubation buffer along with the liver microsomes and incubated at 37° C. for 10 minutes. The reaction was then initiated by the addition of NADPH, previously dissolved in incubation buffer, to give a final concentration of 1 mM and re-incubated at 37° C. Aliquots were removed at 2 and 60 minutes and quenched with an equal volume of cold acetonitrile. After mixing vigorously, the precipitated protein matter was removed by filtration (Multiscreen Solvinert filter plates, Millipore, Bedford, Mass., USA) and the filtrate analysed by reverse phase HPLC with mass spectrometric detection, using single ion monitoring of the [M+H]$^+$ species. Metabolic turnover was determined by comparison of peak areas from the ion chromatograms of the parent compound at 2 and 60 minutes and expressed as percent remaining at 1 hour.

Plasma Incubations:

Human and rat plasma were purchased from Innovative Research Inc. (Southfield. MI, USA). Compounds were taken from 5 mM DMSO stock solutions and added to plasma, which had previously been incubated at 37° C., to give a final concentration of 25 μM and re-incubated. Aliquots were removed at 2 and 60 minutes and quenched with an equal volume of cold acetonitrile. After mixing vigorously, the precipitated protein matter was removed by filtration (Multiscreen Solvinert filter plates, Millipore, Bedford, Mass., USA) and the filtrate analysed by reverse phase HPLC with mass spectrometric detection, using single ion monitoring of the [M+H]$^+$ species. Metabolic turnover was determined by comparison of peak areas from the ion chromatograms of the parent compound at 2 and 60 minutes and expressed as percent remaining at 1 hour.

LogD Determinations:

LogD$_{(PBS)}$ determinations were performed in 96 well microtitre plates using a miniaturised "shake-flask" method. In brief, compounds were taken from 10 mM DMSO stock solutions and added to wells containing equal volumes of phosphate buffered saline (10 mM; pH 7.4) (PBS) and 1-octanol (Sigma-Aldrich, Poole, Dorset, UK) to give a final concentration of 50 μM. The plates were then capped and mixed vigorously for 1 hour on a microtitre plate shaker, after which they were left to stand, allowing the PBS and octanol phases to separate. The PBS layer was analysed by reverse phase HPLC with mass spectrometric detection, using single ion monitoring of the [M+H]$^+$ species. LogD$_{(PBS)}$ was determined by comparison of the peak area from the ion chromatogram of the compound in the PBS phase with that of a 50 μM standard of the same compound dissolved in acetonitrile/water (50:50) and calculated using the following formula:

$$\text{Log}D = \text{Log}\left[\frac{AUCstd - AUCpbs}{AUCpbs}\right]$$

Where AUCstd and AUCpbs are the peak areas from the standard and test ion chromatograms respectively. LogD$_{(PBs)}$ determinations were also made using PBS at pH6.9 and 5.5 by adjusting the pH of the buffer prior to the start of the assay, with 0.1 M HCL.

Human Osteoclast Resorption Assay

Bone resorption was studied using a model where human osteoclast precursor cells were cultured on bovine bone slices for 9 days and allowed to differentiate into bone-resorbing osteoclasts. The formed mature osteoclasts were then allowed to resorb bone. The assay was performed by Pharmatest Services Ltd, Itäinen Pitkakatu 4C, Turku, Finland. After the culture period, bone collagen degradation products were quantified from the culture medium as an index of bone resorption. Inhibitor compounds were added into the cell cultures after the differentiation period and their effects on the resorbing activity of mature osteoclasts were determined. The studies included a baseline group without added compounds and a positive control group where a potent cathepsin K inhibitor E-64 was added.

Human peripheral blood monocytes were suspended to culture medium and allowed to attach to bovine bone slices. The bone slices were transferred into 96-well tissue culture plates containing culture medium with appropriate amounts of important growth factors favouring osteoclast differentiation, including M-CSF, RANK-ligand and TGF-□. The cells were incubated in a $CO_2$ incubator in humidified atmosphere of 95% air and 5% carbon dioxide at 37° C. At day 7 when osteoclast differentiation was complete, the culture medium was replaced with culture medium containing conditions favouring osteoclast activity. The cell culture was continued for an additional 2 days, during which the formed mature osteoclasts were allowed to resorb bone in the presence of vehicle, control inhibitor (E64) or test compounds. At the end of the culture, bone collagen degradation products released into the culture medium were determined using a commercially available ELISA method (CrossLaps® for culture, Nordic Bioscience, Herlev, Denmark) as an index of bone resorption (see Bagger, Y. Z. et al, J. Bone. Miner. Res. 14 (suppl. 1), S370).

In this assay, selected EXAMPLES of the invention exhibited more than 75% inhibition of bone resorption at a concentration of 1000 nM.

Rat Osteoclast Resorption Assay

Bone resorption was studied using a model where mature osteoclasts derived from rat bone were cultured on bovine bone slices for 3 days and allowed to resorb bone in the presence of inhibitor, positive control (E-64) or vehicle. More specifically, tibia, femori and humeri were removed from 1 day old rat pups. The endosteal surfaces of the bones were scraped with a scalpel to release osteoclasts into the culture medium and the osteoclasts were allowed to attach to bovine bone slices. After the culture period, bone collagen degradation products were quantified from the culture medium as an index of bone resorption. The assay was performed by Pharmatest Services Ltd, Itäinen Pitkakatu 4C, Turku, Finland.

In this assay, selected EXAMPLES of the invention exhibited more than 75% inhibition of bone resorption at a concentration of 1000 nM.

TABLE 1

Comparison of biological properties for a selection of preferred compounds and prior art compounds 23/10 and 42/45a

| EXAMPLE | In vitro Ki (nM) vs Cath K | Cell-based % Inh. @ 1 µM Human | Human Plasma Stability % rem. @ 1 h | LogD pH 7.4 |
|---|---|---|---|---|
| Prior art compound 23 (Quibell, M. et.al. Bioorg. Med. Chem., 13, 609-625, 2005); Prior art compound 10 (Quibell, M. et.al. Bioorg. Med. Chem., 12, 5689-5710, 2004); | 87.4 | Lit. 60 | 75 | 1.36 |
| (EXAMPLE 1) Prior art compound 42 (Quibell, M. et.al. Bioorg. Med. Chem., 13, 609-625, 2005); Prior art compound 45a (Quibell, M. et.al. Bioorg. Med. Chem., 12, 5689-5710, 2004); | 8.7 | 55 | 95 | Lit.0.04* 0.56** *UV method **Ion-count method |

TABLE 1-continued
Comparison of biological properties for a selection of preferred compounds and prior art compounds 23/10 and 42/45a
| EXAMPLE | In vitro Ki (nM) vs Cath K | Cell-based % Inh. @ 1 μM Human | Human Plasma Stability % rem. @ 1 h | LogD pH 7.4 |
|---|---|---|---|---|
| 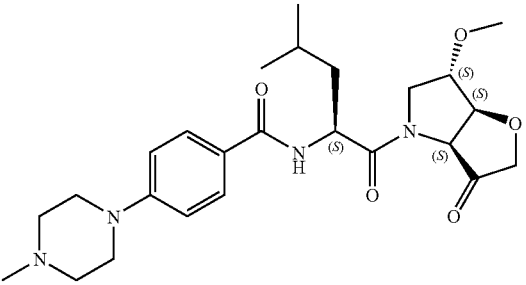 (EXAMPLE 1) | 5.6 | 81 | 96 | 1.18 |
| 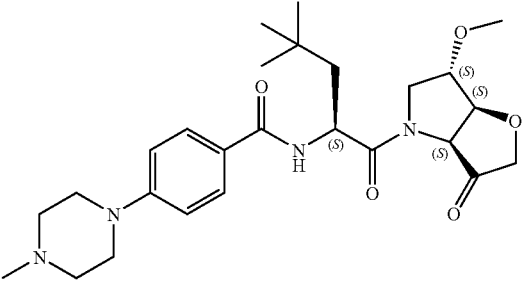 (EXAMPLE 2) | 6.3 | 69 | 93 | 1.00 |
| 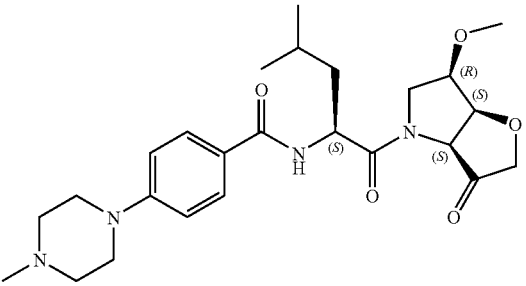 (EXAMPLE 3) | 15.1 | 54 | 87 | 0.42 |
| 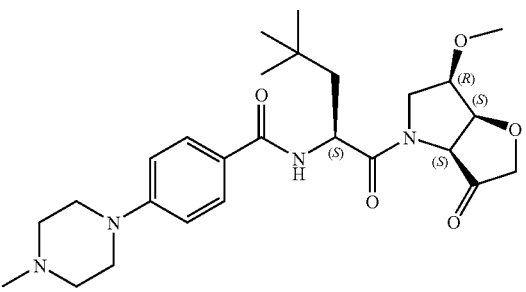 (EXAMPLE 4) | 5.6 | 66 | 89 | 0.84 |

TABLE 1-continued
Comparison of biological properties for a selection of preferred compounds and prior art compounds 23/10 and 42/45a
| EXAMPLE | In vitro Ki (nM) vs Cath K | Cell-based % Inh. @ 1 μM Human | Human Plasma Stability % rem. @ 1 h | LogD pH 7.4 |
|---|---|---|---|---|
| 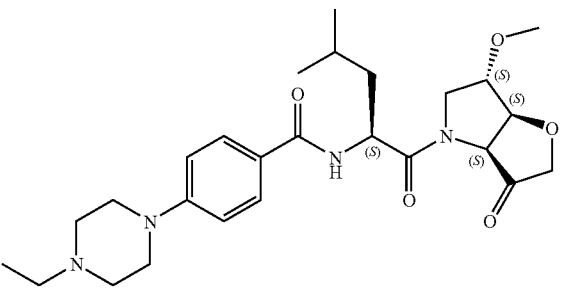 (EXAMPLE 5) | 5.8 | 79 | 96 | 1.05 |
| 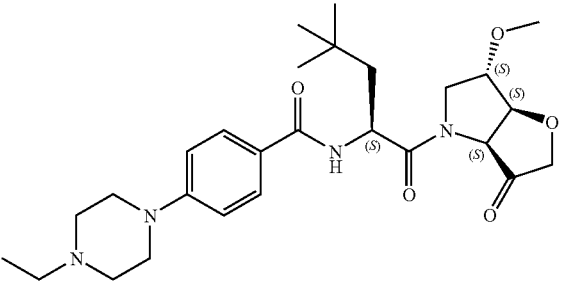 (EXAMPLE 6) | 5.1 | 87 | 100 | 1.46 |
| 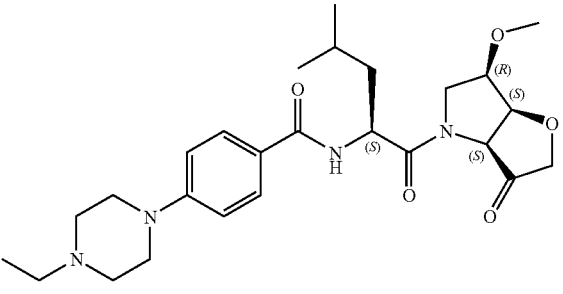 (EXAMPLE 7) | 9.9 | 63 | 93 | 0.89 |
| 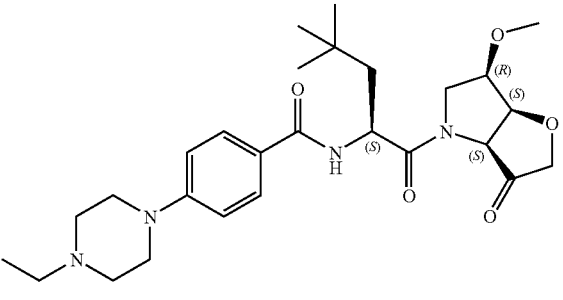 (EXAMPLE 8) | 9.2 | 71 | 92 | 1.09 |

TABLE 1-continued
Comparison of biological properties for a selection of preferred compounds and prior art compounds 23/10 and 42/45a
| EXAMPLE | In vitro Ki (nM) vs Cath K | Cell-based % Inh. @ 1 μM Human | Human Plasma Stability % rem. @ 1 h | LogD pH 7.4 |
|---|---|---|---|---|
| 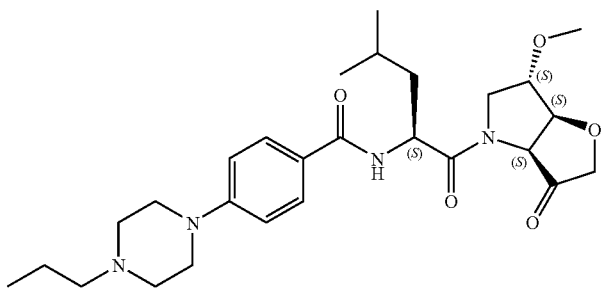 (EXAMPLE 13) | 3.9 | 88 | 93 | 1.64 |
| 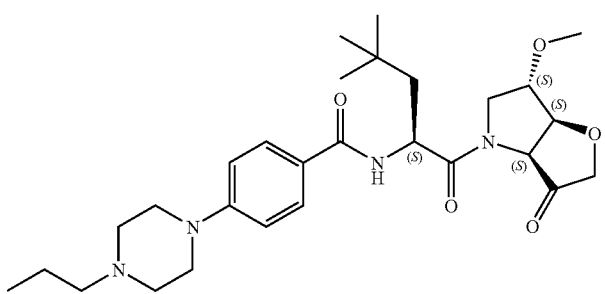 (EXAMPLE 14) | 8.6 | 84 | 98 | 1.74 |
| 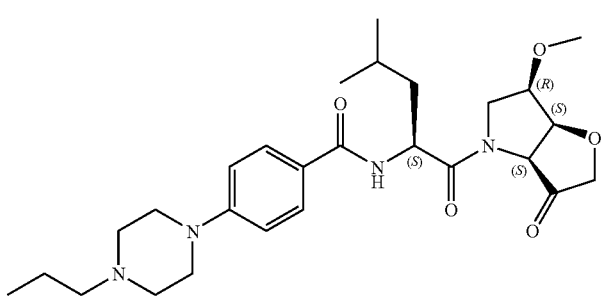 (EXAMPLE 15) | 16.3 | 76 | 92 | 1.34 |
| 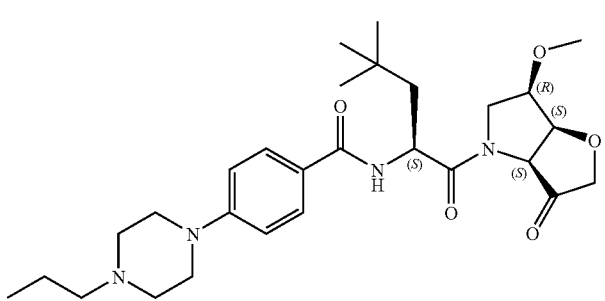 (EXAMPLE 16) | 3.7 | 82 | 97 | 1.69 |

TABLE 1-continued

Comparison of biological properties for a selection of preferred compounds and prior art compounds 23/10 and 42/45a

| EXAMPLE | In vitro Ki (nM) vs Cath K | Cell-based % Inh. @ 1 μM Human | Human Plasma Stability % rem. @ 1 h | LogD pH 7.4 |
|---|---|---|---|---|
| (EXAMPLE 22) | 8.4 | 78 | 91 | 1.2 |
| (EXAMPLE 23) | 11.2 | 25 | 88 | 0.55 |
| (EXAMPLE 24) | 3.5 | 49 | 96 | 0.01 |
| (EXAMPLE 25) | 6.9 | 45 | 92 | 0.56 |

TABLE 1-continued
Comparison of biological properties for a selection of preferred compounds and prior art compounds 23/10 and 42/45a
| EXAMPLE | In vitro Ki (nM) vs Cath K | Cell-based % Inh. @ 1 μM Human | Human Plasma Stability % rem. @ 1 h | LogD pH 7.4 |
|---|---|---|---|---|
| (EXAMPLE 26) 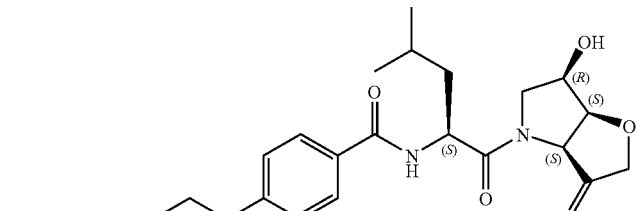 | 8.1 | 42 | 95 | 0.23 |
| (EXAMPLE 27) 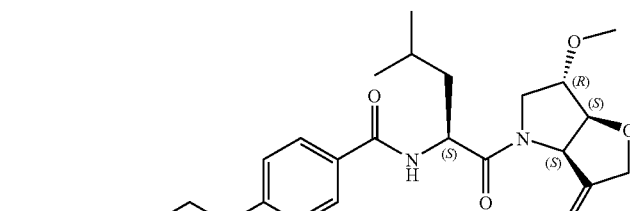 | 6.3 | 82 | 99 | 1.23 |
| (EXAMPLE 28) 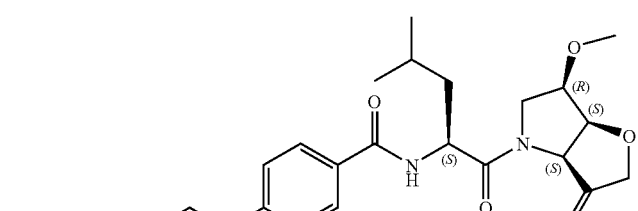 | 14.4 | 44 | 88 | 0.76 |
| (EXAMPLE 38) 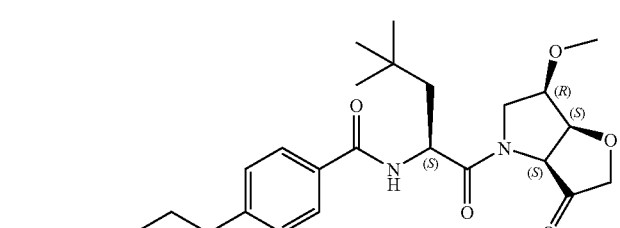 | 8.2 | 70 | 99 | 1.12 |

TABLE 1-continued
Comparison of biological properties for a selection of preferred compounds and prior art compounds 23/10 and 42/45a
| EXAMPLE | In vitro Ki (nM) vs Cath K | Cell-based % Inh. @ 1 μM Human | Human Plasma Stability % rem. @ 1 h | LogD pH 7.4 |
|---|---|---|---|---|
| (EXAMPLE 60) 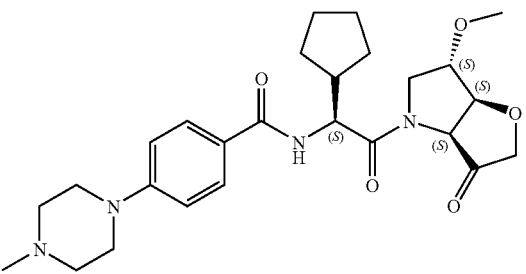 | 1.8 | $IC_{50}$ = 52 nM | 93.6 | 1.36 |
| (EXAMPLE 61) 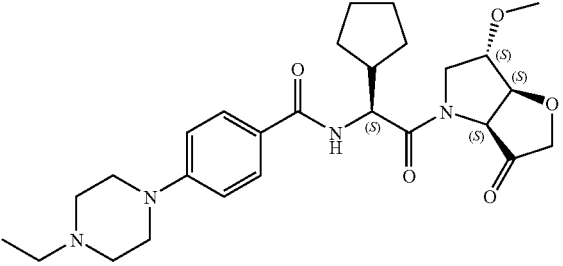 | 3.6 | — | 90.9 | 1.59 |
| (EXAMPLE 77) 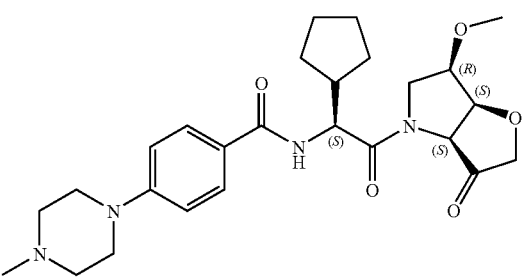 | 4.9 | $IC_{50}$ = 637 nM | 91.8 | 0.75 |
| (EXAMPLE 75) 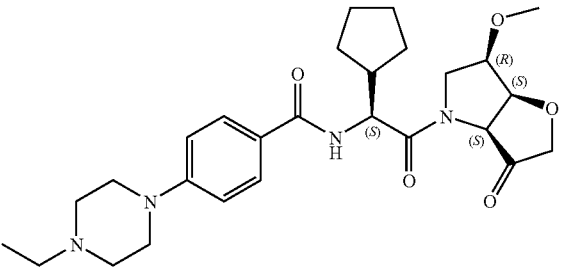 | 3.4 | $IC_{50}$ = 231 nM | 90.7 | 0.95 |

TABLE 2

Prior art WO-A-02057270 in vitro Ki against recombinant human cathepsin K.

| Example No (WO-A-02057270) | Ki (nM) vs Human Cathepsin K |
|---|---|
| 1 | >20000 |
| 2 | >50000 |
| 3 | >4000 |
| 4 | >100000 |
| 5 | >100000 |
| 6 | >20000 |
| 7 | >15000 |
| 8 | 390 |
| 9 | 90 |
| 10 | 87 |
| 11 | 1300 |
| 12 | 170 |
| 13 | 560 |
| 14 | 300 |
| 15 | 60 |
| 16 | 110 |
| 17 | 235 |
| 18 | 130 |
| 19 | 530 |
| 20 | 390 |
| 21 | 210 |
| 22 | 450 |
| 23 | >3000 |
| 24 | >2000 |
| 25 | 620 |
| 26 | >8000 |
| 27 | >20000 |
| 28 | >2500 |
| 29 | >17000 |
| 30 | >100000 |
| 31 | >1500 |
| 32 | >16000 |
| 33 | >36000 |
| 34 | >67000 |
| 35 | >32000 |
| 36 | 570 |
| 37 | >3500 |
| 38 | >4000 |
| 39 | >7500 |
| 40 | >3500 |
| 41 | >45000 |
| 42 | >1500 |
| 43 | >25000 |
| 44 | >40000 |
| 45 | >8500 |
| 46 | >20000 |
| 47 | 830 |
| 48 | >6500 |
| 49 | >6000 |
| 50 | >10000 |
| 51 | >1500 |
| 52 | >25000 |
| 53 | 200 |
| 54 | >2000 |
| 55 | >2000 |
| 56 | >4000 |
| 57 | 390 |
| 58 | >23000 |
| 59 | >2000 |
| 60 | >20000 |
| 61 | >16000 |
| 62 | >10000 |
| 63 | >250 |
| 64 | >8000 |
| 65 | 100 |
| 66 | >2500 |
| 67 | >2000 |
| 68 | >2500 |
| 69 | >15000 |
| 70 | >2500 |
| 71 | >20000 |
| 72 | >20000 |
| 73 | >35000 |
| 74 | >40000 |
| 75 | >50000 |
| 76 | >10000 |
| 77 | >100000 |
| 78 | >2000 |
| 79 | >200 |
| 80 | >150 |
| 81 | >50000 |
| 82 | >50000 |

Selected compounds of the present invention are significantly more potent than those specifically detailed in prior art WO-A-02057270 when assayed in vitro against recombinant human cathepsin K (compare tables 1 and 2).

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

The invention claimed is:

1. A compound of formula (I), or a pharmaceutically acceptable salt, hydrate, ketal derivative or hemiketal derivative thereof, (I)

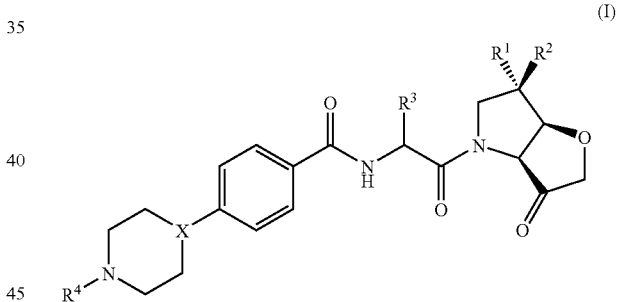

wherein:

X is CH or N;

one of $R^1$ and $R^2$ is H, and the other is selected from OH, OMe, OEt, O"Pr, O$^i$Pr, O-cyclopropyl, O-cyclobutyl, SH, SMe, SEt, S"Pr, S$^i$Pr, S-cyclopropyl, S-cyclobutyl, $NH_2$, NHMe, NHEt, NH"Pr, NH$^i$Pr, NH-cyclopropyl, NH-cyclobutyl, $NMe_2$, $N_3$, SOMe, SOEt, SO"Pr, SO$^i$Pr, SO-cyclopropyl, SO-cyclobutyl, $SO_2$Me, $SO_2$Et, $SO_2$"Pr, $SO_2$$^i$Pr, $SO_2$-cyclopropyl, $SO_2$-cyclobutyl, and

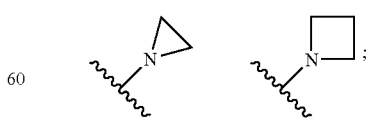

$R^3$ is selected from tert-butylmethyl, iso-propylmethyl, sec-butyl, tert-butyl, cyclopentyl and cyclohexyl;

$R^4$ is $C_{1-8}$ alkyl that is unsubstituted or substituted; or $C_{3-8}$ cycloalkyl that is unsubstituted or substituted.

2. A compound according to claim 1 wherein said compound is of formula Ia

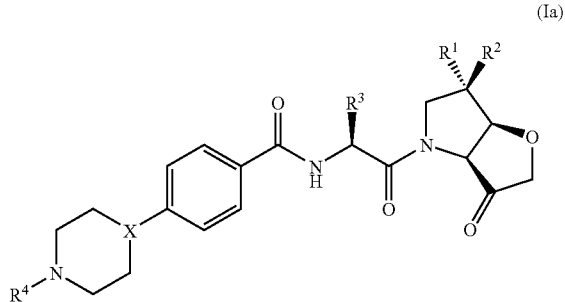

(Ia)

wherein X, $R^1$, $R^2$, $R^3$ and $R^4$ are as defined in claim 1.

3. A compound according to claim 1 wherein X is CH.
4. A compound according to claim 1 wherein X is N.
5. A compound according to claim 1 wherein $R^4$ is an unsubstituted $C_{3-6}$ cycloalkyl group.
6. A compound according to claim 1 wherein $R^4$ is a $C_{1-6}$ alkyl group that is unsubstituted or substituted by one or more $C_{1-6}$ alkoxy groups.
7. A compound according to claim 1 wherein $R^4$ is selected from methyl, ethyl, n-propyl, iso-propyl, cyclopropyl, n-butyl, sec-butyl, iso-butyl, tert-butyl, cyclobutyl and 2-methoxyethyl.
8. A compound according to claim 7 wherein $R^4$ is selected from methyl, ethyl, n-propyl, isopropyl, cyclopropyl, cyclobutyl and 2-methoxyethyl.
9. A compound according to claim 1 wherein $R^3$ is selected from tert-butylmethyl, sec-butyl, tert-butyl, cyclopentyl and cyclohexyl.
10. A compound according to claim 1 wherein $R^3$ is cyclopentyl or cyclohexyl.
11. A compound according to claim 1, wherein one of $R^1$ and $R^2$ is H, and the other is selected from OH, OMe, OEt, O$^n$Pr, O$^i$Pr, O-cyclopropyl, O-cyclobutyl, SH, SMe, SEt, S$^n$Pr, S$^i$Pr, S-cyclopropyl, S cyclobutyl, $NH_2$, NHMe, NHEt, NH$^n$Pr, NH$^i$Pr, NH-cyclopropyl, NH-cyclobutyl, and $NMe_2$.
12. A compound according to claim 1 wherein one of $R^1$ and $R^2$ is H, and the other is selected from OH, OMe, OEt, O$^n$Pr, O$^i$Pr, O-cyclopropyl, O-cyclobutyl, SH, SMe, SEt, S$^n$Pr, S$^i$Pr, S-cyclopropyl, S-cyclobutyl, $NH_2$, NHMe, NHEt, NH$^n$Pr, NH$^i$Pr, $NMe_2$ and $N_3$.
13. A compound according to claim 12 wherein:
$R^1$ is OH, OMe, OEt, SMe, $NH_2$, NHMe, $NMe_2$ or $N_3$ and $R^2$ is H; or
$R^2$ is OH, OMe, OEt, SMe, $NH_2$, NHMe, $NMe_2$ or $N_3$ and $R^1$ is H.
14. A compound according to claim 13 wherein:
$R^1$ is OH, OMe, OEt, $NH_2$, NHMe, SMe or $N_3$, and $R^2$ is H; or
$R^2$ is OH, OMe, $NH_2$ or $N_3$, and $R^1$ is H.
15. A compound according to claim 1 which is selected from the following:
N—((S)-1-((3aS,6S,6aS)-6-hydroxy-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide
N—((S)-1-((3aS,6S,6aS)-6-hydroxy-3-oxodihydro-2H-furo[3,2-b]pyrrol-4(5H,6H,6aH)-yl)-4,4-dimethyl-1-oxopentan-2-yl)-4-(4-isopropylpiperazin-1-yl)benzamide
4-(4-cyclopropylpiperazin-1-yl)-N—((S)-1-((3aS,6S,6aS)-6-hydroxy-3-oxodihydro-2H-furo[3,2-b]pyrrol-4(5H,6H,6aH)-yl)-4,4-dimethyl-1-oxopentan-2-yl)benzamide
4-(4-cyclobutylpiperazin-1-yl)-N—((S)-1-((3aS,6S,6aS)-6-hydroxy-3-oxodihydro-2H-furo[3,2-b]pyrrol-4(5H,6H,6aH)-yl)-4,4-dimethyl-1-oxopentan-2-yl)benzamide
4-(1-cyclopropylpiperidin-4-yl)-N—((S)-1-((3aS,6S,6aS)-6-hydroxy-3-oxodihydro-2H-furo[3,2-b]pyrrol-4(5H,6H,6aH)-yl)-4,4-dimethyl-1-oxopentan-2-yl)benzamide
4-(1-cyclobutylpiperidin-4-yl)-N—((S)-1-((3aS,6S,6aS)-6-hydroxy-3-oxodihydro-2H-furo[3,2-b]pyrrol-4(5H,6H,6aH)-yl)-4,4-dimethyl-1-oxopentan-2-yl)benzamide
N—((S)-1-((3aS,6S,6aS)-6-hydroxy-3-oxodihydro-2H-furo[3,2-b]pyrrol-4(5H,6H,6aH)-yl)-4-methyl-1-oxopentan-2-yl)-4-(4-propylpiperazin-1-yl)benzamide
N—((S)-1-((3aS,6S,6aS)-6-hydroxy-3-oxodihydro-2H-furo[3,2-b]pyrrol-4(5H,6H,6aH)-yl)-4-methyl-1-oxopentan-2-yl)-4-(4-isopropylpiperazin-1-yl)benzamide
4-(4-cyclopropylpiperazin-1-yl)-N—((S)-1-((3aS,6S,6aS)-6-hydroxy-3-oxodihydro-2H-furo[3,2-b]pyrrol-4(5H,6H,6aH)-yl)-4-methyl-1-oxopentan-2-yl)benzamide
4-(4-cyclobutylpiperazin-1-yl)-N—((S)-1-((3aS,6S,6aS)-6-hydroxy-3-oxodihydro-2H-furo[3,2-b]pyrrol-4(5H,6H,6aH)-yl)-4-methyl-1-oxopentan-2-yl)benzamide
4-(1-cyclopropylpiperidin-4-yl)-N—((S)-1-((3aS,6S,6aS)-6-hydroxy-3-oxodihydro-2H-furo[3,2-b]pyrrol-4(5H,6H,6aH)-yl)-4-methyl-1-oxopentan-2-yl)benzamide
4-(1-cyclobutylpiperidin-4-yl)-N—((S)-1-((3aS,6S,6aS)-6-hydroxy-3-oxodihydro-2H-furo[3,2-b]pyrrol-4(5H,6H,6aH)-yl)-4-methyl-1-oxopentan-2-yl)benzamide
4-(4-ethylpiperazin-1-yl)-N-((2S,3S)-1-((3aS,6S,6aS)-6-hydroxy-3-oxodihydro-2H-furo[3,2-b]pyrrol-4(5H,6H,6aH)-yl)-3-methyl-1-oxopentan-2-yl)benzamide
N-((2S,3S)-1-((3aS,6S,6aS)-6-hydroxy-3-oxodihydro-2H-furo[3,2-b]pyrrol-4(5H,6H,6aH)-yl)-3-methyl-1-oxopentan-2-yl)-4-(4-propylpiperazin-1-yl)benzamide
N-((2S,3S)-1-((3aS,6S,6aS)-6-hydroxy-3-oxodihydro-2H-furo[3,2-b]pyrrol-4(5H,6H,6aH)-yl)-3-methyl-1-oxopentan-2-yl)-4-(4-isopropylpiperazin-1-yl)benzamide
4-(4-cyclopropylpiperazin-1-yl)-N-((2S,3S)-1-((3aS,6S,6aS)-6-hydroxy-3-oxodihydro-2H-furo[3,2-b]pyrrol-4(5H,6H,6aH)-yl)-3-methyl-1-oxopentan-2-yl)benzamide
4-(4-cyclobutylpiperazin-1-yl)-N-((2S,3S)-1-((3aS,6S,6aS)-6-hydroxy-3-oxodihydro-2H-furo[3,2-b]pyrrol-4(5H,6H,6aH)-yl)-3-methyl-1-oxopentan-2-yl)benzamide
4-(1-cyclopropylpiperidin-4-yl)-N-((2S,3S)-1-((3aS,6S,6aS)-6-hydroxy-3-oxodihydro-2H-furo[3,2-b]pyrrol-4(5H,6H,6aH)-yl)-3-methyl-1-oxopentan-2-yl)benzamide
4-(1-cyclobutylpiperidin-4-yl)-N-((2S,3S)-1-((3aS,6S,6aS)-6-hydroxy-3-oxodihydro-2H-furo[3,2-b]pyrrol-4(5H,6H,6aH)-yl)-3-methyl-1-oxopentan-2-yl)benzamide
4-(4-ethylpiperazin-1-yl)-N—((S)-1-((3aS,6S,6aS)-6-hydroxy-3-oxodihydro-2H-furo[3,2-b]pyrrol-4(5H,6H,6aH)-yl)-3,3-dimethyl-1-oxobutan-2-yl)benzamide
N—((S)-1-((3aS,6S,6aS)-6-hydroxy-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide N—((S)-1-((3aS,6S,6aS)-6-hydroxy-3-oxodihydro-2H-furo[3,2-b]pyrrol-4(5H,6H,6aH)-yl)-3,3-dimethyl-1-oxobutan-2-yl)-4-(4-isopropylpiperazin-1-yl)benzamide 4-(4-cyclopropylpiperazin-1-yl)-N—((S)-1-((3aS,6S,6aS)-6-hydroxy-3-oxodihydro-2H-furo[3,2-b]pyrrol-4(5H,6H,6aH)-yl)-3,3-dimethyl-1-oxobutan-2-yl)benzamide 4-(4-cyclobutylpiperazin-1-yl)-N—((S)-1-((3aS,6S,6aS)-6-hydroxy-3-oxodihydro-2H-furo[3,2-b]pyrrol-4(5H,6H,6aH)-yl)-3,3-dimethyl-1-oxobutan-2-yl)benzamide 4-(1-cyclopropylpiperidin-4-yl)-N—((S)-1-((3aS,6S,6aS)-6-hydroxy-3-oxodihydro-2H-furo[3,2-b]pyrrol-4(5H,6H,6aH)-yl)-3,3-dimethyl-1-oxobutan-2-yl)benzamide 4-(1-cyclobutylpiperidin-4-yl)-N—((S)-1-((3aS,6S,6aS)-6-hydroxy-3-oxodihydro-2H-furo[3,2-b]pyrrol-4(5H,6H,6aH)-yl)-3,3-dimethyl-1-oxobutan-2-yl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclopentyl-2-((3aS,6S,6aS)-6-hydroxy-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclohexyl-2-((3aS,6S,6aS)-6-hydroxy-3-oxodihydro-2H-furo[3,2-b]pyrrol-4(5H,6H,6aH)-yl)-2-oxoethyl)benzamide N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)-4-(4-methylpiperazin-1-yl)benzamide 4-(4-ethylpiperazin-1-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide 4-(4-isopropylpiperazin-1-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)-4-(4-(2-methoxyethyl)piperazin-1-yl)benzamide 4-(4-cyclopropylpiperazin-1-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide 4-(4-cyclobutylpiperazin-1-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)-4-(1-propylpiperidin-4-yl)benzamide 4-(1-isopropylpiperidin-4-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)-4-(1-(2-methoxyethyl)piperidin-4-yl)benzamide 4-(1-cyclopropylpiperidin-4-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide 4-(1-cyclobutylpiperidin-4-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)-4-(4-methylpiperazin-1-yl)benzamide 4-(4-ethylpiperazin-1-yl)-N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)benzamide N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)-4-(4-propylpiperazin-1-yl)benzamide 4-(4-isopropylpiperazin-1-yl)-N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)benzamide N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)-4-(4-(2-methoxyethyl)piperazin-1-yl)benzamide 4-(4-cyclopropylpiperazin-1-yl)-N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)benzamide 4-(4-cyclobutylpiperazin-1-yl)-N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)benzamide N—((S)-1 ((3aS,6S,6aS)-6-methoxy-3-oxodihydro-2H-furo[3,2-b]pyrrol-4(5H,6H,6aH)-yl)-4-methyl-1-oxopentan-2-0)-4-(1-propylpiperidin-4-yl)benzamide 4-(1-cyclopropylpiperidin-4-yl)-N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)benzamide 4-(1-cyclobutylpiperidin-4-yl)-N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)benzamide N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)-4-(4-methylpiperazin-1-yl)benzamide 4-(4-ethylpiperazin-1-yl)-N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)-4-(4-propylpiperazin-1-yl)benzamide 4-(4-isopropylpiperazin-1-yl)-N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)-4-(1-(2-methoxyethyl)piperazin-4-yl)benzamide 4-(4-cyclopropylpiperazin-1-yl)-N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)benzamide 4-(4-cyclobutylpiperazin-1-yl)-N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)-4-(1-methylpiperidin-4-yl)benzamide 4-(1-ethylpiperidin-4-yl)-N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)-4-(1-propylpiperidin-4-yl)benzamide 4-(1-isopropylpiperidin-4-yl)-N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)-4-(1-(2-methoxyethyl)piperidin-4-yl)benzamide 4-(1-cyclopropylpiperidin-4-yl)-N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)benzamide 4-(1-cyclobutylpiperidin-4-yl)-N-((2S,3S)-1-((3aS,6S,6aS)-6-methoxy-3-oxodihydro-2H-furo[3,2-b]pyrrol-4(5H,6H,6aH)-yl)-3-methyl-1-oxopentan-2-yl)benzamide N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)-4-(4-methylpiperazin-1-yl)benzamide 4-(4-ethylpiperazin-1-yl)-N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)benzamide N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide 4-(4-isopropylpiperazin-1-yl)-N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)benzamide N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)-4-(4-(2-methoxyethyl)piperazin-1-yl)benzamide 4-(4-cyclopropylpiperazin-1-yl)-N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)benzamide 4-(4-cyclobutylpiperazin-1-yl)-N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)benzamide N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)-4-(1-propylpiperidin-4-yl)benzamide 4-(1-cyclopropylpiperidin-4-yl)-N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)benzamide 4-(1-cyclobutylpiperidin-4-yl)-N—((S)-1-((3aS,6S,6aS)-6-methoxy-3-oxodihydro-2H-furo[3,2-b]pyrrol-4(5H,6H,6aH)-yl)-3,3-dimethyl-1-oxobutan-2-yl)benzamide N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)benzamide N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(1-methylpiperidin-4-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(1-ethylpiperidin-4-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclohexyl-2-((3aS,6S,6aS)-6-methoxy-3-oxodihydro-2-furo[3,2-b]pyrrol-4(5H,6H,6aH)-yl)-2-oxoethyl)-4-(1-isopropylpiperidin-4-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(1-(2-methoxyethyl)piperidin-4-yl)benzamide N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclohexyl-2-((3aS,6S,6aS)-6-methoxy-3-oxodihydro-2H-furo[3,2-b]pyrrol-4(5H,6H,6aH)-yl)-2-oxoethyl)benzamide N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)-4-(4-methylpiperazin-1-yl)benzamide N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)-4-(4-ethylpiperazin-1-yl)benzamide N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)-4-(4-isopropylpiperazin-1-yl)benzamide N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)-4-(4-(2-methoxyethyl)piperazin-1-yl)benzamide 4-(4-cyclopropylpiperazin-1-yl)-N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)benzamide 4-(4-cyclobutylpiperazin-1-yl)-N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)-4-(1-propylpiperidin-4-yl)benzamide N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)-4-(1-isopropylpiperidin-4-yl)benzamide N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)-4-(1-(2-methoxyethyl)piperidin-4-yl)benzamide 4-(1-cyclopropylpiperidin-4-yl)-N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)benzamide 4-(1-cyclobutylpiperidin-4-yl)-N—((S)-1-((3aS,6S,6aS)-6-ethoxy-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)-4-(4-methylpiperazin-1-yl)benzamide N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)-4-(4-ethylpiperazin-1-yl)benzamide N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)-4-(4-propylpiperazin-1-yl)benzamide N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)-4-(4-isopropylpiperazin-1-yl)benzamide N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)-4-(4-(2-methoxyethyl)piperazin-1-yl)benzamide 4-(4-cyclopropylpiperazin-1-yl)-N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)benzamide 4-(4-cyclobutylpiperazin-1-yl)-N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)benzamide N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)-4-(1-propylpiperidin-4-yl)benzamide 4-(1-cyclopropylpiperidin-4-yl)-N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)benzamide 4-(1-cyclobutylpiperidin-4-yl)-N—((S)-1-((3aS,6S,6aS)-6-ethoxy-3-oxodihydro-2H-furo[3,2-b]pyrrol-4(5H,6H,6aH)-yl)-4-methyl-1-oxopentan-2-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(4-methylpiperazin-1-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(4-ethylpiperazin-1-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(4-propylpiperazin-1-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(4-isopropylpiperazin-1-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(4-(2-methoxyethyl)piperazin-1-yl)benzamide 4-(4-cyclopropylpiperazin-1-yl)-N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)benzamide 4-(4-cyclobutylpiperazin-1-yl)-N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(1-methylpiperidin-4-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(1-ethylpiperidin-4-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(1-propylpiperidin-4-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(1-isopropylpiperidin-4-yl)benzamide N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)-4-(1-(2-methoxyethyl)piperidin-4-yl)benzamide 4-(1-cyclopropylpiperidin-4-yl)-N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)benzamide 4-(1-cyclobutylpiperidin-4-yl)-N-((2S,3S)-1-((3aS,6S,6aS)-6-ethoxy-3-oxodihydro-2H-furo[3,2-b]pyrrol-4(5H,6H,6aH)-yl)-3-methyl-1-oxopentan-2-yl)benzamide N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)-4-(4-methylpiperazin-1-yl)benzamide N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)-4-(4-ethylpiperazin-1-yl)benzamide N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)-4-(4-isopropylpiperazin-1-yl)benzamide N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)-4-(4-(2-methoxyethyl)piperazin-1-yl)benzamide 4-(4-cyclopropylpiperazin-1-yl)-N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)benzamide 4-(4-cyclobutylpiperazin-1-yl)-N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)benzamide N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)-4-(1-propylpiperidin-4-yl)benzamide 4-(1-cyclopropylpiperidin-4-yl)-N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)benzamide 4-(1-cyclobutylpiperidin-4-yl)-N—((S)-1-((3aS,6S,6aS)-6-ethoxy-3-oxodihydro-2H-furo[3,2-b]pyrrol-4(5H,6H,6aH)-yl)-3,3-dimethyl-1-oxobutan-2-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(1-methylpiperidin-4-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(1-ethylpiperidin-4-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(1-(2-methoxyethyl)piperidin-4-yl)benzamide N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclopentyl-2-((3aS,6S,6aS)-6-ethoxy-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(1-methylpiperidin-4-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(1-ethylpiperidin-4-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(1-(2-methoxyethyl)piperidin-4-yl)benzamide N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclohexyl-2-((3aS,6S,6aS)-6-ethoxy-3-oxodihydro-2H-furo[3,2-b]pyrrol-4(5H,6H,6aH)-yl)-2-oxoethyl)benzamide N—((S)-1-((3aS,6S,6aR)-6-amino-3-oxodihydro-2H-furo[3,2-b]pyrrol-4(5H,6H,6aH)-yl)-4,4-dimethyl-1-oxopentan-2-yl)-4-(1-propylpiperazin-1-yl)benzamide N—((S)-1-((3aS,6S,6aR)-6-amino-3-oxodihydro-2H-furo[3,2-b]pyrrol-4(5H,6H,6aH)-yl)-4,4-dimethyl-1-oxopentan-2-yl)-4-(1-cyclopropylpiperazin-1-yl)benzamide N—((S)-1-((3aS,6S,6aR)-6-amino-3-oxodihydro-2H-furo[3,2-b]pyrrol-4(5H,6H,6aH)-yl)-4,4-dimethyl-1-oxopentan-2-yl)-4-(1-cyclobutylpiperazin-1-yl)benzamide N-((2S,3S)-1-((3aS,6S,6aR)-6-amino-3-oxodihydro-2H-furo[3,2-b]pyrrol-4(5H,6H,6aH)-yl)-3-methyl-1-oxopentan-2-yl)-4-(4-ethylpiperazin-1-yl)benzamide N-((2S,3S)-1-((3aS,6S,6aR)-6-amino-3-oxodihydro-2H-furo[3,2-b]pyrrol-4(5H,6H,6aH)-yl)-3-methyl-1-oxopentan-2-yl)-4-(4-propylpiperazin-1-yl)benzamide N-((2S,3S)-1-((3aS,6S,6aR)-6-amino-3-oxodihydro-2H-furo[3,2-b]pyrrol-4(5H,6H,6aH)-yl)-3-methyl-1-oxopentan-2-yl)-4-(4-isopropylpiperazin-1-yl)benzamide N-((2S,3S)-1-((3aS,6S,6aR)-6-amino-3-oxodihydro-2H-furo[3,2-b]pyrrol-4(5H,6H,6aH)-yl)-3-methyl-1-oxopentan-2-yl)-4-(4-cyclopropylpiperazin-1-yl)benzamide N-((2S,3S)-1-((3aS,6S,6aR)-6-amino-3-oxodihydro-2H-furo[3,2-b]pyrrol-4(5H,6H,6aH)-yl)-3-methyl-1-oxopentan-2-yl)-4-(4-cyclobutylpiperazin-1-yl)benzamide N—((S)-1-((3aS,6S,6aR)-6-amino-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide N—((S)-1-((3aS,6S,6aR)-6-amino-3-oxodihydro-2H-furo[3,2-b]pyrrol-4(5H,6H,6aH)-yl)-3,3-di-methyl-1-oxobutan-2-yl)-4-(4-cyclopropylpiperazin-1-yl)benzamide N—((S)-1-((3aS,6S,6aR)-6-amino-3-oxodihydro-2H-furo[3,2-b]pyrrol-4(5H,6H,6aH)-yl)-3,3-di-methyl-1-oxobutan-2-yl)-4-(4-cyclobutylpiperazin-1-yl)benzamide N—(S)-2-((3aS,6S,6aR)-6-amino-3-oxodihydro-2H-furo[3,2-b]pyrrol-4(5H,6H,6aH)-yl)-1-cyclopentyl-2-oxoethyl)-4-(4-propylpiperazin-1-yl)benzamide N—(S)-2-((3aS,6S,6aR)-6-amino-3-oxodihydro-2H-furo[3,2-b]pyrrol-4(5H,6H,6aH)-yl)-1-cyclopentyl-2-oxoethyl)-4-(4-cyclopropylpiperazin-1-yl)benzamide N—(S)-2-((3aS,6S,6aR)-6-amino-3-oxodihydro-2H-furo[3,2-b]pyrrol-4(5H,6H,6aH)-yl)-1-cyclopentyl-2-oxoethyl)-4-(4-cyclobutylpiperazin-1-yl)benzamide N—(S)-2-((3aS,6S,6aR)-6-amino-3-oxodihydro-2H-furo[3,2-b]pyrrol-4(5H,6H,6aH)-yl)-1-cyclohexyl-2-oxoethyl)-4-(4-ethylpiperazin-1-yl)benzamide N—(S)-2-((3aS,6S,6aR)-6-amino-3-oxodihydro-2H-furo[3,2-b]pyrrol-4(5H,6H,6aH)-yl)-1-cyclohexyl-2-oxoethyl)-4-(propylpiperazin-1-yl)benzamide N—(S)-2-((3aS,6S,6aR)-6-amino-3-oxodihydro-2H-furo[3,2-b]pyrrol-4(5H,6H,6aH)-yl)-1-cyclohexyl-2-oxoethyl)-4-(isopropylpiperazin-1-yl)benzamide N—(S)-2-((3aS,6S,6aR)-6-amino-3-oxodihydro-2H-furo[3,2-b]pyrrol-4(5H,6H,6aH)-yl)-1-cyclohexyl-2-oxoethyl)-4-(cyclopropylpiperazin-1-yl)benzamide N—(S)-2-((3aS,6S,6aR)-6-amino-3-oxodihydro-2H-furo[3,2-b]pyrrol-4(5H,6H,6aH)-yl)-1-cyclohexyl-2-oxoethyl)-4-(cyclobutylpiperazin-1-yl)benzamide N—((S)-1-((3aS,6S,6aR)-6-(methylamino)-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide 4-(4-cyclopropylpiperazin-1-yl)-N—((S)-1-((3aS,6S,6aR)-6-(methylamino)-3-oxodihydro-2H-furo[3,2-b]pyrrol-4(5H,6H,6aH)-yl)-4,4-dimethyl-1-oxopentan-2-yl)benzamide 4-(4-cyclobutylpiperazin-1-yl)-N—((S)-1-((3aS,6S,6aR)-6-(methylamino)-3-oxodihydro-2H-furo[3,2-b]pyrrol-4(5H,6H,6aH)-yl)-4,4-dimethyl-1-oxopentan-2-yl)benzamide 4-(1-cyclopropylpiperidin-4-yl)-N—((S)-1-((3aS,6S,6aR)-6-(methylamino)-3-oxodihydro-2H-furo[3,2-b]pyrrol-4(5H,6H,6aH)-yl)-4,4-dimethyl-1-oxopentan-2-yl)benzamide 4-(1-cyclobutylpiperidin-4-yl)-N—((S)-1-((3aS,6S,6aR)-6-(methylamino)-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aR)-6-(methylamino)-3-oxodihydro-2H-furo[3,2-b]pyrrol-4(5H,6H,6aH)-yl)-4-methyl-1-oxopentan-2-yl)-4-(4-propylpiperazin-1-yl)benzamide 4-(4-cyclopropylpiperazin-1-yl)-N—((S)-1-((3aS,6S, 6aR)-6-(methylamino)-3-oxodihydro-2H-furo[3,2-b] pyrrol-4(5H,6H,6aH)-yl)-4-methyl-1-oxopentan-2-yl) benzamide 4-(4-cyclobutylpiperazin-1-yl)-N—((S)-1-((3aS,6S,6aR)- 6-(methylamino)-3-oxodihydro-2H-furo[3,2-b]pyrrol-4(5H,6H,6aH)-yl)-4-methyl-1-oxopentan-2-yl)benzamide 4-(4-ethylpiperazin-1-yl)-N-((2S,3S)-1-((3aS,6S,6aR)-6-(methylamino)-3-oxodihydro-2H-furo[3,2-b]pyrrol-4 (5H,6H,6aH)-yl)-3-methyl-1-oxopentan-2-yl)benzamide N-((2S,3S)-1-((3aS,6S,6aR)-6-(methylamino)-3-oxodihydro-2H-furo[3,2-b]pyrrol-4(5H,6H,6aH)-yl)-3-methyl-1-oxopentan-2-yl)-4-(4-propylpiperazin-1-yl)benzamide 4-(4-isopropylpiperazin-1-yl-N-((2S,3S)-1-((3aS,6S, 6aR)-6-(methylamino)-3-oxodihydro-2H-furo[3,2-b] pyrrol-4(5H,6H,6aH)-yl)-3-methyl-1-oxopentan-2-yl)-) benzamide 4-(4-(2-methoxyethyl)piperazin-1-yl)-N-((2S,3S)-1-((3aS,6S,6aR)-6-(methylamino)-3-oxodihydro-2H-furo[3,2-b]pyrrol-4(5H,6H,6aH)-yl)-3-methyl-1-oxopentan-2-yl)benzamide 4-(4-cyclopropylpiperazin-1-yl)-N-((2S,3S)-1-((3aS,6S, 6aR)-6-(methylamino)-3-oxodihydro-2H-furo[3,2-b] pyrrol-4(5H,6H,6aH)-yl)-3-methyl-1-oxopentan-2-yl) benzamide 4-(4-cyclobutylpiperazin-1-yl)-N-((2S,3S)-1-((3aS,6S, 6aR)-6-(methylamino)-3-oxodihydro-2H-furo[3,2-b] pyrrol-4(5H,6H,6aH)-yl)-3-methyl-1-oxopentan-2-yl) benzamide N-((2S,3S)-1-((3aS,6S,6aR)-6-(methylamino)-3-oxodihydro-2H-furo[3,2-b]pyrrol-4(5H,6H,6aH)-yl)-3-methyl-1-oxopentan-2-yl)-4-(1-propylpiperidin-4-yl)benzamide 4-(1-isopropylpiperidin-4-yl)-N-((2S,3S)-1-((3aS,6S, 6aR)-6-(methylamino)-3-oxodihydro-2H-furo[3,2-b] pyrrol-4(5H,6H,6aH)-yl)-3-methyl-1-oxopentan-2-yl) benzamide 4-(1-cyclopropylpiperidin-4-yl)-N-((2S,3S)-1-((3aS,6S, 6aR)-6-(methylamino)-3-oxodihydro-2H-furo[3,2-b] pyrrol-4(5H,6H,6aH)-yl)-3-methyl-1-oxopentan-2-yl) benzamide 4-(1-cyclobutylpiperidin-4-yl)-N-((2S,3S)-1-((3aS,6S, 6aR)-6-(methylamino)-3-oxodihydro-2H-furo[3,2-b] pyrrol-4(5H,6H,6aH)-yl)-3-methyl-1-oxopentan-2-yl) benzamide N—((S)-1-((3aS,6S,6aR)-6-(methylamino)-3-oxodihydro-2H-furo[3,2-pyrrol-4(5H,6H,6aH)-yl)-3,3-dimethyl-1-oxobutan-2-yl)-4-(4-propylpiperazin-1-yl)benzamide 4-(4-cyclopropylpiperazin-1-yl)-N—((S)-1-((3aS,6S, 6aR)-6-(methylamino)-3-oxodihydro-2H-furo[3,2-b] pyrrol-4(5H,6H,6aH)-yl)-3,3-dimethyl-1-oxobutan-2-yl)benzamide 4-(4-cyclobutylpiperazin-1-yl)-N—((S)-1-((3aS,6S,6aR)- 6-(methylamino)-3-oxodihydro-2H-furo[3,2-b]pyrrol-4(5H,6H,6aH)-yl)-3,3-dimethyl-1-oxobutan-2-yl)benzamide N—((S)-1-((3aS,6S,6aR)-6-(methylamino)-3-oxodihydro-2H-furo[3,2-b]pyrrol-4(5H,6H,6aH)-yl)-3,3-dimethyl-1-oxobutan-2-yl)-4-(1-propylpiperidin-4-yl)benzamide 4-(1-cyclopropylpiperidin-4-yl)-N—((S)-1-((3aS,6S, 6aR)-6-(methylamino)-3-oxodihydro-2H-furo[3,2-b] pyrrol-4(5H,6H,6aH)-yl)-3'3-di-methyl-1-oxobutan-2-yl)benzamide 4-(1-cyclobutylpiperidin-4-yl)-N—((S)-1-((3aS,6S,6aR)- 6-(methylamino)-3-oxodihydro-2H-furo[3,2-b]pyrrol-4(5H,6H,6aH)-yl)-3,3-di-methyl-1-oxobutan-2-yl)benzamide N—((S)-1-cyclopentyl-2-((3aS,6S,6aR)-6-(methylamino)-3-oxodihydro-2H-furo[3,2-b]pyrrol-4(5H,6H, 6aH)-yl)-2-oxoethyl)-4-(4-propylpiperazin-1-yl)benzamide N—((S)-1-cyclopentyl-2-((3aS,6S,6aR)-6-(methylamino)-3-oxodihydro-2H-furo[3,2-b]pyrrol-4(5H,6H, 6aH)-yl)-2-oxoethyl)-4-(4-cyclopropylpiperazin-1-yl) benzamide 4-(4-cyclobutylpiperazin-1-yl)-N—((S)-1-cyclopentyl-2-((3aS,6S,6aR)-6-(methylamino)-3-oxodihydro-2H-furo[3,2-b]pyrrol-4(5H,6H,6aH)-yl)-2-oxoethyl)benzamide N—((S)-1-cyclopentyl-2-((3aS,6S,6aR)-6-(methylamino)-3-oxodihydro-2H-furo[3,2-b]pyrrol-4(5H,6H, 6aH)-yl)-2-oxoethyl)-4-(1-propylpiperidin-4-yl)benzamide N—((S)-1-cyclopentyl-2-((3aS,6S,6aR)-6-(methylamino)-3-oxodihydro-2H-furo[3,2-b]pyrrol-4(5H,6H, 6aH)-yl)-2-oxoethyl)-4-(1-cyclopropylpiperidin-4-yl) benzamide 4-(1-cyclobutylpiperidin-4-yl)-N—((S)-1-cyclopentyl-2-((3aS,6S,6aR)-6-(methylamino)-3-oxodihydro-2H-furo[3,2-b]pyrrol-4(5H,6H,6aH)-yl)-2-oxoethyl)benzamide N—((S)-1-cyclohexyl-2-((3aS,6S,6aR)-6-(methylamino)-3-oxodihydro-2H-furo[3,2-b]pyrrol-4(5H,6H, 6aH)-yl)-2-oxoethyl)-4-(4-ethylpiperazin-1-yl)benzamide N—((S)-1-cyclohexyl-2-((3aS,6S,6aR)-6-(methylamino)-3-oxodihydro-2H-furo[3,2-b]pyrrol-4(5H,6H, 6aH)-yl)-2-oxoethyl)-4-(4-propylpiperazin-1-yl)benzamide N—((S)-1-cyclohexyl-2-((3aS,6S,6aR)-6-(methylamino)-3-oxodihydro-2H-furo[3,2-b]pyrrol-4(5H,6H, 6aH)-yl)-2-oxoethyl)-4-(4-isopropylpiperazin-1-yl) benzamide N—((S)-1-cyclohexyl-2-((3aS,6S,6aR)-6-(methylamino)-3-oxodihydro-2H-furo[3,2-b]pyrrol-4(5H,6H, 6aH)-yl)-2-oxoethyl)-4-(4-cyclopropylpiperazin-1-yl) benzamide 4-(4-cyclobutylpiperazin-1-yl)-N—((S)-1-cyclohexyl-2-((3aS,6S,6aR)-6-(methylamino)-3-oxodihydro-2H-furo[3,2-b]pyrrol-4(5H,6H,6aH)-yl)-2-oxoethyl)benzamide N—((S)-1-cyclohexyl-2-((3aS,6S,6aR)-6-(methylamino)-3-oxodihydro-2H-furo[3,2-b]pyrrol-4(5H,6H, 6aH)-yl)-2-oxoethyl)-4-(1-propylpiperidin-4-yl)benzamide N—((S)-1-cyclohexyl-2-((3aS,6S,6aR)-6-(methylamino)-3-oxodihydro-2H-furo[3,2-b]pyrrol-4(5H,6H, 6aH)-yl)-2-oxoethyl)-4-(1-cyclopropylpiperidin-4-yl) benzamide 4-(1-cyclobutylpiperidin-4-yl)-N—((S)-1-cyclohexyl-2-((3aS,6S,6aR)-6-(methylamino)-3-oxodihydro-2H-furo[3,2-b]pyrrol-4(5H,6H,6aH)-yl)-2-oxoethyl)benzamide 4-(4-methylpiperazin-1-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide 4-(4-ethylpiperazin-1-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide 4-(4-isopropylpiperazin-1-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl) benzamide 4-(4-(2-methoxyethyl)piperazin-1-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide 4-(4-cyclopropylpiperazin-1-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide 4-(4-cyclobutylpiperazin-1-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide 4-(1-ethylpiperidin-4-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)-4-(1-propylpiperidin-4-yl)benzamide 4-(1-isopropylpiperidin-4-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide 4-(1-(2-methoxyethyl)piperidin-4-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide 4-(1-cyclopropylpiperidin-4-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide 4-(1-cyclobutylpiperidin-4-yl)-N—((S)-1-((3aS,6S,6aS)-6-(methylthio)-3-oxodihydro-2H-furo[3,2-b]pyrrol-4(5H,6H,6aH)-yl)-4,4-dimethyl-1-oxopentan-2-yl)benzamide 4-(4-methylpiperazin-1-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide 4-(4-ethylpiperazin-1-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)-4-(4-propylpiperazin-1-yl)benzamide 4-(4-isopropylpiperazin-1-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide 4-(4-(2-methoxyethyl)piperazin-1-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide 4-(4-cyclopropylpiperazin-1-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide 4-(4-cyclobutylpiperazin-1-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)-4-(1-propylpiperidin-4-yl)benzamide 4-(1-isopropylpiperidin-4-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide 4-(1-cyclopropylpiperidin-4-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide 4-(1-cyclobutylpiperidin-4-yl)-N—((S)-1-((3aS,6S,6aS)-6-(methylthio)-3-oxodihydro-2H-furo[3,2-b]pyrrol-4(5H,6H,6aH)-yl)-4-methyl-1-oxopentan-2-yl)benzamide 4-(4-methylpiperazin-1-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(4-ethylpiperazin-1-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)-4-(4-propylpiperazin-1-yl)benzamide 4-(4-isopropylpiperazin-1-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(4-(2-methoxyethyl)piperazin-1-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(4-cyclopropylpiperazin-1-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(4-cyclobutylpiperazin-1-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(1-methylpiperidin-4-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(1-ethylpiperidin-4-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)-4-(1-propylpiperidin-4-yl)benzamide 4-(1-isopropylpiperidin-4-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(1-(2-methoxyethyl)piperidin-4-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(1-cyclopropylpiperidin-4-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(1-cyclobutylpiperidin-4-yl)-N-((2S,3S)-1-((3aS,6S,6aS)-6-(methylthio)-3-oxodihydro-2H-furo[3,2-b]pyrrol-4(5H,6H,6aH)-yl)-3-methyl-1-oxopentan-2-yl)benzamide 4-(4-methylpiperazin-1-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide 4-(4-ethylpiperazin-1-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide 4-(4-isopropylpiperazin-1-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide 4-(4-(2-methoxyethyl)piperazin-1-yl)-N—((S)-1-((3aS,6S,6aS)-6-(methylthio)-3-oxodihydro-2H-furo[3,2-b]pyrrol-4(5H,6H,6aH)-yl)-3,3-di-methyl-1-oxobutan-2-yl)benzamide 4-(4-cyclopropylpiperazin-1-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide 4-(4-cyclobutylpiperazin-1-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide 4-(1-ethylpiperidin-4-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)-4-(1-propylpiperidin-4-yl)benzamide 4-(1-isopropylpiperidin-4-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide 4-(1-cyclopropylpiperidin-4-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide 4-(1-cyclobutylpiperidin-4-yl)-N—((S)-1-((3aS,6S,6aS)-6-(methylthio)-3-oxodihydro-2H-furo[3,2-b]pyrrol-4(5H,6H,6aH)-yl)-3,3-dimethyl-1-oxobutan-2-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(4-methylpiperazin-1-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(4-ethylpiperazin-1-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(4-propylpiperazin-1-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(1-methylpiperidin-4-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(1-ethylpiperidin-4-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(1-propylpiperidin-4-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(1-(2-methoxyethyl)piperidin-4-yl)benzamide N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclopentyl-2-((3aS,6S,6aS)-6-(methylthio)-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(4-methylpiperazin-1-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(4-ethylpiperazin-1-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(4-propylpiperazin-1-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(1-methylpiperidin-4-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(1-ethylpiperidin-4-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(1-propylpiperidin-4-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(1-(2-methoxyethyl)piperidin-4-yl)benzamide N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclohexyl-2-((3aS,6S,6aS)-6-(methylthio)-3-oxodihydro-2H-furo[3,2-b]pyrrol-4(5H,6H,6aH)-yl)-2-oxoethyl)benzamide N—((S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(4-methylpiperazin-1-yl)benzamide N—((S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(4-ethylpiperazin-1-yl)benzamide N—((S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide N—((S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(4-isopropylpiperazin-1-yl)benzamide N—((S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(4-(2-methoxyethyl)piperazin-1-yl)benzamide N—((S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(4-cyclopropylpiperazin-1-yl)benzamide N—((S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(4-cyclobutylpiperazin-1-yl)benzamide N—((S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(1-propylpiperidin-4-yl)benzamide N—((S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(1-isopropylpiperidin-4-yl)benzamide N—((S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(1-(2-methoxyethyl)piperidin-4-yl)benzamide N—((S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(1-cyclopropylpiperidin-4-yl)benzamide N—((S)-1-((3aS,6S,6aS)-6-azido-3-oxodihydro-2H-furo[3,2-b]pyrrol-4(5H,6H,6aH)-yl)-4,4-dimethyl-1-oxopentan-2-yl)-4-(1-cyclobutylpiperidin-4-yl)benzamide N—((S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(4-methylpiperazin-1-yl)benzamide N—((S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(4-ethylpiperazin-1-yl)benzamide N—((S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(4-propylpiperazin-1-yl)benzamide N—((S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(4-isopropylpiperazin-1-yl)benzamide N—((S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(4-(2-methoxyethyl)piperazin-1-yl)benzamide N—((S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(4-cyclopropylpiperazin-1-yl)benzamide N—((S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(4-cyclobutylpiperazin-1-yl)benzamide N—((S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(1-propylpiperidin-4-yl)benzamide N—((S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(1-cyclopropylpiperidin-4-yl)benzamide N—((S)-1-((3aS,6S,6aS)-6-azido-3-oxodihydro-2H-furo[3,2-b]pyrrol-4(5H,6H,6aH)-yl)-4-methyl-1-oxopentan-2-yl)-4-(1-cyclobutylpiperidin-4-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(4-methylpiperazin-1-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(4-ethylpiperazin-1-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(4-propylpiperazin-1-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(4-isopropylpiperazin-1-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(4-(2-methoxyethyl)piperazin-1-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(4-cyclopropylpiperazin-1-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(4-cyclobutylpiperazin-1-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(1-methylpiperidin-4-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(1-ethylpiperidin-4-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(1-propylpiperidin-4-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(1-isopropylpiperidin-4-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(1-(2-methoxyethyl)piperidin-4-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(1-cyclopropylpiperidin-4-yl)benzamide N-((2S,3S)-1-((3aS,6S,6aS)-6-azido-3-oxodihydro-2H-furo[3,2-b]pyrrol-4(5H,6H,6aH)-yl)-3-methyl-1-oxopentan-2-yl)-4-(1-cyclobutylpiperidin-4-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(4-methylpiperazin-1-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(4-ethylpiperazin-1-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(4-isopropylpiperazin-1-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(4-(2-methoxyethyl)piperazin-1-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(4-cyclopropylpiperazin-1-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(4-cyclobutylpiperazin-1-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(1-propylpiperidin-4-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(1-cyclopropylpiperidin-4-yl)benzamide N—((S)-1-((3aS,6S,6aS)-6-azido-3-oxodihydro-2H-furo[3,2-b]pyrrol-4(5H,6H,6aH)-yl)-3,3-dimethyl-1-oxobutan-2-yl)-4-(1-cyclobutylpiperidin-4-yl)benzamide N—((S)-1-cyclopentyl-2-((3aS,6S,6aS)-6-azido-3-oxodihydro-2H-furo[3,2-b]pyrrol-4(5H,6H,6aH)-yl)-2-oxoethyl)-4-(4-methylpiperazin-1-yl)benzamide N—((S)-1-cyclopentyl-2-((3aS,6S,6aS)-6-azido-3-oxodihydro-2H-furo[3,2-b]pyrrol-4(5H,6H,6aH)-yl)-2-oxoethyl)-4-(4-ethylpiperazin-1-yl)benzamide N—((S)-1-cyclopentyl-2-((3aS,6S,6aS)-6-azido-3-oxodihydro-2H-furo[3,2-b]pyrrol-4(5H,6H,6aH)-yl)-2-oxoethyl)-4-(4-propylpiperazin-1-yl)benzamide N—((S)-1-cyclopentyl-2-((3aS,6S,6aS)-6-azido-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclopentyl-2-((3aS,6S,6aS)-6-azido-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclopentyl-2-((3aS,6S,6aS)-6-azido-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclopentyl-2-((3aS,6S,6aS)-6-azido-3-oxodihydro-2H-furo[3,2-b]pyrrol-4(5H,6H,6aH)-yl)-2-oxoethyl)benzamide N—((S)-1-cyclopentyl-2-((3aS,6S,6aS)-6-azido-3-oxodihydro-2H-furo[3,2-b]pyrrol-4(5H,6H,6aH)-yl)-2-oxoethyl)-4-(1-propylpiperidin-4-yl)benzamide N—((S)-1-cyclopentyl-2-((3aS,6S,6aS)-6-azido-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclopentyl-2-((3aS,6S,6aS)-6-azido-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(4-methylpiperazin-1-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(4-ethylpiperazin-1-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(4-propylpiperazin-1-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclohexyl-2-((3aS,6S,6aS)-6-azido-3-oxodihydro-2H-furo[3,2-b]pyrrol-4(5H,6H,6aH)-yl)-2-oxoethyl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(1-methylpiperidin-4-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(1-ethylpiperidin-4-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(1-propylpiperidin-4-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(1-(2-methoxyethyl)piperidin-4-yl)benzamide N—((S)-1-cyclohexyl-2-((3aS,6S,6aS)-6-azido-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclohexyl-2-((3aS,6S,6aS)-6-azido-3-oxodihydro-2H-furo[3,2-b]pyrrol-4(5H,6H,6aH)-yl)-2-oxoethyl)benzamide N—((S)-1-((3aS,6R,6aS)-6-hydroxy-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide N—((S)-1-((3aS,6R,6aS)-6-hydroxy-3-oxodihydro-2H-furo[3,2-b]pyrrol-4(5H,6H,6aH)-yl)-4,4-dimethyl-1-oxopentan-2-yl)-4-(4-isopropylpiperazin-1-yl)benzamide 4-(4-cyclopropylpiperazin-1-yl)-N—((S)-1-((3aS,6R,6aS)-6-hydroxy-3-oxodihydro-2H-furo[3,2-b]pyrrol-4(5H,6H,6aH)-yl)-4,4-dimethyl-1-oxopentan-2-yl)benzamide 4-(4-cyclobutylpiperazin-1-yl)-N—((S)-1-((3aS,6R,6aS)-6-hydroxy-3-oxodihydro-2H-furo[3,2-b]pyrrol-4(5H,6H,6aH)-yl)-4,4-dimethyl-1-oxopentan-2-yl)benzamide 4-(1-cyclopropylpiperidin-4-yl)-N—((S)-1-((3aS,6R,6aS)-6-hydroxy-3-oxodihydro-2H-furo[3,2-b]pyrrol-4(5H,6H,6aH)-yl)-4,4-dimethyl-1-oxopentan-2-yl)benzamide 4-(1-cyclobutylpiperidin-4-yl)-N—((S)-1-((3aS,6R,6aS)-6-hydroxy-3-oxodihydro-2H-furo[3,2-b]pyrrol-4(5H,6H,6aH)-yl)-4,4-dimethyl-1-oxopentan-2-yl)benzamide N—((S)-1-((3aS,6R,6aS)-6-hydroxy-3-oxodihydro-2H-furo[3,2-b]pyrrol-4(5H,6H,6aH)-yl)-4-methyl-1-oxopentan-2-yl)-4-(4-propylpiperazin-1-yl)benzamide N—((S)-1-((3aS,6R,6aS)-6-hydroxy-3-oxodihydro-2H-furo[3,2-b]pyrrol-4(5H,6H,6aH)-yl)-4-methyl-1-oxopentan-2-yl)-4-(4-isopropylpiperazin-1-yl)benzamide 4-(4-cyclopropylpiperazin-1-yl)-N—((S)-1-((3aS,6R,6aS)-6-hydroxy-3-oxodihydro-2H-furo[3,2-b]pyrrol-4(5H,6H,6aH)-yl)-4-methyl-1-oxopentan-2-yl)benzamide 4-(4-cyclobutylpiperazin-1-yl)-N—((S)-1-((3aS,6R,6aS)-6-hydroxy-3-oxodihydro-2H-furo[3,2-b]pyrrol-4(5H,6H,6aH)-yl)-4-methyl-1-oxopentan-2-yl)benzamide 4-(1-cyclopropylpiperidin-4-yl)-N—((S)-1-((3aS,6R,6aS)-6-hydroxy-3-oxodihydro-2H-furo[3,2-b]pyrrol-4(5H,6H,6aH)-yl)-4-methyl-1-oxopentan-2-yl)benzamide 4-(1-cyclobutylpiperidin-4-yl)-N—((S)-1-((3aS,6R,6aS)-6-hydroxy-3-oxodihydro-2H-furo[3,2-b]pyrrol-4(5H,6H,6aH)-yl)-4-methyl-1-oxopentan-2-yl)benzamide 4-(4-ethylpiperazin-1-yl)-N-((2S,3S)-1-((3aS,6R,6aS)-6-hydroxy-3-oxodihydro-2H-furo[3,2-b]pyrrol-4(5H,6H,6aH)-yl)-3-methyl-1-oxopentan-2-yl)benzamide N-((2S,3S)-1-((3aS,6R,6aS)-6-hydroxy-3-oxodihydro-2H-furo[3,2-b]pyrrol-4(5H,6H,6aH)-yl)-3-methyl-1-oxopentan-2-yl)-4-(4-propylpiperazin-1-yl)benzamide N-((2S,3S)-1-((3aS,6R,6aS)-6-hydroxy-3-oxodihydro-2H-furo[3,2-b]pyrrol-4(5H,6H,6aH)-yl)-3-methyl-1-oxopentan-2-yl)-4-(4-isopropylpiperazin-1-yl)benzamide 4-(4-cyclopropylpiperazin-1-yl)-N-((2S,3S)-1-((3aS,6R,6aS)-6-hydroxy-3-oxodihydro-2H-furo[3,2-b]pyrrol-4(5H,6H,6aH)-yl)-3-methyl-1-oxopentan-2-yl)benzamide 4-(4-cyclobutylpiperazin-1-yl)-N-((2S,3S)-1-((3aS,6R,6aS)-6-hydroxy-3-oxodihydro-2H-furo[3,2-b]pyrrol-4(5H,6H,6aH)-yl)-3-methyl-1-oxopentan-2-yl)benzamide 4-(1-cyclopropylpiperidin-4-yl)-N-((2S,3S)-1-((3aS,6R,6aS)-6-hydroxy-3-oxodihydro-2H-furo[3,2-b]pyrrol-4(5H,6H,6aH)-yl)-3-methyl-1-oxopentan-2-yl)benzamide 4-(1-cyclobutylpiperidin-4-yl)-N-((2S,3S)-1-((3aS,6R,6aS)-6-hydroxy-3-oxodihydro-2H-furo[3,2-b]pyrrol-4(5H,6H,6aH)-yl)-3-methyl-1-oxopentan-2-yl)benzamide 4-(4-ethylpiperazin-1-yl)-N—((S)-1-((3aS,6R,6aS)-6-hydroxy-3-oxodihydro-2H-furo[3,2-b]pyrrol-4(5H,6H,6aH)-yl)-3,3-dimethyl-1-oxobutan-2-yl)benzamide ((S)-1-((3aS,6R,6aS)-6-hydroxy-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide N—((S)-1-((3aS,6R,6aS)-6-hydroxy-3-oxodihydro-2H-furo[3,2-b]pyrrol-4(5H,6H,6aH)-yl)-3,3-dimethyl-1-oxobutan-2-yl)-4-(4-isopropylpiperazin-1-yl)benzamide 4-(4-cyclopropylpiperazin-1-yl)-N—((S)-1-((3aS,6R,6aS)-6-hydroxy-3-oxodihydro-2H-furo[3,2-b]pyrrol-4(5H,6H,6aH)-yl)-3,3-dimethyl-1-oxobutan-2-yl)benzamide 4-(4-cyclobutylpiperazin-1-yl)-N—((S)-1-((3aS,6R,6aS)-6-hydroxy-3-oxodihydro-2H-furo[3,2-b]pyrrol-4(5H,6H,6aH)-yl)-3,3-dimethyl-1-oxobutan-2-yl)benzamide 4-(1-cyclopropylpiperidin-4-yl)-N—((S)-1-((3aS,6R,6aS)-6-hydroxy-3-oxodihydro-2H-furo[3,2-b]pyrrol-4(5H,6H,6aH)-yl)-3,3-dimethyl-1-oxobutan-2-yl)benzamide 4-(1-cyclobutylpiperidin-4-yl)-N—((S)-1-((3aS,6R,6aS)-6-hydroxy-3-oxodihydro-2H-furo[3,2-b]pyrrol-4(5H,6H,6aH)-yl)-3,3-dimethyl-1-oxobutan-2-yl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclopentyl-2-((3aS,6R,6aS)-6-hydroxy-3-oxodihydro-2H-furo[3,2-b]pyrrol-4(5H,6H,6aH)-yl)-2-oxoethyl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(1-(2-methoxyethyl)piperidin-4-yl)benzamide N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclohexyl-2-((3aS,6R,6aS)-6-hydroxy-3-oxodihydro-2H-furo[3,2-b]pyrrol-4(5H,6H,6aH)-yl)-2-oxoethyl)benzamide N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)-4-(4-methylpiperazin-1-yl)benzamide 4-(4-ethylpiperazin-1-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide 4-(4-isopropylpiperazin-1-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide 4-(4-(2-methoxyethyl)piperazin-1-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide 4-(4-cyclopropylpiperazin-1-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide 4-(4-cyclobutylpiperazin-1-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide 4-(1-cyclopropylpiperidin-4-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide 4-(1-cyclobutylpiperidin-4-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide 4-(4-ethylpiperazin-1-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)-4-(4-propylpiperazin-1-yl)benzamide 4-(4-isopropylpiperazin-1-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide 4-(4-(2-methoxyethyl)piperazin-1-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide 4-(4-cyclopropylpiperazin-1-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide 4-(4-cyclobutylpiperazin-1-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide 4-(1-cyclopropylpiperidin-4-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide 4-(1-cyclobutylpiperidin-4-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)-4-(4-methylpiperazin-1-yl)benzamide 4-(4-ethylpiperazin-1-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)-4-(4-propylpiperazin-1-yl)benzamide 4-(4-isopropylpiperazin-1-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide 4-(4-(2-methoxyethyl)piperazin-1-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide 4-(4-cyclopropylpiperazin-1-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide 4-(4-cyclobutylpiperazin-1-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide 4-(1-ethylpiperidin-4-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)-4-(1-propylpiperidin-4-yl)benzamide 4-(1-isopropylpiperidin-4-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide 4-(1-cyclopropylpiperidin-4-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide 4-(1-cyclobutylpiperidin-4-yl)-N-((2S,3S)-1-((3aS,6R,6aS)-6-methoxy-3-oxodihydro-2H-furo[3,2-b]pyrrol-4(5H,6H,6aH)-yl)-3-methyl-1-oxopentan-2-yl)benzamide N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)-4-(4-methylpiperazin-1-yl)benzamide 4-(4-ethylpiperazin-1-yl)-N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)benzamide N—((S)-1-((3aS,6R,6aS)-6-methoxy-3-oxodihydro-2H-furo[3,2-pyrrol-4(5H,6H,6aH)-yl)-3,3-dimethyl-1-oxobutan-2-yl)-4-(4-propylpiperazin-1-yl)benzamide 4-(4-isopropylpiperazin-1-yl)-N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)benzamide N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)-4-(4-(2-methoxyethyl)piperazin-1-yl)benzamide 4-(4-cyclopropylpiperazin-1-yl)-N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)benzamide 4-(4-cyclobutylpiperazin-1-yl)-N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)benzamide 4-(1-cyclopropylpiperidin-4-yl)-N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)benzamide 4-(1-cyclobutylpiperidin-4-yl)-N—((S)-1-((3aS,6R,6aS)-6-methoxy-3-oxodihydro-2H-furo[3,2-b]pyrrol-4(5H,6H,6aH)-yl)-3,3-dimethyl-1-oxobutan-2-yl)benzamide N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)benzamide N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(4-methylpiperazin-1-yl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(4-ethylpiperazin-1-yl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(4-propylpiperazin-1-yl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(4-isopropylpiperazin-1-yl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(4-(2-methoxyethyl)piperazin-1-yl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(4-cyclopropylpiperazin-1-yl)benzamide 4-(4-cyclobutylpiperazin-1-yl)-N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(1-ethylpiperidin-4-yl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(1-propylpiperidin-4-yl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(1-isopropylpiperidin-4-yl)benzamide N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)-4-(1-cyclopropylpiperidin-4-yl)benzamide 4-(1-cyclobutylpiperidin-4-yl)-N—((S)-1-cyclohexyl-2-((3aS,6R,6aS)-6-methoxy-3-oxodihydro-2H-furo[3,2-b]pyrrol-4(5H,6H,6aH)-yl)-2-oxoethyl)benzamide N—((S)-1-((3aS,6R,6aR)-6-amino-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide N—((S)-1-((3aS,6R,6aR)-6-amino-3-oxodihydro-2H-furo[3,2-b]pyrrol-4(5H,6H,6aH)-yl)-4,4-dimethyl-1-oxopentan-2-yl)-4-(4-cyclopropylpiperazin-1-yl)benzamide N—((S)-1-((3aS,6R,6aR)-6-amino-3-oxodihydro-2H-furo[3,2-b]pyrrol-4(5H,6H,6aH)-yl)-4,4-dimethyl-1-oxopentan-2-yl)-4-(4-cyclobutylpiperazin-1-yl)benzamide N-((2S,3S)-1-((3aS,6R,6aR)-6-amino-3-oxodihydro-2H-furo[3,2-b]pyrrol-4(5H,6H,6aH)-yl)-3-methyl-1-oxopentan-2-yl)-4-(4-ethylpiperazin-1-yl)benzamide N-((2S,3S)-1-((3aS,6R,6aR)-6-amino-3-oxodihydro-2H-furo[3,2-b]pyrrol-4(5H,6H,6aH)-yl)-3-methyl-1-oxopentan-2-yl)-4-(4-propylpiperazin-1-yl)benzamide N-((2S,3S)-1-((3aS,6R,6aR)-6-amino-3-oxodihydro-2H-furo[3,2-b]pyrrol-4(5H,6H,6aH)-yl)-3-methyl-1-oxopentan-2-yl)-4-(4-isopropylpiperazin-1-yl)benzamide N-((2S,3S)-1-((3aS,6R,6aR)-6-amino-3-oxodihydro-2H-furo[3,2-b]pyrrol-4(5H,6H,6aH)-yl)-3-methyl-1-oxopentan-2-yl)-4-(4-cyclopropylpiperazin-1-yl)benzamide N-((2S,3S)-1-((3aS,6R,6aR)-6-amino-3-oxodihydro-2H-furo[3,2-b]pyrrol-4(5H,6H,6aH)-yl)-3-methyl-1-oxopentan-2-yl)-4-(4-cyclobutylpiperazin-1-yl)benzamide N—((S)-1-((3aS,6R,6aR)-6-amino-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide N—((S)-1-((3aS,6R,6aR)-6-amino-3-oxodihydro-2H-furo[3,2-b]pyrrol-4(5H,6H,6aH)-yl)-3,3-dimethyl-1-oxobutan-2-yl)-4-(4-cyclopropylpiperazin-1-yl)benzamide N—((S)-1-((3aS,6R,6aR)-6-amino-3-oxodihydro-2H-furo[3,2-b]pyrrol-4(5H,6H,6aH)-yl)-3,3-dimethyl-1-oxobutan-2-yl)-4-(4-cyclobutylpiperazin-1-yl)benzamide N—((S)-2-((3aS,6R,6aR)-6-amino-3-oxodihydro-2H-furo[3,2-b]pyrrol-4(5H,6H,6aH)-yl)-1-cyclopentyl-2-oxoethyl)-4-(4-propylpiperazin-1-yl)benzamide N—((S)-2-((3aS,6R,6aR)-6-amino-3-oxodihydro-2H-furo[3,2-b]pyrrol-4(5H,6H,6aH)-yl)-1-cyclopentyl-2-oxoethyl)-4-(4-cyclopropylpiperazin-1-yl)benzamide N—((S)-2-((3aS,6R,6aR)-6-amino-3-oxodihydro-2H-furo[3,2-b]pyrrol-4(5H,6H,6aH)-yl)-1-cyclopentyl-2-oxoethyl)-4-(4-cyclobutylpiperazin-1-yl)benzamide N—((S)-2-((3aS,6R,6aR)-6-amino-3-oxodihydro-2H-furo[3,2-b]pyrrol-4(5H,6H,6aH)-yl)-1-cyclohexyl-2-oxoethyl)-4-(4-ethylpiperazin-1-yl)benzamide N—((S)-2-((3aS,6R,6aR)-6-amino-3-oxodihydro-2H-furo[3,2-b]pyrrol-4(5H,6H,6aH)-yl)-1-cyclohexyl-2-oxoethyl)-4-(4-propylpiperazin-1-yl)benzamide N—((S)-2-((3aS,6R,6aR)-6-amino-3-oxodihydro-2H-furo[3,2-b]pyrrol-4(5H,6H,6aH)-yl)-1-cyclohexyl-2-oxoethyl)-4-(4-isopropylpiperazin-1-yl)benzamide N—((S)-2-((3aS,6R,6aR)-6-amino-3-oxodihydro-2H-furo[3,2-b]pyrrol-4(5H,6H,6aH)-yl)-1-cyclohexyl-2-oxoethyl)-4-(4-cyclopropylpiperazin-1-yl)benzamide N—((S)-2-((3aS,6R,6aR)-6-amino-3-oxodihydro-2H-furo[3,2-b]pyrrol-4(5H,6H,6aH)-yl)-1-cyclohexyl-2-oxoethyl)-4-(4-cyclobutylpiperazin-1-yl)benzamide N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(4-methylpiperazin-1-yl)benzamide N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(4-ethylpiperazin-1-yl)benzamide N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(4-isopropylpiperazin-1-yl)benzamide N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(4-(2-methoxyethyl)piperazin-1-yl)benzamide N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(4-cyclopropylpiperazin-1-yl)benzamide N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(4-cyclobutylpiperazin-1-yl)benzamide N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(1-propylpiperidin-4-yl)benzamide N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(1-isopropylpiperidin-4-yl)benzamide N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(1-(2-methoxyethyl)piperidin-4-yl)benzamide N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(1-cyclopropylpiperidin-4-yl)benzamide N—((S)-1-((3aS,6R,6aS)-6-azido-3-oxodihydro-2H-furo[3,2-b]pyrrol-4(5H,6H,6aH)-yl)-4,4-dimethyl-1-oxopentan-2-yl)-4-(1-cyclobutylpiperidin-4-yl)benzamide N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(4-methylpiperazin-1-yl)benzamide N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(4-ethylpiperazin-1-yl)benzamide N—((S)-1-((3aS,6R,6aS)-6-azido-3-oxodihydro-2H-furo[3,2-pyrrol-4(5H,6H,6aH)-yl)-4-methyl-1-oxopentan-2-yl)-4-(4-propylpiperazin-1-yl)benzamide N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(4-isopropylpiperazin-1-yl)benzamide N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(4-(2-methoxyethyl)piperazin-1-yl)benzamide N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(4-cyclopropylpiperazin-1-yl)benzamide N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(4-cyclobutylpiperazin-1-yl)benzamide N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(1-propylpiperidin-4-yl)benzamide N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(1-cyclopropylpiperidin-4-yl)benzamide N—((S)-1-((3aS,6R,6aS)-6-azido-3-oxodihydro-2H-furo[3,2-b]pyrrol-4(5H,6H,6aH)-yl)-4-methyl-1-oxopentan-2-yl)-4-(1-cyclobutylpiperidin-4-yl)benzamide N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(4-methylpiperazin-1-yl)benzamide N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(4-ethylpiperazin-1-yl)benzamide N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(4-propylpiperazin-1-yl)benzamide N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(4-isopropylpiperazin-1-yl)benzamide N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(4-(2-methoxyethyl)piperazin-1-yl)benzamide N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(4-cyclopropylpiperazin-1-yl)benzamide N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(4-cyclobutylpiperazin-1-yl)benzamide N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(1-methylpiperidin-4-yl)benzamide N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(1-ethylpiperidin-4-yl)benzamide N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(1-propylpiperidin-4-yl)benzamide N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(1-isopropylpiperidin-4-yl)benzamide N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(1-(2-methoxyethyl)piperidin-4-yl)benzamide N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(1-cyclopropylpiperidin-4-yl)benzamide N-((2S,3S)-1-((3aS,6R,6aS)-6-azido-3-oxodihydro-2H-furo[3,2-b]pyrrol-4(5H,6H,6aH)-yl)-3-methyl-1-oxopentan-2-yl)-4-(1-cyclobutylpiperidin-4-yl)benzamide N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(4-methylpiperazin-1-yl)benzamide N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(4-ethylpiperazin-1-yl)benzamide N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(4-propylpiperazin-1-yl)benzamide N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(4-isopropylpiperazin-1-yl)benzamide N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(4-(2-methoxyethyl)piperazin-1-yl)benzamide N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(4-cyclopropylpiperazin-1-yl)benzamide N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(4-cyclobutylpiperazin-1-yl)benzamide N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(1-propylpiperidin-4-yl)benzamide N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(1-cyclopropylpiperidin-4-yl)benzamide N—((S)-1-((3aS,6R,6aS)-6-azido-3-oxodihydro-2H-furo[3,2-b]pyrrol-4(5H,6H,6aH)-yl)-3,3-dimethyl-1-oxobutan-2-yl)-4-(1-cyclobutylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(4-methylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(4-ethylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(4-propylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(4-isopropylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(4-(2-methoxyethyl)piperazin-1-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(4-cyclopropylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(4-cyclobutylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(1-propylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(1-cyclopropylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclopentyl-2-oxoethyl)-4-(1-cyclobutylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(4-methylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(4-ethylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(4-propylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(4-isopropylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(4-(2-methoxyethyl)piperazin-1-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(4-cyclopropylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(4-cyclobutylpiperazin-1-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(1-methylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(1-ethylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(1-propylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(1-isopropylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(1-(2-methoxyethyl)piperidin-4-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(1-cyclopropylpiperidin-4-yl)benzamide N—((S)-2-((3aS,6R,6aS)-6-azido-3-oxodihydro-2H-furo[3,2-b]pyrrol-4(5H,6H,6aH)-yl)-1-cyclohexyl-2-oxoethyl)-4-(1-cyclobutylpiperidin-4-yl)benzamide.

16. A pharmaceutical or veterinary composition comprising a compound according to claim 1 and a pharmaceutically acceptable or veterinarily acceptable diluent, excipient and/or carrier.

17. A process for preparing a pharmaceutical or veterinary composition, said process comprising admixing a compound according to claim 1 with a pharmaceutically acceptable or veterinarily acceptable diluent, excipient and/or carrier.

18. A compound according to claim 1 which is selected from the following:

N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)-4-(4-methylpiperazin-1-yl)benzamide;

N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)-4-(4-methylpiperazin-1-yl)benzamide;

N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)-4-(4-methylpiperazin-1-yl)benzamide;

4-(4-ethylpiperazin-1-yl)-N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)benzamide;

4-(4-ethylpiperazin-1-yl)-N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)benzamide;

4-(4-ethylpiperazin-1-yl)-N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)benzamide;

4-(4-ethylpiperazin-1-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide;

N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)-4-(4-propylpiperazin-1-yl)benzamide;

N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide;

N—((S)-1-((3aS,6R,6aS)-6-methoxy-3-oxodihydro-2H-furo[3,2-b]pyrrol-4(5H,6H,6aH)-yl)-4-methyl-1-oxopentan-2-yl)-4-(4-propylpiperazin-1-yl)benzamide;

N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide;

4-(4-isopropylpiperazin-1-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide;

N—((S)-1-((3aS,6S,6aS)-6-methoxy-3-oxodihydro-2H-furo[3,2-b]pyrrol-4(5H,6H,6aH)-yl)-4-methyl-1-oxopentan-2-yl)-4-(4-(2-methoxyethyl)piperazin-1-yl)benzamide;

N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)-4-(1-propylpiperidin-4-yl)benzamide;

N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-methylpiperazin-1-yl)benzamide;

N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-ethylpiperazin-1-yl)benzamide; and N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(4-ethylpiperazin-1-yl)benzamide.

19. A compound according to claim 18 which is selected from the following:

N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)-4-(4-methylpiperazin-1-yl)benzamide;

N—((S)-1-((3aS,6S,6aS)-6-methoxy-3-oxodihydro-2H-furo[3,2-b]pyrrol-4(5H,6H,6aH)-yl)-4,4-dimethyl-1-oxopentan-2-yl)-4-(4-propylpiperazin-1-yl)benzamide;

4-(4-isopropylpiperazin-1-yl)-N—((S)-1-((3aS,6R,6aS)-6-methoxy-3-oxodihydro-2H-furo[3,2-b]pyrrol-4(5H,6H,6aH)-yl)-4,4-dimethyl-1-oxopentan-2-yl)benzamide;

N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-methylpiperazin-1-yl)benzamide;

N—((S)-1-cyclopentyl-2-((3aS,6S,6aS)-6-methoxy-3-oxodihydro-2H-furo[3,2-b]pyrrol-4(5H,6H,6aH)-yl)-2-oxoethyl)-4-(4-ethylpiperazin-1-yl)benzamide; and N—((S)-1-cyclopentyl-2-((3aS,6R,6aS)-6-methoxy-3-oxodihydro-2H-furo[3,2-b]pyrrol-4(5H,6H,6aH)-yl)-2-oxoethyl)-4-(4-ethylpiperazin-1-yl)benzamide.

\* \* \* \* \*